US012692247B2

(12) United States Patent
Bhamra et al.

(10) Patent No.: US 12,692,247 B2
(45) Date of Patent: Jul. 28, 2026

(54) PHENYL- AND PYRIDOPYRAZOLE DERIVATIVES AS INHIBITORS OF DDR1

(71) Applicant: Redx Pharma Limited, Macclesfield (GB)

(72) Inventors: Inder Bhamra, Macclesfield (GB); Clifford D. Jones, Macclesfield (GB); Ana Varela Rodriguez, Macclesfield (GB)

(73) Assignee: Redx Pharma Limited, Macclesfield (GB)

( * ) Notice: Subject to any disclaimer, the term of this patent is extended or adjusted under 35 U.S.C. 154(b) by 304 days.

(21) Appl. No.: 18/294,014

(22) PCT Filed: Aug. 15, 2022

(86) PCT No.: PCT/GB2022/052122

§ 371 (c)(1),
(2) Date: Jan. 31, 2024

(87) PCT Pub. No.: WO2023/021278

PCT Pub. Date: Feb. 23, 2023

(65) Prior Publication Data

US 2024/0336592 A1 Oct. 10, 2024

(30) Foreign Application Priority Data

Aug. 16, 2021 (GB) .................................... 2111740

(51) Int. Cl.

| | |
|---|---|
| *C07D 401/12* | (2006.01) |
| *A61K 31/4725* | (2006.01) |
| *A61K 31/496* | (2006.01) |
| *A61K 31/506* | (2006.01) |
| *A61K 31/5377* | (2006.01) |
| *C07D 401/14* | (2006.01) |
| *C07D 405/14* | (2006.01) |
| *C07D 413/14* | (2006.01) |
| *C07D 471/04* | (2006.01) |
| *C07D 487/04* | (2006.01) |
| *C07D 491/08* | (2006.01) |

(52) U.S. Cl.

CPC ........ *C07D 401/12* (2013.01); *A61K 31/4725* (2013.01); *A61K 31/496* (2013.01); *A61K 31/506* (2013.01); *A61K 31/5377* (2013.01); *C07D 401/14* (2013.01); *C07D 405/14* (2013.01); *C07D 413/14* (2013.01); *C07D 471/04* (2013.01); *C07D 487/04* (2013.01); *C07D 491/08* (2013.01)

(58) Field of Classification Search

CPC .. C07D 401/12; C07D 401/14; C07D 405/14; C07D 413/14; C07D 471/04; C07D 487/04; C07D 491/08; A61K 31/4725; A61K 31/496; A61K 31/506; A61K 31/5377

See application file for complete search history.

(56) References Cited

U.S. PATENT DOCUMENTS

| | | | |
|---|---|---|---|
| 2005/0054670 | A1 | 3/2005 | Tegley et al. |
| 2011/0152273 | A1 | 6/2011 | Arikawa et al. |

FOREIGN PATENT DOCUMENTS

| | | | |
|---|---|---|---|
| WO | WO-2002/096873 | A1 | 12/2002 |
| WO | WO-2005/021532 | A1 | 3/2005 |
| WO | WO-2012/164103 | A2 | 12/2012 |
| WO | WO-2017/137334 | A1 | 8/2017 |
| WO | WO2021/013084 | A1 * | 1/2021 |
| WO | WO-2023/021278 | A1 | 2/2023 |

OTHER PUBLICATIONS

GB Search Report for GB Application No. 2111740.3 dated Jan. 17, 2022.

International Search Report and Written Opinion for International Application No. PCT/GB22/52122 dated Nov. 2, 2022.

Wang et al., "Structure-based design of tetrahydroisoquinoline-7-carboxamides as selective discoidin domain receptor 1 (DDR1) inhibitors." Journal of Medicinal Chemistry 59,12 (2016): 5911-5916.

International Preliminary Report on Patentability for International Application No. PCT/GB22/52122 dated Feb. 13, 2024.

GB Search Report for GB Application No. 2115838.1 dated Mar. 30, 2022.

International Search Report and Written Opinion for Application No. PCT/GB22/52778 dated Feb. 15, 2024.

* cited by examiner

*Primary Examiner* — Brandon J Fetterolf

(74) *Attorney, Agent, or Firm* — Foley Hoag LLP; Dana M. Gordon; Shejla S. Pollozi

(57) ABSTRACT

This invention relates to novel compounds and pharmaceutical compositions comprising novel isoquinolone compounds. More specifically, the invention relates to compounds useful as inhibitors of discoidin domain receptor 1 (DDR1) and discoidin domain receptor 2 (DDR2). The compounds are particularly useful in the treatment of cancer and fibrotic diseases.

22 Claims, No Drawings

PHENYL- AND PYRIDOPYRAZOLE DERIVATIVES AS INHIBITORS OF DDR1

RELATED APPLICATIONS

This application is a U.S. National Stage filing under 35 U.S.C. § 371 of PCT Application No. PCT/GB22/52122, filed Aug. 15, 2022; which claims the benefit of priority to Great Britain Patent Application No. 2111740.3, filed Aug. 16, 2021.

This invention relates to novel compounds and pharmaceutical compositions comprising the novel compounds. More specifically, the invention relates to compounds useful as inhibitors of discoidin domain receptor 1 (DDR1) and discoidin domain receptor 2 (DDR2). The compounds are particularly useful in the treatment of cancer and fibrotic diseases

BACKGROUND

Discoidin Domain Receptors (DDRs) DDR1 and DDR2 are type 1 transmembrane Receptor Tyrosine Kinases (RTKs) with collagen receptor functionality (Vogel et al, Mol. Cell, 1997). DDRs contain characteristic collagen binding discoidin domains in the N-terminal extracellular domain. These domains are proceeded by an extracellular juxtamembrane domain, a single transmembrane domain, a cytosolic juxtamembrane domain and a catalytic kinase domain prior to a short C-terminal tail. Five isoforms of DDR1 (DRR1a-e) have been identified which arise from alternative splicing of the cytoplasmic region. No alternative isoforms of DDR2 have been identified. DDR1 and DDR2 have broadly (but not completely) mutually exclusive expression profiles in epithelial cell and stroma respectively. DDRs are activated by binding to collagens with broad specificity but with distinct preference for certain collagen types. Upon activation DDRs are known to regulate cell adhesion, proliferation and remodelling of the extracellular matrix. It is recognised that DDRs are upregulated in response to cellular activity and many forms of tissue injury and as such DDRs are implicated in diseases including cancer, atherosclerosis as well as diseases characterised by fibrosis and inflammation. Inhibitors of DDR kinase activity may be of benefit as therapeutic agents in these disease areas.

DDR1 and DDR2 overexpression and/or activation has been linked to multiple forms of cancer as summarised in a recent review (Elkamhawy et al, Int. J. Mol. Sci., 2021). Studies have shown that elevated DDR expression levels and/or mutations can be found in a number of cancer cell lines as well as primary tumour tissues including lung, pancreas, prostate, breast, brain, ovary, liver and others. DDR1 was found to be a prognostic marker for non-small-cell lung carcinoma (NSCLC) patients. A recent study demonstrated that siRNA-mediated downregulation of DDR1 suppressed melanoma cell malignancy, migration, invasion, and survival. DDR1 protein was also found to be expressed in 63% of serous ovarian cancer tissue, but not in normal ovarian surface epithelium. Involvement of DDR1 in glioblastoma cell invasion and epithelial-mesenchymal transition (EMT) has also been demonstrated. DDR1 expression was found in 50.5% of gastric cancer tissues. DDR1 was found to control triple-negative breast cancer growth by modulating tumour-infiltrating CD4+ and CD8+ T cells. There is also strong evidence indicating that DDR2 could be a potential biomarker and a molecular target for a variety of cancers. For instance, DDR2 overexpression was reported to contribute to NSCLC, thyroid carcinoma, Hodgkin's lymphoma, nasopharyngeal carcinomas, prostate cancer, as well as to head and neck squamous cell carcinoma. According to studies DDR2 contributes to breast cancer metastasis by stabilizing the SNAIL1 protein. DDR2 has also been shown to be a favourable independent predictor of recurrence and outcome in primary breast cancers. In addition to the essential roles of the wild type of DDR in cancer pathology and prognosis, various mutations of DDR1 and/or DDR2 have also been reported in numerous types of cancer cells, for instance, G1486T(DDR1) and A496S(DDR1) in lung cancer, N502S(DDR1), A533S(DDR1), and A803V(DDR1) in acute myeloid leukemia (AML), and S768R(DDR2) in squamous cell carcinoma. DDRs also play a role in cancer growth by controlling how tumour cells interact with their surrounding collagen matrix. This role of DDRs becomes more prominent when considering their role as extracellular matrix receptors. The extracellular matrix (ECM) confers structural properties to tissues around the tumour, as well as regulating cell proliferation, survival, migration, and invasion. The physiological interactions between tumour cells and their immediate microenvironment, represented by the extracellular matrix, are disrupted in metastatic cancers. As a key component of the tumour extracellular matrix, type I collagen shows high density and distorted architecture in malignant cancer, linking it to tumour formation and metastasis. Therefore, the discovery of DDRs as collagen receptors represents a new target in the regulation of tumour progression.

DDRs also appear to play a central role in the modulation of inflammation and fibrosis. Modulation of fibrosis and inflammation has been demonstrated in several organs including lung and kidney. In lung DDR-1 deficient mice show reduced bleomycin induced pulmonary injury (Vogel et al, Am. J. Respir. Crit. Care Med., 2006) and both DDR1 and DDR2 have been demonstrated to have increased expression in patients with fibrotic lung disease (Bian et al, ERJ Open Res., 2016). In kidney, DDR1 expression is elevated in patients with lupus nephritis and Goodpasture's syndrome as well as mouse models of glomerulonephritis (Kerroch et al, FASEB journal, 2012) and in the tubules of mice that have undergone unilatereal ureteral obstruction (UUO) (Guerrot et al, Am. J. Pathol., 2011). Several studies have demonstrated that DDR1-null mice are protected from angiotensin II-mediated proteinuria, glomerular fibrosis and inflammation as well as showing reduced collagen deposition, tubular macrophage infiltration and pro-inflamatory cytokine levels following the UUO procedure. Finally, COL3A3 KO mice (the mouse model for human Alport syndrome, crossed on to DDR1-null mice have mice have reduced renal fibrosis and inflammation as a consequence of reduced TGF-β mediated signalling and reduced levels of the pro-inflammatory cytokine IL-6 (Dorison, Cell Adhesion and Migration, 2018).

Small molecule inhibitors of DDR1 and DDR2 kinase activity have been disclosed in the prior art and inhibitory activity of DDR1 and/or DDR2 has been demonstrated to give rise to efficacious effects in mouse models of cancer and fibrotic disease (Richter et al, ACS Chem. Biol., 2019; Wang et al, J. Med. Chem., 2018; Zhu et al, J. Med. Chem., 2019). Such reports support the hypothesis that inhibitors of DDR kinase activity may be of benefit as therapeutic agents for the treatment of human cancer and fibrotic disease.

Furthermore, it is an aim of certain embodiments of this invention to provide new compounds useful in treating diseases such as cancer and fibrotic diseases. The compounds may be inhibitors of DDR1 and/or DDR2. It is an aim of certain embodiments of this invention to provide compounds which have comparable activity to existing DDR1 and/or DDR2 inhibitors. It is an aim of certain embodiments of this invention to provide compounds which have increased activity relative to existing DDR1 and/or DDR2 inhibitors.

Certain embodiments of the present invention satisfy some or all of the above aims.

BRIEF SUMMARY OF THE DISCLOSURE

The present invention provides a compound of formula (I) and pharmaceutically acceptable salts thereof:

(I)

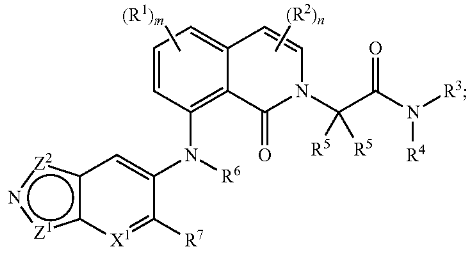

wherein

- $Z^1$ and $Z^2$ are each selected from —$CR^{8a}$— and —$NR^{8b}$—, wherein one of $Z^1$ and $Z^2$ is —$CR^{8a}$— and the other is —$NR^{8b}$—; and wherein the ring comprising $Z^1$ and $Z^2$ is a pyrazole;
- $X^1$ is independently selected from $CR^{7a}$ and N;
- $R^1$ and $R^2$ are each independently selected at each occurrence from halo, nitro, cyano, $NR^9R^{10}$, $OR^{11}$, $SR^9$, $SO_2NR^9R^9$, $SO_2R^9$, $CO_2R^9$, $C(O)R^9$, $CONR^9R^9$, $C_1$-$C_4$-alkyl, $C_1$-$C_4$-alkyl substituted with $NR^9R^{10}$, $C_1$-$C_4$-alkyl substituted with $OR^1$, $C_2$-$C_4$-alkenyl, $C_2$-$C_4$-alkynyl, $C_1$-$C_4$-haloalkyl and cyclopropyl;
- $R^3$ is independently selected from H and $C_1$-$C_4$-alkyl;
- $R^4$ is independently selected from $C_1$-$C_6$-alkyl, $C_1$-$C_6$-haloalkyl, $C_0$-$C_4$-alkylene-$R^{4a}$; wherein $R^{4a}$ is independently selected from: $C_3$-$C_8$-cycloalkyl, phenyl, 5-, 6-, 9- or 10-membered heteroaryl and 4- to 10-membered heterocycloalkyl; wherein said heterocycloalkyl or heteroaryl group may be monocyclic or bicyclic; wherein said cycloalkyl or heterocycloalkyl group is optionally substituted with a single $R^{12}$ group and/or from 1 to 4 $R^{13}$ groups and wherein said phenyl or heteroaryl group is optionally substituted with a single $R^{12}$ group and/or from 1 to 3 $R^{14}$ groups;
- or $R^3$ and $R^4$, together with the nitrogen atom to which they are attached together form a 4- to 10-membered heterocycloalkyl group or a 5-, or 9-membered heteroaryl group; wherein said heterocycloalkyl or heteroaryl group may be monocyclic or bicyclic; wherein said heterocycloalkyl group is optionally substituted with a single $R^{12}$ group and/or from 1 to 4 $R^{13}$ groups and wherein said heteroaryl group is optionally substituted with a single $R^{12}$ group and/or from 1 to 3 $R^{14}$ groups;
- $R^5$ is independently at each occurrence selected from H, halo and $C_1$-$C_4$-alkyl, or the two $R^5$ groups and the carbon atom to which they are attached may together form a $C_3$-$C_6$ cycloalkyl ring;
- $R^6$ is independently selected from H, $C_1$-$C_4$-alkyl, $C_1$-$C_4$-haloalkyl and cyclopropyl;

- $R^7$ and $R^{7a}$ are each independently selected from H, halo, nitro, cyano, $NR^9R^{10}$, $OR^{11}$, $SR^9$, $SO_2NR^9R^9$, $SO_2R^9$, $CO_2R^9$, $C(O)R^9$, $CONR^9R^9$, $C_1$-$C_4$-alkyl, $C_1$-$C_4$-alkyl substituted with $NR^9R^{10}$, $C_1$-$C_4$-alkyl substituted with $OR^1$, $C_2$-$C_4$-alkenyl, $C_2$-$C_4$-alkynyl, $C_1$-$C_4$-haloalkyl and cyclopropyl;
- $R^{8a}$ is independently selected from H, halo, nitro, cyano, $NR^9R^{10}$, $OR^{11}$, $SR^9$, $SO_2NR^9R^9$, $SO_2R^9$, $CO_2R^9$, $C(O)R^9$, $CONR^9R^9$, $C_1$-$C_4$-alkyl, $C_1$-$C_4$-alkyl substituted with $NR^9R^{10}$, $C_1$-$C_4$-alkyl substituted with $OR^1$, $C_2$-$C_4$-alkenyl, $C_2$-$C_4$-alkynyl, $C_1$-$C_4$-haloalkyl and $C_0$-$C_4$-alkylene-$R^{8c}$;
- $R^{8b}$ is independently selected from H, $C_1$-$C_4$-alkyl, $C_2$-$C_4$-alkyl substituted with $NR^9R^{10}$, $C_2$-$C_4$-alkyl substituted with $OR^1$, $C_3$-$C_4$-alkenyl, $C_3$-$C_4$-alkynyl, $C_1$-$C_4$-haloalkyl and $C_0$-$C_4$-alkylene-$R^{8c}$;
- $R^{8c}$ is independently selected from $C_3$-$C_6$-cycloalkyl and 3- to 7-membered heterocycloalkyl; wherein said heterocycloalkyl group is attached to the $C_0$-$C_4$-alkylene via a carbon atom in the heterocycloalkyl ring; wherein said cycloalkyl or heterocycloalkyl group is optionally substituted with from 1 to 4 $R^{13}$ groups;
- $R^9$ is independently at each occurrence selected from H and $C_1$-$C_4$-alkyl; or two $R^9$ groups, together with the nitrogen atom to which they are attached together form a $C_5$-$C_8$-heterocycloalkyl group optionally substituted with from 0 to 4 $R^{13}$ groups;
- $R^{10}$ is independently at each occurrence selected from H, $C_1$-$C_4$-alkyl, C(O)—$C_1$-$C_4$-alkyl and $S(O)_2$—$C_1$-$C_4$-alkyl; or $R^9$ and $R^{10}$, together with the nitrogen atom to which they are attached together form a $C_5$-$C_8$-heterocycloalkyl group optionally substituted with from 0 to 4 $R^{13}$ groups;
- $R^{11}$ is independently at each occurrence selected from H, $C_1$-$C_4$-alkyl, C(O)—$C_1$-$C_4$-alkyl and $C_1$-$C_4$-haloalkyl;
- $R^{12}$ is independently selected from $C_3$-$C_6$-cycloalkyl, phenyl, 5- or 6-membered heteroaryl and 3- to 6-membered-heterocycloalkyl; wherein said cycloalkyl or heterocycloalkyl group is optionally substituted with from 1 to 4 $R^{13}$ groups and wherein said phenyl or heteroaryl group is optionally substituted with from 1 to 3 $R^{14}$ groups;
- $R^{13}$ is independently at each occurrence selected from =O, halo, nitro, cyano, $NR^8R^9$, $OR^{14}$, $SR^8$, $SO_2NR^8R^8$, $CO_2R^8$, $C(O)R^8$, $CONR^8R^8$, $C_1$-$C_4$-alkyl, $C_1$-$C_4$-alkyl substituted with $OR^1$, $C_1$-$C_4$-alkyl substituted with $NR^9R^{10}$, $C_2$-$C_4$-alkenyl, $C_2$-$C_4$-alkynyl, $C_1$-$C_4$-haloalkyl, $C_6$-$C_{10}$-aryl, and $C_3$-$C_6$-cycloalkyl;
- $R^{14}$ is independently at each occurrence selected from halo, nitro, cyano, $NR^8R^9$, $OR^{10}$, $SR^8$, $SO_2R^8$, $SO_2NR^8R^8$, $CO_2R^8$, $C(O)R^8$, $CONR^8R^8$, $C_1$-$C_4$-alkyl, $C_2$-$C_4$-alkenyl, $C_2$-$C_4$-alkynyl, $C_1$-$C_4$-haloalkyl, $C_1$-$C_4$-alkyl substituted with $OR^1$, $C_1$-$C_4$-alkyl substituted with $NR^8R^9$ and cyclopropyl;
- m is an integer selected from 0, 1, 2 and 3;
- n is an integer selected from 0, 1 and 2;
- wherein any of the aforementioned alkyl, alkylene or cyclopropyl groups is optionally substituted, where chemically possible, by 1 to 5 substituents which are each independently at each occurrence selected from the group consisting of: halo, oxo, fluoro, nitro, cyano, $NR^aR^b$, $OR^a$, $SR^a$, $CO_2R^a$, $C(O)R^a$, $CONR^aR^a$, $C_1$-$C_4$-alkyl, $C_1$-$C_4$-haloalkyl and cyclopropyl; wherein $R^a$ is independently at each occurrence selected from H, $C_1$-$C_4$-alkyl and $C_1$-$C_4$-haloalkyl; and $R^b$ is independently at each occurrence selected from H, $C_1$-$C_4$-alkyl, C(O)—$C_1$-$C_4$-alkyl and $S(O)_2$—$C_1$-$C_4$-alkyl.

In an embodiment, the compound of formula (I) is a compound of formula (II):

(II)

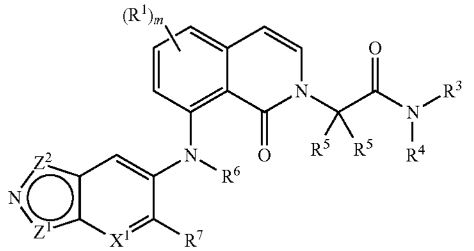

wherein $Z^1$, $Z^2$, $X^1$, $R^1$, $R^3$, $R^4$, $R^5$, $R^6$, $R^7$ and m are as described above for compounds of formula (I).

In an embodiment, the compound of formula (I) is a compound of formula (III):

(III)

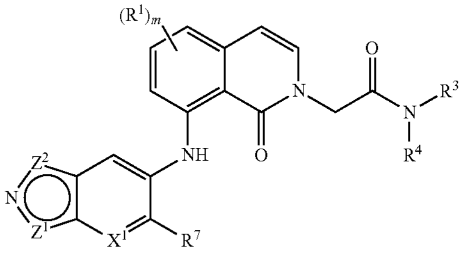

wherein $Z^1$, $Z^2$, $X^1$, $R^1$, $R^3$, $R^4$, $R^7$ and m are as described above for compounds of formula (I).

In an embodiment, the compound of formula (I) is a compound of formula (IV):

(IV)

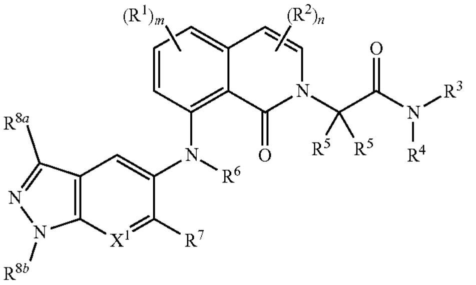

wherein $X^1$, $R^1$, $R^2$, $R^3$, $R^4$, $R^5$, $R^6$, $R^1$, $R^{8a}$, $R^{8b}$, m and n are as described above for compounds of formula (I).

In an embodiment, the compound of formula (I) is a compound of formula (V):

(V)

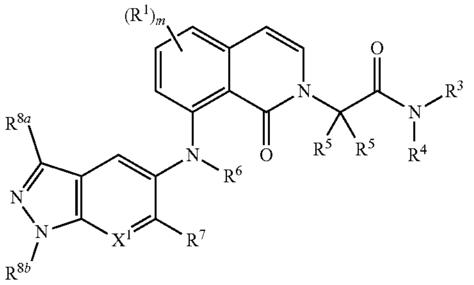

wherein $X^1$, $R^1$, $R^3$, $R^4$, $R^5$, $R^6$, $R^7$, $R^{8a}$, $R^{8b}$ and m are as described above for compounds of formula In an embodiment, the compound of formula (I) is a compound of formula (VI):

(VI)

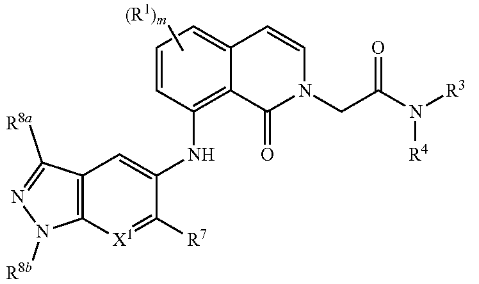

wherein $Z^1$, $Z^2$, $X^1$, $R^1$, $R^3$, $R^4$, $R^1$, $R^{8a}$, $R^{8b}$ and m are as described above for compounds of formula (I).

In an embodiment, the compound of formula (I) is a compound of formula (VII):

(VII)

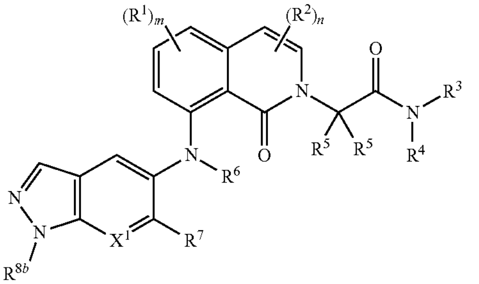

wherein $X^1$, $R^1$, $R^2$, $R^3$, $R^4$, $R^5$, $R^6$, $R^7$, $R^{8b}$, m and n are as described above for compounds of formula (I).

In an embodiment, the compound of formula (I) is a compound of formula (VIII):

(VIII)

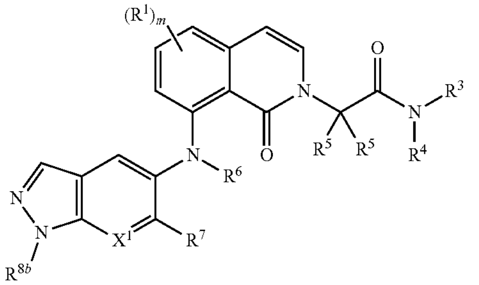

wherein $X^1$, $R^1$, $R^3$, $R^4$, $R^5$, $R^6$, $R^7$, $R^{8b}$ and m are as described above for compounds of formula (I).

In an embodiment, the compound of formula (I) is a compound of formula (IX):

(IX)

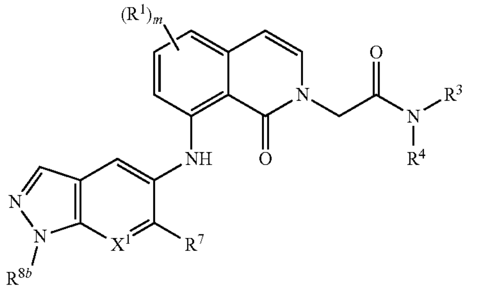

wherein $X^1$, $R^1$, $R^3$, $R^4$, $R^7$, $R^{8b}$ and m are as described above for compounds of formula (I).

In an embodiment, the compound of formula (I) is a compound of formula (X):

(X)

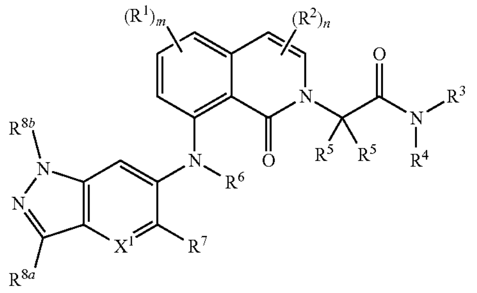

wherein $X^1$, $R^1$, $R^2$, $R^3$, $R^4$, $R^5$, $R^6$, $R^1$, $R^{8a}$, $R^{8b}$, m and n are as described above for compounds of formula (I).

In an embodiment, the compound of formula (I) is a compound of formula (XI):

(XI)

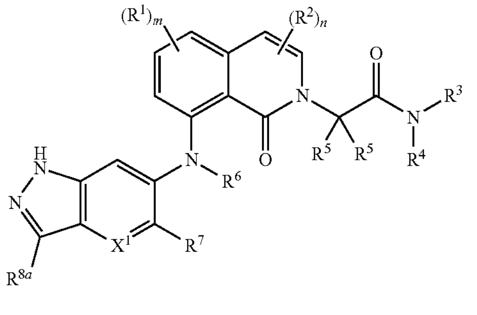

wherein $X^1$, $R^1$, $R^2$, $R^3$, $R^4$, $R^5$, $R^6$, $R^7$, $R^{8a}$, m and n are as described above for compounds of formula (I).

In an embodiment, the compound of formula (I) is a compound of formula (XII):

(XII)

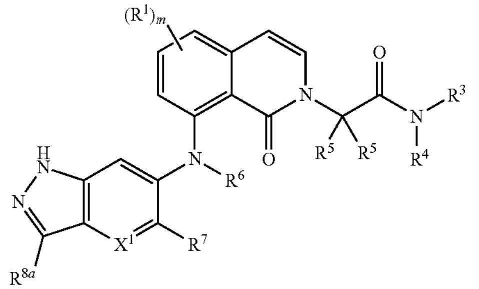

wherein $X^1$, $R^1$, $R^3$, $R^4$, $R^5$, $R^6$, $R^7$, $R^{8a}$ and m are as described above for compounds of formula (I).

In an embodiment, the compound of formula (I) is a compound of formula (XIII):

(XIII)

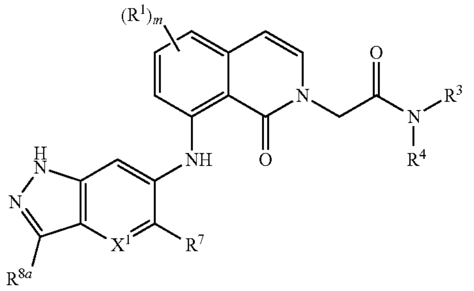

wherein $X^1$, $R^1$, $R^3$, $R^4$, $R^7$, $R^{8a}$ and m are as described above for compounds of formula (I).

In an embodiment, the compound of formula (I) is a compound of formula (XIV):

(XIV)

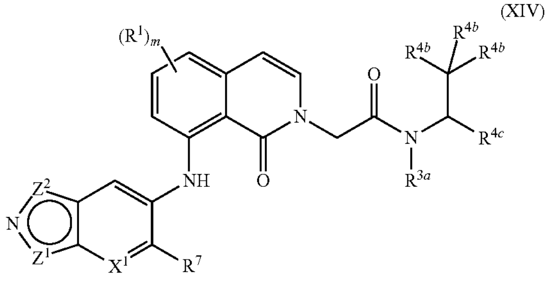

wherein $Z^1$, $Z^2$, $X^1$, $R^1$, $R^7$ and m are as described above for compounds of formula (I) and wherein $R^{4b}$ is at each occurrence selected from H and F; wherein at least two $R^{4b}$ groups are F;

$R^{3a}$ is independently selected from H and $C_1$-$C_4$-alkyl;

$R^{4c}$ is independently selected from H, $C_1$-$C_4$-alkyl and $C_4$-$C_6$-cycloalkyl; or $R^{3a}$ and $R^{4c}$, together with the carbon and nitrogen to which they are attached, form a 4- to 6-membered heterocycloalkyl group.

In an embodiment, the compound of formula (I) is a compound of formula (XV):

(XV)

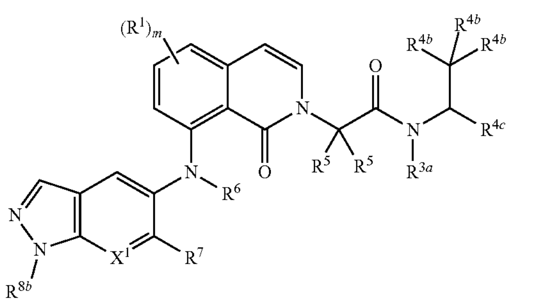

wherein $X^1$, $R^1$, $R^5$, $R^6$, $R^7$, $R^{8b}$ and m are as described above for compounds of formula (I); and wherein $R^{3a}$, $R^{4b}$ and $R^{4c}$ are as described above for formula (XIV).

The following embodiments apply to compounds of any of formulae (I)-(XV). These embodiments are independent and interchangeable. Any one embodiment may be combined with any other embodiment, where chemically allowed. In other words, any of the features described in the following embodiments may (where chemically allowable) be combined with the features described in one or more other embodiments. In particular, where a compound is exemplified or illustrated in this specification, any two or more of the embodiments listed below, expressed at any level of generality, which encompass that compound may be combined to provide a further embodiment which forms part of the present disclosure.

It may be either that $Z^1$ is $NR^{8b}$ and $Z^2$ is CH or that $Z^1$ is $CR^{8a}$ and $Z^2$ is NH.

It may be that $Z^1$ is $NR^{8b}$ and $Z^2$ is $CR^{8a}$. It may be that $Z^1$ is $NR^{8b}$ and $Z^2$ is CH. It may be that $Z^1$ is NMe and $Z^2$ is $CR^{8a}$. It may be that $Z^1$ is NMe and $Z^2$ is CH.

It may be that $Z^1$ is $CR^{8a}$ and $Z^2$ is $NR^{8b}$. It may be that $Z^1$ is $CR^{8a}$ and $Z^2$ is NH.

It may be that $X^1$ is N. It may be that $X^1$ is $CR^{7a}$.

m may be 0.

m may be 1. Where m is 1, it may be that the single $R^1$ group is situated ortho to $NR^6$. Where m is 1, it may be that the single $R^1$ group is situated para to $NR^6$. Where m is 1, it may be that the single $R^1$ group is situated para to $NR^6$.

m may be 2.

$R^1$ may be independently at each occurrence selected from halo, nitro, cyano, $OR^{11}$, $C_1$-$C_4$-alkyl, $C_1$-$C_4$-alkyl substituted with $NR^9R^{10}$, $C_1$-$C_4$-alkyl substituted with $OR^{11}$, $C_1$-$C_4$-haloalkyl and cyclopropyl. $R^1$ may be independently at each occurrence selected from halo, $OR^1$, $C_1$-$C_4$-alkyl, $C_1$-$C_4$-haloalkyl and cyclopropyl. $R^1$ may be independently at each occurrence selected from halo and $C_1$-$C_4$-alkyl. $R^1$ may be independently at each occurrence halo, e.g. fluoro. $R^1$ may be independently at each occurrence $C_1$-$C_4$-alkyl, e.g. methyl.

It may be that m is 1, the single $R^1$ group is F and is situated ortho to $NR^6$.

n may be 0.

n may be 1. n may be 2.

$R^2$ may be independently at each occurrence selected from halo, nitro, cyano, $OR^1$, $C_1$-$C_4$-alkyl, $C_1$-$C_4$-alkyl substituted with $NR^9R^{10}$, $C_1$-$C_4$-alkyl substituted with $OR^1$, $C_1$-$C_4$-haloalkyl and cyclopropyl. $R^2$ may be independently at each occurrence selected from halo, $OR^1$, $C_1$-$C_4$-alkyl, $C_1$-$C_4$-haloalkyl and cyclopropyl. $R^2$ may be independently at each occurrence selected from halo and $C_1$-$C_4$-alkyl. $R^2$ may be independently at each occurrence halo, e.g. fluoro. $R^2$ may be independently at each occurrence $C_1$-$C_4$-alkyl, e.g. methyl.

$R^5$ may be independently at each occurrence selected from H, fluoro and $C_1$-$C_4$-alkyl. $R^5$ may be independently at each occurrence selected from H, fluoro and $C_1$-$C_4$-alkyl, or the two $R^5$ groups and the carbon atom to which they are attached may together form a $C_3$-$C_6$ cycloalkyl ring. $R^5$ may be independently at each occurrence selected from H and $C_1$-$C_4$-alkyl, or the two $R^5$ groups and the carbon atom to which they are attached may together form a $C_3$-$C_6$ cycloalkyl ring. $R^5$ may be independently at each occurrence selected from H and $C_1$-$C_4$-alkyl, e.g. methyl.

It may be that $R^5$ is at each occurrence H. It may be that $R^5$ is at one occurrence H and at the other occurrence $C_1$-$C_4$-alkyl, e.g. methyl. It may be that $R^5$ is at each occurrence $C_1$-$C_4$-alkyl, e.g. methyl.

$R^6$ may be H. $R^6$ may be $C_1$-$C_4$-alkyl, e.g. methyl.

It may be that $R^7$ is H. $R^7$ may be independently selected from halo, nitro, cyano, $OR^1$, $C_1$-$C_4$-alkyl, $C_1$-$C_4$-alkyl substituted with $NR^9R^{10}$, $C_1$-$C_4$-alkyl substituted with $OR^1$, $C_1$-$C_4$-haloalkyl and cyclopropyl. $R^7$ may be independently selected from halo, $OR^1$, $C_1$-$C_4$-alkyl, $C_1$-$C_4$-haloalkyl and cyclopropyl. $R^7$ may be independently selected from halo and $C_1$-$C_4$-alkyl. If present, $R^7$ may be halo, e.g. fluoro. $R^7$ may be $C_1$-$C_4$-alkyl, e.g. methyl.

It may be that $R^{7a}$ is H. $R^{7a}$ may be independently selected from halo, nitro, cyano, $OR^1$, $CO_2R^9$, $CONR^9R^9$, $C_1$-$C_4$-alkyl, $C_1$-$C_4$-alkyl substituted with $NR^9R^{10}$, $C_1$-$C_4$-alkyl substituted with $OR^1$, $C_1$-$C_4$-haloalkyl and cyclopropyl. $R^{7a}$ may be independently selected from halo, $OR^1$, $C_1$-$C_4$-alkyl, $C_1$-$C_4$-haloalkyl and cyclopropyl.

It may be that $R^7$ is H and $X^1$ is N. It may be that $R^7$ is H and $X^1$ is $CR^{7a}$. It may be that $R^7$ is H and $X^1$ is CH. It may be that $R^7$ is H and $X^1$ is $CR^{7a}$, wherein $R^{7a}$ is independently selected from halo, nitro, cyano, $OR^1$, $CO_2R^9$, $CONR^9R^9$, $C_1$-$C_4$-alkyl, $C_1$-$C_4$-alkyl substituted with $NR^9R^{10}$, $C_1$-$C_4$-alkyl substituted with $OR^1$, $C_1$-$C_4$-haloalkyl and cyclopropyl.

$R^{8a}$ may be H. $R^{8a}$ may be selected from halo, $C_1$-$C_4$-alkyl, $C_1$-$C_4$-alkyl substituted with $NR^9R^{10}$, $C_1$-$C_4$-alkyl substituted with $OR^1$, $C_1$-$C_4$-haloalkyl and $C_0$-$C_4$-alkylene-$R^{8c}$. $R^{8a}$ may be selected from H, halo, $C_1$-$C_4$-alkyl, $C_1$-$C_4$-haloalkyl and cyclopropyl. $R^{8a}$ may be selected from H, $C_1$-$C_4$-alkyl, $C_1$-$C_4$-haloalkyl and cyclopropyl. $R^{8a}$ may be selected from $C_1$-$C_4$-alkyl (e.g. methyl) and $C_1$-$C_4$-haloalkyl (e.g. $CF_3$). $R^{8a}$ may be $C_1$-$C_4$-alkyl (e.g. methyl).

$R^{8b}$ may be H. $R^{8b}$ may be selected from $C_1$-$C_4$-alkyl, $C_2$-$C_4$-alkyl substituted with $NR^9R^{10}$, $C_2$-$C_4$-alkyl substituted with $OR^{11}$, $C_1$-$C_4$-haloalkyl and $C_0$-$C_4$-alkylene-$R^{8c}$. $R^{8b}$ may be selected from H, $C_1$-$C_4$-alkyl and cyclopropyl. $R^{8b}$ may be $C_1$-$C_4$-alkyl (e.g. methyl).

$R^{8b}$ is independently selected from H, $C_1$-$C_4$-alkyl, $C_2$-$C_4$-alkyl substituted with $NR^9R^{10}$, $C_2$-$C_4$-alkyl substituted with $OR^1$, $C_3$-$C_4$-alkenyl, $C_3$-$C_4$-alkynyl, $C_1$-$C_4$-haloalkyl and $C_0$-$C_4$-alkylene-$R^{8c}$.

It may be that $R^{8a}$ is H and $R^{8b}$ is $C_1$-$C_4$-alkyl (e.g. methyl).

It may be that $R^9$ is independently at each occurrence selected from H and $C_1$-$C_4$-alkyl.

It may be that $R^{10}$ is independently at each occurrence selected from H, $C_1$-$C_4$-alkyl, C(O)—$C_1$-$C_4$-alkyl and $S(O)_2$—$C_1$-$C_4$-alkyl. It may be that $R^{10}$ is independently at each occurrence selected from H and $C_1$-$C_4$-alkyl.

It may be that $R^{11}$ is independently at each occurrence selected from H, $C_1$-$C_4$-alkyl and $C_1$-$C_4$-haloalkyl. It may be that $R^{11}$ is independently at each occurrence selected from H and $C_1$-$C_4$-alkyl. It may be that $R^{11}$ is independently at each occurrence $C_1$-$C_4$-alkyl, e.g. methyl.

$R^{12}$ may be independently selected from 5- or 6-membered heteroaryl, wherein said heteroaryl group is optionally substituted with from 1 to 3 $R^{14}$ groups. $R^{12}$ may be independently selected from 5-membered heteroaryl, e.g. imidazole, wherein said heteroaryl group is optionally substituted with from 1 to 3 $R^{14}$ groups.

$R^{13}$ may be independently at each occurrence selected from oxo, fluoro, $OR^1$, $CO_2R^9$, $CO_2NR^9R^9$, $C_1$-$C_4$-alkyl, $C_1$-$C_4$-alkyl substituted with $NR^9R^{10}$, $C_1$-$C_4$-alkyl substituted with $OR^1$, $C_1$-$C_4$-haloalkyl and cyclopropyl. $R^{13}$ may be independently at each occurrence selected from oxo, $OR^1$, $C_1$-$C_4$-alkyl and cyclopropyl. $R^{13}$ may be independently at each occurrence selected from oxo and $C_1$-$C_4$-alkyl. $R^{13}$ may be independently at each occurrence $C_1$-$C_4$-alkyl, e.g. methyl.

$R^{14}$ may be independently at each occurrence selected from halo, nitro, cyano, $OR^1$, $C_1$-$C_4$-alkyl, $C_1$-$C_4$-alkyl substituted with $NR^8R^9$, $C_1$-$C_4$-alkyl substituted with $OR^1$, $C_1$-$C_4$-haloalkyl and cyclopropyl. $R^{14}$ may be independently at each occurrence selected from halo, $OR^1$, $C_1$-$C_4$-alkyl, $C_1$-$C_4$-haloalkyl and cyclopropyl. $R^{14}$ may be independently at each occurrence selected from halo and $C_1$-$C_4$-alkyl. $R^{14}$ may be independently at each occurrence halo, e.g. fluoro. $R^{14}$ may be independently at each occurrence $C_1$-$C_4$-alkyl, e.g. methyl.

It may be that:

$R^3$ is H; and $R^4$ is independently selected from $C_1$-$C_6$-alkyl, $C_1$-$C_6$-haloalkyl, $C_0$-$C_4$-alkylene-$R^{4a}$; wherein $R^{4a}$ is independently selected from: $C_3$-$C_8$-cycloalkyl, phenyl, 5-, 6-, 9- or 10-membered heteroaryl and 4- to 10-membered heterocycloalkyl; wherein said heterocycloalkyl or heteroaryl group may be monocyclic or bicyclic; wherein said cycloalkyl or heterocycloalkyl group is optionally substituted with a single $R^{12}$ group and/or from 1 to 4 $R^{13}$ groups and wherein said phenyl or heteroaryl group is optionally substituted with a single $R^{12}$ group and/or from 1 to 3 $R^{14}$ groups;

or $R^3$ and $R^4$, together with the nitrogen atom to which they are attached together form a 4- to 10-membered heterocycloalkyl group or a 5-, or 9-membered heteroaryl group; wherein said heterocycloalkyl group is optionally substituted with a single $R^{12}$ group and/or from 1 to 4 $R^{13}$ groups and wherein said heteroaryl group is optionally substituted with a single $R^{12}$ group and/or from 1 to 3 $R^{14}$ groups.

It may be that:

$R^3$ is H; and $R^4$ is independently selected from $C_1$-$C_6$-alkyl, $C_1$-$C_6$-haloalkyl, $C_0$-$C_4$-alkylene-$R^{4a}$; wherein $R^{4a}$ is independently selected from: $C_3$-$C_8$-cycloalkyl, phenyl, 5-, 6-, 9- or 10-membered heteroaryl and 4- to 10-membered heterocycloalkyl; wherein said heterocycloalkyl or heteroaryl group may be monocyclic or bicyclic; wherein said cycloalkyl or heterocycloalkyl group is optionally substituted with from 1 to 4 $R^{13}$ groups and wherein said phenyl or heteroaryl group is optionally substituted with from 1 to 3 $R^{14}$ groups;

or $R^3$ and $R^4$, together with the nitrogen atom to which they are attached together form a 4- to 10-membered heterocycloalkyl group or a 5-, or 9-membered heteroaryl group; wherein said heterocycloalkyl group is optionally substituted with from 1 to 4 $R^{13}$ groups and wherein said heteroaryl group is optionally substituted with from 1 to 3 $R^{14}$ groups.

It may be that $R^3$ is H.

It may be that $R^4$ is selected from $C_1$-$C_6$-alkyl, $C_1$-$C_6$-haloalkyl and $C_0$-$C_4$-alkylene-$R^{4a}$ It may be that $R^4$ is selected from $C_1$-$C_6$-alkyl and $C_1$-$C_6$-haloalkyl. It may be that $R^4$ is selected from $C_2$-$C_3$-alkyl and $C_2$-$C_3$-haloalkyl. It may be that $R^4$ is $C_1$-$C_4$-haloalkyl. It may be that $R^4$ is $C_2$-$C_3$-haloalkyl. It may be that $R^4$ is 2,2,2-trifluoroethyl.

Illustrative $R^4$ groups include:

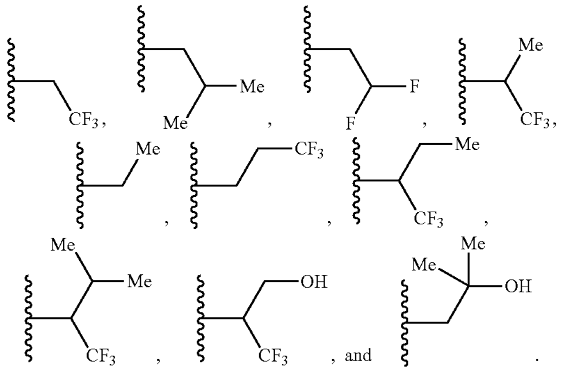

It may be that $R^4$ is $C_0$-$C_4$-alkylene-$R^{4a}$. It may be that $R^4$ is $CH_2$—$R^{4a}$. It may be that $R^4$ is $R^{4a}$.

It may be that $R^{4a}$ is independently selected from $C_3$-$C_8$-cycloalkyl, phenyl, 5-, 6-, 9- or 10-membered heteroaryl, 4- to 10-membered heterocycloalkyl, wherein said heterocycloalkyl or heteroaryl group may be monocyclic or bicyclic; wherein said cycloalkyl or heterocycloalkyl group is optionally substituted with from 1 to 4 $R^{13}$ groups and wherein said phenyl or heteroaryl group is optionally substituted with from 1 to 3 $R^{14}$ groups.

It may be that $R^{4a}$ is selected from $C_3$-$C_8$-cycloalkyl and 4- to 10-membered heterocycloalkyl, wherein said cycloalkyl or heterocycloalkyl group is optionally substituted with a single $R^{12}$ group and/or from 1 to 4 $R^{13}$ groups. It may be that $R^{4a}$ is selected from $C_3$-$C_8$-cycloalkyl and 4- to 10-membered heterocycloalkyl, wherein said cycloalkyl or heterocycloalkyl group is optionally substituted with from 1 to 4 $R^{13}$ groups.

It may be that $R^4$ is selected from $CH_2$—$C_3$-$C_8$-cycloalkyl and $CH_2$-4- to 10-membered heterocycloalkyl, wherein said cycloalkyl or heterocycloalkyl group is optionally substituted with a single $R^{12}$ group and/or from 1 to 4 $R^{13}$ groups. It may be that $R^4$ is selected from $CH_2$—$C_3$-$C_8$-cycloalkyl and $CH_2$-4- to 10-membered heterocycloalkyl, wherein said cycloalkyl or heterocycloalkyl group is optionally substituted with from 1 to 4 $R^{13}$ groups.

It may be that $R^4$ is selected from $C_3$-$C_8$-cycloalkyl and 4- to 10-membered heterocycloalkyl, wherein said cycloalkyl or heterocycloalkyl group is optionally substituted with a single $R^{12}$ group and/or from 1 to 4 $R^{13}$ groups. It may be that $R^4$ is selected from $C_3$-$C_8$-cycloalkyl and 4- to 10-membered heterocycloalkyl, wherein said cycloalkyl or heterocycloalkyl group is optionally substituted with from 1 to 4 $R^{13}$ groups.

Illustrative $R^4$ groups include:

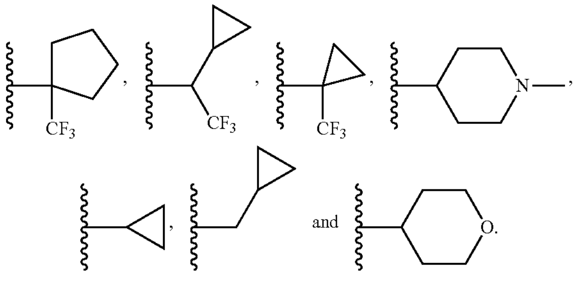

, , , , , and .

It may be that $R^{4a}$ is independently selected from: phenyl and 5- or 6-membered heteroaryl; wherein said phenyl or heteroaryl group is optionally substituted with a single $R^{12}$ group and/or from 1 to 3 $R^{14}$ groups. It may be that $R^{4a}$ is independently selected from: phenyl and 5- or 6-membered heteroaryl; wherein said phenyl or heteroaryl group is optionally substituted with from 1 to 3 $R^{14}$ groups. It may be that $R^{4a}$ is independently phenyl; wherein said phenyl group is optionally substituted with a single $R^{12}$ group and/or from 1 to 3 $R^{14}$ groups. It may be that $R^{4a}$ is independently phenyl; wherein said phenyl group is optionally substituted with from 1 to 3 $R^{14}$ groups. It may be that $R^{4a}$ is independently 5- or 6-membered heteroaryl; wherein said heteroaryl group is optionally substituted with a single $R^{12}$ group and/or from 1 to 3 $R^{14}$ groups. It may be that $R^{4a}$ is independently 5- or 6-membered heteroaryl; wherein said heteroaryl group is optionally substituted with from 1 to 3 $R^{14}$ groups.

It may be that $R^4$ is independently selected from $CH_2$-phenyl or $CH_2$-5- or 6-membered heteroaryl wherein said phenyl or heteroaryl group is optionally substituted with a single $R^{12}$ group and/or from 1 to 3 $R^{14}$ groups. It may be that $R^4$ is independently selected from $CH_2$-phenyl or $CH_2$-5- or 6-membered heteroaryl wherein said phenyl or heteroaryl group is optionally substituted with from 1 to 3 $R^{14}$ groups. It may be that $R^4$ is independently $CH_2$-phenyl wherein said phenyl is optionally substituted with a single $R^{12}$ group and/or from 1 to 3 $R^{14}$ groups. It may be that $R^4$ is independently $CH_2$-phenyl wherein said phenyl group is optionally substituted with from 1 to 3 $R^{14}$ groups. It may be that $R^4$ is independently $CH_2$-5- or 6-membered heteroaryl wherein said heteroaryl group is optionally substituted with a single $R^{12}$ group and/or from 1 to 3 $R^{14}$ groups. It may be that $R^4$ is independently $CH_2$-5- or 6-membered heteroaryl wherein said heteroaryl group is optionally substituted with from 1 to 3 $R^{14}$ groups.

It may be that $R^4$ is independently selected from phenyl or 5- or 6-membered heteroaryl wherein said phenyl or heteroaryl group is optionally substituted with a single $R^{12}$ group and/or from 1 to 3 $R^{14}$ groups. It may be that $R^4$ is independently selected from phenyl or 5- or 6-membered heteroaryl wherein said phenyl or heteroaryl group is optionally substituted with from 1 to 3 $R^{14}$ groups. It may be that $R^4$ is independently phenyl wherein said phenyl group is optionally substituted with a single $R^{12}$ group and/or from 1 to 3 $R^{14}$ groups. It may be that $R^4$ is independently phenyl wherein said phenyl group is optionally substituted with from 1 to 3 $R^{14}$ groups. It may be that $R^4$ is independently 5- or 6-membered heteroaryl wherein said heteroaryl group is optionally substituted with a single $R^{12}$ group and/or from 1 to 3 $R^{14}$ groups. It may be that $R^4$ is independently 5- or 6-membered heteroaryl wherein said heteroaryl group is optionally substituted with from 1 to 3 $R^{14}$ groups.

It may be that $R^4$ is independently selected from phenyl or 6-membered heteroaryl wherein said phenyl or 6-membered heteroaryl group is substituted at the meta position with 1 $R^{14}$ group. It may be that the $R^{14}$ group is selected from $C_1$-$C_4$-alkyl substituted with $OR^{11}$, $C_1$-$C_4$-alkyl and $C_1$-$C_4$-haloalkyl. It may be that the $R^{14}$ group at the meta position is $C_1$-$C_4$-alkyl substituted with $OR^1$ e.g. —$(CH_3)_2$—OH. It may be that the $R^{14}$ group at the meta position is $C_1$-$C_4$-haloalkyl e.g. $CF_3$.

It may be that $R^4$ is a 6-membered heteroaryl group. It may be that $R^4$ is phenyl. It may be that $R^4$ is phenyl substituted at the meta position with 1 $R^{14}$ group. It may be that $R^{14}$ is $R^{14a}$. Illustrative $R^4$ groups include:

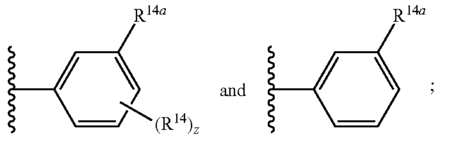

and ;

wherein $R^{14a}$ is selected from halo, nitro, cyano, $NR^8R^9$, $OR^{10}$, $SR^8$, $SO_2R^8$, $SO_2NR^8R^8$, $CO_2R^8$, $C(O)R^8$, $CONR^8R^8$, $C_1$-$C_4$-alkyl, $C_2$-$C_4$-alkenyl, $C_2$-$C_4$-alkynyl, $C_1$-$C_4$-haloalkyl, $C_1$-$C_4$-alkyl substituted with $OR^1$, $C_1$-$C_4$-alkyl substituted with $NR^8R^9$ and cyclopropyl; and wherein z is an integer selected from 1 and 2.

Illustrative $R^4$ groups include:

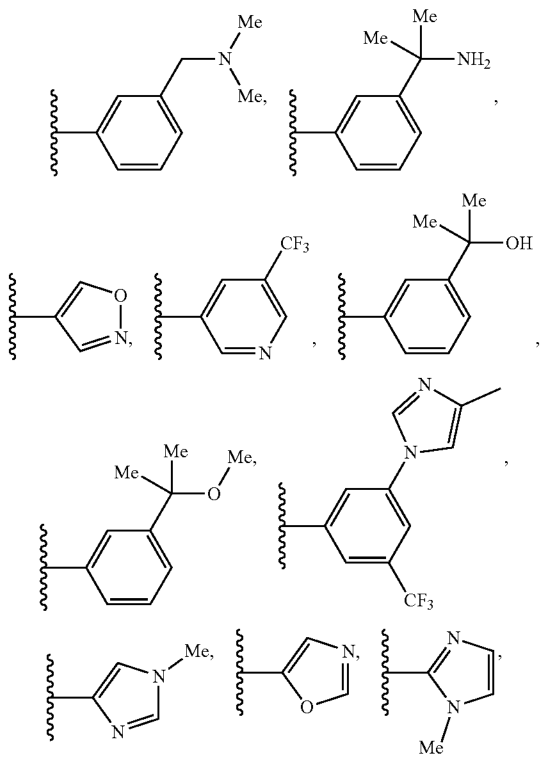

-continued

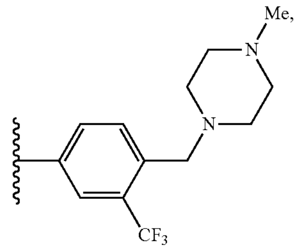 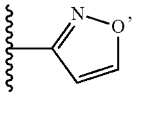

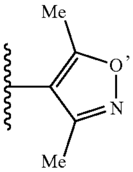 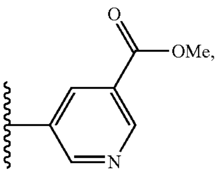 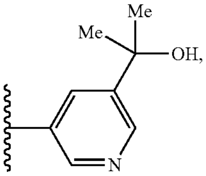

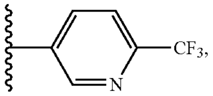 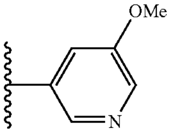 ,

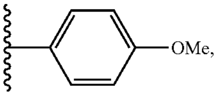 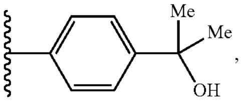 ,

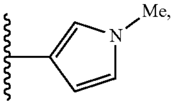 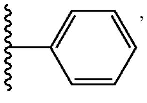 , 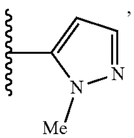 ,

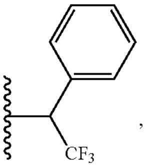 , 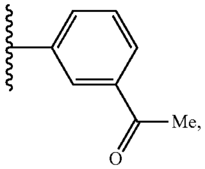 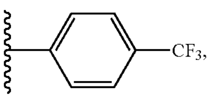

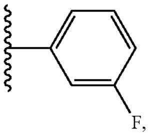 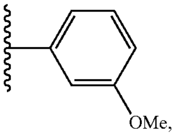 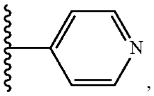 ,

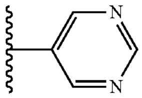 and 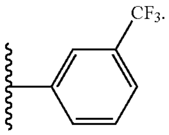

It may be that $R^3$ and $R^4$, together with the nitrogen atom to which they are attached together form a 4- to 10-membered heterocycloalkyl group or a 5-, or 9-membered heteroaryl group; wherein said heterocycloalkyl group is optionally substituted with a single $R^{12}$ group and/or from 1 to 4 $R^{13}$ groups and wherein said heteroaryl group is optionally substituted with a single $R^{12}$ group and/or from 1 to 3 $R^{14}$ groups. It may be that $R^3$ and $R^4$, together with the nitrogen atom to which they are attached together form a 4- to 10-membered heterocycloalkyl group or a 5-, or 9-membered heteroaryl group; wherein said heterocycloalkyl group is optionally substituted with from 1 to 4 $R^{13}$ groups and wherein said heteroaryl group is optionally substituted with from 1 to 3 $R^{14}$ groups.

It may be that $R^3$ and $R^4$, together with the nitrogen atom to which they are attached together form a 5-, or 9-membered heteroaryl group; wherein heteroaryl group is optionally substituted with a single $R^{12}$ group and/or from 1 to 3 $R^{14}$ groups. It may be that $R^3$ and $R^4$, together with the nitrogen atom to which they are attached together form a 5-, or 9-membered heteroaryl group; wherein said heteroaryl group is optionally substituted with from 1 to 3 $R^{14}$ groups. It may be that $R^3$ and $R^4$, together with the nitrogen atom to which they are attached together form a 5-membered heteroaryl group; wherein heteroaryl group is optionally substituted with a single $R^{12}$ group and/or from 1 to 3 $R^{14}$ groups. It may be that $R^3$ and $R^4$, together with the nitrogen atom to which they are attached together form a 5-membered heteroaryl group; wherein said heteroaryl group is optionally substituted with from 1 to 3 $R^{14}$ groups.

Illustrative $NR^3R^4$ groups include:

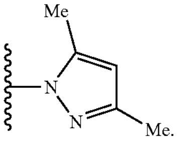 [SMILES: *n1nc(C)cc1C]

It may be that $R^3$ and $R^4$, together with the nitrogen atom to which they are attached together form a 4- to 10-membered heterocycloalkyl group; wherein said heterocycloalkyl group is optionally substituted with a single $R^{12}$ group and/or from 1 to 4 $R^{13}$ groups. It may be that $R^3$ and $R^4$, together with the nitrogen atom to which they are attached together form a 4- to 10-membered heterocycloalkyl group; wherein said heterocycloalkyl group is optionally substituted with from 1 to 4 $R^{13}$ groups. It may be that said heterocycloalkyl group is 7- to 10-membered bicyclic heterocycloalkyl group. It may be that said heterocyclic group is 7- to 10-membered bridged bicyclic heterocycloalkyl group. It may be that said heterocyclic group is a monocyclic 4- to 7-membered heterocycloalkyl group. It may be that said heterocyclic group is a monocyclic 5- to 6-membered heterocycloalkyl group. It may be that said heterocyclic group is pyrrolidine. It may be that said heterocyclic group is piperidine. It may be that said heterocyclic group is morpholine. It may be that said heterocyclic group is piperazine. For the absence of doubt the heterocycloalkyl groups mentioned in this paragraph are optionally substituted with a single $R^{12}$ group and/or from 1 to 4 $R^{13}$ groups. It may be that the heterocycloalkyl groups mentioned in this paragraph are optionally substituted with from 1 to 4 $R^{13}$ groups. It may be that said heterocyclic group is pyrrolidine and is substituted at the 2 position with 1 $R^{13}$ group. It may be that said heterocyclic group is pyrrolidine and is substituted at the 3 position with 1 $R^{13}$ group. It may be that said heterocyclic group is piperidine and is substituted at the 2 position with 1 $R^{13}$ group. It may be that said heterocyclic group is piperidine and is substituted at the 3 position with 1 $R^{13}$ group. It may be that said heterocyclic group is piperidine and is substituted at the 4 position with 1 $R^{13}$ group. It may be that said heterocyclic group is morpholine and is substituted at the 2 position with 1 $R^{13}$ group. It may be that said heterocyclic group is morpholine and is substituted at the 3 position with 1 $R^{13}$ group. It may be that the $R^{13}$ group is selected from $C_1$-$C_4$-alkyl, $C_1$-$C_4$-alkyl substituted with $OR^{11}$ e.g. —$(CH_3)_2$—OH, and $C_1$-$C_4$-haloalkyl, e.g. —$CF_3$. It may be that the $R^{13}$ group is $C_1$-$C_4$-haloalkyl, e.g. —$CHF_2$ or —$CF_3$.

Illustrative $NR^3R^4$ groups include:

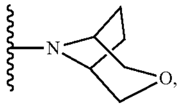, 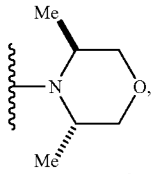, 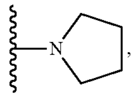,

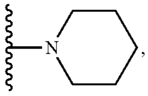, 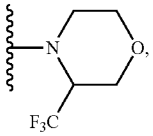, 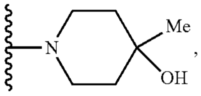,

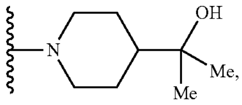, 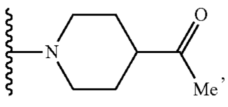,

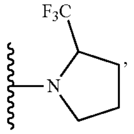, 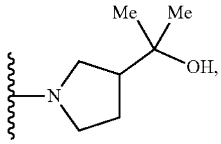,

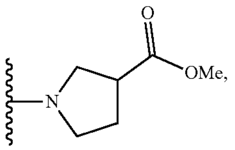, 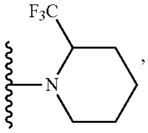, 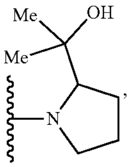,

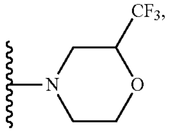, 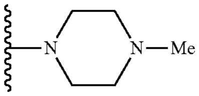 and

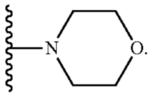.

It may be that $R^3$ and $R^4$ are selected such that $NR^3R^4$ comprises a $CHF_2$ group or a $CF_3$ group.

It may be that $NR^3R^4$ has the formula

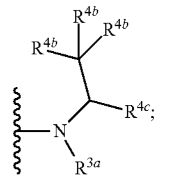;

wherein $R^{4b}$ is at each occurrence selected from H and F; wherein at least one $R^{4b}$ group is F;

$R^{3a}$ is independently selected from H and $C_1$-$C_4$-alkyl;

$R^{4c}$ is independently selected from H, $C_1$-$C_4$-alkyl and $C_4$-$C_6$-cycloalkyl; or $R^{3a}$ and $R^{4c}$, together with the carbon and nitrogen to which they are attached, form a 4- to 6-membered heterocycloalkyl group.

It may be that at least two $R^{4b}$ groups are F. It may be that two $R^{4b}$ groups are F and one $R^{4b}$ group is H. It may be that each $R^{4b}$ group is F.

It may be that $R^{3a}$ is independently selected from H and $C_1$-$C_4$-alkyl; and $R^{4c}$ is independently selected from H, $C_1$-$C_4$-alkyl and $C_4$-$C_6$-cycloalkyl. It may be that $R^{3a}$ is H; and $R^{4c}$ is independently selected from H, $C_1$-$C_4$-alkyl and $C_4$-$C_6$-cycloalkyl. Said alkyl or cycloalkyl group may be unsubstituted.

It may be that $R^{3a}$ and $R^{4c}$, together with the carbon and nitrogen to which they are attached, form a 4- to 6-membered heterocycloalkyl group. It may be that $R^{3a}$ and $R^{4c}$, together with the carbon and nitrogen to which they are attached, form a 5-membered heterocycloalkyl group. Said heterocycloalkyl group might be unsubstituted.

The compound of formula (I) may be selected from:

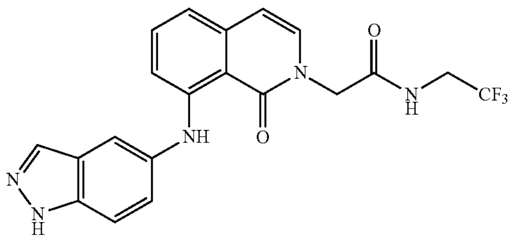

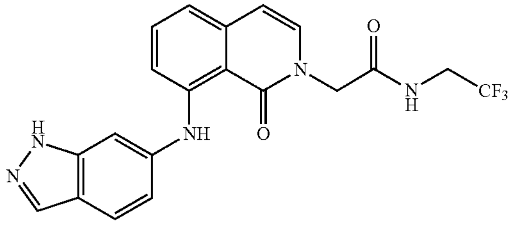

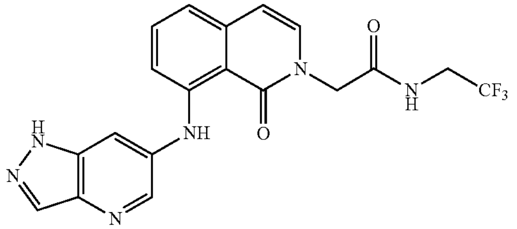

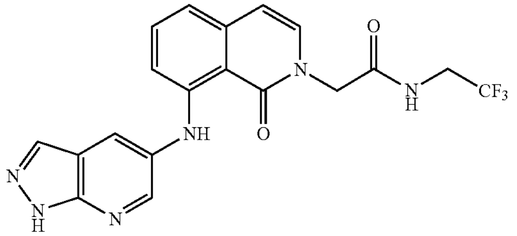

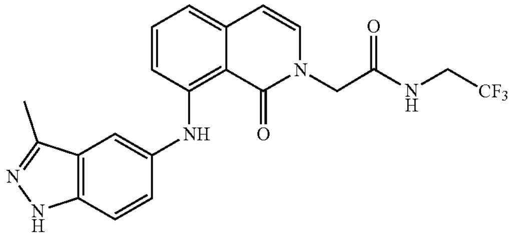

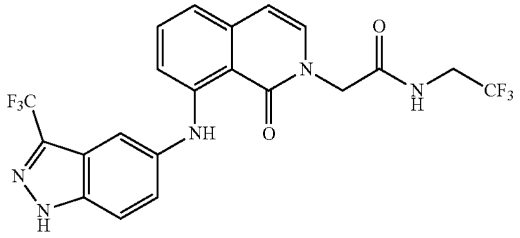

-continued
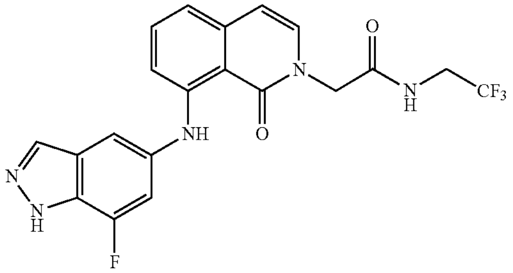
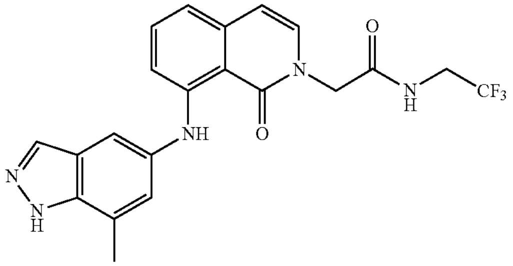
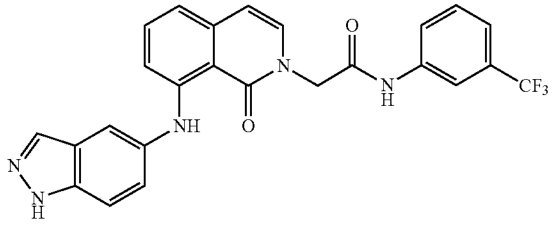
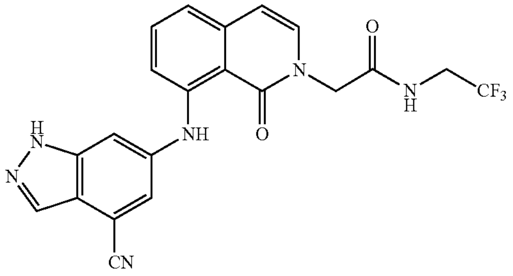
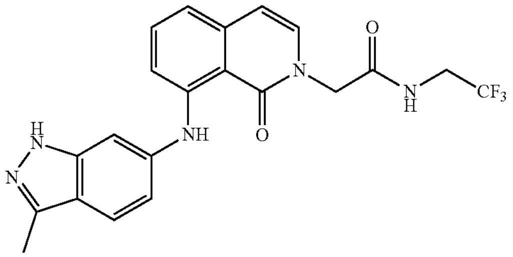
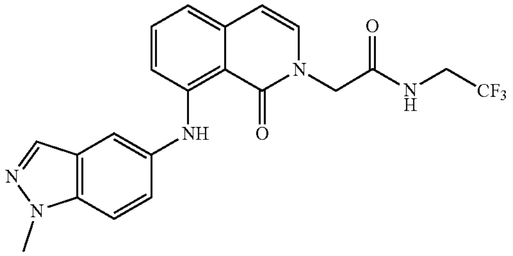
-continued
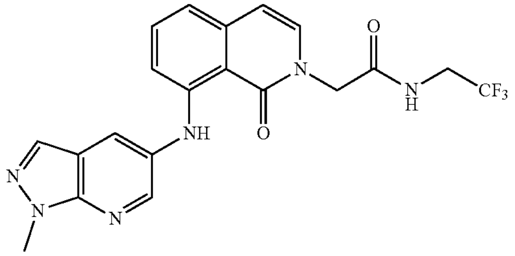
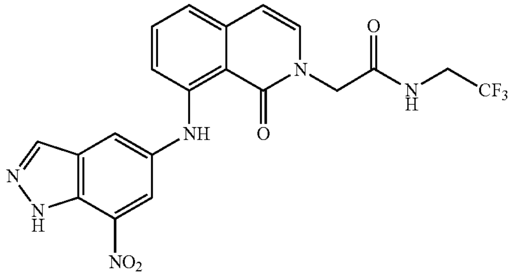
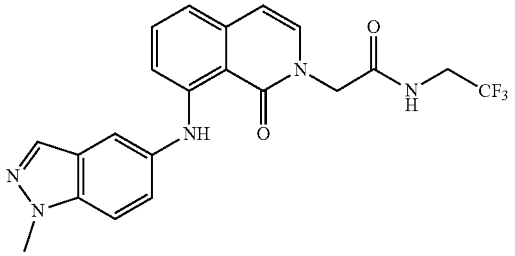
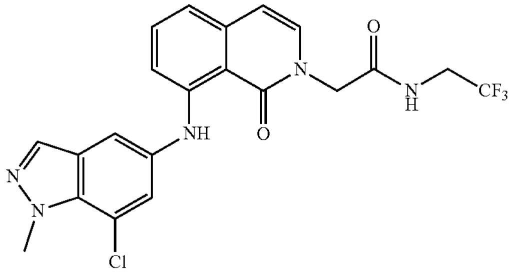
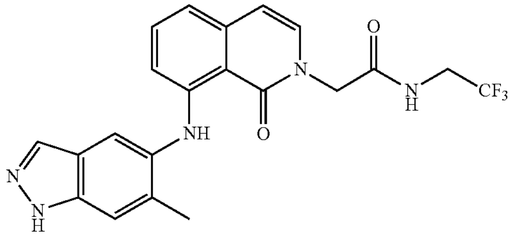
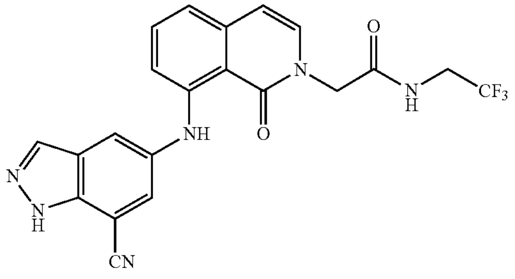

-continued
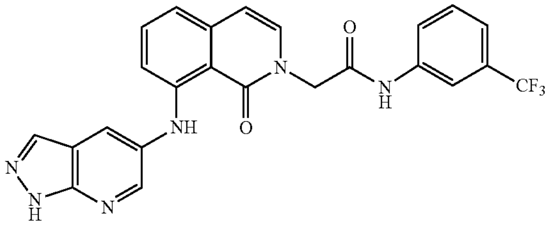
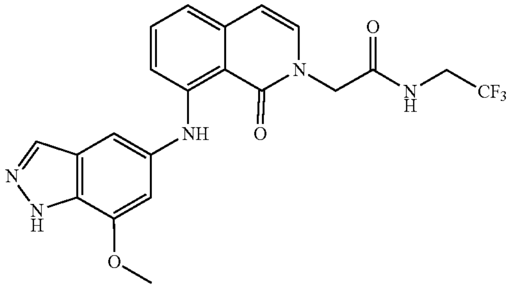
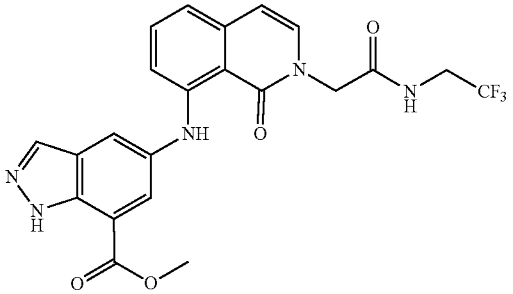
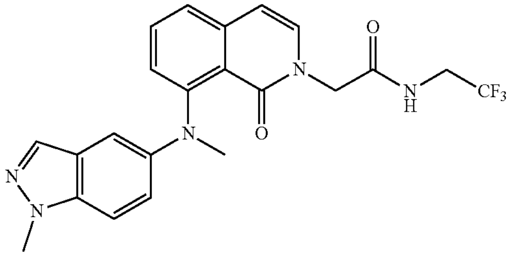
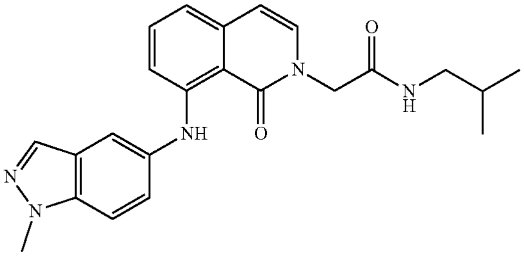
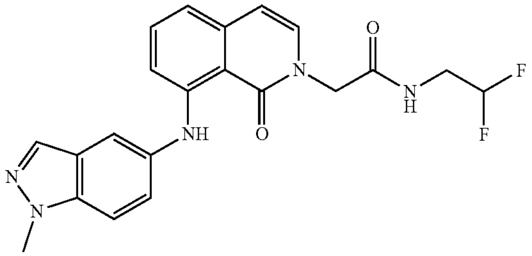
-continued
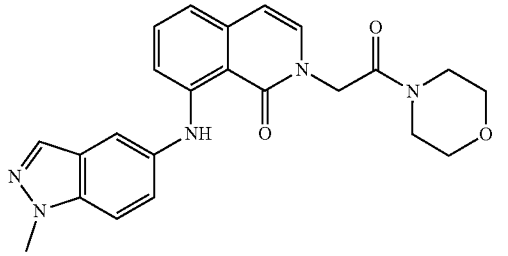
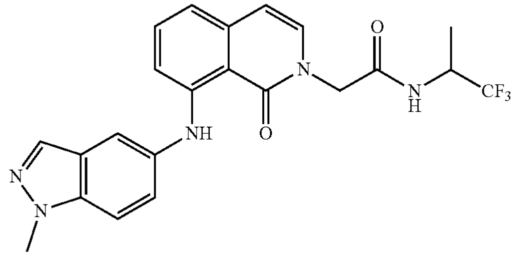
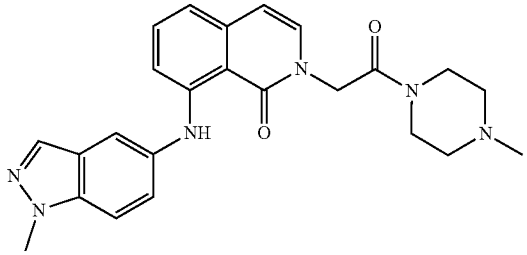
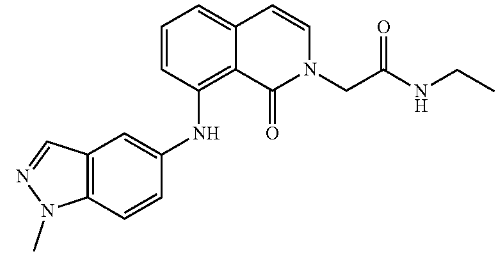
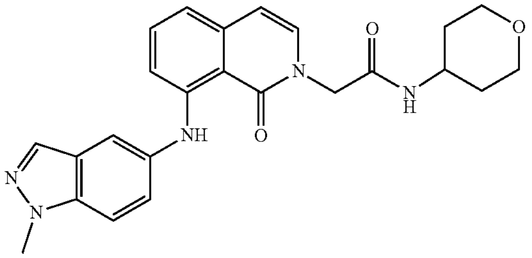
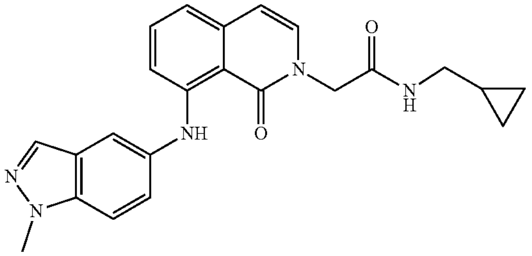

-continued
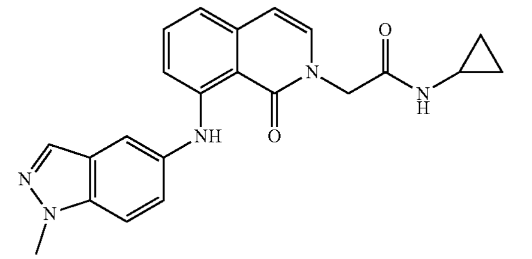
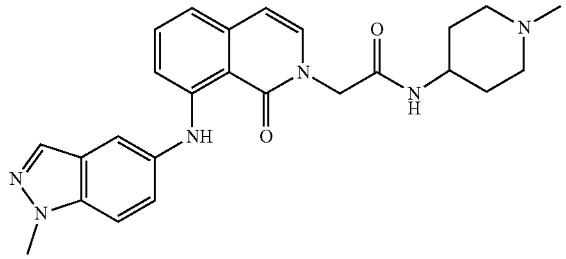
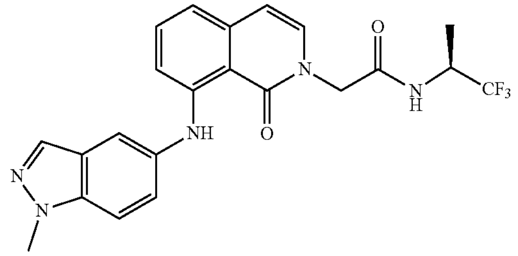
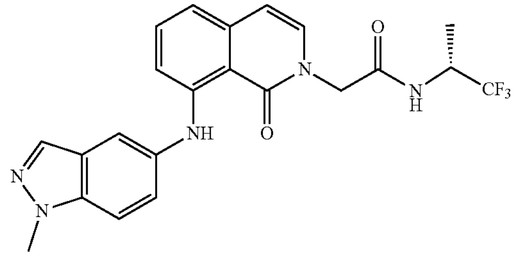
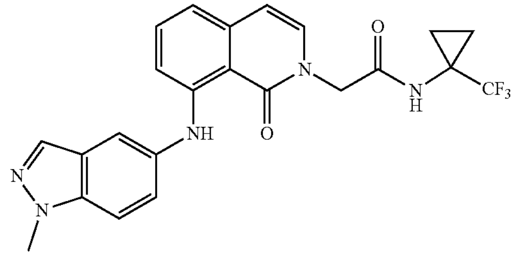
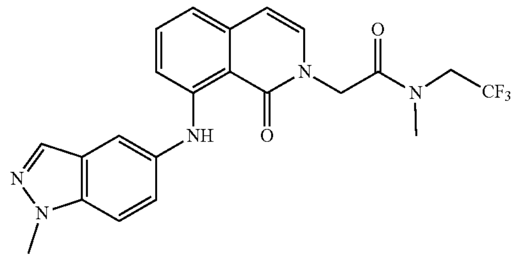
-continued
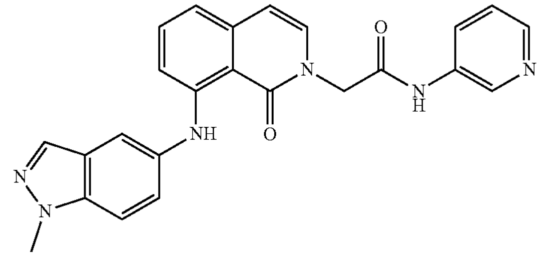
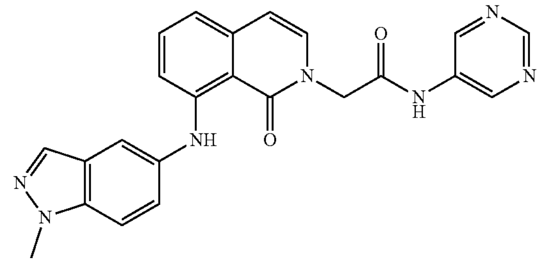
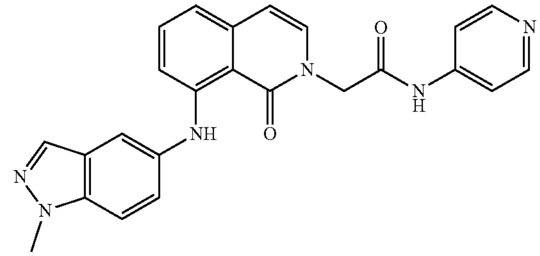
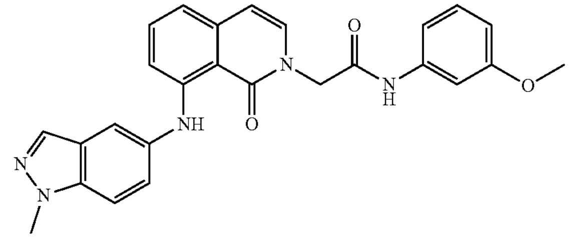
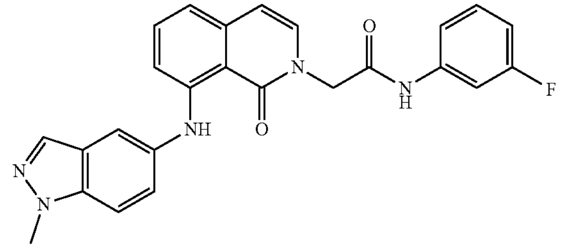
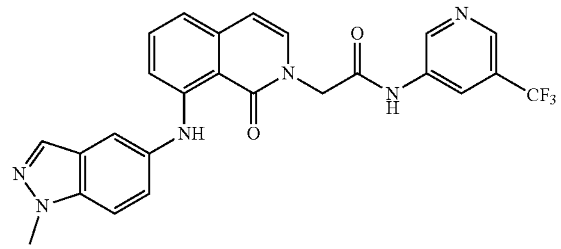

-continued
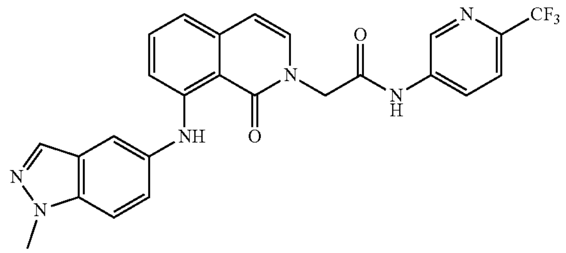
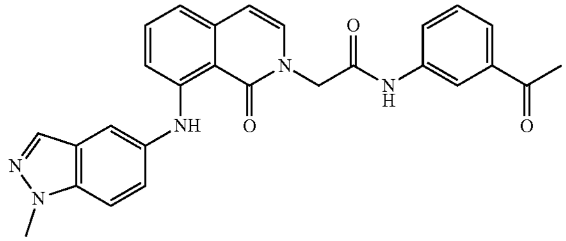
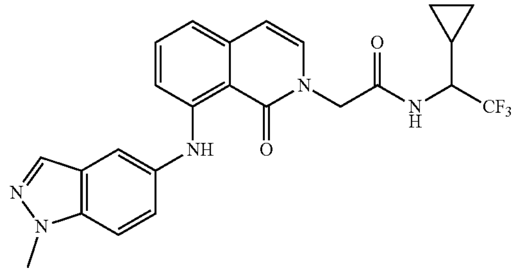
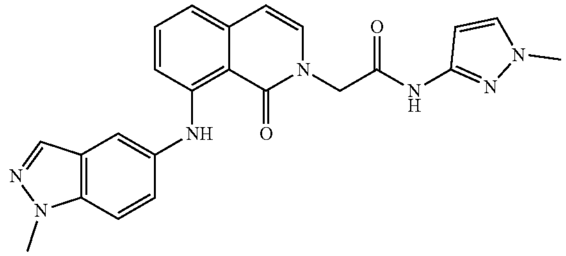
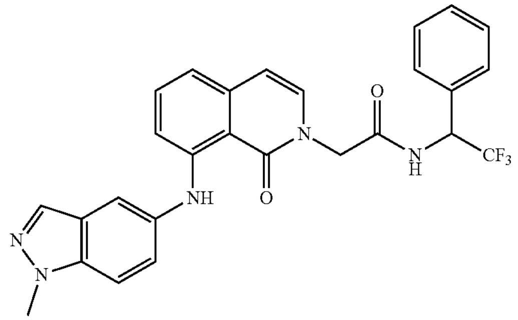
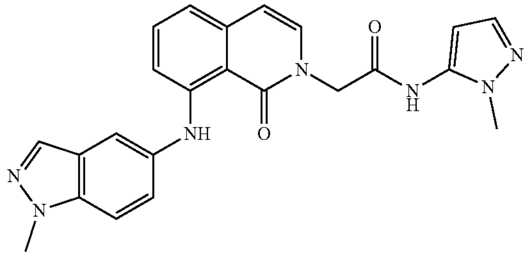
-continued
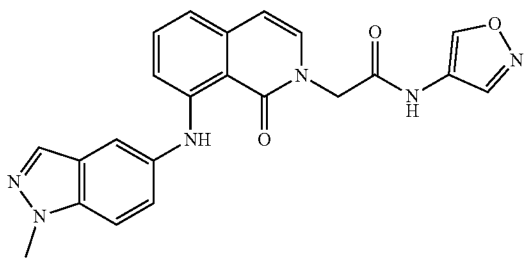
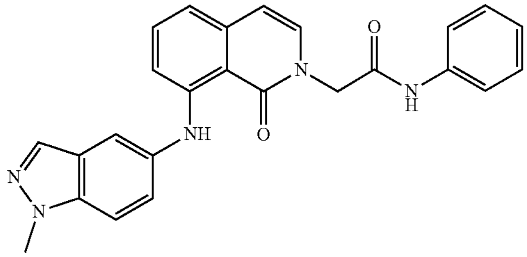
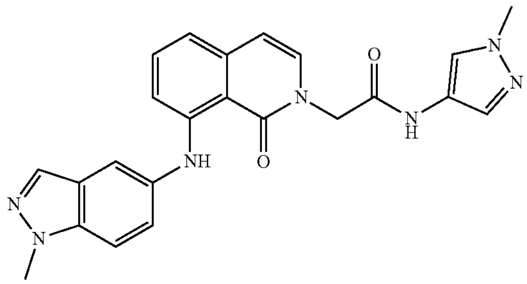
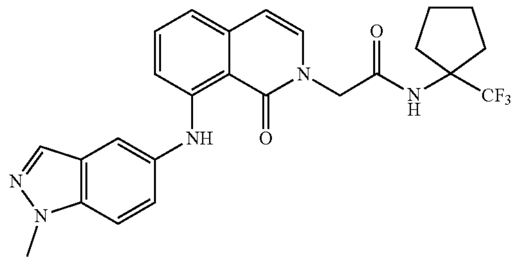
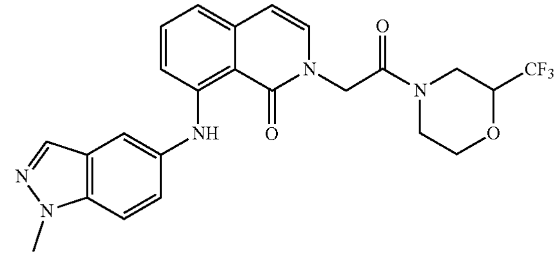
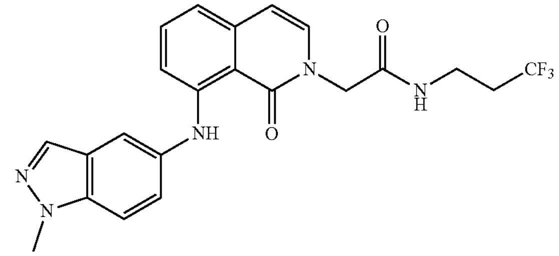

-continued
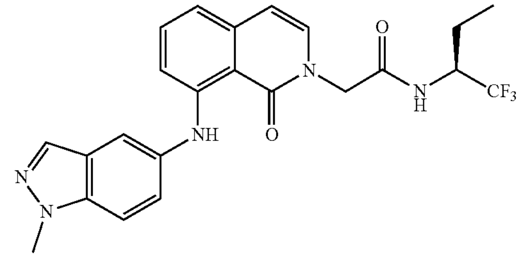
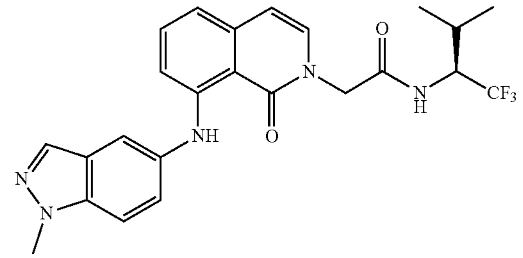
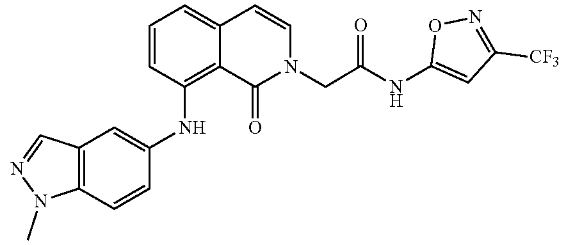
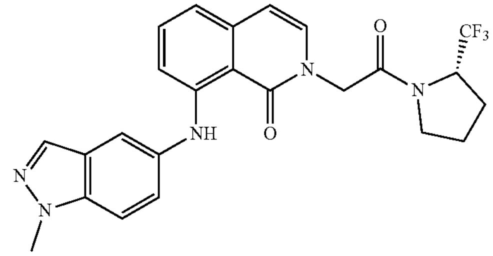
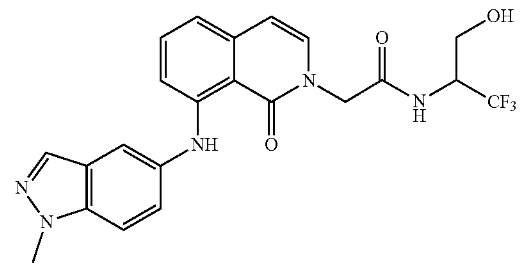
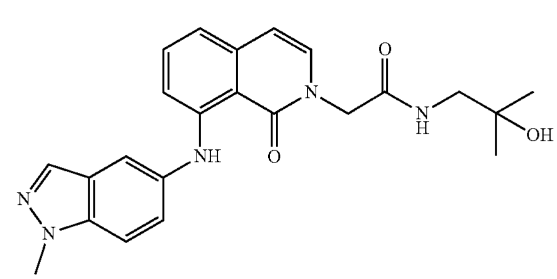
-continued
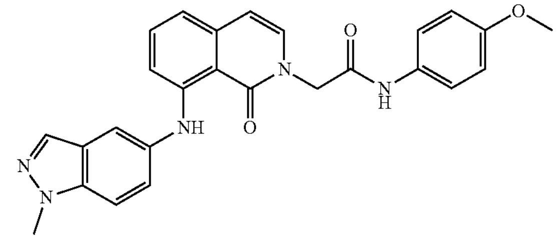
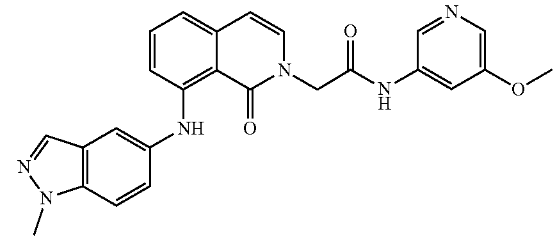
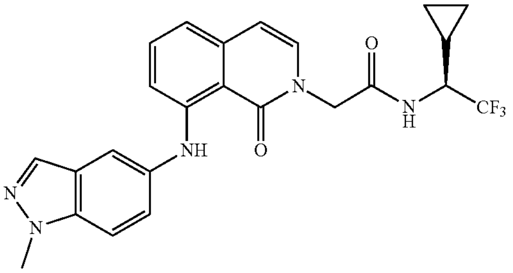
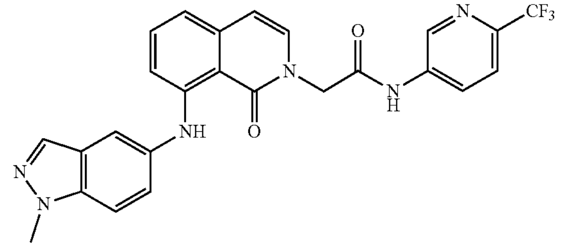
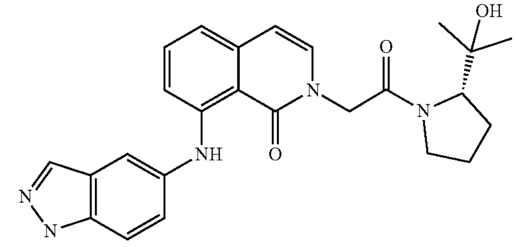
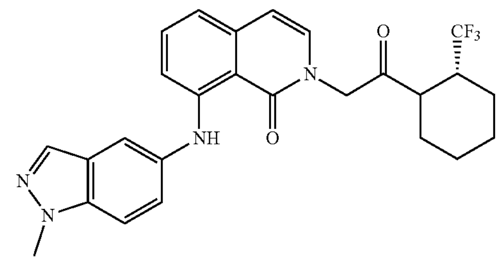

-continued
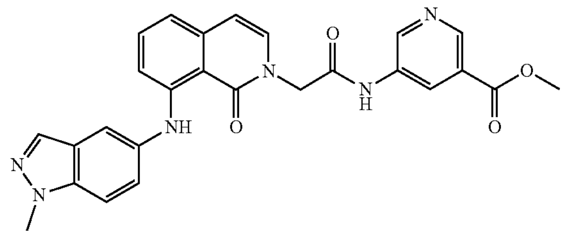
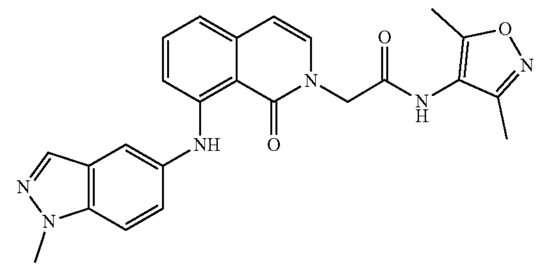
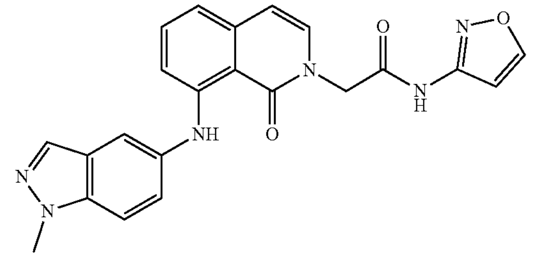
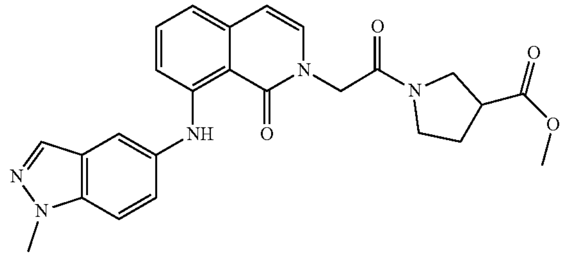
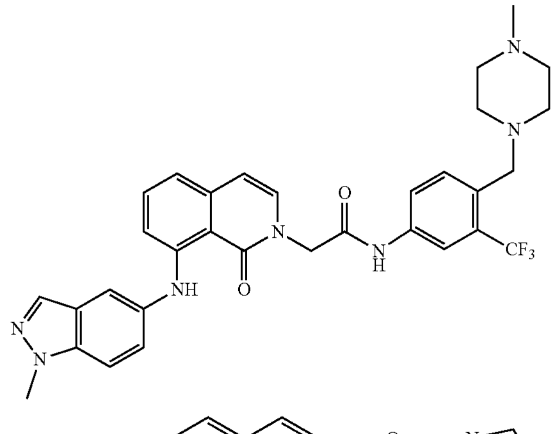
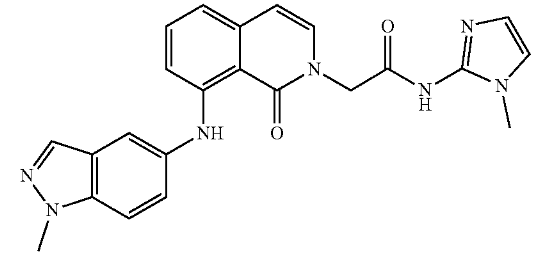
-continued
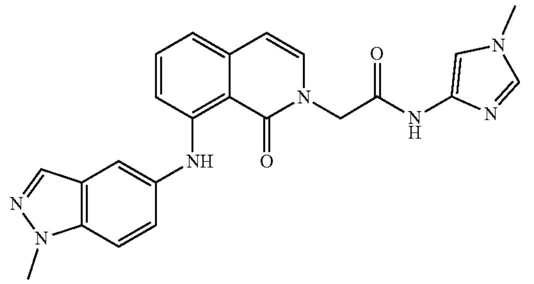
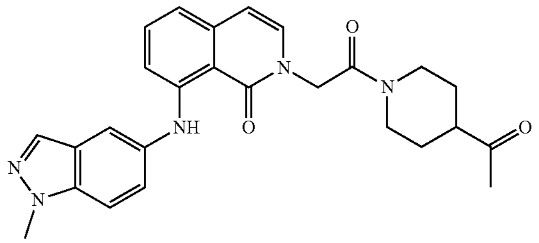
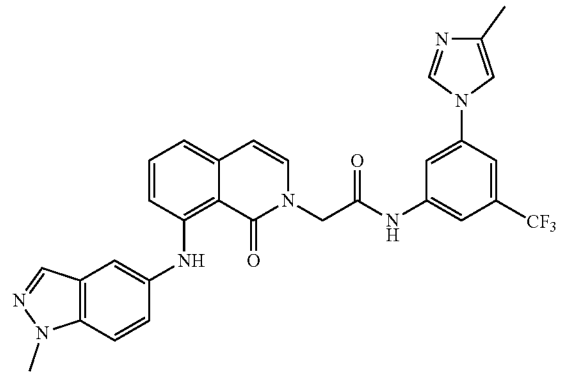
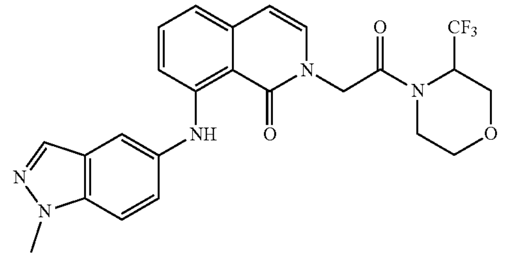
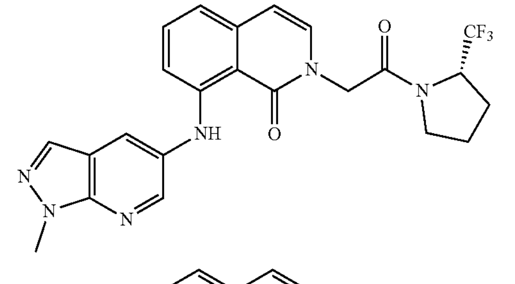
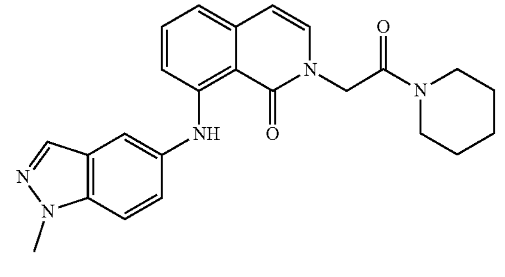

-continued
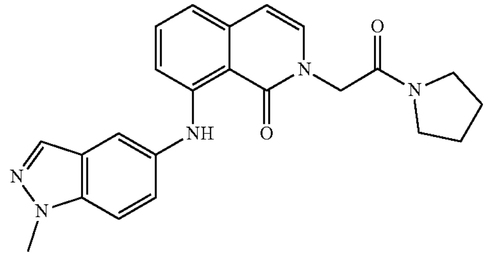
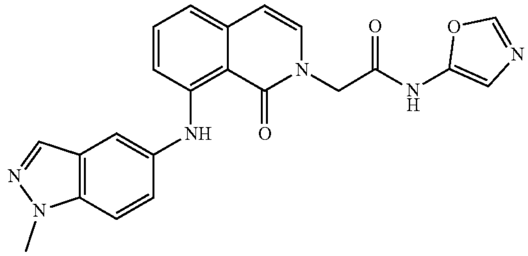
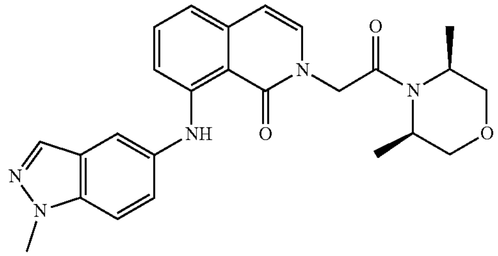
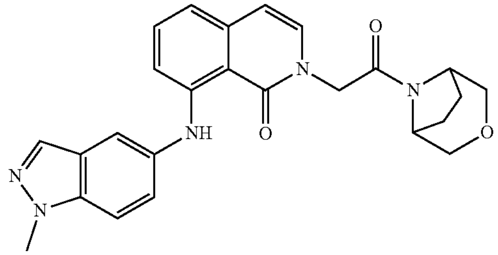
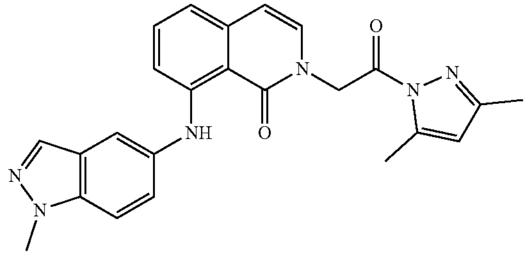
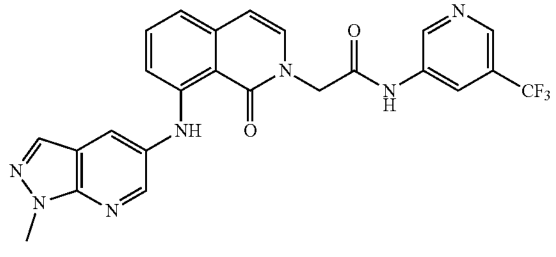
-continued
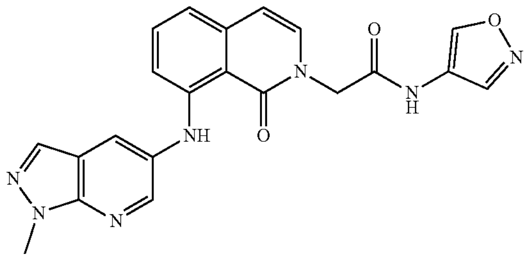
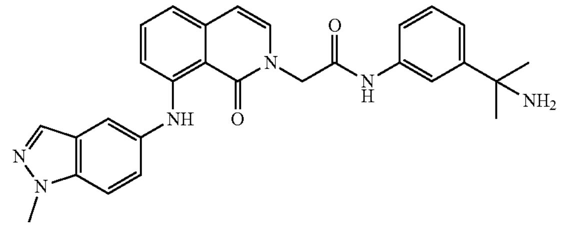
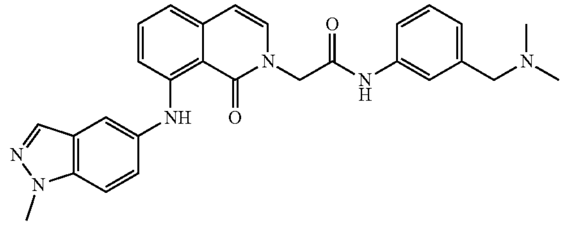
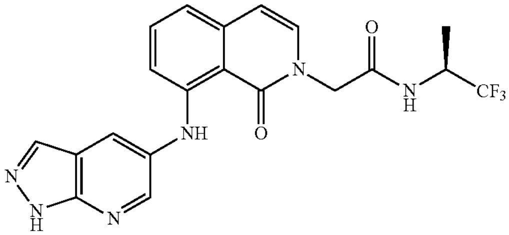
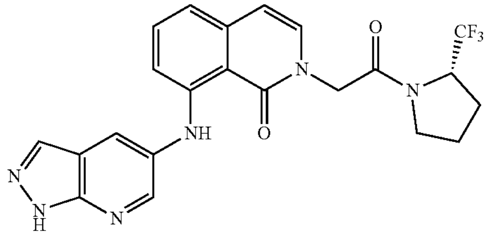
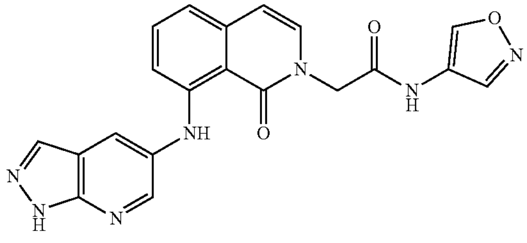
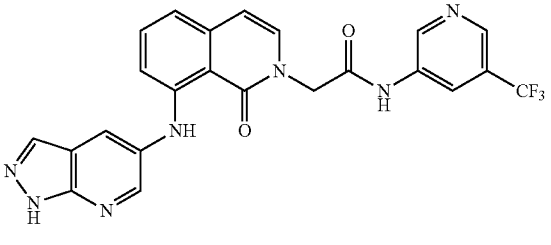

-continued
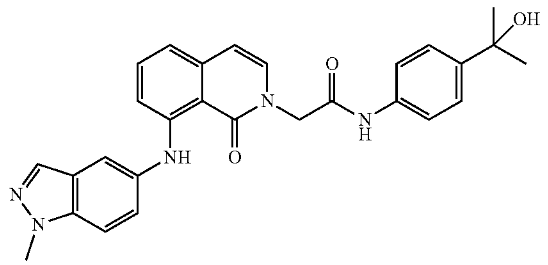
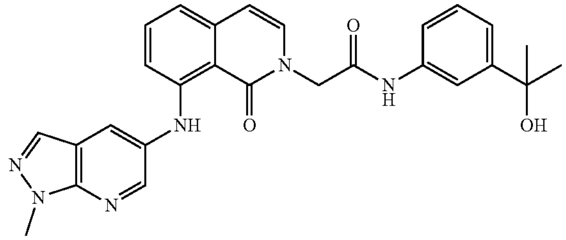
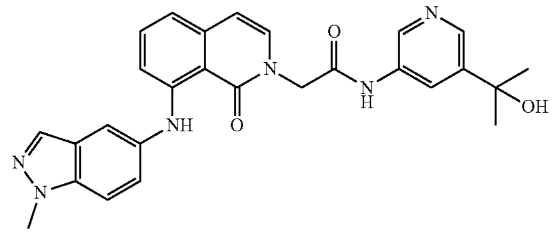
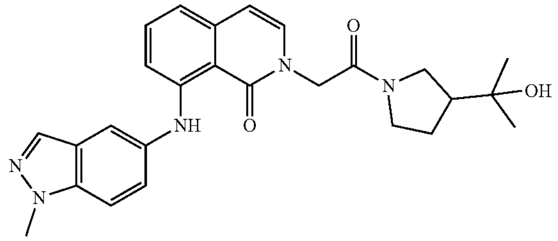
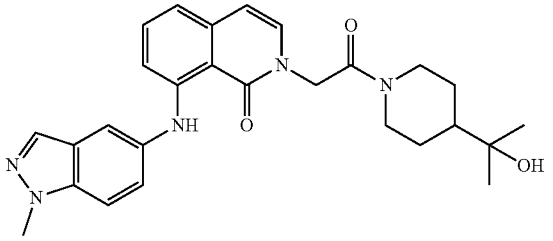
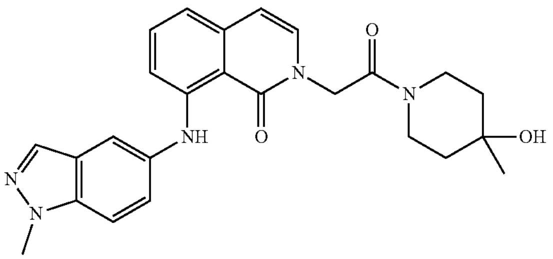
-continued
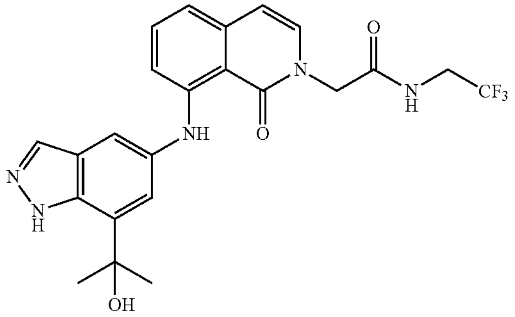
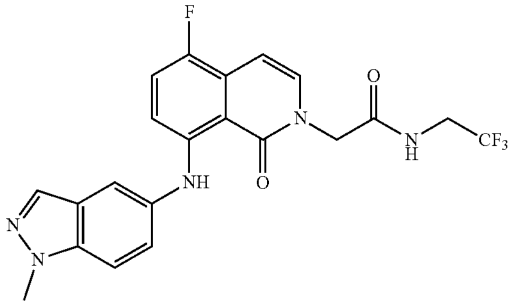
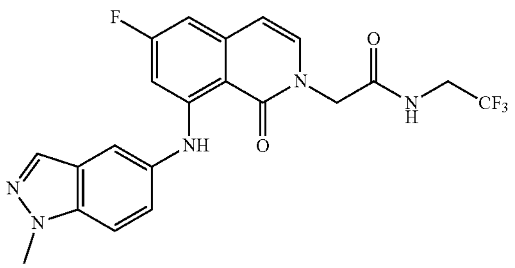
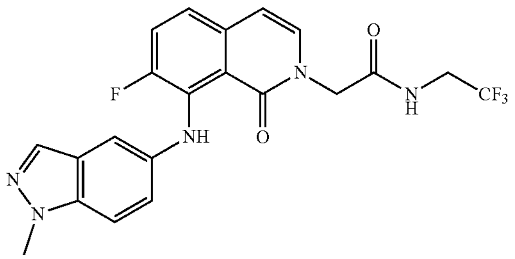
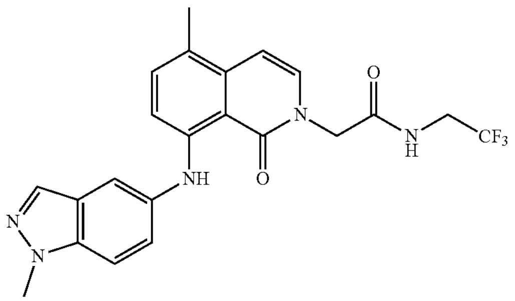
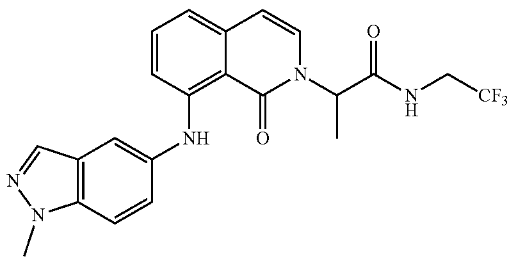

-continued
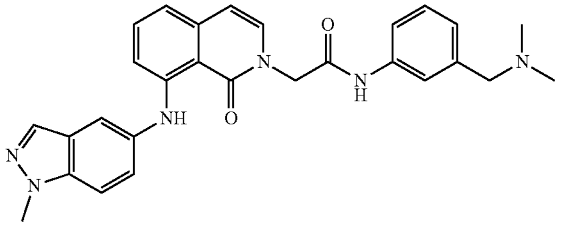
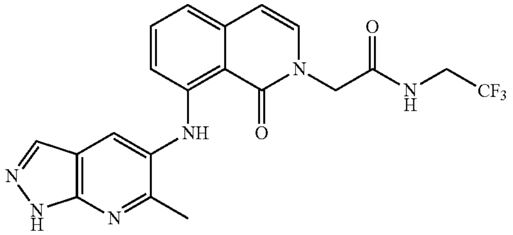
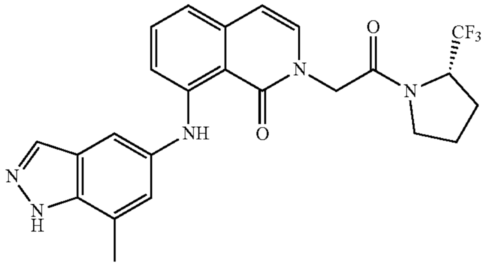
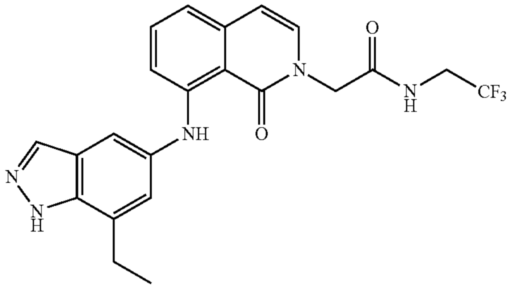
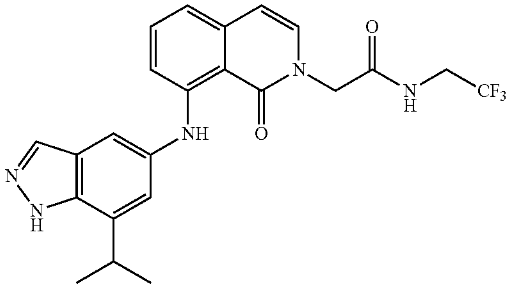
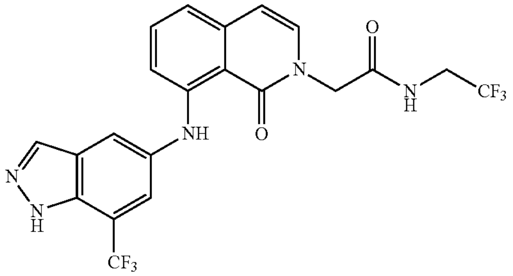
-continued
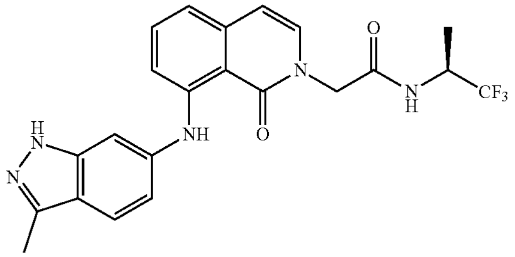
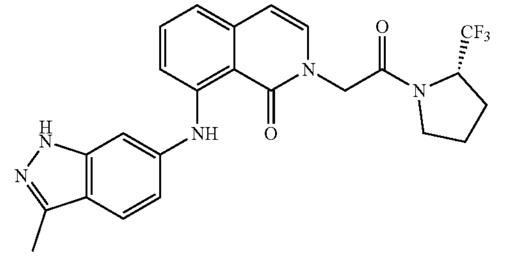
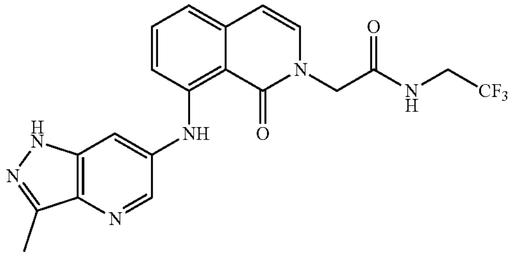
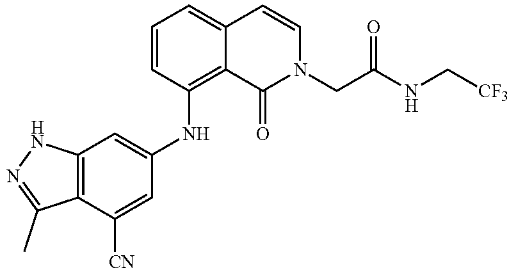
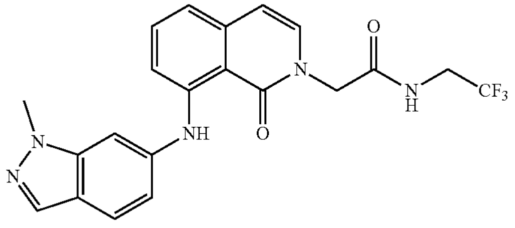
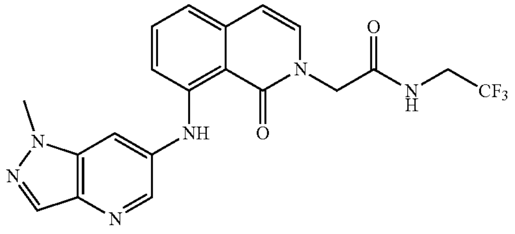

-continued
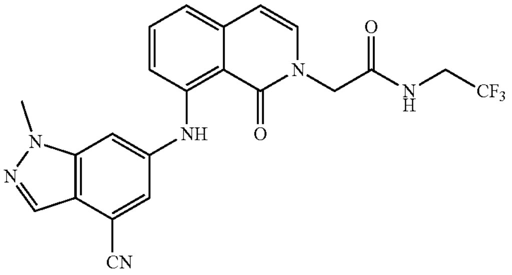
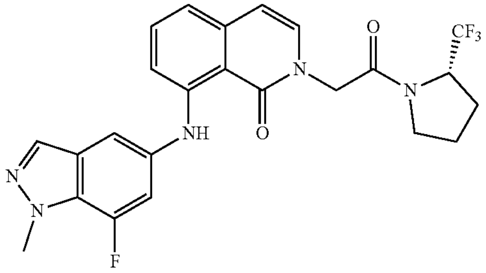
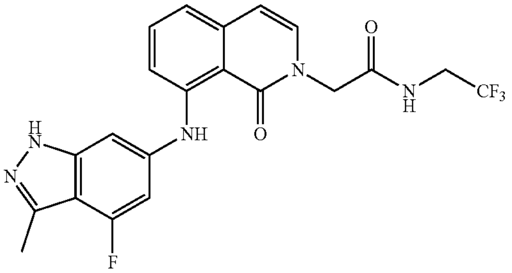
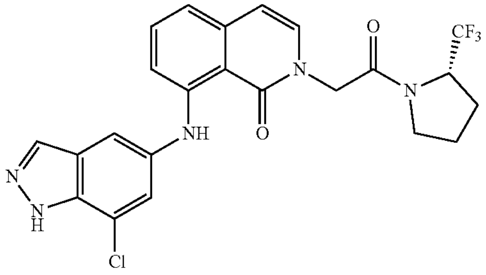
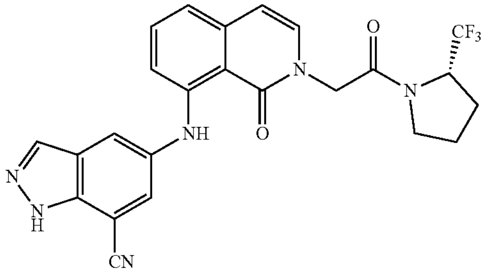
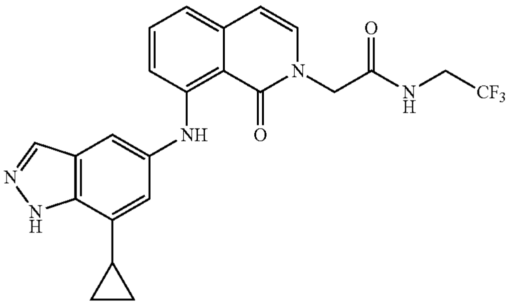
-continued
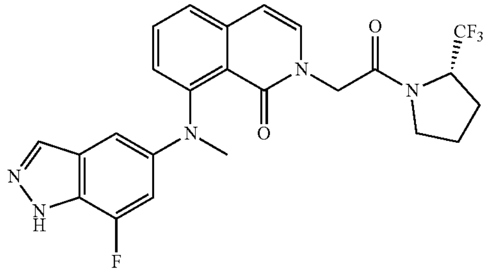
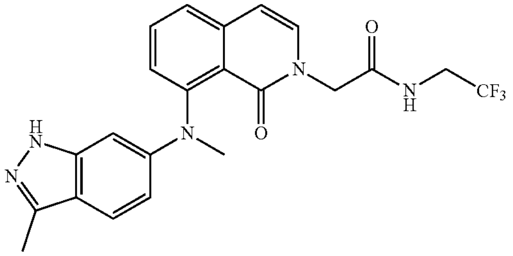
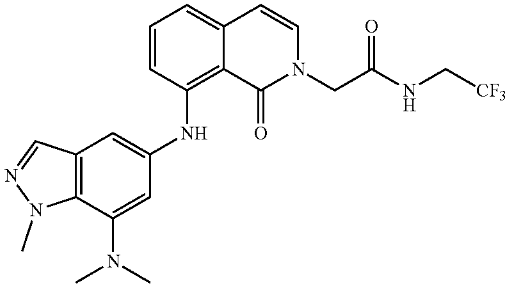
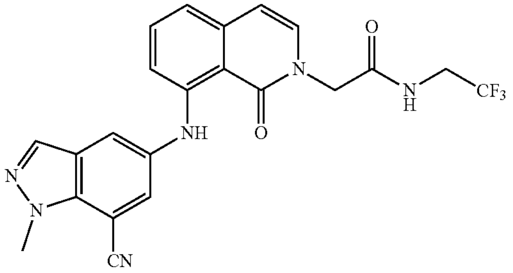
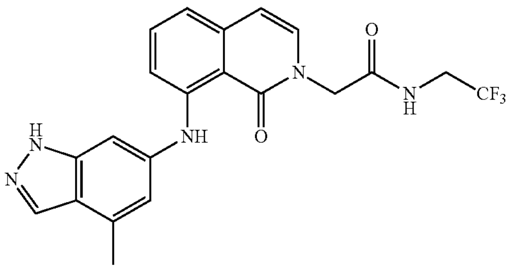
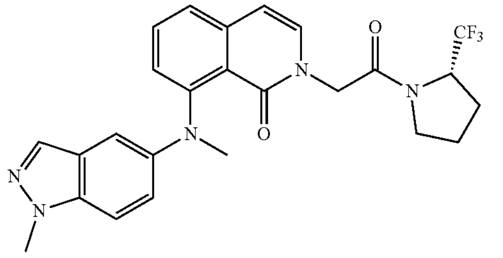

-continued
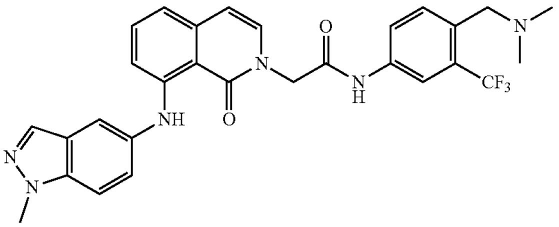
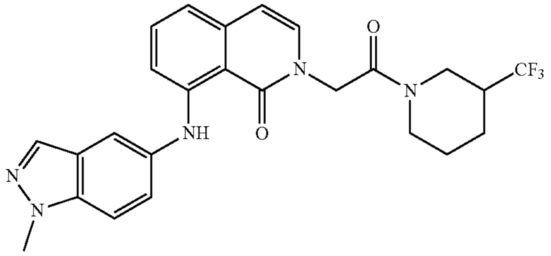
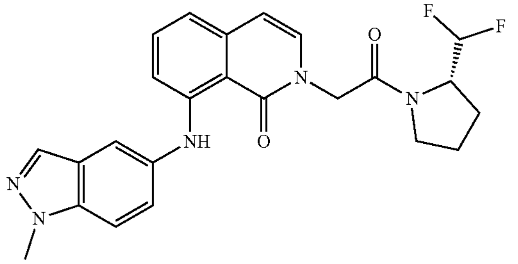
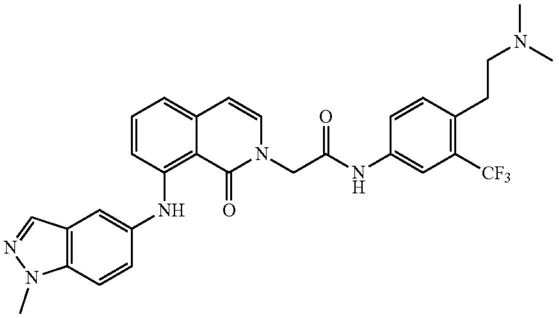
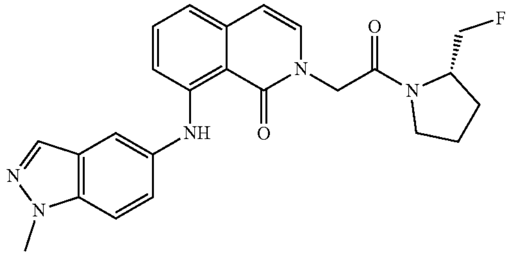
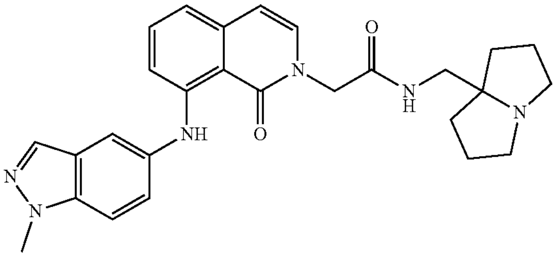
-continued
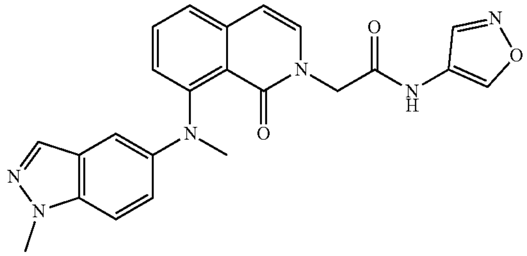
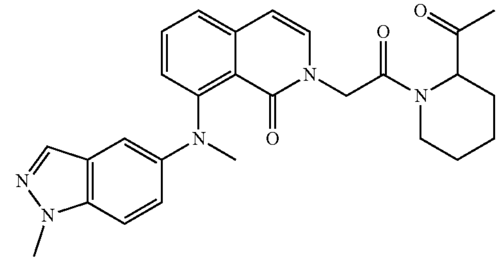
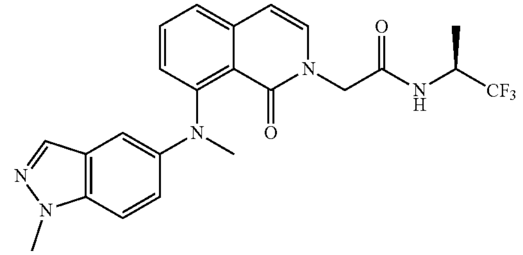
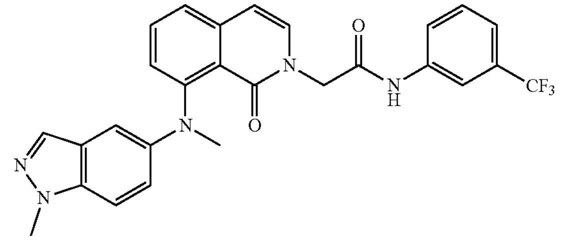
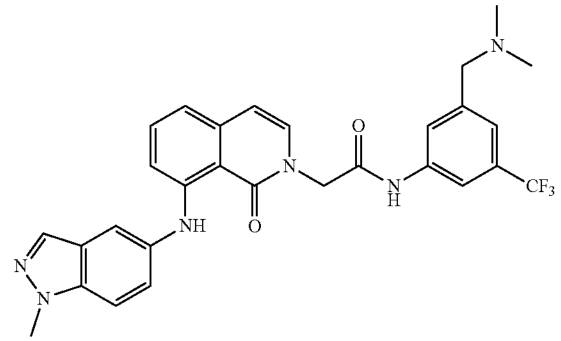
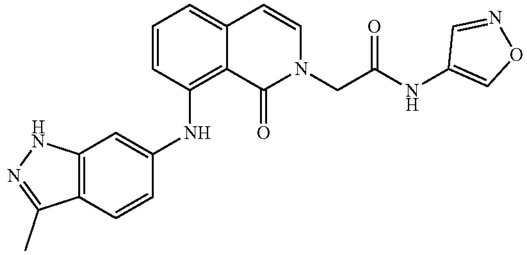

-continued
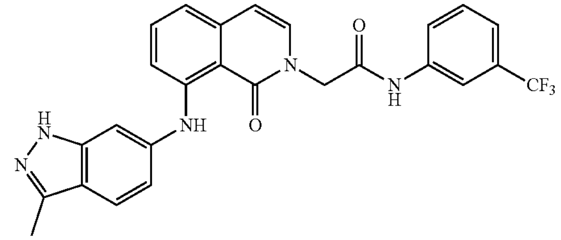
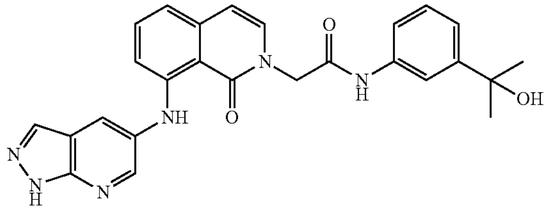
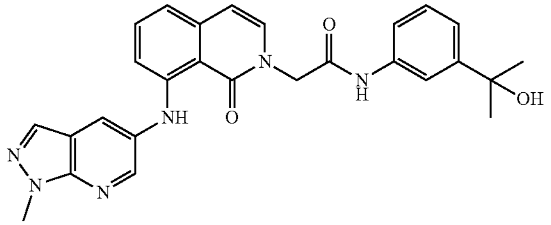
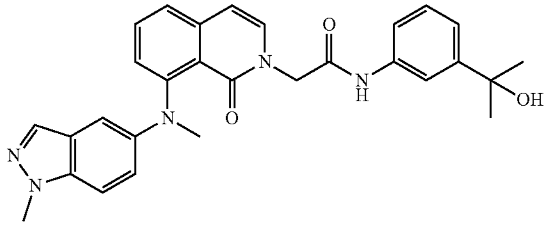
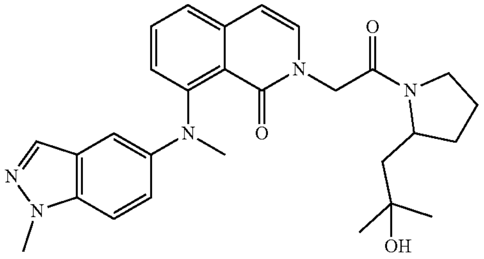
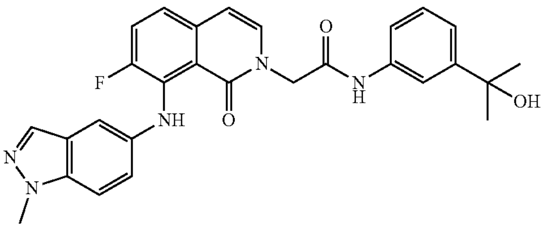
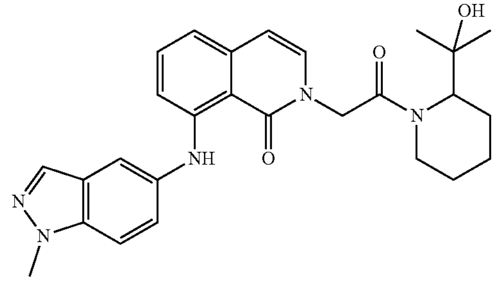
-continued
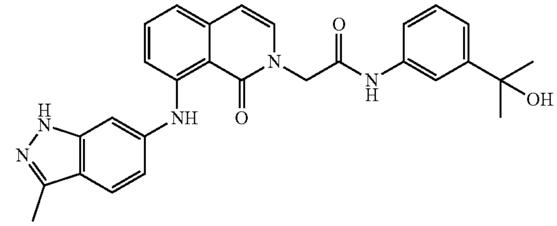
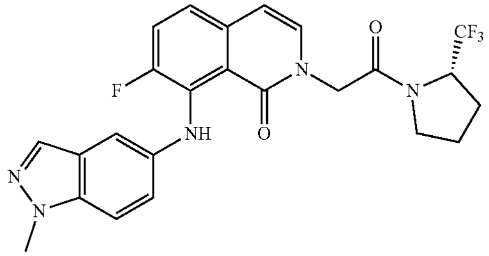
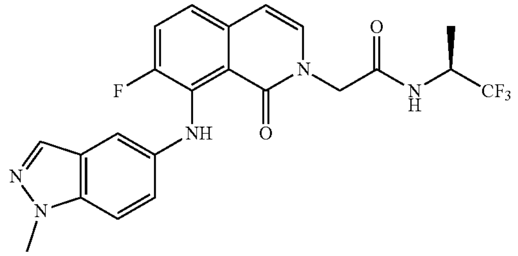
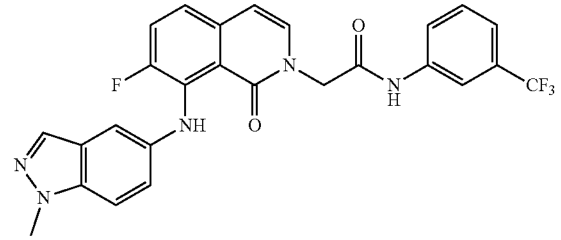
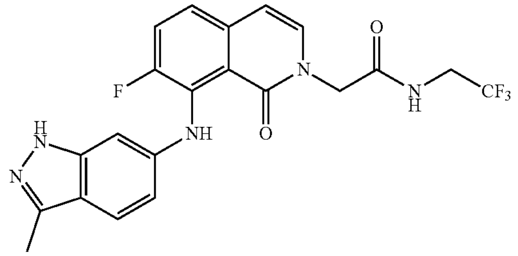
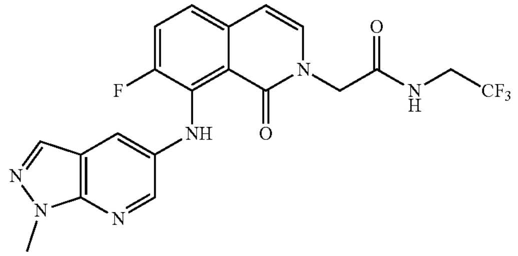

-continued

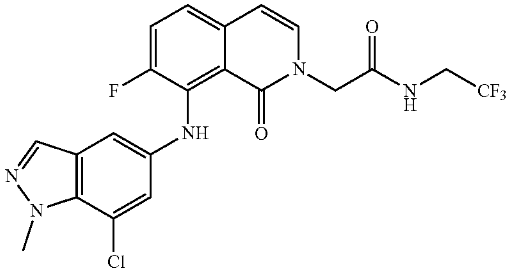

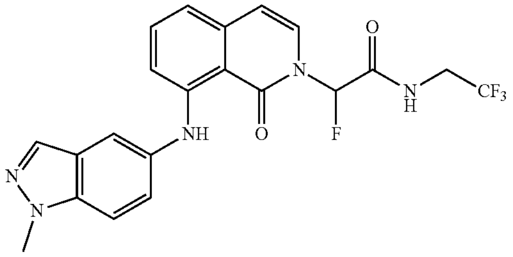

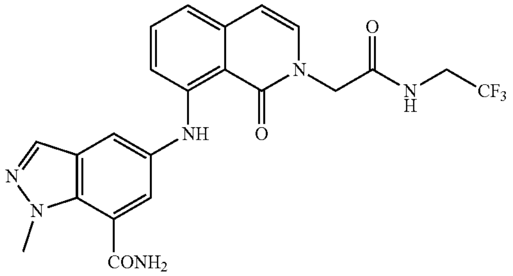

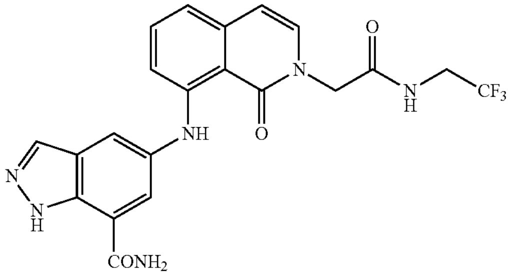

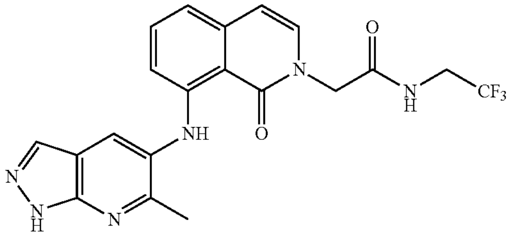

and

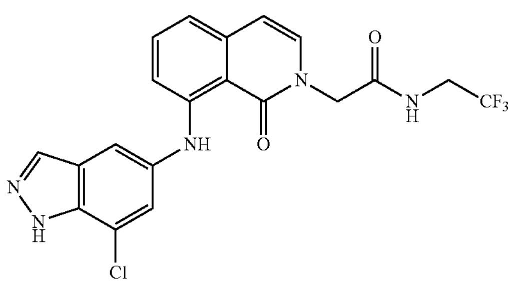

-continued

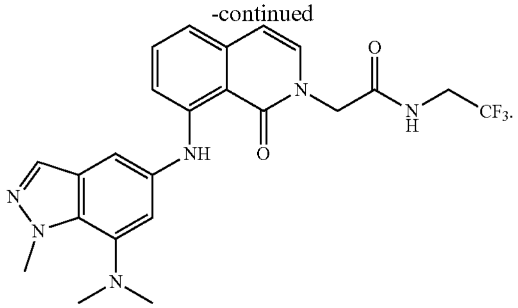

In an aspect of the invention there is provided the compounds of the present invention for use as a medicament.

In accordance with another aspect, there is provided a compound of the present invention for use in the treatment of a condition which is modulated by DDR1 and/or DDR2. A compound of any formula disclosed herein may be for use in the treatment of a condition treatable by the inhibition of DDR1 and/or DDR2.

In another aspect of the invention, there is provided a compound of the present invention for use in the treatment of a disease or disorder selected from: renal conditions, liver conditions, inflammatory conditions, cardiovascular conditions, acute and chronic organ transplant rejection, fibrotic diseases and cancer.

In an aspect of the invention there is provided a method of treating a disease or disorder which is modulated by DDR1 and/or DDR2 wherein the method comprises administering a therapeutic amount of a compound of the invention, to a patient in need thereof.

The method of treatment may be a method of treating a condition treatable by the inhibition of DDR1 and/or DDR2.

The invention also provides a method of treating a disease or disorder selected from: renal conditions, liver conditions, inflammatory conditions, cardiovascular conditions, acute and chronic organ transplant rejection, fibrotic diseases and cancer wherein the method comprises administering a therapeutic amount of a compound of any formula disclosed herein, to a patient in need thereof.

Renal conditions include, acute kidney injury and chronic renal disease with and without proteinuria including end-stage renal disease (ESRD). This includes decreased creatinine clearance and decreased glomerular filtration rate, micro albuminuria, albuminuria and proteinuria, glomerulosclerosis with expansion of reticulated mesangial matrix with or without significant hypercellularity (particularly diabetic nephropathy and amyloidosis), focal thrombosis of glomerular capillaries (particularly thrombotic microangiopathies), global fibrinoid necrosis, ischemic lesions, malignant nephrosclerosis (such as ischemic retraction, reduced renal blood flow and renal arteriopathy), swelling and proliferation of intracapillary (endothelial and mesangial) and/or extracapillary cells (crescents) like in glomerular nephritis entities, focal segmental glomerular sclerosis, IgA nephropathy, vasculitis/systemic diseases as well as acute and chronic kidney transplant rejection. Early and advanced Alport syndrome are also included amongst renal conditions.

Inflammatory conditions include, arthritis, osteoarthritis, multiple sclerosis, systemic lupus erythematodes, inflammatory bowel disease, abnormal evacuation disorder and the like as well as inflammatory airways diseases such as idiopathic pulmonary fibrosis (IPF), chronic obstructive pulmonary disease (COPD) or chronic asthma. Further conditions of the respiratory system include other diffuse parenchymal lung diseases of different etiologies including iatrogenic drug-induced fibrosis, occupational and/or environmental induced fibrosis, systemic diseases and vasculitis, granulomatous diseases (sarcoidosis, hypersensitivity pneumonia), collagen vascular disease, radiation induced fibrosis.

Vascular conditions include atherosclerosis, thrombotic vascular disease as well as thrombotic microangiopathies, proliferative arteriopathy (such as swollen myointimal cells surrounded by mucinous extracellular matrix and nodular thickening), atherosclerosis, decreased vascular compliance (such as stiffness, reduced ventricular compliance and reduced vascular compliance), endothelial dysfunction and the like.

Cardiovascular conditions include acute coronary syndrome, coronary heart disease, myocardial infarction, arterial and pulmonary hypertension, cardiac arrhythmia such as atrial fibrillation, stroke and other vascular damage.

Fibrotic diseases include, but are not limited to myocardial and vascular fibrosis, renal fibrosis, liver fibrosis, pulmonary fibrosis, skin fibrosis, scleroderma and encapsulating peritonitis, systemic sclerosis, Alport syndrome, Chronic kidney disease, NASH, Interstitial lung diseases and Systemic Sclerosis.

In certain embodiments compounds of the invention are for use in the treatment of or are used in a method of treatment of cancer. Examples include but are not limited to: liver cancer, bladder cancer, hepatoma, squamous carcinoma of the lung, non-small cell lung cancer, adenocarcinoma of the lung, small-cell lung cancer, various types of head and neck cancer, breast cancer, colon cancer, colorectal cancer, cancer of the peritoneum, hepatocellular cancer, gastrointestinal cancer, esophageal cancer, endometrial or uterine carcinoma, salivary gland carcinoma, squamous cell cancer, pituitary cancer, astrocytoma, soft tissue sarcoma, pancreatic cancer, glioblastoma, cervical cancer, ovarian cancer, kidney cancer, liver cancer, prostate cancer, vulval cancer, thyroid cancer, hepatic carcinoma, brain cancer, endometrial cancer, testis cancer, cholangiocarcinoma, gallbladder carcinoma, gastric cancer and melanoma. In certain embodiments, the cancer is selected from bladder cancer, pancreatic cancer, breast cancer, lung cancer, ovarian cancer and glioblastoma.

In another aspect of the invention there is provided a pharmaceutical composition, wherein the composition comprises a compound of the invention and pharmaceutically acceptable excipients.

In an embodiment the pharmaceutical composition may be a combination product comprising an additional pharmaceutically active agent.

In an aspect of the present invention there is provided the use of a compound of the invention in the manufacture of a medicament for use in the treatment of any condition disclosed herein.

DETAILED DESCRIPTION

Given below are definitions of terms used in this application. Any term not defined herein takes the normal meaning as the skilled person would understand the term.

The term "halo" refers to one of the halogens, group 17 of the periodic table. In particular, the term refers to fluorine, chlorine, bromine and iodine. Preferably, the term refers to chlorine or fluorine.

The term "alkyl" refers to a linear or branched hydrocarbon chain. For example, the term "$C_{1-6}$ alkyl" refers to a linear or branched hydrocarbon chain containing 1, 2, 3, 4, 5 or 6 carbon atoms, for example methyl, ethyl, n-propyl, iso-propyl, n-butyl, sec-butyl, tert-butyl, n-pentyl and n-hexyl. "Alkylene" groups may likewise be linear or branched and is divalent, i.e. it attached at two positions to other portions of the molecule. Furthermore, an alkylene group may, for example, correspond to one of those alkyl groups listed in this paragraph. The alkyl and alkylene groups may be unsubstituted or substituted by one or more substituents.

The term "haloalkyl" refers to a hydrocarbon chain substituted with at least one halogen atom independently chosen at each occurrence, for example fluorine, chlorine, bromine and iodine. For example, the term "$C_{1-6}$ haloalkyl" refers to a linear or branched hydrocarbon chain containing 1, 2, 3, 4, 5 or 6 carbon atoms substituted with at least one halogen. The halogen atom may be present at any position on the hydrocarbon chain. For example, $C_{1-8}$ haloalkyl may refer to chloromethyl, fluoromethyl, trifluoromethyl, chloroethyl e.g. 1-chloromethyl and 2-chloroethyl, trichloroethyl e.g. 1,2,2-trichloroethyl, 2,2,2-trichloroethyl, fluoroethyl e.g. 1-fluoromethyl and 2-fluoroethyl, trifluoroethyl e.g. 1,2,2-trifluoroethyl and 2,2,2-trifluoroethyl, chloropropyl, trichloropropyl, fluoropropyl, trifluoropropyl. The term "fluoroalkyl" refers to a hydrocarbon chain substituted with at least one fluorine atom.

The term "alkenyl" refers to a branched or linear hydrocarbon chain containing at least one double bond. For example, the term "$C_{2-6}$ alkenyl" refers to a branched or linear hydrocarbon chain containing at least one double bond and having 2, 3, 4, 5 or 6 carbon atoms. The double bond(s) may be present as the E or Z isomer. The double bond may be at any possible position of the hydrocarbon chain. For example, the "$C_{2-6}$ alkenyl" may be ethenyl, propenyl, butenyl, butadienyl, pentenyl, pentadienyl, hexenyl and hexadienyl.

The term "alkynyl" refers to a branched or linear hydrocarbon chain containing at least one triple bond. For example, the term "$C_{2-6}$ alkynyl" refers to a branched or linear hydrocarbon chain containing at least one triple bond and having 2, 3, 4, 5 or 6 carbon atoms. The triple bond may be at any possible position of the hydrocarbon chain. For example, the "$C_{2-6}$ alkynyl" may be ethynyl, propynyl, butynyl, pentynyl and hexynyl.

The term "heteroalkyl" refers to a branched or linear hydrocarbon chain containing at least one heteroatom selected from N, O and S positioned between any carbon in the chain or at an end of the chain. For example, the term "$C_{1-8}$ heteroalkyl" refers to a branched or linear hydrocarbon chain containing 1, 2, 3, 4, 5, or 6 carbon atoms and at least one heteroatom selected from N, O and S positioned between any carbon in the chain or at an end of the chain. For example, the hydrocarbon chain may contain one or two heteroatoms. The $C_{1-6}$ heteroalkyl may be bonded to the rest of the molecule through a carbon or a heteroatom. For example, the "$C_{1-8}$ heteroalkyl" may be $C_{1-6}$ N-alkyl, $C_{1-6}$ N,N-alkyl, or $C_{1-6}$ O-alkyl.

The term "heterocycle" refers to a saturated, unsaturated or aromatic ring system containing at least one heteroatom selected from N, O or S. A "heterocyclic" system may contain 1, 2, 3 or 4 heteroatoms, for example 1 or 2. A "heterocyclic" system may be monocyclic or a fused polycyclic ring system, for example, bicyclic or tricyclic. A "heterocyclic" moiety may contain from 3 to 14 carbon atoms, for example, 3 to 8 carbon atoms in a monocyclic system and 7 to 14 carbon atoms in a polycyclic system. "Heterocyclic" encompasses heterocycloalkyl moieties, heterocycloalkenyl moieties and heteroaryl moieties. For example, the heterocyclic group may be: oxirane, aziridine, azetidine, oxetane, tetrahydrofuran, pyrrolidine, imidazolidine, succinimide, pyrazolidine, oxazolidine, isoxazolidine, thiazolidine, isothiazolidine, piperidine, morpholine, thiomorpholine, piperazine, and tetrahydropyran. Heteroaryl includes groups such as pyridones and N-alkyl-pyridones.

The term "$C_{3-8}$ cycloalkyl" refers to a saturated hydrocarbon ring system containing 3, 4, 5, 6, 7 or 8 carbon atoms. For example, the "$C_{3-8}$ cycloalkyl" may be cyclopropyl, cyclobutyl, cyclopentyl, cyclohexyl, cycloheptyl and cyclooctyl.

The term "$C_{3-8}$ cycloalkenyl" refers to an unsaturated hydrocarbon ring system containing 3, 4, 5, 6, 7 or 8 carbon atoms that is not aromatic. The ring may contain more than one double bond provided that the ring system is not aromatic. For example, the "$C_{3-8}$ cycloalkyl" may be cyclopropenyl, cyclobutenyl, cyclopentenyl, cyclopentadienyl, cyclohexenyl, cyclohexadienly, cycloheptenyl, cycloheptadiene, cyclooctenyl and cycloatadienyl.

The term "heterocycloalkyl" refers to a saturated hydrocarbon ring system containing carbon atoms and at least one heteroatom within the ring selected from N, O and S. For example, there may be 1, 2 or 3 heteroatoms, optionally 1 or 2. The "heterocycloalkyl" may be bonded to the rest of the molecule through any carbon atom or heteroatom. The "heterocycloalkyl" may have one or more, e.g. one or two, bonds to the rest of the molecule: these bonds may be through any of the atoms in the ring. For example, the "heterocycloalkyl" may be a "$C_{3-8}$ heterocycloalkyl". The term "$C_{3-8}$ heterocycloalkyl" refers to a saturated hydrocarbon ring system containing 3, 4, 5, 6, 7 or 8 atoms at least one of the atoms being a heteroatom within the ring selected from N, O and S. The "heterocycloalkyl" may be oxirane, aziridine, azetidine, oxetane, tetrahydrofuran, pyrrolidine, imidazolidine, succinimide, pyrazolidine, oxazolidine, isoxazolidine, thiazolidine, isothiazolidine, piperidine, morpholine, thiomorpholine, piperazine, and tetrahydropyran.

The term "aromatic" when applied to a substituent as a whole means a single ring or polycyclic ring system with 4n+2 electrons in a conjugated π system within the ring or ring system where all atoms contributing to the conjugated π system are in the same plane.

The term "aryl" refers to an aromatic hydrocarbon ring system. The ring system has 4n+2 electrons in a conjugated π system within a ring where all atoms contributing to the conjugated π system are in the same plane. For example, the "aryl" may be phenyl and naphthyl. The aryl system itself may be substituted with other groups.

The term "heteroaryl" refers to an aromatic hydrocarbon ring system with at least one heteroatom within a single ring or within a fused ring system, selected from O, N and S. The ring or ring system has 4n+2 electrons in a conjugated π system where all atoms contributing to the conjugated π system are in the same plane. For example, the "heteroaryl" may be imidazole, oxazole, isoxazole, thiazole, isothiazole, thiene, furan, thianthrene, pyrrole, benzimidazole, pyrazole, pyrazine, pyridine, pyrimidine and indole.

A bond terminating in a " " represents that the bond is connected to another atom that is not shown in the structure. A bond terminating inside a cyclic structure and not terminating at an atom of the ring structure represents that the bond may be connected to any of the atoms in the ring structure where allowed by valency.

A bond drawn as a solid line and a dotted line represents a bond which can be either a single bond or a double bond, where chemically possible. For example, the bond drawn below could be a single bond or a double bond.

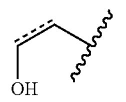

Where a moiety is substituted, it may be substituted at any point on the moiety where chemically possible and consistent with atomic valency requirements. The moiety may be substituted by one or more substituents, e.g. 1, 2, 3 or 4 substituents; optionally there are 1 or 2 substituents on a group. Where there are two or more substituents, the substituents may be the same or different.

Substituents are only present at positions where they are chemically possible, the person skilled in the art being able to decide (either experimentally or theoretically) without inappropriate effort which substitutions are chemically possible and which are not.

Ortho, meta and para substitution are well understood terms in the art. For the absence of doubt, "ortho" substitution is a substitution pattern where adjacent carbons possess a substituent, whether a simple group, for example the fluoro group in the example below, or other portions of the molecule, as indicated by the bond ending in " ".

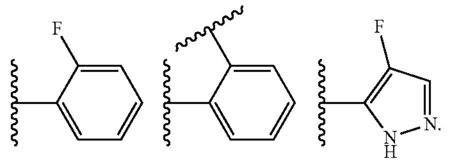

"Meta" substitution is a substitution pattern where two substituents are on carbons one carbon removed from each other, i.e. with a single carbon atom between the substituted carbons. In other words there is a substituent on the second atom away from the atom with another substituent. For example the groups below are meta substituted.

"Para" substitution is a substitution pattern where two substituents are on carbons two carbons removed from each other, i.e. with two carbon atoms between the substituted carbons. In other words there is a substituent on the third atom away from the atom with another substituent. For example the groups below are para substituted.

Throughout the description the disclosure of a compound also encompasses pharmaceutically acceptable salts, solvates and stereoisomers thereof.

Where a compound has a stereocentre, both (R) and (S) stereoisomers are contemplated by the invention, equally mixtures of stereoisomers or a racemic mixture are completed by the present application. Where a compound of the invention has two or more stereocentres any combination of (R) and (S) stereoisomers is contemplated. The combination of (R) and (S) stereoisomers may result in a diastereomeric mixture or a single diastereoisomer. The compounds of the invention may be present as a single stereoisomer or may be mixtures of stereoisomers, for example racemic mixtures and other enantiomeric mixtures, and diasteroemeric mixtures. Where the mixture is a mixture of enantiomers the enantiomeric excess may be any of those disclosed above. Where the compound is a single stereoisomer the compounds may still contain other diasteroisomers or enantiomers as impurities. Hence a single stereoisomer does not necessarily have an enantiomeric excess (e.e.) or diastereomeric excess (d.e.) of 100% but could have an e.e. or d.e. of about at least 85%, at least 60% or less. For example, the e.e. or d.e. may be 90% or more, 90% or more, 80% or more, 70% or more, 60% or more, 50% or more, 40% or more, 30% or more, 20% or more, or 10% or more.

The invention contemplates pharmaceutically acceptable salts of the compounds of the invention. These may include the acid addition and base salts of the compounds. These may be acid addition and base salts of the compounds. In addition the invention contemplates solvates of the compounds. These may be hydrates or other solvated forms of the compound.

Suitable acid addition salts are formed from acids which form non-toxic salts. Examples include the acetate, aspartate, benzoate, besylate, bicarbonate/carbonate, bisulfate/sulfate, borate, camsylate, citrate, edisylate, esylate, formate, fumarate, gluceptate, gluconate, glucuronate, hexafluorophosphate, hibenzate, hydrochloride/chloride, hydrobromide/bromide, hydroiodide/iodide, isethionate, lactate, malate, maleate, malonate, mesylate, methylsulfate, naphthylate, 1,5-naphthalenedisulfonate, 2-napsylate, nicotinate, nitrate, orotate, oxalate, palmitate, pamoate, phosphate/hydrogen phosphate/dihydrogen phosphate, saccharate, stearate, succinate, tartrate, tosylate and trifluoroacetate salts.

Suitable base salts are formed from bases which form non-toxic salts. Examples include the aluminium, arginine, benzathine, calcium, choline, diethylamine, diolamine, glycine, lysine, magnesium, meglumine, olamine, potassium, sodium, tromethamine and zinc salts. Hemisalts of acids and bases may also be formed, for example, hemisulfate and hemicalcium salts. For a review on suitable salts, see "Handbook of Pharmaceutical Salts: Properties, Selection, and Use" by Stahl and Wermuth (Wiley-VCH, Weinheim, Germany, 2002).

Pharmaceutically acceptable salts of compounds of formula (I) may be prepared by one or more of three methods:

(i) by reacting the compound of the invention with the desired acid or base;

(ii) by removing an acid- or base-labile protecting group from a suitable precursor of the compound of the invention or by ring-opening a suitable cyclic precursor, for example, a lactone or lactam, using the desired acid or base; or (iii) by converting one salt of the compound of the invention to another by reaction with an appropriate acid or base or by means of a suitable ion exchange column.

All three reactions are typically carried out in solution. The resulting salt may precipitate out and be collected by filtration or may be recovered by evaporation of the solvent. The degree of ionisation in the resulting salt may vary from completely ionised to almost non-ionised.

The compounds of the invention may exist in both unsolvated and solvated forms. The term 'solvate' is used herein to describe a molecular complex comprising the compound of the invention and a stoichiometric amount of one or more pharmaceutically acceptable solvent molecules, for example, ethanol. The term 'hydrate' is employed when said solvent is water.

Included within the scope of the invention are complexes such as clathrates, drug-host inclusion complexes wherein, in contrast to the aforementioned solvates, the drug and host are present in stoichiometric or non-stoichiometric amounts. Also included are complexes of the drug containing two or more organic and/or inorganic components which may be in stoichiometric or non-stoichiometric amounts. The resulting complexes may be ionised, partially ionised, or non-ionised. For a review of such complexes, see J Pharm Sci, 64 (8), 1269-1288 by Haleblian (August 1975).

Hereinafter all references to compounds of any formula include references to salts, solvates and complexes thereof and to solvates and complexes of salts thereof.

The compounds of the invention include compounds of a number of formula as herein defined, including all polymorphs and crystal habits thereof, prodrugs and isomers thereof (including optical, geometric and tautomeric isomers) as hereinafter defined and isotopically-labelled compounds of the invention.

The present invention also includes all pharmaceutically acceptable isotopically-labelled compounds of the invention wherein one or more atoms are replaced by atoms having the same atomic number, but an atomic mass or mass number different from the atomic mass or mass number most commonly found in nature.

Examples of isotopes suitable for inclusion in the compounds of the invention include isotopes of hydrogen, such as $^{2}H$ and $^{3}H$, carbon, such as $^{11}C$, $^{13}C$ and $^{14}C$, chlorine, such as $^{36}C_1$, fluorine, such as $^{18}F$, iodine, such as $^{123}I$ and $^{125}I$, nitrogen, such as $^{13}N$ and $^{15}N$, oxygen, such as $^{15}O$, $^{17}O$ and $^{18}O$, phosphorus, such as $^{32}P$, and sulphur, such as $^{35}S$.

Certain isotopically-labelled compounds, for example, those incorporating a radioactive isotope, are useful in drug and/or substrate tissue distribution studies. The radioactive isotopes tritium, i.e. $^{3}H$, and carbon-14, i.e. $^{14}C$, are particularly useful for this purpose in view of their ease of incorporation and ready means of detection.

Substitution with heavier isotopes such as deuterium, i.e. $^{2}H$, may afford certain therapeutic advantages resulting from greater metabolic stability, for example, increased in vivo half-life or reduced dosage requirements, and hence may be preferred in some circumstances.

Before purification, the compounds of the present invention may exist as a mixture of enantiomers depending on the synthetic procedure used. The enantiomers can be separated by conventional techniques known in the art. Thus the invention covers individual enantiomers as well as mixtures thereof.

For some of the steps of the process of preparation of the compounds of the invention, it may be necessary to protect potential reactive functions that are not wished to react, and to cleave said protecting groups in consequence. In such a case, any compatible protecting radical can be used. In particular methods of protection and deprotection such as those described by T. W. GREENE (Protective Groups in Organic Synthesis, A. Wiley-Interscience Publication, 1981) or by P. J. Kocienski (Protecting groups, Georg Thieme Verlag, 1994), can be used. All of the above reactions and the preparations of novel starting materials used in the preceding methods are conventional and appropriate reagents and reaction conditions for their performance or preparation as well as procedures for isolating the desired products will be well-known to those skilled in the art with reference to literature precedents and the examples and preparations hereto.

Also, the compounds of the present invention as well as intermediates for the preparation thereof can be purified according to various well-known methods, such as for example crystallization or chromatography.

One or more compounds of the invention may be combined with one or more pharmaceutical agents, for example anti-inflammatory agents, anti-fibrotic agents, chemotherapeutics, anti cancer agents, immunosuppressants, anti-tumour vaccines, cytokine therapy, or tyrosine kinase inhibitors, for the treatment of conditions modulated by the inhibition of ROCK, for example fibrotic diseases, autoimmune, inflammatory-fibrotic conditions, inflammatory conditions, central nervous system disorders, or cancer.

The method of treatment or the compound for use in the treatment of renal conditions, liver conditions, inflammatory conditions, cardiovascular conditions, acute and chronic organ transplant rejection, fibrotic diseases and cancer as defined hereinbefore may be applied as a sole therapy or be a combination therapy with an additional active agent.

The method of treatment or the compound for use in the treatment of renal conditions, liver conditions, inflammatory conditions, cardiovascular conditions, acute and chronic organ transplant rejection, fibrotic diseases and cancer. The additional active agents may be one or more active agents used to treat the condition being treated by the compound of the invention and additional active agent. The additional active agents may include one or more of the following active agents:—

(i) steroids such as corticosteroids, including glucocorticoids and mineralocorticoids, for example aclometasone, aclometasone dipropionate, aldosterone, amcinonide, beclomethasone, beclomethasone dipropionate, betamethasone, betamethasone dipropionate, betamethasone sodium phosphate, betamethasone valerate, budesonide, clobetasone, clobetasone butyrate, clobetasol propionate, cloprednol, cortisone, cortisone acetate, cortivazol, deoxycortone, desonide, desoximetasone, dexamethasone, dexamethasone sodium phosphate, dexamethasone isonicotinate, difluorocortolone, fluclorolone, flumethasone, flunisolide, fluocinolone, fluocinolone acetonide, fluocinonide, fluocortin butyl, fluorocortisone, fluorocortolone, fluocortolone caproate, fluocortolone pivalate, fluorometholone, fluprednidene, fluprednidene acetate, flurandrenolone, fluticasone, fluticasone propionate, halcinonide, hydrocortisone, hydrocortisone acetate, hydrocortisone butyrate, hydrocortisone aceponate, hydrocortisone buteprate, hydrocortisone valerate, icomethasone, icomethasone enbutate, meprednisone, methylprednisolone, mometasone paramethasone, mometasone furoate monohydrate, prednicarbate, prednisolone, prednisone, tixocortol, tixocortol pivalate, triamcinolone, triamcinolone acetonide, triamcinolone alcohol and their respective pharmaceutically acceptable derivatives. A combination of steroids may be used, for example a combination of two or more steroids mentioned in this paragraph;

(ii) TNF inhibitors for example etanercept; monoclonal antibodies (e.g. infliximab (Remicade), adalimumab (Humira), certolizumab pegol (Cimzia), golimumab (Simponi)); fusion proteins (e.g. etanercept (Enbrel)); and 5-$HT_{2A}$ agonists (e.g. 2,5-dimethoxy-4-iodoamphetamine, TCB-2, lysergic acid diethylamide (LSD), lysergic acid dimethylazetidide);

(iii) anti-inflammatory drugs, for example non-steroidal anti-inflammatory drugs;

(iv) dihydrofolate reductase inhibitors/antifolates, for example methotrexate, trimethoprim, brodimoprim, tetroxoprim, iclaprim, pemetrexed, ralitrexed and pralatrexate; and (v) immunosuppressants for example cyclosporins, tacrolimus, sirolimus pimecrolimus, angiotensin II inhibitors (e.g. Valsartan, Telmisartan, Losartan, Irbesatan, Azilsartan, Olmesartan, Candesartan, Eprosartan) and ACE inhibitors e.g. sulfhydryl-containing agents (e.g. Captopril, Zofenopril), dicarboxylate-containing agents (e.g. Enalapril, Ramipril, Quinapril, Perindopril, Lisinopril, Benazepril, Imidapril, Zofenopril, Trandolapril), phosphate-containing agents (e.g. Fosinopril), casokinins, lactokinins and lactotripeptides.

(vi) Anti-fibrotic agents for example: Pirfenidone, Nintedanib, Anti-IL-13 monoclonal antibodies (e.g. Tralokinumab, QAX576, Lebrikizumab), simtuzumab, FG-3019, lysophosphatidic acid receptor antagonists (e.g. BMS-986020, AM966), LOXL2 inhibitors, BET bromodomain inhibitors (e.g. JQ1), HDAC inhibitors (e.g. Vorinostat), thrombin inhibitors (e.g. Dabigatran), FactorXa inhibitors (e.g. Apixban, Rivaroxaban) 15PGDH inhibitors, anti-avβ6 monoclonal antibodies (e.g. BG00011), Anti-CTGF monoclonal antibodies (e.g. FG-3019), PAR1 inhibitors, Nox4 inhibitors and PAI-1 inhibitors.

The method of treatment or the compound for use in the treatment of cancer may involve, in addition to the compound of the invention, conventional surgery or radiotherapy or chemotherapy. Such chemotherapy may include one or more of the following categories of anti-tumor agents:

(i) antiproliferative/antineoplastic drugs and combinations thereof, such as alkylating agents (for example cis-platin, oxaliplatin, carboplatin, cyclophosphamide, nitrogen mustard, uracil mustard, bendamustin, melphalan, chlorambucil, chlormethine, busulphan, temozolamide, nitrosoureas, ifosamide, melphalan, pipobroman, triethylene-melamine, triethylenethiophoporamine, carmustine, lomustine, stroptozocin and dacarbazine); antimetabolites (for example gemcitabine and antifolates such as fluoropyrimidines like 5-fluorouracil and tegafur, raltitrexed, methotrexate, pemetrexed, cytosine arabinoside, floxuridine, cytarabine, 6-mercaptopurine, 6-thioguanine, fludarabine phosphate, pentostatine, and gemcitabine and hydroxyurea); antibiotics (for example anthracyclines like adriamycin, bleomycin, doxorubicin, daunomycin, epirubicin, idarubicin, mitomycin-C, dactinomycin and mithramycin); antimitotic agents (for example *vinca* alkaloids like vincristine, vinblastine, vindesine and vinorelbine and taxoids like taxol and taxotere and polokinase inhibitors); proteasome inhibitors, for example carfilzomib and bortezomib; interferon therapy; and topoisomerase inhibitors (for example epipodophyllotoxins like etoposide and teniposide, amsacrine, topotecan, mitoxantrone and camptothecin); bleomcin, dactinomycin, daunorubicin, doxorubicin, epirubicin, idarubicin, ara-C, paclitaxel (Taxol™), nabpaclitaxel, docetaxel, mithramycin, deoxyco-formycin, mitomycin-C, L-asparaginase, interferons (especially IFN-α), etoposide, and teniposide;

(ii) cytostatic agents such as antiestrogens (for example tamoxifen, fulvestrant, toremifene, raloxifene, droloxifene and iodoxyfene), antiandrogens (for example bicalutamide, flutamide, nilutamide and cyproterone acetate), LHRH antagonists or LHRH agonists (for example goserelin, leuprorelin and buserelin), progestogens (for example megestrol acetate), aromatase inhibitors (for example as anastrozole, letrozole, vorazole and exemestane) and inhibitors of 5α-reductase such as finasteride; and navelbene, CPT-II, anastrazole, letrazole, capecitabine, reloxafme, cyclophosphamide, ifosamide, and droloxafine;

(iii) anti-invasion agents, for example dasatinib and bosutinib (SKI-606), and metalloproteinase inhibitors, inhibitors of urokinase plasminogen activator receptor function or antibodies to Heparanase;

(iv) inhibitors of growth factor function: for example such inhibitors include growth factor antibodies and growth factor receptor antibodies, for example the anti-erbB2 antibody trastuzumab [Herceptin™], the anti-EGFR antibody panitumumab, the anti-erbB1 antibody cetuximab, tyrosine kinase inhibitors, for example inhibitors of the epidermal growth factor family (for example EGFR family tyrosine kinase inhibitors such as gefitinib, erlotinib, 6-acrylamido-N-(3-chloro-4-fluorophenyl)-7-(3-morpholinopropoxy)-quinazolin-4-amine (CI 1033), erbB2 tyrosine kinase inhibitors such as lapatinib) and antibodies to costimulatory molecules such as CTLA-4, 4-IBB and PD-I, or antibodies to cytokines (IL-10, TGF-beta); inhibitors of the hepatocyte growth factor family; inhibitors of the insulin growth factor family; modulators of protein regulators of cell apoptosis (for example Bcl-2 inhibitors); inhibitors of the platelet-derived growth factor family such as imatinib and/or nilotinib (AMN107); inhibitors of serine/threonine kinases (for example Ras/Raf signalling inhibitors such as farnesyl transferase inhibitors, for example sorafenib, tipifarnib and lonafarnib), inhibitors of cell signalling through MEK and/or AKT kinases, c-kit inhibitors, abl kinase inhibitors, PI3 kinase inhibitors, Plt3 kinase inhibitors, CSF-1R kinase inhibitors, IGF receptor, kinase inhibitors; aurora kinase inhibitors and cyclin dependent kinase inhibitors such as CDK2 and/or CDK4 inhibitors; and CCR2, CCR4 or CCR6 modulator;

(v) antiangiogenic agents such as those which inhibit the effects of vascular endothelial growth factor, for example the anti-vascular endothelial cell growth factor antibody bevacizumab (Avastin™); thalidomide; lenalidomide; and for example, a VEGF receptor tyrosine kinase inhibitor such as vandetanib, vatalanib, sunitinib, axitinib and pazopanib;

(vi) gene therapy approaches, including for example approaches to replace aberrant genes such as aberrant p53 or aberrant BRCA1 or BRCA2;

(vii) immunotherapy approaches, including for example antibody therapy such as alemtuzumab, rituximab, ibritumomab tiuxetan (Zevalin®) and ofatumumab; interferons such as interferon α; interleukins such as IL-2 (aldesleukin); interleukin inhibitors for example IRAK4 inhibitors; cancer vaccines including prophylactic and treatment vaccines such as HPV vaccines, for example Gardasil, Cervarix, Oncophage and Sipuleucel-T (Provenge); gp100; dendritic cell-based vaccines (such as Ad.p53 DC); and toll-like receptor modulators for example TLR-7 or TLR-9 agonists; and (viii) cytotoxic agents for example fludaribine (fludara), cladribine, pentostatin (Nipent™);

(ix) steroids such as corticosteroids, including glucocorticoids and mineralocorticoids, for example aclometasone, aclometasone dipropionate, aldosterone, amcinonide, beclomethasone, beclomethasone dipropionate, betamethasone, betamethasone dipropionate, betamethasone sodium phosphate, betamethasone valerate, budesonide, clobetasone, clobetasone butyrate, clobetasol propionate, cloprednol, cortisone, cortisone acetate, cortivazol, deoxycortone, desonide, desoximetasone, dexamethasone, dexamethasone sodium phosphate, dexamethasone isonicotinate, difluorocortolone, fluclorolone, flumethasone, flunisolide, fluocinolone, fluocinolone acetonide, fluocinonide, fluocortin butyl, fluorocortisone, fluorocortolone, fluocortolone caproate, fluocortolone pivalate, fluorometholone, fluprednidene, fluprednidene acetate, flurandrenolone, fluticasone, fluticasone propionate, halcinonide, hydrocortisone, hydrocortisone acetate, hydrocortisone butyrate, hydrocortisone aceponate, hydrocortisone buteprate, hydrocortisone valerate, icomethasone, icomethasone enbutate, meprednisone, methylprednisolone, mometasone paramethasone, mometasone furoate monohydrate, prednicarbate, prednisolone, prednisone, tixocortol, tixocortol pivalate, triamcinolone, triamcinolone acetonide, triamcinolone alcohol and their respective pharmaceutically acceptable derivatives. A combination of steroids may be used, for example a combination of two or more steroids mentioned in this paragraph;

(x) targeted therapies, for example PI3Kd inhibitors, for example idelalisib and perifosine; PD-1, PD-L1, PD-L2 and CTL4-A modulators, antibodies and vaccines; other IDO inhibitors (such as indoximod); anti-PD-1 monoclonal antibodies (such as MK-3475 and nivolumab); anti-PD-L1 monoclonal antibodies (such as MEDI-4736 and RG-7446); anti-PD-L2 monoclonal antibodies; and anti-CTLA-4 antibodies (such as ipilimumab);

(xii) chimeric antigen receptors, anticancer vaccines and arginase inhibitors.

Such combination treatment may be achieved by way of the simultaneous, sequential or separate dosing of the individual components of the treatment. Such combination products employ the compounds of this invention within a therapeutically effective dosage range described hereinbefore and the other pharmaceutically-active agent within its approved dosage range.

Compounds of the invention may exist in a single crystal form or in a mixture of crystal forms or they may be amorphous. Thus, compounds of the invention intended for pharmaceutical use may be administered as crystalline or amorphous products. They may be obtained, for example, as solid plugs, powders, or films by methods such as precipitation, crystallization, freeze drying, or spray drying, or evaporative drying. Microwave or radio frequency drying may be used for this purpose.

For the above-mentioned compounds of the invention the dosage administered will, of course, vary with the compound employed, the mode of administration, the treatment desired and the disorder indicated. For example, if the compound of the invention is administered orally, then the daily dosage of the compound of the invention may be in the range from 0.01 micrograms per kilogram body weight (μg/kg) to 100 milligrams per kilogram body weight (mg/kg).

A compound of the invention, or pharmaceutically acceptable salt thereof, may be used on their own but will generally be administered in the form of a pharmaceutical composition in which the compounds of the invention, or pharmaceutically acceptable salt thereof, is in association with a pharmaceutically acceptable adjuvant, diluent or carrier. Conventional procedures for the selection and preparation of suitable pharmaceutical formulations are described in, for example, "Pharmaceuticals—The Science of Dosage Form Designs", M. E. Aulton, Churchill Livingstone, 1988.

Depending on the mode of administration of the compounds of the invention, the pharmaceutical composition which is used to administer the compounds of the invention will preferably comprise from 0.05 to 99% w (percent by weight) compounds of the invention, more preferably from 0.05 to 80% w compounds of the invention, still more preferably from 0.10 to 70% w compounds of the invention, and even more preferably from 0.10 to 50% w compounds of the invention, all percentages by weight being based on total composition.

The pharmaceutical compositions may be administered topically (e.g. to the skin) in the form, e.g., of creams, gels, lotions, solutions, suspensions, or systemically, e.g. by oral administration in the form of tablets, capsules, syrups, powders or granules; or by parenteral administration in the form of a sterile solution, suspension or emulsion for injection (including intravenous, subcutaneous, intramuscular, intravascular or infusion); by rectal administration in the form of suppositories; or by inhalation in the form of an aerosol.

For oral administration the compounds of the invention may be admixed with an adjuvant or a carrier, for example, lactose, saccharose, sorbitol, mannitol; a starch, for example, potato starch, corn starch or amylopectin; a cellulose derivative; a binder, for example, gelatine or polyvinylpyrrolidone; and/or a lubricant, for example, magnesium stearate, calcium stearate, polyethylene glycol, a wax, paraffin, and the like, and then compressed into tablets. If coated tablets are required, the cores, prepared as described above, may be coated with a concentrated sugar solution which may contain, for example, gum arabic, gelatine, talcum and titanium dioxide. Alternatively, the tablet may be coated with a suitable polymer dissolved in a readily volatile organic solvent.

For the preparation of soft gelatine capsules, the compounds of the invention may be admixed with, for example, a vegetable oil or polyethylene glycol. Hard gelatine capsules may contain granules of the compound using either the above-mentioned excipients for tablets. Also liquid or semisolid formulations of the compound of the invention may be filled into hard gelatine capsules. Liquid preparations for oral application may be in the form of syrups or suspensions, for example, solutions containing the compound of the invention, the balance being sugar and a mixture of ethanol, water, glycerol and propylene glycol. Optionally such liquid preparations may contain colouring agents, flavouring agents, sweetening agents (such as saccharine), preservative agents and/or carboxymethylcellulose as a thickening agent or other excipients known to those skilled in art.

For intravenous (parenteral) administration the compounds of the invention may be administered as a sterile aqueous or oily solution.

The size of the dose for therapeutic purposes of compounds of the invention will naturally vary according to the nature and severity of the conditions, the age and sex of the animal or patient and the route of administration, according to well-known principles of medicine.

Dosage levels, dose frequency, and treatment durations of compounds of the invention are expected to differ depending on the formulation and clinical indication, age, and comorbid medical conditions of the patient.

Throughout the description and claims of this specification, the words "comprise" and "contain" and variations of them mean "including but not limited to", and they are not intended to (and do not) exclude other moieties, additives, components, integers or steps. Throughout the description and claims of this specification, the singular encompasses the plural unless the context otherwise requires. In particular, where the indefinite article is used, the specification is to be understood as contemplating plurality as well as singularity, unless the context requires otherwise.

Features, integers, characteristics, compounds, chemical moieties or groups described in conjunction with a particular aspect, embodiment or example of the invention are to be understood to be applicable to any other aspect, embodiment or example described herein unless incompatible therewith. All of the features disclosed in this specification (including any accompanying claims, abstract and drawings), and/or all of the steps of any method or process so disclosed, may be combined in any combination, except combinations where at least some of such features and/or steps are mutually exclusive. The invention is not restricted to the details of any foregoing embodiments. The invention extends to any novel one, or any novel combination, of the features disclosed in this specification (including any accompanying claims, abstract and drawings), or to any novel one, or any novel combination, of the steps of any method or process so disclosed.

The reader's attention is directed to all papers and documents which are filed concurrently with or previous to this specification in connection with this application and which are open to public inspection with this specification, and the contents of all such papers and documents are incorporated herein by reference.

The compounds of the invention may be prepared according to or analogously to the General Schemes 1-11 and Examples 1 to 104.

EXAMPLES AND SYNTHESIS

Experimental Procedures

Solvents, reagents and starting materials were purchased from commercial vendors and used as received unless otherwise described. All reactions were performed at room temperature unless otherwise stated. Compound identity and purity confirmations were performed by LCMS UV using a Waters Acquity SQ Detector 2 (ACQ-SQD2 #LCA081). The diode array detector wavelength was set to acquire spectra at a wavelength of 254 nM and the MS was in positive and negative electrospray mode (m/z: 150-800). A 2 μL aliquot was injected onto a guard column (0.2 μm×2 mm filters) and UPLC column (C18, 50×2.1 mm, <2 μm) in sequence maintained at 40° C. The samples were eluted at a flow rate of 0.6 mL/min with a mobile phase system composed of A (0.1% (v/v) Formic Acid in Water) and B (0.1% (v/v) Formic Acid in Acetonitrile) according to the gradients outlined in Table 1 below (Methods 1 and 2). Retention times RT are reported in minutes. The following methods were also used on occasions when described throughout the experimental section, gradients are detailed in table 1. Method 3 utilised a Shimadzu 2020 series spectrometer equipped with a binary pump and diode array detector (acquisition wavelength 214 and 254 nm) and the MS was in positive and negative electrospray mode (m/z: 100-900). 2 μL Aliquot were injected onto an Agilent Poroshell 120 EC-C18 column (2.7 μm, 4.6×50 mm) maintained at 35° C. and eluted at 1.0 ml/min using mobile phase consisting of: A: 0.05% Formic acid in water (v/v), B: 0.05% Formic acid in ACN(v/v). Method 4 utilised a Agilent Technologies 1290 series spectrometer equipped with a binary pump and diode array detector (acquisition wavelength 214 and 254 nm) and the MS was in positive electrospray mode (m/z: 70-1000). 2 μL Aliquots were injected onto an Agilent Eclipse Plus RRHD C18, (1.8 μm, 3.0×50 mm) column maintained at 40° C. and eluted at 0.8 ml/min using mobile phase consisting of: A: 0.05% Formic acid in water (v/v), B: 0.05% Formic acid in ACN(v/v).

TABLE 1

| Time (min) | % A | % B |
|---|---|---|
| Method 1 (Long acidic) | | |
| 0 | 95 | 5 |
| 1.1 | 95 | 5 |
| 6.1 | 5 | 95 |
| 7 | 5 | 95 |
| 7.5 | 95 | 5 |
| 8 | 95 | 5 |
| Method 2 (Short acidic) | | |
| 0 | 95 | 5 |
| 0.3 | 95 | 5 |
| 2 | 5 | 95 |
| 2.6 | 95 | 5 |
| 3 | 95 | 5 |
| Method 3 | | |
| 0.01 | 85 | 15 |
| 1.0 | 85 | 15 |
| 4.0 | 0 | 100 |
| 4.5 | 0 | 100 |
| 4.51 | 85 | 15 |
| 5.0 | 85 | 15 |
| Method 4 | | |
| 0.00 | 80 | 20 |
| 2.65 | 20 | 80 |
| 3.00 | 20 | 80 |

NMR was also used to characterise final compounds. NMR spectra were obtained on a Bruker AVIII 400 Nanobay with 5 mm BBFO probe. Optionally, compound Rf values on silica thin layer chromatography (TLC) plates were measured.

Compound purification was performed by flash column chromatography on silica or by preparative LCMS. LCMS purification was performed using a Waters 3100 Mass detector in positive and negative electrospray mode (m/z: 150-800) with a Waters 2489 LUV/Vis detector. Samples were eluted at a flow rate of 20 mL/min on a XBridge™ prep C18 5 μM OBD 19×100 mm column with a mobile phase system composed of A (0.1% (v/v) Formic Acid in Water) and B (0.1% (v/v) Formic Acid in Acetonitrile) according to the gradient outlined in Table 2 below.

TABLE 2

| Time (min) | % A | % B |
|---|---|---|
| 0 | 90 | 10 |
| 1.5 | 90 | 10 |
| 11.7 | 5 | 95 |
| 13.7 | 5 | 95 |
| 14 | 90 | 90 |
| 15 | 90 | 90 |

Synthesis of Intermediates

Scheme 1 below describes the synthesis of several intermediates that are common to certain examples and indicates a synthetic approach that could be adopted to prepare other examples by selecting an appropriately functionalised building block in place of one or more of those in Scheme 1, as detailed in the description of the preparation of individual examples.

Scheme 1

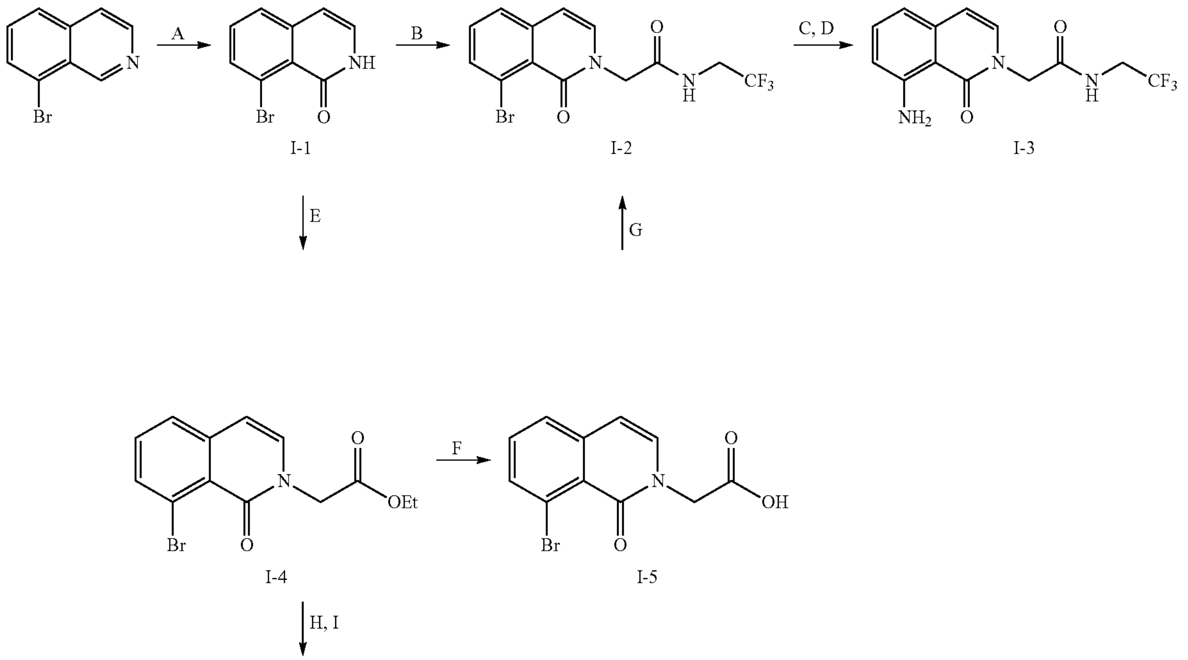

I-1 I-2 I-3 I-4 I-5

-continued

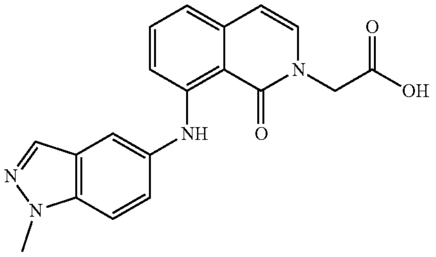

I-6

STEP A. Synthesis of Intermediate I-1, 8-Bromo-2H-isoquinolin-1-one

To a solution of 8-Bromoisoquinoline (5.0 g, 24 mmol) in dichloromethane (60 mL) at 0° C. was added m-CPBA (8.1 g, 36 mmol) in portions over 5 min. The mixture was warmed to rt and stirred for 4 h. The reaction was quenched by addition of saturated aqueous $Na_2S_2O_3$, and the layers were separated. The organic layer was washed with saturated aqueous $NaHCO_3$ and the combined aqueous layers were extracted three times with dichloromethane. The combined organic layers were dried over $Na_2SO_4$ and concentrated under reduced pressure to give the crude N-oxide intermediate as a yellow solid.

The N-oxide was dissolved in acetic anhydride (45.6 mL, 483 mmol), heated to 140° C. and stirred for 3 h. The mixture was cooled to rt and concentrated under reduced pressure to give a brown oil, which was dissolved in methanol (20 mL). Saturated aqueous $NaHCO_3$ (20 mL, 365 mmol) was added, and the mixture was stirred at rt overnight, concentrated under reduced pressure, then cooled to 0° C. 2M HCl was added dropwise until pH 3, then the stirring was stopped, and the mixture was left to sit for 30 min. The resulting brown solid was collected by filtration, dissolved in methanol, and concentrated under reduced pressure to give 8-bromo-2H-isoquinolin-1-one (Intermediate I-1, 5.4 g, 24 mmol, 99% yield) as a brown solid.

UPLC-MS ($ES^+$, Method 2): 1.34 min, m/z 223.9/225.8 $[M+H]^+$.

$^1H$ NMR (400 MHz, DMSO-$d_6$) δ 11.28 (s, 1H), 7.69 (d, J=7.7 Hz, 1H), 7.64 (d, J=7.9 Hz, 1H), 7.49 (t, J=7.8 Hz, 1H), 7.19 (t, J=6.5 Hz, 1H), 6.54 (d, J=7.0 Hz, 1H).

STEP B. Synthesis of Intermediate I-2, 2-(8-bromo-1-oxo-2-isoquinolyl)-N-(2,2,2-trifluoroethyl) acetamide To a solution of 8-bromo-2H-isoquinolin-1-one (Intermediate I-1, 2.8 g, 13 mmol) in dichloromethane (25 mL) were added $Cs_2CO_3$ (10.2 g, 31 mmol) and 2-chloro-N-(2,2,2-trifluoroethyl)acetamide (2.4 g, 14 mmol), and the mixture was stirred at rt overnight. EtOAc was added and the mixture was washed with Brine, dried over $Na_2SO_4$ and concentrated under reduced pressure. The crude product was purified by normal phase chromatography (25 g column, 0 to 5% methanol in dichloromethane) to give 2-(8-bromo-1-oxo-2-isoquinolyl)-N-(2,2,2-trifluoroethyl)acetamide (Intermediate I-2, 1.1 g, 3 mmol, 24% yield) as an orange solid.

UPLC-MS ($ES^+$, Method 2): 1.60 min, m/z 363.0/364.9 $[M+H]^+$.

$^1H$ NMR (400 MHz, DMSO-$d_6$) δ 8.91 (t, J=6.5 Hz, 1H), 7.74 (dd, J=1.3, 7.8 Hz, 1H), 7.67 (dd, J=1.1, 8.0 Hz, 1H), 7.53 (t, J=7.8 Hz, 1H), 7.49 (d, J=7.3 Hz, 1H), 6.63 (d, J=7.4 Hz, 1H), 4.64 (s, 2H), 3.97 (q, J=5.5 Hz, 2H).

STEPS C, D. Synthesis of Intermediate I-3, 2-(8-amino-1-oxo-2-isoquinolyl)-N-(2,2,2-trifluoroethyl) acetamide STEP C. A solution of 2-(8-bromo-1-oxo-2-isoquinolyl)-N-(2,2,2-trifluoroethyl) acetamide (Intermediate I-2, 1.4 g, 3.9 mmol), tert-butylcarbamate (677 mg, 5.8 mmol) and $Cs_2CO_3$ (2.5 g, 7.7 mmol) in 1,4-Dioxane (30 mL) was degassed with $N_2$ for 10 min. Tris (dibenzylideneacetone) dipalladium (0) (177 mg, 0.19 mmol) and 4,5-bis(diphenylphosphino)-9,9-dimethylxanthene (223 mg, 0.39 mmol) were added, the vial was sealed, the mixture was heated at 100° C. and stirred overnight. The mixture was filtered through a Celite pad, washing with MeOH, and concentrated under reduced pressure. The crude product was purified by normal phase chromatography (25 g column, 55-70% EtOAc in petrol) to give the carbamate intermediate tert-butyl N-[1-oxo-2-[2-oxo-2-(2,2,2-trifluoroethylamino) ethyl]-8-isoquinolyl]carbamate (1.5 g, 3.6 mmol, 94% yield) as a yellow solid.

UPLC-MS ($ES^+$, Method 2): 1.86 min, m/z 400.1 $[M+H]^+$.

$^1H$ NMR (400 MHz, DMSO-$d_6$) δ 12.08 (s, 1H), 8.93 (t, J=6.4 Hz, 1H), 8.28 (d, J=7.3 Hz, 1H), 7.65 (t, J=8.1 Hz, 1H), 7.46 (d, J=7.3 Hz, 1H), 7.25 (d, J=7.0 Hz, 1H), 6.68 (d, J=7.4 Hz, 1H), 4.69 (s, 2H), 4.01-3.96 (m, 2H), 1.49 (s, 9H).

STEP D. To a solution of tert-butyl N-[1-oxo-2-[2-oxo-2-(2,2,2-trifluoroethylamino)ethyl]-8-isoquinolyl]carbamate (1.6 g, 4 mmol) in acetonitrile (20 mL) and dichloromethane (10 mL) was added HCl (4 M in dioxane, 4 mL, 16 mmol) dropwise, the mixture was stirred at rt overnight. The mixture was concentrated under reduced pressure and the crude product was purified by SCX cartridge (10 g, washing with methanol then 7 M ammonia in methanol). The basic fraction was concentrated under reduced pressure to afford 2-(8-amino-1-oxo-2-isoquinolyl)-N-(2,2,2-trifluoroethyl)acetamide (Intermediate I-3, 580 mg, 2 mmol, 48% yield) as a brown solid.

UPLC-MS ($ES^+$, Short acidic): 1.36 min, m/z 300.2 $[M+H]^+$.

$^1H$ NMR (400 MHz, DMSO-$d_6$) δ 8.84 (t, J=6.3 Hz, 1H), 7.30-7.19 (m, 4H), 6.60-6.56 (m, 2H), 6.36 (d, J=7.7 Hz, 1H), 4.56 (s, 2H), 3.96 (dq, J=6.3, 9.8 Hz, 2H).

STEP E. Synthesis of Intermediate I-4, ethyl 2-(8-bromo-1-oxo-2-isoquinolyl)acetate To a solution of 8-bromo-2H-isoquinolin-1-one (Intermediate I-1, 2.5 g, 11 mmol) in dichloromethane (25 mL) were added ethyl bromoacetate (2.5 mL, 22 mmol) and $Cs_2CO_3$ (9.1 g, 28 mmol), and the mixture was stirred at rt overnight. Water was added, the layers were separated, the aqueous layer was extracted three times with dichloromethane. The combined organic layers were washed with Brine, dried over $Na_2SO_4$, and concentrated under reduced pressure. The crude product was purified by normal phase chromatography (25 g column, 0 to 5% methanol in dichloromethane) to give ethyl 2-(8-bromo-1-oxo-2-isoquinolyl)acetate (Intermediate I-4, 2.6 g, 8.4 mmol, 76% yield) as an orange solid.

UPLC-MS ($ES^+$, Short acidic): 1.66 min, m/z 310.0/311.9 $[M+H]^+$.

$^1H$ NMR (400 MHz, DMSO-$d_6$) δ 7.76 (dd, J=1.2, 7.7 Hz, 1H), 7.68 (dd, J=1.1, 8.0 Hz, 1H), 7.57-7.52 (m, 2H), 6.67 (d, J=7.4 Hz, 1H), 4.72 (s, 2H), 4.13 (q, J=7.1 Hz, 2H), 1.20 (t, J=7.1 Hz, 3H).

STEP F. Synthesis of Intermediate I-5, 2-(8-bromo-1-oxo-2-isoquinolyl)acetic acid Ethyl 2-(8-bromo-1-oxo-2-isoquinolyl)acetate (Intermediate I-4, 5.5 g, 16 mmol) was suspended in THE (30 mL) and methanol (20 mL) and a solution of lithium hydroxide (561 mg, 23 mmol) in water (10 mL) was added. The mixture was stirred at rt for 2 h, then concentrated under reduced pressure. The aqueous solution was acidified to pH 4 using 2M HCl. The resulting precipitate was collected by filtration, dissolved in MeOH and concentrated under reduced pressure, to give 2-(8-bromo-1-oxo-2-isoquinolyl) acetic acid (Intermediate I-5, 4.0 g, 14 mmol, 91% yield) as a pale brown solid.

UPLC-MS ($ES^+$, Short acidic): 1.34 min, m/z 283.9 $[M+H]^+$.

$^1H$ NMR (400 MHz, DMSO-$d_6$) δ 13.01 (s, 1H), 7.75 (dd, J=1.2, 7.7 Hz, 1H), 7.67 (dd, J=1.1, 7.9 Hz, 1H), 7.56-7.51 (m, 2H), 6.64 (d, J=7.4 Hz, 1H), 4.63 (s, 2H).

STEP G. Synthesis of Intermediate I-2, 2-(8-bromo-1-oxo-2-isoquinolyl)-N-(2,2,2-trifluoroethyl) acetamide To a solution of 2-(8-bromo-1-oxo-2-isoquinolyl)acetic acid (Intermediate I-5, 770 mg, 2.7 mmol), N,N-diisopropylethylamine (0.95 mL, 5.5 mmol) and trifluoroethylamine (0.33 mL, 4.1 mmol) in dichloromethane (25 mL) and DMF (5 mL) was added HATU (1.56 g, 4.1 mmol) and the mixture was stirred at rt overnight. The mixture was diluted into DCM and water. The aqueous layer was extracted three times with dichloromethane. The combined organic layers were washed with Brine, dried over $Na_2SO_4$ and concentrated under reduced pressure. The crude product was purified by normal phase chromatography (40 g column, 0 to 5% methanol in dichloromethane) to give 2-(8-bromo-1-oxo-2-isoquinolyl)-N-(2,2,2-trifluoroethyl)acetamide (Intermediate I-2, 503 mg, 1.4 mmol, 51% yield) as an off-white solid. See Step B for characterisation.

STEPs H, I. Synthesis of Intermediate I-6, 2-[8-[(1-methylindazol-5-yl)amino]-1-oxo-2-isoquinolyl] acetic acid Step H. Ethyl 2-(8-bromo-1-oxo-2-isoquinolyl)acetate (Intermediate I-4, 940 mg, 2.4 mmol) was suspended in toluene (12 mL). 1-Methyl-1h-indazol-5-amine (480 mg, 3.3 mmol) and $Cs_2CO_3$ (1.5 g, 4.5 mmol) were added and the mixture was degassed with N2 for 5 min before adding 4,5-bis (diphenylphosphino)-9,9-dimethylxanthene (167 mg, 0.3 mmol) and tris(dibenzylideneacetone) dipalladium (0) (138 mg, 0.15 mmol), sealing the reaction vial and heating to 110° C. overnight. The mixture was cooled and partitioned between dichloromethane and water. The aqueous phase was extracted three times with dichloromethane and the combined organic layers were washed with brine, dried over $Na_2SO_4$ and concentrated under reduced pressure. The crude product was purified by normal phase chromatography (25 g column, eluting with 20-90% EtOAc in petrol) to give intermediate ethyl ester ethyl 2-[8-[(1-methylindazol-5-yl)amino]-1-oxo-2-isoquinolyl]acetate (663 mg, 1.8 mmol, 73% yield) as a brown solid.

UPLC-MS ($ES^+$, Short acidic): 1.83 min. m/z 377.3 $[M+H]^+$.

$^1H$ NMR (400 MHz, DMSO-$d_6$) δ 10.88 (s, 1H), 7.99 (d, J=0.9 Hz, 1H), 7.70-7.66 (m, 2H), 7.40 (t, J=7.9 Hz, 1H), 7.40 (d, J=7.3 Hz, 1H), 7.32 (dd, J=2.0, 8.9 Hz, 1H), 6.88 (d, J=8.6 Hz, 1H), 6.83 (d, J=7.3 Hz, 1H), 6.57 (d, J=7.4 Hz, 1H), 4.75 (s, 2H), 4.18 (q, J=7.1 Hz, 2H), 4.06 (s, 3H), 1.24 (t, J=7.1 Hz, 3H).

Step H. Ethyl 2-[8-[(1-methylindazol-5-yl)amino]-1-oxo-2-isoquinolyl]acetate (660 mg, 1.5 mmol) was dissolved in THE (5 mL) and methanol (4 mL), and a solution of lithium hydroxide (74 mg, 3.1 mmol) in water (3 mL) was added. The mixture was stirred at rt for 1.5 h, then it was concentrated under reduced pressure and acidified to pH 4 using 1 M HCl. The resulting precipitate was collected by filtration, washing with water, and dissolved in methanol. The product was concentrated under reduced pressure to give 2-[8-[(1-methylindazol-5-yl)amino]-1-oxo-2-isoquinolyl]acetic acid (Intermediate I-6, 482 mg, 1.4 mmol, 90% yield) as a yellow solid.

UPLC-MS ($ES^+$, Short acidic): 1.60 min, m/z 349.1 $[M+H]^+$.

$^1H$ NMR (400 MHz, DMSO-$d_6$) δ 11.00 (s, 1H), 7.99 (d, J=0.8 Hz, 1H), 7.69-7.65 (m, 2H), 7.41-7.35 (m, 2H), 7.32 (dd, J=2.1, 8.6 Hz, 1H), 6.88 (d, J=8.3 Hz, 1H), 6.82 (d, J=7.1 Hz, 1H), 6.53 (d, J=7.3 Hz, 1H), 4.61 (s, 2H), 4.06 (s, 3H) (OH peak not seen).

Table 2 describes intermediates which were synthesised in an analogous fashion to I-1, 8-Bromo-2H-isoquinolin-1-one, replacing 8-bromoisoquinoline with the appropriate building block.

TABLE 2

| Building block | Intermediate | UPLCMS ($ES^+$) | $^1H$ NMR (400 MHz, DMSO-$d_6$) |
|---|---|---|---|
| 5-bromo-8-nitroisoquinoline | 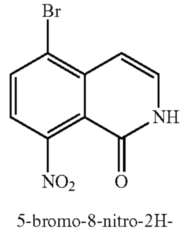<br>5-bromo-8-nitro-2H-isoquinolin-1-one<br>I-7 | Method 2: 1.46 min, m/z 268.9/270.8 $[M + H]^+$ | 12.02 (s, 1H), 8.22 (d, J = 8.2 Hz, 1H), 7.70 (d, J = 8.2 Hz, 1H), 7.56 (d, J = 8.1 Hz, 1H), 6.80 (d, J = 6.3 Hz, 1H). |

Table 3 describes intermediates which were synthesised in an analogous fashion to 1-2, 2-(8-bromo-1-oxo-2-isoquinolyl)-N-(2,2,2-trifluoroethyl) acetamide (via step G, scheme 1), replacing 2-trifluoroethylamine with the appropriate building block.

TABLE 3

| Building block | Intermediate | UPLCMS ($ES^+$) | $^1H$ NMR (400 MHz, DMSO-$d_6$) |
|---|---|---|---|
| 3-trifluoromethylaniline | 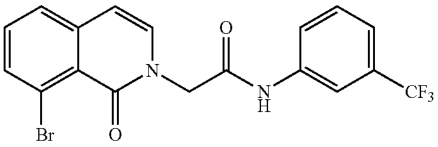 2-(8-bromo-1-oxo-2-isoquinolyl)-N-[3-(trifluoromethyl)phenyl]acetamide I-8 | Method 2: 1.83 min, m/z 425.0/427.0 $[M + H]^+$ | 10.74 (s, 1H), 8.12 (s, 1H), 7.79-7.74 (m, 2H), 7.69 (dd, J = 1.1, 8.1 Hz, 1H), 7.59 (t, J = 8.0 Hz, 1H), 7.57-7.53 (m, 2H), 7.43 (d, J = 7.8 Hz, 1H), 6.67 (d, J = 7.4 Hz, 1H), 4.79 (s, 2H). |
| (2S)-2-(trifluoromethyl)pyrrolidine | 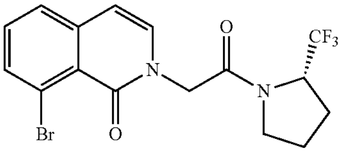 8-bromo-2-[2-oxo-2-[(2S)-2-(trifluoromethyl)pyrrolidin-1-yl]ethyl]isoquinolin-1-one I-14 | Method 3: 3.88 min, m/z 404.0 $[M + H]^+$ | |
| (1S)-2,2,2-trifluoro-1-methyl-ethylamine | 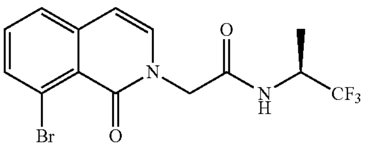 I-15 | Method 3: 3.68 min, m/z 397.0 $[M + H]^+$ | |

Intermediates in table 4 could be prepared from intermediates in table 3 using the method described in steps C and D of scheme 1

TABLE 4

| Building block | Structure/Name | UPLCMS ($ES^+$) | $^1H$ NMR (400 MHz, DMSO-$d_6$) |
|---|---|---|---|
| I-8, 2-(8-bromo-1-oxo-2-isoquinolyl)-N-[3-(trifluoromethyl)phenyl] acetamide | 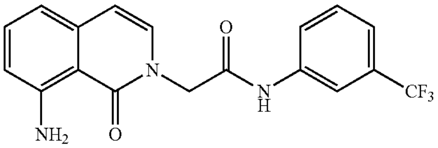 2-(8-bromo-1-oxo-2-isoquinolyl)-N-[3-(trifluoromethyl)phenyl]acetamide I-9 | Method 2: 1.75 min, m/z 362.4 $[M + H]^+$ | 10.69 (s, 1H), 8.12 (s, 1H), 7.77 (d, J = 7.7 Hz, 1H), 7.58 (t, J = 8.0 Hz, 1H), 7.42 (d, J = 7.7 Hz, 1H), 7.31-7.21 (m, 4H), 6.61 (dd, J = 0.9, 7.7 Hz, 1H), 6.58 (dd, J = 1.0, 8.1 Hz, 1H), 6.40 (d, J = 7.4 Hz, 1H), 4.72 (s, 2H). |
| I-14, 8-bromo-2-[2-oxo-2-[(2S)-2-(trifluoromethyl)pyrrolidin-1-yl]ethyl] isoquinolin-1-one | 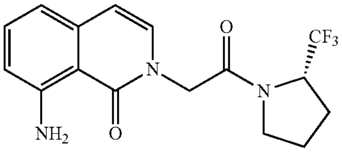 I-16 | Method 3: 4.25 min, m/z 346.00 $[M + H]^+$ | |

TABLE 4-continued

| Building block | Structure/Name | UPLCMS ($ES^+$) | $^1H$ NMR (400 MHz, DMSO-$d_6$) |
|---|---|---|---|
| I-15 | 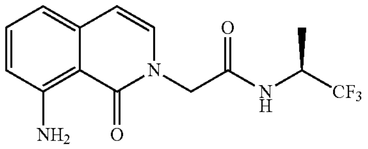 2-(8-amino-1-oxo-2-isoquinolyl)-N-[(1S)-2,2,2-trifluoro-1-methyl-ethyl]acetamide I-17 | Method 3: 3.48 min, m/z 314.2 $[M + H]^+$ | d 8.78 (d, J = 8.9 Hz, 1H), 7.31-7.18 (m, 4H), 6.62-6.56 (m, 2H), 6.36 (d, J = 7.7 Hz, 1H), 4.67-4.58 (m, 1H), 4.58-4.51 (m, 2H), 1.29 (d, J = 7.0 Hz, 3H). |

Table 5 describes intermediates that were prepared in an analogous fashion to 1-6 from 1-4 in scheme 1, replacing 1-methyl-1H-indazole-5-amine with the appropriate building block in step H.

TABLE 5

| Building block | Structure/Name | UPLCMS ($ES^+$) | $^1H$ NMR (400 MHz, DMSO-$d_6$) |
|---|---|---|---|
| 1-tetrahydropyran-2-ylpyrazolo[3,4-b]pyridine-5-amine | 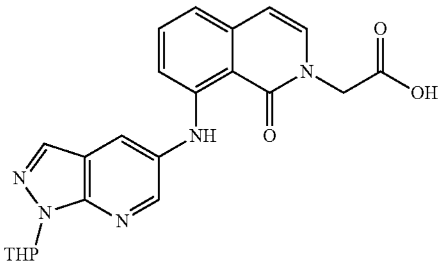 2-[1-oxo-8-[(1-tetrahydropyran-2-ylpyrazolo[3,4-b]pyridine-5-yl)amino]-2-isoquinolyl]acetic acid I-12 | Method 2: 1.71 min, | 13.04 (s, 1H), 11.01 (s, 1H), 8.53 (d, J = 2.4 Hz, 1H), 8.23 (d, J = 2.3 Hz, 1H), 8.18 (s, 1H), 7.44-7.38 (m, 2H), 6.89 (d, J = 7.4 Hz, 1H), 6.85 (d, J = 8.2 Hz, 1H), 6.58 (d, J = 7.4 Hz, 1H), 6.02 (dd, J = 2.3, 10.4 Hz, 1H), 4.67 (s, 2H), 3.95-3.93 (m, 1H), 3.71-3.70 (m, 1H), 2.08-2.05 (m, 1H), 1.97-1.96 (m, 1H), 1.82-1.77 (m, 1H), 1.63-1.58 (m, 3H). |
| 1-methyl-1H-pyrazolo[3,4-b]pyridine-5-amine | 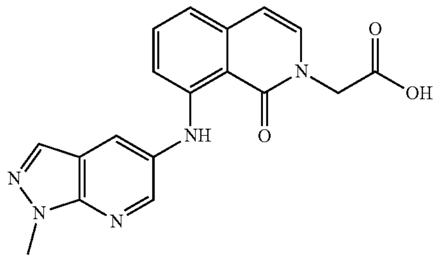 2-[8-[(1-methylpyrazolo[3,4-b]pyridine-5-yl)amino]-1-oxo-2-isoquinolyl]acetic acid I-13 | Method 2: 1.44 min, m/z 350.6 $[M + H]^+$ | 13.04 (s, 1H), 10.97 (s, 1H), 8.51 (d, J = 2.4 Hz, 1H), 8.20 (d, J = 2.3 Hz, 1H), 8.10 (s, 1H), 7.43-7.38 (m, 2H), 6.88 (d, J = 7.6 Hz, 1H), 6.81 (d, J = 7.8 Hz, 1H), 6.57 (d, J = 7.3 Hz, 1H), 4.67 (s, 2H), 4.08 (s, 3H). |

TABLE 5-continued

| Building block | Structure/Name | UPLCMS ($ES^+$) | $^1H$ NMR (400 MHz, $DMSO-d_6$) |
|---|---|---|---|
| N, 1-dimethylindazol-5-amine (MI1) | 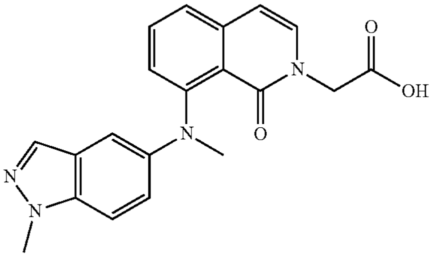 2-[8-[methyl-(1-methylindazol-5-yl)amino]-1-oxo-2-isoquinolyl]acetic acid I-18 | Method 3: 3.48 min, m/z 363.0 $[M + H]^+$ | |
| 3-methyl-1-(tetrahydro-2H-pyran-2-yl)-1H-indazol-6-amine (Requires THP deprotection) | 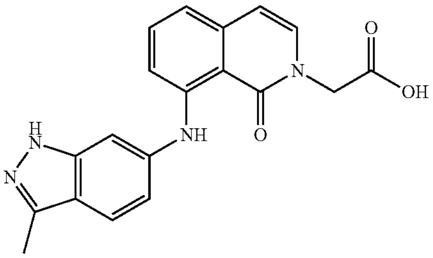 2-[8-[(3-methyl-1H-indazol-6-yl)amino]-1-oxo-2-isoquinolyl]acetic acid I-19 | Method 4: 1.19 min, m/z 349.0 $[M + H]^+$ | |

Synthesis of Methylated Aniline Indazoles

Methylated Indazole 1 (MI1)

Scheme 2

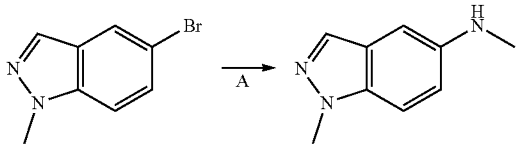

MI1

STEP A. A solution of 5-bromo-1-methyl-1H-indazole (900 mg, 4.3 mmol), methanamine (2 M in THF, 795 mg, 25.6 mmol), $Cs_2CO_3$ (2.8 g, 8.5 mmol) and t-Buxphos-Pd-G3 (338 mg, 0.43 mmol) in dioxane (20 mL) was stirred at 100° C. under $N_2$ overnight. The mixture was concentrated and purified by normal phase chromatography (25 g column, 10 to 50% EtOAc in petrol) then purified by reverse phase chromatography (12 g column, 25% MeCN in water) to give N,1-dimethylindazol-5-amine as a yellow solid (MI1, 67 mg, 0.42 mmol, 10% yield).

UPLCMS (Method 4): 0.550 min, m/z, 162.2 [M+H].

$^1H$ NMR (400 MHz, $DMSO-d_6$) δ 7.75 (s, 1H), 7.39 (d, J=8.9 Hz, 1H), 6.87 (dd, J=2.1, 8.9 Hz, 1H), 6.59 (d, J=1.8 Hz, 1H), 5.49-5.42 (m, 1H), 3.97 (s, 3H), 2.72 (d, J=5.2 Hz, 3H).

Methylated Indazole 2 (MI2)

Scheme 3

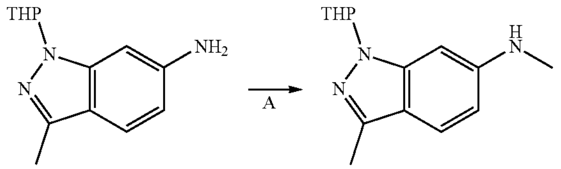

MI2

STEP A. A mixture of 3-methyl-1-(tetrahydro-2H-pyran-2-yl)-1H-indazol-6-amine (1 g, 4.32 mmol), sodium methoxide (2.34 g, 43 mmol) and formaldehyde (195 mg, 6.5 mmol) in MeOH (15 mL) was stirred at rt for 16 h. $NaBH_4$ (327 mg, 8.65 mmol) was added to the mixture and it was stirred for 4 h. On completion, the reaction mixture was diluted with water (10 mL) and extracted with EtOAc (3×50 mL). The combined extracts were washed with brine (3×10 mL), dried over $Na_2SO_4$ and evaporated.

The residue was purified by column chromatography (0-100% EtOAc in petrol) to afford N,3-dimethyl-1-(tetrahydro-2H-pyran-2-yl)-1H-indazol-6-amine (MI2, 0.42 g, 1.7 mmol, 40% yield) as a white solid.

UPLCMS (Method 3): 3.35 min, m/z, 246.3 [M+H].

$^1H$ NMR (400 MHz, $CDCl_3$) δ 7.38 (d, J=8.6 Hz, 1H), 6.50 (d, J=8.7 Hz, 1H), 6.47 (s, 1H), 5.55 (dd, J=1.9, 10.0 Hz, 1H), 4.13-4.07 (m, 1H), 3.97-3.97 (m, 1H), 3.80-3.73 (m, 1H), 2.93 (s, 3H), 2.67-2.57 (m, 1H), 2.50 (s, 3H), 2.20-2.15 (m, 1H), 2.06-2.01 (m, 1H), 1.83-1.64 (m, 3H).

Methylated Indazole 3 (MI3)

Scheme 4

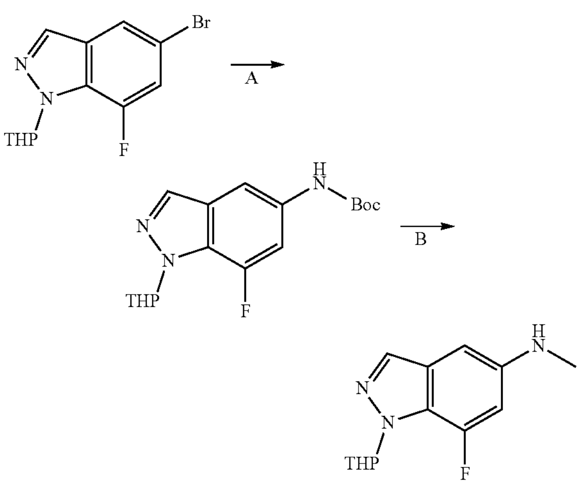

MI3

STEP A. A solution of 5-bromo-7-fluoro-1-tetrahydropyran-2-yl-indazole (650 mg, 2.2 mmol), $NH_2$-Boc (509 mg, 4.4 mmol), $Cs_2CO_3$ (1.42 g, 4.4 mmol), Xantphos (403.0 mg, 0.44 mmol) and $Pd_2(dba)_3$ (255 mg, 0.44 mmol) in 1,4-dioxane (7 mL) was stirred at 100° C. under $N_2$ overnight. The mixture was filtered through a Celite pad washing with EtOAc and concentrated in vacuo to give tert-butyl N-(7-fluoro-1-tetrahydropyran-2-yl-indazol-5-yl)carbamate (500 mg, 1.5 mmol, 69% yield) as a brown solid which was used in the next step without further purification.

UPLCMS ($ES^+$, Method 3): 4.37 min, m/z 336.2 $[M+H]^+$.

STEP B. A solution of tert-butyl N-(7-fluoro-1-tetrahydropyran-2-yl-indazol-5-yl)carbamate (50 mg, 0.15 mmol), and $LiAlH_4$ (0.8 mL, 0.76 mmol), in THE (5 mL) was stirred at 60° C. overnight. Water (3 mL) was added followed by NaOH (10% aqueous) until pH11 was achieved. The mixture was further diluted with water, extracted with DCM and the organics, dried ($Na_2SO_4$), filtered and concentrated to afford 7-fluoro-N-methyl-1-tetrahydropyran-2-yl-indazol-5-amine (30 mg, 81%) as a white solid. UPLCMS ($ES^+$, Method 3): 3.28 min, m/z 250.0 $[M+H]^+$.

EXAMPLES

Example 1, 2-[8-(1H-indazol-5-ylamino)-1-oxo-2-isoquinolyl]-N-(2,2,2-trifluoroethyl)acetamide Scheme 5

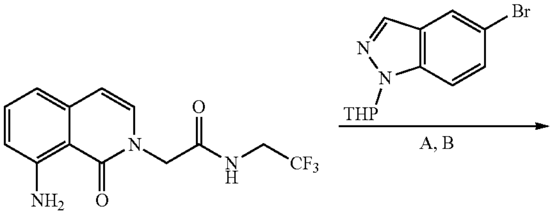

I-3

-continued

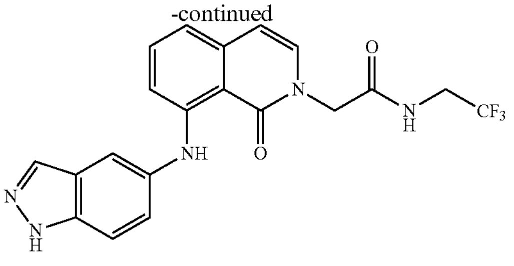

1

STEP A. 2-(8-amino-1-oxo-2-isoquinolyl)-N-(2,2,2-trifluoroethyl)acetamide (Intermediate I-3, 50 mg, 0.17 mmol), 5-bromo-1-tetrahydropyran-2-yl-pyrazolo[3,4-b]pyridine (52 mg, 0.18 mmol), tris(dibenzylideneacetone)dipalladium (0) (8 mg, 0.01 mmol), tbubrettphos (8 mg, 0.02 mmol), potassium carbonate (46 mg, 0.33 mmol) and acetic acid (glacial) (5 μL, 0.08 mmol) were dissolved in tert-butanol (2 mL), the vial was sealed and degassed, and the mixture was stirred at 110° C. overnight. The mixture was cooled to rt and filtered through a Celite pad, washing with EtOAc, concentrated under reduced pressure and purified by normal phase chromatography (12 g column, 0 to 5% methanol in dichloromethane) to give THP-protected intermediate 2-[1-oxo-8-[(1-tetrahydropyran-2-ylindazol-5-yl)amino]-2-isoquinolyl]-N-(2,2,2-trifluoroethyl)acetamide (61 mg, 0.12 mmol, 73% yield) as an orange solid.

UPLC-MS ($ES^+$, Method 2): 1.85 min, m/z 500.3 $[M+H]^+$ $^1H$ NMR (400 MHz, DMSO-$d_6$) δ 8.91 (t, J=6.4 Hz, 1H), 8.06 (s, 1H), 7.76 (d, J=8.7 Hz, 1H), 7.68 (d, J=1.8 Hz, 1H), 7.41-7.32 (m, 3H), 6.90 (d, J=8.2 Hz, 1H), 6.84 (d, J=7.8 Hz, 1H), 6.54 (d, J=7.4 Hz, 1H), 5.85 (dd, J=2.6, 9.6 Hz, 1H), 4.67 (s, 2H), 3.99 (qd, J=5.5, 9.6 Hz, 2H), 3.93-3.88 (m, 1H), 3.77-3.72 (m, 2H), 2.07-1.97 (m, 2H), 1.79-1.74 (m, 2H), 1.63-1.57 (m, 2H).

STEP B. To a solution of 2-[1-oxo-8-[(1-tetrahydropyran-2-ylindazol-5-yl)amino]-2-isoquinolyl]-N-(2,2,2-trifluoroethyl)acetamide (60 mg, 0.12 mmol) in methanol (1 mL) and acetonitrile (1 mL) was added HCl (4 M in dioxane, 0.3 mL, 1.2 mmol) dropwise, and the mixture was stirred overnight. The mixture was concentrated in vacuo, purified by reverse phase chromatography (4 g column, 10 to 60% MeCN in water, 0.1% formic acid) and dried under vacuum overnight to give 2-[8-(1H-indazol-5-ylamino)-1-oxo-2-isoquinolyl]-N-(2,2,2-trifluoroethyl)acetamide (12 mg, 0.03 mmol, 24% yield) as a yellow solid.

UPLC-MS ($ES^+$, Method 1): 3.54 min, m/z 416.1 $[M+H]^+$.

$^1H$ NMR (400 MHz, DMSO-$d_6$) δ 13.07 (s, 1H), 10.92 (s, 1H), 8.91 (t, J=6.3 Hz, 1H), 8.02 (s, 1H), 7.66 (d, J=1.4 Hz, 1H), 7.58 (d, J=8.8 Hz, 1H), 7.40-7.34 (m, 2H), 7.27 (dd, J=1.9, 8.8 Hz, 1H), 6.87 (d, J=7.8 Hz, 1H), 6.81 (d, J=7.1 Hz, 1H), 6.53 (d, J=7.4 Hz, 1H), 4.66 (s, 2H), 3.98 (dq, J=6.6, 9.7 Hz, 2H).

Examples synthesised following the same procedure as Example 1 (Scheme 5) replacing 5-bromo-1-tetrahydropyran-2-yl-pyrazolo[3,4-b]pyridine in step A with the appropriate building block and replacing I-3 with the appropriate aniline intermediate when required are described in table 6.

TABLE 6

| Building block | Structure/Name | UPLCMS1 ($ES^+$) | $^1H$ NMR (400 MHz, DMSO-$d_6$) |
|---|---|---|---|
| 6-bromo-1-tetrahydropyran-2-yl-indazole | 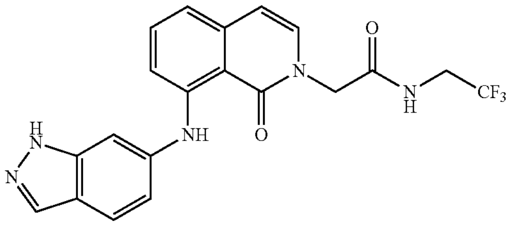 2-[8-(1H-indazol-6-ylamino)-1-oxo-2-isoquinolyl]-N-(2,2,2-trifluoroethyl)acetamide Example 2 | Method 1: 3.61 min, m/z 416.0 $[M + H]^+$ | 12.85 (s, 1H), 11.20 (s, 1H), 8.92 (t, J = 6.3 Hz, 1H), 8.00 (s, 1H), 7.73 (d, J = 8.1 Hz, 1H), 7.48 (t, J = 8.0 Hz, 1H), 7.43 (s, 1H), 7.39 (d, J = 7.3 Hz, 1H), 7.22 (d, J = 8.3 Hz, 1H), 7.00 (dd, J = 1.8, 8.6 Hz, 1H), 6.92 (d, J = 7.1 Hz, 1H), 6.57 (d, J = 7.4 Hz, 1H), 4.68 (s, 2H), 3.98 (q, J = 5.3 Hz, 2H). |
| 6-bromo-1-tetrahydropyran-2-yl-pyrazolo[4,3-b]pyridine | 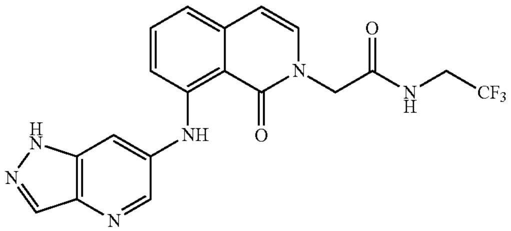 2-[1-oxo-8-(1H-pyrazolo[4,3-b]pyridine-6-ylamino)-2-isoquinolyl]-N-(2,2,2-trifluoroethyl)acetamide Example 4 | Method 1: 3.12 min, m/z 417.1 $[M + H]^+$ | 13.09 (s, 1H), 11.29 (s, 1H), 8.93 (t, J = 6.3 Hz, 1H), 8.42 (d, J = 2.3 Hz, 1H), 8.21 (t, J = 1.5 Hz, 1H), 7.89 (d, J = 1.4 Hz, 1H), 7.51 (t, J = 8.0 Hz, 1H), 7.42 (d, J = 7.3 Hz, 1H), 7.21 (d, J = 8.2 Hz, 1H), 6.99 (d, J = 7.8 Hz, 1H), 6.60 (d, J = 7.4 Hz, 1H), 4.70 (s, 2H), 3.98 (dq, J = 6.3, 9.8 Hz, 2H). |
| 5-bromo-1-tetrahydropyran-2-yl-pyrazolo[3,4-b]pyridine | 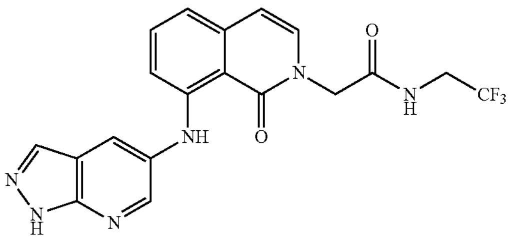 2-[1-oxo-8-(1H-pyrazolo[3,4-b]pyridine-5-ylamino)-2-isoquinolyl]-N-(2,2,2-trifluoroethyl)acetamide Example 7 | Method 1: 3.29 min, m/z 417.1 $[M + H]^+$ | 13.67 (s, 1H), 10.93 (s, 1H), 8.92 (t, J = 6.4 Hz, 1H), 8.45 (d, J = 2.4 Hz, 1H), 8.17 (d, J = 2.7 Hz, 1H), 8.10 (d, J = 1.2 Hz, 1H), 7.42-7.37 (m, 2H), 6.86 (d, J = 7.1 Hz, 1H), 6.78 (d, J = 8.1 Hz, 1H), 6.55 (d, J = 7.4 Hz, 1H), 4.68 (s, 2H), 3.98 (dq, J = 6.5, 9.8 Hz, 2H). |
| 5-bromo-3-methyl-1-tetrahydropyran-2-yl-indazole | 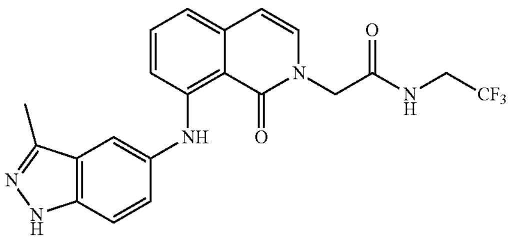 2-[8-[(3-methyl-1H-indazol-5-yl)amino]-1-oxo-2-isoquinolyl]-N-(2,2,2-trifluoroethyl)acetamide Example 68 | Method 1: 3.57 min, m/z 430.2 $[M + H]^+$ | 12.64 (s, 1H), 10.90 (s, 1H), 8.92 (t, J = 6.5 Hz, 1H), 7.57 (s, 1H), 7.49 (d, J = 8.5 Hz, 1H), 7.40-7.34 (m, 2H), 7.26 (dd, J = 1.8, 8.8 Hz, 1H), 6.81 (t, J = 7.7 Hz, 2H), 6.52 (d, J = 7.4 Hz, 1H), 4.66 (s, 2H), 3.98 (dq, J = 6.3, 9.8 Hz, 2H), 2.46 (s, 3H). |

TABLE 6-continued

| Building block | Structure/Name | UPLCMS1 ($ES^+$) | $^1H$ NMR (400 MHz, DMSO-$d_6$) |
|---|---|---|---|
| tetrahydropyran-2-yl-3-(trifluoromethyl) indazole | 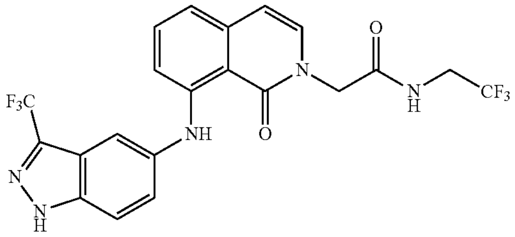 2-[1-oxo-8-[[3-(trifluoromethyl)-1H-indazol-5-yl]amino]-2-isoquinolyl]-N-(2,2,2-trifluoroethyl)acetamide Example 70 | Method 1: 4.08 min, m/z 484.0 $[M + H]^+$ | 14.00 (s, 1H), 11.09 (s, 1H), 8.92 (t, J = 6.3 Hz, 1H), 7.74 (d, J = 9.0 Hz, 1H), 7.60 (s, 1H), 7.48-7.42 (m, 2H), 7.38 (d, J = 7.3 Hz, 1H), 6.97 (d, J = 8.3 Hz, 1H), 6.89 (d, J = 7.1 Hz, 1H), 6.56 (d, J = 7.4 Hz, 1H), 4.67 (s, 2H), 3.98 (td, J = 9.7, 16.0 Hz, 2H). |
| 5-bromo-7-fluoro-1-tetrahydropyran-2-yl-indazole | 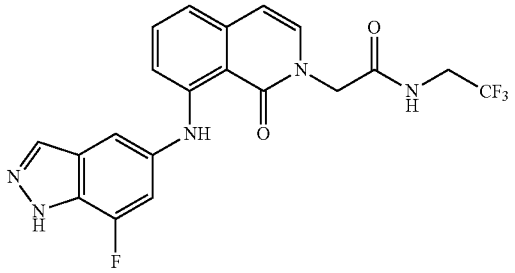 2-[8-[(7-fluoro-1H-indazol-5-yl)amino]-1-oxo-2-isoquinolyl]-N-(2,2,2-trifluoroethyl)acetamide Example 83 | Method 1: 3.60 min, m/z 434.4 $[M + H]^+$ | 13.62 (s, 1H), 10.97 (s, 1H), 8.91 (t, J = 6.4 Hz, 1H), 8.12 (s, 1H), 7.51 (s, 1H), 7.44-7.36 (m, 2H), 7.17 (d, J = 11.6 Hz, 1H), 6.95 (d, J = 8.3 Hz, 1H), 6.87 (d, J = 7.1 Hz, 1H), 6.55 (d, J = 7.4 Hz, 1H), 4.67 (s, 2H), 3.98 (dq, J = 6.6, 9.7 Hz, 2H). |
| 5-bromo-7-methyl-1-tetrahydropyran-2-yl-indazole | 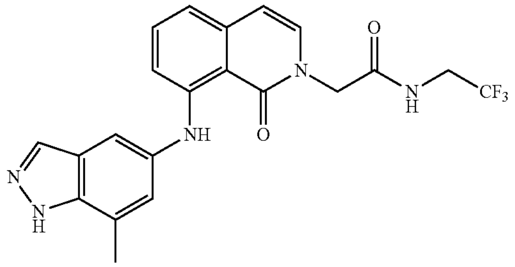 2-[8-[(7-methyl-1H-indazol-5-yl)amino]-1-oxo-2-isoquinolyl]-N-(2,2,2-trifluoroethyl)acetamide Example 85 | Method 1: 3.61 min, m/z 430.6 $[M + H]^+$ | 13.15 (s, 1H), 10.89 (s, 1H), 8.90 (t, J = 6.4 Hz, 1H), 8.01 (s, 1H), 7.47 (s, 1H), 7.38-7.33 (m, 2H), 7.05 (s, 1H), 6.86 (d, J = 8.3 Hz, 1H), 6.80 (d, J = 6.9 Hz, 1H), 6.52 (d, J = 7.5 Hz, 1H), 4.66 (s, 2H), 3.98 (dq, J = 6.4, 9.8 Hz, 2H), 2.53 (s, 3H). |
| 5-bromo-1-tetrahydropyran-2-yl-indazole + 1-9 | 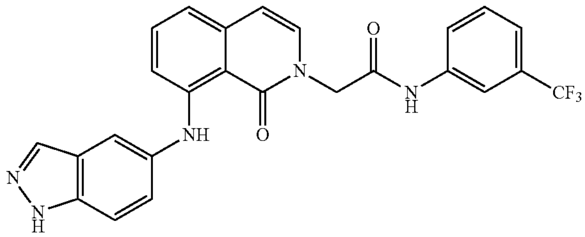 2-[8-(1H-indazol-5-ylamino)-1-oxo-2-isoquinolyl]-N-[3-(trifluoromethyl)phenyl]acetamide Example 5 | Method 1: 4.24 min, m/z 478.2 $[M + H]^+$ | 13.06 (s, 1H), 10.91 (s, 1H), 10.75 (s, 1H), 8.13 (s, 1H), 8.01 (s, 1H), 7.78 (d, J = 7.7 Hz, 1H), 7.65 (s, 1H), 7.62-7.54 (m, 2H), 7.45-7.37 (m, 3H), 7.27 (dd, J = 1.8, 8.7 Hz, 1H), 6.87 (d, J = 8.3 Hz, 1H), 6.84 (d, J = 7.5 Hz, 1H), 6.57 (d, J = 7.7 Hz, 1H), 4.82 (s, 2H). |

TABLE 6-continued

| Building block | Structure/Name | UPLCMS1 ($ES^+$) | $^1H$ NMR (400 MHz, DMSO-$d_6$) |
|---|---|---|---|
| 6-bromo-1-tetrahydropyran-2-yl-indazole-4-carbonitrile | 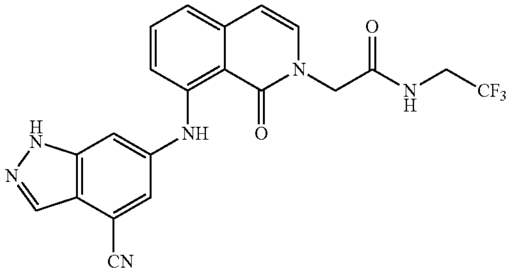 2-[8-[(4-cyano-1H-indazol-6-yl)amino]-1-oxo-2-isoquinolyl]-N-(2,2,2-trifluoroethyl)acetamide Example 91 | Method 3: 3.74 min, m/z 441.3 $[M + H]^+$ | 11.23 (s, 1H), 9.00 (br s, 1H), 8.20 (s, 1H), 7.84 (s, 1H), 7.60 (s, 1H), 7.54 (t, J = 8.0 Hz, 1H), 7.44 (d, J = 7.3 Hz, 1H), 7.23 (d, J = 8.1 Hz, 1H), 7.02 (d, J = 7.4 Hz, 1H), 6.63 (d, J = 7.4 Hz, 1H), 4.73 (s, 2H), 4.08-3.96 (m, 2H). One NH signal not observed. |
| 6-bromo-1-tetrahydropyran-2-yl-1-methyl indazole | 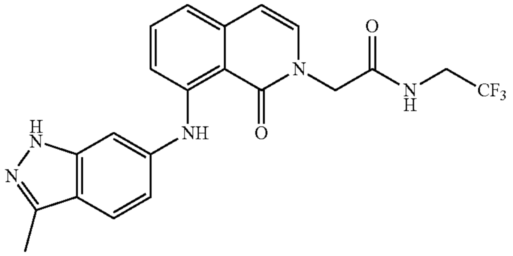 2-[8-[(3-methyl-1H-indazol-6-yl)amino]-1-oxo-2-isoquinolyl]-N-(2,2,2-trifluoroethyl)acetamide Example 100 | Method 4: 1.99 min, m/z 430.2 $[M + H]^+$ | 12.44 (s, 1H), 11.19 (s, 1H), 8.94 (t, J = 6.1 Hz, 1H), 7.68 (d, J = 8.6 Hz, 1H), 7.48 (t, J = 8.0 Hz, 1H), 7.39 (d, J = 7.3 Hz, 1H), 7.35 (s, 1H), 7.21 (d, J = 8.0 Hz, 1H), 6.97 (dd, J = 1.6, 8.6 Hz, 1H), 6.92 (d, J = 7.6 Hz, 1H), 6.58 (d, J = 7.4 Hz, 1H), 4.69 (s, 2H), 3.99 (dq, J = 6.7, 9.5 Hz, 2H), 2.45 (s, 3H). |
| 5-bromo-6-methyl-1-tetrahydropyran-2-yl-pyrazolo[3,4-b]pyridine | 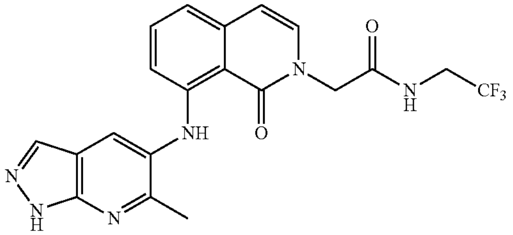 2-[8-[(6-methyl-1H-pyrazolo[3,4-b]pyridine-5-yl)amino]-1-oxo-2-isoquinolyl]-N-(2,2,2-trifluoroethyl)acetamide Example 109 | Method 3: 3.45 min, m/z 431.3 $[M + H]^+$ | 13.58 (s, 1H), 10.84 (s, 1H), 9.02 (t, J = 6.4 Hz, 1H), 8.20 (s, 1H), 8.11 (s, 1H), 7.47-7.40 (m, 2H), 6.91 (d, J = 8.1 Hz, 1H), 6.62 (d, J = 7.4 Hz, 1H), 6.53 (d, J = 8.2 Hz, 1H), 4.76 (s, 2H), 4.06 (dq, J = 6.8, 9.5 Hz, 2H), 2.56 (s, 3H). |
| Intermediate I-16 and 5-bromo-7-methyl-1-tetrahydropyran-2-yl-indazole | 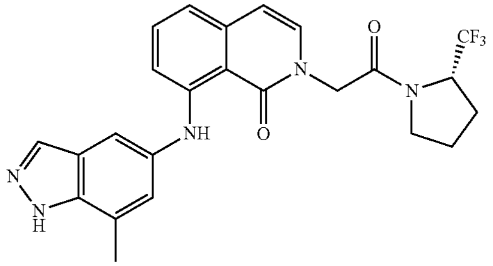 8-[(7-methyl-1H-indazol-5-yl)amino]-2-[2-oxo-2-[(2S)-2-(trifluoromethyl)pyrrolidin-1-yl]ethyl]isoquinolin-1-one Example 113 | Method 3: 4.00 min, m/z 470.3 $[M + H]^+$ | 13.17 (s, 1H), 10.92 (s, 1H), 8.02 (s, 1H), 7.49 (s, 1H), 7.39 (t, J = 7.9 Hz, 1H), 7.30 (d, J = 7.2 Hz, 1H), 7.06 (s, 1H), 6.89 (d, J = 8.2 Hz, 1H), 6.81 (d, J = 7.6 Hz, 1H), 6.54 (d, J = 7.5 Hz, 1H), 4.93-4.83 (m, 2H), 4.82-4.76 (m, 1H), 3.80-3.67 (m, 2H), 2.54 (s, 3H), 2.13-1.97 (m, 4H). |

TABLE 6-continued

| Building block | Structure/Name | UPLCMS1 ($ES^+$) | $^1H$ NMR (400 MHz, DMSO-$d_6$) |
|---|---|---|---|
| 5-bromo-7-ethyl-1-tetrahydropyran-2-yl-indazole | 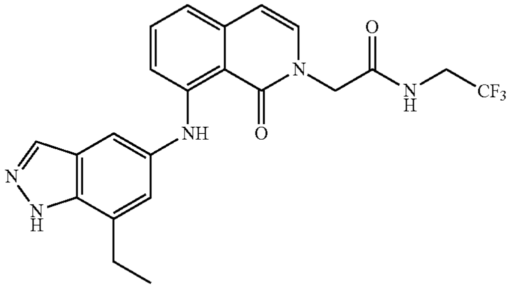 2-[8-[(7-ethyl-1H-indazol-5-yl)amino]-1-oxo-2-isoquinolyl]-N-(2,2,2-trifluoroethyl)acetamide Example 114 | Method 4: 1.76 min, m/z 444.2 $[M + H]^+$ | 13.15 (s, 1H), 10.90 (s, 1H), 8.90 (s, 1H), 8.01 (s, 1H), 7.48 (d, J = 1.8 Hz, 1H), 7.36 (dd, J = 16.8, 7.8 Hz, 2H), 7.04 (d, J = 1.8 Hz, 1H), 6.88 (d, J = 8.3 Hz, 1H), 6.79 (d, J = 7.6 Hz, 1H), 6.51 (d, J = 7.3 Hz, 1H), 4.65 (s, 2H), 3.96 (dt, J = 10.0, 5.0 Hz, 2H), 2.90 (q, J = 7.5 Hz, 2H), 1.29 (t, J = 7.5 Hz, 3H). |
| 5-bromo-7-isopropyl-1-tetrahydropyran-2-yl-indazole | 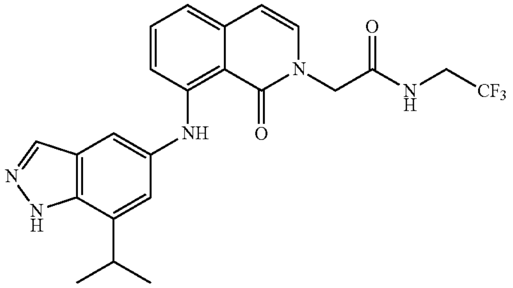 2-[8-[(7-isopropyl-1H-indazol-5-yl)amino]-1-oxo-2-isoquinolyl]-N-(2,2,2-trifluoroethyl)acetamide Example 115 | Method 4: 1.76 min, m/z 458.2 $[M + H]^+$ | 13.12 (s, 1H), 10.92 (s, 1H), 8.87 (t, J = 6.3 Hz, 1H), 8.01 (s, 1H), 7.49 (d, J = 1.8 Hz, 1H), 7.41-7.29 (m, 2H), 7.05 (d, J = 1.9 Hz, 1H), 6.89 (d, J = 8.2 Hz, 1H), 6.83-6.75 (m, 1H), 6.51 (d, J = 7.3 Hz, 1H), 4.66 (s, 2H), 4.04-3.90 (m, 2H), 3.39 (p, J = 6.9 Hz, 1H), 1.33 (d, J = 6.8 Hz, 6H). |
| 5-bromo-1-tetrahydropyran-2-yl-7-(trifluoromethyl) indazole | 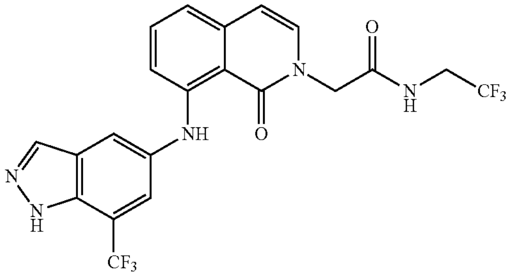 2-[1-oxo-8-[[7-(trifluoromethyl)-1H-indazol-5-yl]amino]-2-isoquinolyl]-N-(2,2,2-trifluoroethyl)acetamide Example 116 | Method 3: 3.92 min, m/z 484.3 $[M + H]^+$ | 11.02 (s, 1H), 8.91 (t, J = 6.3 Hz, 1H), 8.24 (s, 1H), 8.02 (d, J = 1.8 Hz, 1H), 7.62 (s, 1H), 7.42 (t, J = 8.0 Hz, 1H), 7.37 (d, J = 7.3 Hz, 1H), 6.88 (dd, J = 8.0, 3.9 Hz, 2H), 6.55 (d, J = 7.3 Hz, 1H), 4.67 (s, 2H), 3.97 (qd, J = 9.8, 6.2 Hz, 2H). |
| Intermediate I-17 and 6-bromo-3-methyl-1-tetrahydropyran-2-yl-indazole | 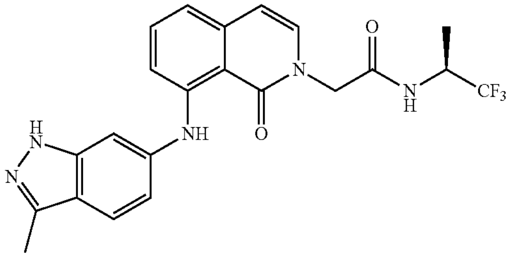 2-[8-[(3-methyl-1H-indazol-6-yl)amino]-1-oxo-2-isoquinolyl]-N-[(1S)-2,2,2-trifluoro-1-methyl-ethyl]acetamide Example 127 | Method 4: 1.80 min, m/z 444.1 $[M + H]^+$ | 12.40 (s, 1H), 11.17 (s, 1H), 8.82 (d, J = 8.0 Hz, 1H), 7.65 (d, J = 12.0 Hz, 1H), 7.48-7.44 (m, 1H), 7.36-7.33 (m, 2H), 7.20-7.17 (m, 1H), 6.95 (dd, J = 8.0, 4.0 Hz, 1H), 6.90 (d, J = 8.0 Hz, 1H), 6.55 (d, J = 8.0 Hz, 1H), 4.7-4.57 (m, 3H), 2.45 (s, 3H), 1.28 (d, J = 8.0 Hz, 3H). |

TABLE 6-continued

| Building block | Structure/Name | UPLCMS1 (ES$^+$) | $^1$H NMR (400 MHz, DMSO-$d_6$) |
|---|---|---|---|
| Intermediate I-16 and 6-bromo-3-methyl-1-tetrahydropyran-2-yl-indazole | 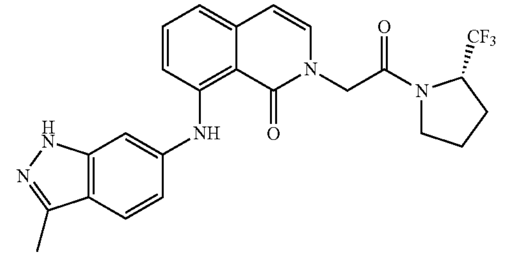 8-[(3-methyl-1H-indazol-6-yl)amino]-2-[2-oxo-2-[(2S)-2-(trifluoromethyl)pyrrolidin-1-yl]ethyl]isoquinolin-1-one Example 134 | Method 3: 4.02 min, m/z 470.2 [M + H]$^+$ | 12.39 (s, 1H), 11.16 (d, J = 20.0 Hz, 1H), 7.65 (d, J = 8.5 Hz, 1H), 7.47 (t, J = 8.0 Hz, 1H), 7.33-7.29 (m, 2H), 7.19 (d, J = 8.1 Hz, 1H), 6.97-6.90 (m, 2H), 6.56 (d, J = 7.3 Hz, 1H), 5.10-4.74 (m, 3H), 3.74-3.69 (m, 2H), 2.46 (s, 3H), 2.09-1.96 (m, 4H). |
| 6-bromo-3-methyl-1-tetrahydropyran-2-yl-pyrazolo[4,3-b]pyridine | 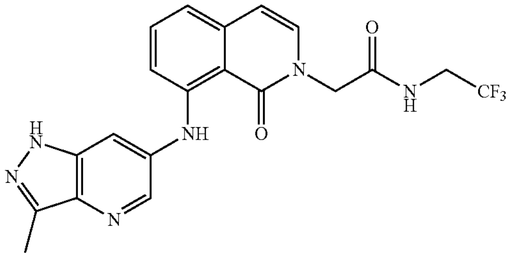 2-[8-[(3-methyl-1H-pyrazolo[4,3-b]pyridin-6-yl)amino]-1-oxo-2-isoquinolyl]-N-(2,2,2-trifluoroethyl)acetamide Example 153 | Method 3: 3.32 min, m/z 431.2 [M + H]$^+$ | 11.26 (s, 1H), 8.35 (s, 1H), 7.79 (s, 1H), 7.49 (t, J = 7.8 Hz, 1H), 7.40 (d, J = 7.3 Hz, 1H), 7.17 (d, J = 8.2 Hz, 1H), 6.97 (d, J = 7.7 Hz, 1H), 6.59 (d, J = 7.3 Hz, 1H), 4.69 (s, 2H), 4.03-3.93 (m, 2H), 2.50 (s, 3H). |
| 6-bromo-3-methyl-1-tetrahydropyran-2-yl-indazole-4-carbonitrile | 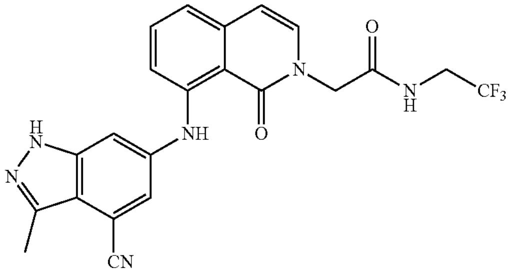 2-[8-[(4-cyano-3-methyl-1H-indazol-6-yl)amino]-1-oxo-2- | Method 3: 3.75 min, m/z 455.2 [M + H]$^+$ | 12.97 (s, 1H), 11.22 (s, 1H), 8.92 (t, J = 6.4 Hz, 1H), 7.69 (s, 1H), 7.56 (s, 1H), 7.51 (t, J = 8.0 Hz, 1H), 7.40 (d, J = 8.0 Hz, 1H), 7.22 (d, J = 8.0 Hz, 1H), 7.00 (d, J = 8.0 Hz, 1H), 6.59 (d, J = 8.0 Hz, 1H), 4.68 (s, 2H), 3.99-3.94 (m, 2H), 2.62 (s, 3H). |

[1]For examples where alternative HPLC and mass spectrometry methods were used, these are referred to in the individual example entries Example 3, 2-[8-[(1-methylindazol-5-yl)amino]-1-oxo-2-isoquinolyl]-N-(2,2,2-trifluoroethyl)acetamide Scheme 6

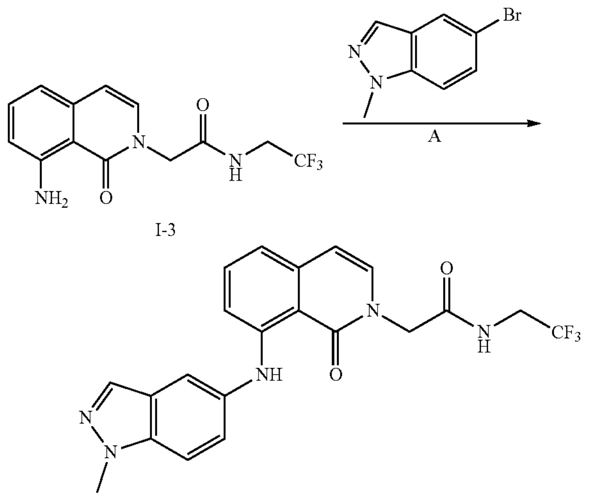

I-3

2

STEP A. 2-(8-amino-1-oxo-2-isoquinolyl)-N-(2,2,2-trifluoroethyl)acetamide (Intermediate I-3, 50 mg, 0.17 mmol), 5-Bromo-1-methyl-1H-indazole (39 mg, 0.18 mmol), tris (dibenzylideneacetone)dipalladium (0) (8 mg, 0.01 mmol), tbubrettphos (8 mg, 0.02 mmol), potassium carbonate (46 mg, 0.33 mmol) and acetic acid (glacial) (5 μL, 0.08 mmol) were dissolved in tert-butanol (2 mL), the vial was sealed and degassed, and the mixture was stirred at 110° C. overnight. The mixture was cooled to rt and filtered through a Celite pad, washing with EtOAc, concentrated under reduced pressure, purified by reverse phase chromatography (12 g column, 35 to 60% acetonitrile in water, 0.1% formic acid) and dried under vacuum overnight to give 2-[8-[(1-methylindazol-5-yl)amino]-1-oxo-2-isoquinolyl]-N-(2,2,2-trifluoroethyl) acetamide (32 mg, 0.07 mmol, 44% yield) as a yellow solid.

UPLC-MS ($ES^+$, Method 1): 3.88 min, m/z 430.2 $[M+H]^+$ (100%).

$^1$H NMR (400 MHz, DMSO-$d_6$) δ 10.94 (s, 1H), 8.92 (t, J=6.2 Hz, 1H), 7.99 (d, J=0.9 Hz, 1H), 7.67 (d, J=8.9 Hz, 1H), 7.65 (d, J=1.9 Hz, 1H), 7.38 (t, J=8.0 Hz, 1H), 7.36 (d, J=7.3 Hz, 1H), 7.31 (dd, J=2.0, 8.9 Hz, 1H), 6.87 (dd, J=0.9, 8.4 Hz, 1H), 6.82 (dd, J=0.9, 7.7 Hz, 1H), 6.53 (d, J=7.4 Hz, 1H), 4.67 (s, 2H), 4.06 (s, 3H), 3.98 (q, J=5.4 Hz, 2H).

Examples synthesised following the same procedure as Example 3 (Scheme 6) replacing 5-Bromo-1-methyl-1H-indazole in step A with the appropriate building block and replacing I-3 with I-9 when required are described in table 7.

TABLE 7

| Building block | Structure/Name | UPLCMS[1] ($ES^+$) | $^1$H NMR (400 MHz, DMSO-$d_6$) |
|---|---|---|---|
| 5-bromo-1-methyl-pyrazolo[3,4-b]pyridine | 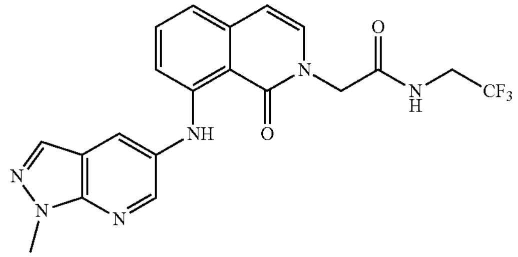 2-[8-[(1-methylpyrazolo[3,4-b]pyridin-5-yl)amino]-1-oxo-2-isoquinolyl]-N-(2,2,2-trifluoroethyl)acetamide Example 40 | Method 1: 3.82 min, m/z 431.3 $[M + H]^+$ | 10.96 (s, 1H), 8.92 (t, J = 6.4 Hz, 1H), 8.50 (d, J = 2.3 Hz, 1H), 8.19 (d, J = 2.2 Hz, 1H), 8.10 (s, 1H), 7.43-7.36 (m, 2H), 6.88 (d, J = 7.5 Hz, 1H), 6.79 (d, J = 8.1 Hz, 1H), 6.56 (d, J = 7.4 Hz, 1H), 4.68 (s, 2H), 4.08 (s, 3H), 3.98 (dq, J = 6.2, 9.7 Hz, 2H). |
| 5-bromo-7-nitro-1H- indazole | 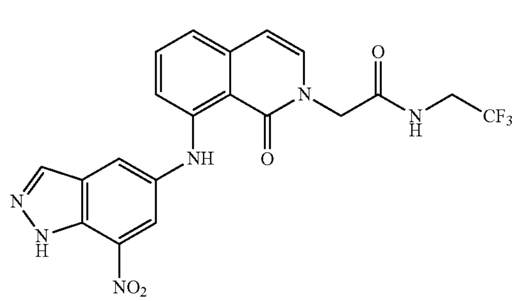 2-[8-[(7-nitro-1H-indazol-5-yl)amino]-1-oxo-2-isoquinolyl]-N-(2,2,2-trifluoroethyl)acetamide Example 86 | Method 1: 3.64 min, m/z 461.4 $[M + H]^+$ | 13.92 (s, 1H), 11.13 (s, 1H), 8.93 (t, J = 6.1 Hz, 1H), 8.36 (s, 1H), 8.27 (s, 1H), 8.24 (s, 1H), 7.46 (t, J = 7.9 Hz, 1H), 7.40 (d, J = 7.7 Hz, 1H), 7.00 (d, J = 8.0 Hz, 1H), 6.94 (d, J = 7.6 Hz, 1H), 6.58 (d, J = 7.2 Hz, 1H), 4.69 (s, 2H), 3.98 (dq, J = 6.4, 9.8 Hz, 2H). |

TABLE 7-continued

| Building block | Structure/Name | UPLCMS[1] ($ES^+$) | $^1H$ NMR (400 MHz, DMSO-$d_6$) |
|---|---|---|---|
| 5-Bromo-1-methy-1H-lindazole + I-9 | 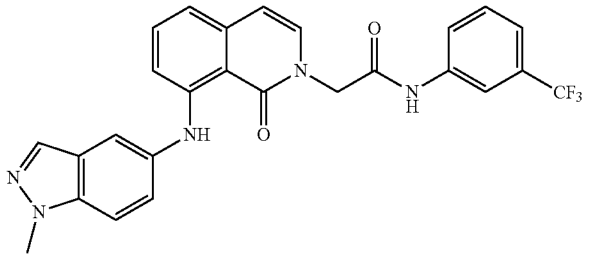 2-[8-[(1-methylindazol-5-yl)amino]-1-oxo-2-isoquinolyl]-N-[3-(trifluoromethyl)phenyl]acetamide Example 6 | Method 1: 4.53 min, m/z 492 $[M + H]^+$ | 10.93 (s, 1H), 10.75 (s, 1H), 8.13 (s, 1H), 7.98 (d, J = 0.9 Hz, 1H), 7.78 (d, J = 9.2 Hz, 1H), 7.68-7.65 (m, 2H), 7.59 (t, J = 8.1 Hz, 1H), 7.43-7.38 (m, 3H), 7.31 (dd, J = 2.3, 8.5 Hz, 1H), 6.86 (dd, J = 7.0, 14.3 Hz, 2H), 6.57 (d, J = 7.4 Hz, 1H), 4.82 (s, 2H), 4.05 (s, 3H). |
| 5-Bromo-7-chloro-1-methyl-1H-indazole | 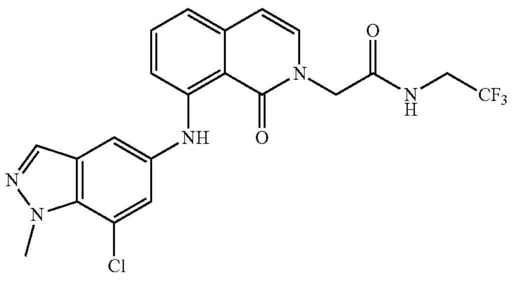 2-{8-[(7-chloro-1-methyl-1H-indazol-5-yl)amino]-1-oxo-1,2-dihydroisoquinolin-2-yl}-N-(2,2,2-trifluoroethyl)acetamide Example 102 | Method 4: 2.56 min, m/z 464.2 $[M + H]^+$ | 10.99 (s, 1H), 8.92 (t, J = 6.2 Hz, 1H), 8.08 (s, 1H), 7.68 (d, J = 1.5 Hz, 1H), 7.47-7.36 (m, 3H), 6.94 (d, J = 8.2 Hz, 1H), 6.89 (d, J = 7.5 Hz, 1H), 6.56 (d, J = 7.2 Hz, 1H), 4.68 (s, 2H), 4.33 (s, 3H), 3.98 (dq, J = 6.5, 9.7 Hz, 2H). |
| 6-bromo-1-methyl-indazole | 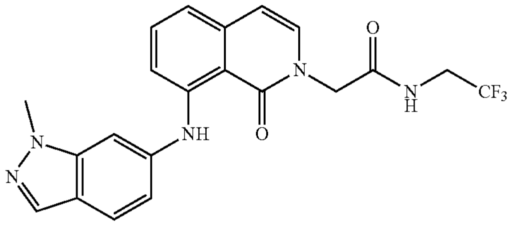 2-[8-[(1-methylindazol-6-yl)amino]-1-oxo-2-isoquinolyl]-N-(2,2,2-trifluoroethyl)acetamide Example 107 | Method 3: 3.88 min, m/z 430.0 $[M + H]^+$ | 11.27 (s, 1H), 8.91 (t, J = 6.3 Hz, 1H), 7.96 (s, 1H), 7.71 (d, J = 8.6 Hz, 1H), 7.53 - 7.44 (m, 2H), 7.38 (d, J = 7.3 Hz, 1H), 7.25 (d, J = 8.2 Hz, 1H), 7.05 (dd, J = 8.6, 1.7 Hz, 1H), 6.92 (d, J = 7.6 Hz, 1H), 6.56 (d, J = 7.3 Hz, 1H), 4.67 (s, 2H), 4.03-3.92 (m, 5H). |
| 6-bromo-1-methyl-pyrazolo[4,3-b]pyridine | 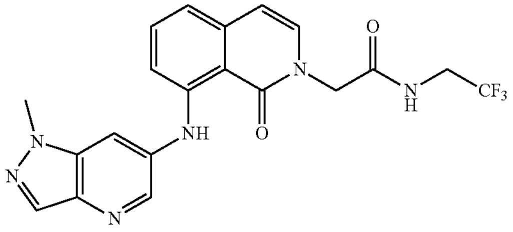 2-[8-[(1-methylpyrazolo[4,3-b]pyridin-6-yl)amino]-1-oxo-2-isoquinolyl]-N-(2,2,2-trifluoroethyl)acetamide Example 108 | Method 4: 1.50 min, m/z 431.1 $[M + H]^+$ | 11.43 (s, 1H), 8.95 (t, J = 6.2 Hz, 1H), 8.44 (d, J = 2.1 Hz, 1H), 8.19 (s, 1H), 8.07 (s, 1H), 7.54 (t, J = 7.9 Hz, 1H), 7.43 (d, J = 7.3 Hz, 1H), 7.31 (d, J = 8.3 Hz, 1H), 7.02 (d, J = 7.7 Hz, 1H), 6.63 (d, J = 7.3 Hz, 1H), 4.72 (s, 2H), 4.05 (s, 3H), 4.03-3.96 (m, 2H). |

TABLE 7-continued

| Building block | Structure/Name | UPLCMS[1] ($ES^+$) | $^1H$ NMR (400 MHz, DMSO-$d_6$) |
|---|---|---|---|
| 6-bromo-1-methyl-indazole-4-carbonitrile | 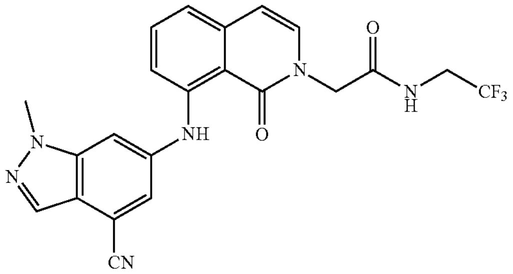 2-[8-[(4-cyano-1-methyl-indazol-6-yl)amino]-1-oxo-2-isoquinolyl]-N-(2,2,2-trifluoroethyl)acetamide Example 110 | Method 4: 2.27 min, m/z 455.2 [M + H]+ | 11.35 (s, 1H), 8.91 (t, J = 6.7 Hz, 1H), 8.15 (d, J = 0.8 Hz, 1H), 7.91 (s, 1H), 7.68 (d, J = 1.6 Hz, 1H), 7.51 (t, J = 7.9 Hz, 1H), 7.40 (d, J = 7.3 Hz, 1H), 7.28 (d, J = 7.8 Hz, 1H), 7.01 (d, J = 7.5 Hz, 1H), 6.59 (d, J = 7.4 Hz, 1H), 4.68 (s, 2H), 4.05 (s, 3H), 3.96 (dq, J = 6.4, 9.7 Hz, 2H). |
| Intermediate I-16 and 5-bromo-7-fluoro-1-methyl-indazole | 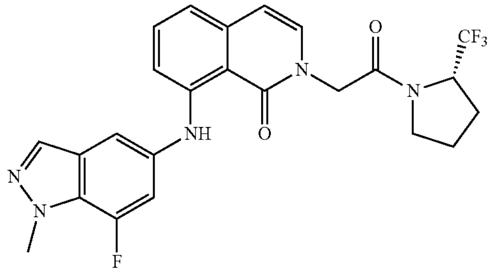 8-[(7-fluoro-1-methyl-indazol-5-yl)amino]-2-[2-oxo-2-[(2S)-2-(trifluoromethyl)pyrrolidin-1-yl]ethyl]isoquinolin-1-one Example 123 | Method 3: 4.40 min, m/z 488.25 $[M + H]^+$ | 10.98 (d, J = 16.0 Hz, 1H), 8.04 (s, 1H), 7.49 (s, 1H), 7.42 (t, J = 8.0 Hz, 1H), 7.30 (d, J = 4.0 Hz, 1H), 7.19 (d, J = 12.0 Hz, 1H), 6.97 (d, J = 8.0 Hz, 1H), 6.87 (d, J = 8.0 Hz, 1H), 6.55 (d, J = 8.0 Hz, 1H), 5.00-4.72 (m, 3H), 4.17 (s, 3H), 3.72 (m, 2H), 2.06 (m, 4H). |
| 6-bromo-4-fluoro-3-methyl-1H-indazole | 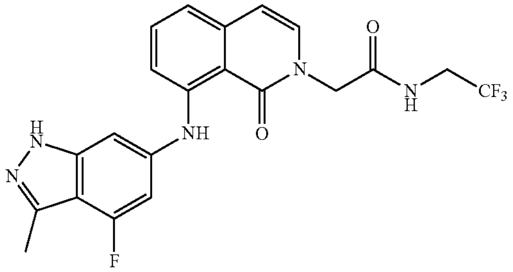 2-[8-[(4-fluoro-3-methyl-1H-indazol-6-yl)amino]-1-oxo-2-isoquinolyl]-N-(2,2,2-trifluoroethyl)acetamide Example 128 | Method 4: 1.56 min, m/z 446.1 $[M + H]^+$ | 12.64 (s, 1H), 11.19 (s, 1H), 8.90 (t, J = 6.5 Hz, 1H), 7.50 (t, J = 8.0 Hz, 1H), 7.38 (d, J = 7.3 Hz, 1H), 7.26 (d, J = 8.2 Hz, 1H), 7.15 (s, 1H), 6.97 (d, J = 7.7 Hz, 1H), 6.73 (d, J = 12.1 Hz, 1H), 6.58 (d, J = 7.3 Hz, 1H), 4.67 (s, 2H), 3.97 (dd, J = 9.9, 6.4 Hz, 2H), 2.53 (s, 3H). |
| Intermediate I-16 and 5-bromo-7-chloro-1H-indazole | 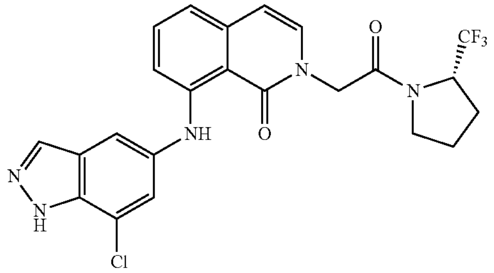 8-[(7-chloro-3a,7a-dihydro-1H-indazol-5-yl)amino]-2-[2-oxo-2-[(2S)-2-(trifluoromethyl)pyrrolidin-1-yl]ethyl]isoquinolin-1-one Example 129 | Method 4: 2.44 min, m/z 488.1 $[M + H]^+$ | 13.57 (s, 1H), 10.94 (d, J = 16.5 Hz, 1H), 8.14 (s, 1H), 7.66 (d, J = 1.7 Hz, 1H), 7.44-7.36 (m, 2H), 7.30 (d, J = 7.1 Hz, 1H), 6.87 (dd, J = 11.2, 7.9 Hz, 2H), 6.55 (d, J = 7.3 Hz, 1H), 5.10-4.73 (m, 3H), 3.83-3.64 (m, 2H), 2.17-1.95 (m, 4H). |

TABLE 7-continued

| Building block | Structure/Name | UPLCMS[1] (ES$^+$) | $^1$H NMR (400 MHz, DMSO-$d_6$) |
|---|---|---|---|
| Intermediate I-16 and 5-bromo-1H-indazole-7-carbonitrile | 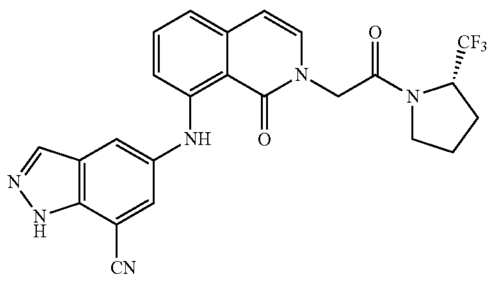 5-[[1-oxo-2-[2-oxo-2-[(2S)-2-(trifluoromethyl)pyrrolidin-1-yl]ethyl]-8-isoquinolyl]amino]-1H-indazol-7-carbonitrile Example 145 | Method 3: 3.94 min, m/z 481.2 [M + H]$^+$ | 10.98 (d, J = 15.2 Hz, 1H), 8.24 (s, 1H), 8.07 (d, J = 4.8 Hz, 1H), 7.88 (d, J = 2.0 Hz, 1H), 7.42 (t, J = 8.0 Hz, 1H), 7.31 (d, J = 6.6 Hz, 1H), 6.88 (dd, J = 8.0, 2.4 Hz, 2H), 6.56 (d, J = 7.6 Hz, 1H), 5.03-4.61 (m, 3H), 3.80-3.63 (m, 2H), 2.09-1.96 (m, 4H). |

[1]For examples where alternative HPLC and mass spectrometry methods were used, these are referred to in the individual example entries Example 52, 2-[8-[(7-chloro-1H-indazol-5-yl)amino]-1-oxo-2-isoquinolyl]-N-(2,2,2-trifluoroethyl)acetamide Scheme 7

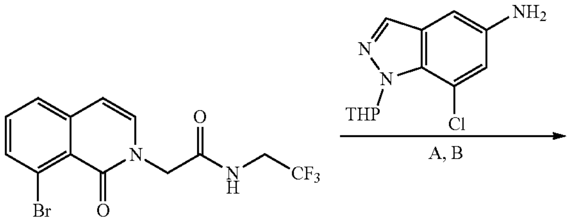

I-2

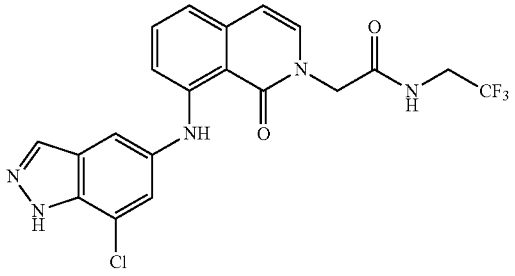

52

STEP A. 2-(8-Bromo-1-oxo-2-isoquinolyl)-N-(2,2,2-trifluoroethyl)acetamide (Intermediate I-2, 50 mg, 0.14 mmol), $Cs_2CO_3$ (90 mg, 0.28 mmol) and 7-chloro-1-tetrahydropyran-2-yl-indazol-5-amine (42 mg, 0.17 mmol) were dissolved in Toluene (2 mL). The vial was degassed with $N_2$ for 10 minutes before 4,5-bis(diphenylphosphino)-9,9-dimethylxanthene (8 mg, 0.01 mmol) 0 and tris (dibenzylideneacetone)dipalladium (0) (6.3 mg, 0.01 mmol) were added, the vial was sealed and the mixture was heated to 110° C. and stirred overnight. The mixture was filtered through a Celite pad, washing with methanol, and concentrated in vacuo. The crude product was purified by reverse phase chromatography (12 g column, 20 to 70% acetonitrile in water, 0.1% formic acid) to give the THP-protected intermediate 2-[8-[(7-chloro-1-tetrahydropyran-2-yl-indazol-5-yl)amino]-1-oxo-2-isoquinolyl]-N-(2,2,2-trifluoroethyl)acetamide (36 mg, 0.07 mmol, 49% yield) as a yellow solid.

UPLC-MS (ES$^+$, Method 2): 2.07 min. m/z 534.2 [M+H]$^+$.

$^1$H NMR (400 MHz, DMSO-$d_6$) δ 11.02 (s, 1H), 8.92 (t, J=6.3 Hz, 1H), 8.17 (s, 1H), 7.83-7.80 (m, 1H), 7.72 (d, J=1.7 Hz, 1H), 7.42-7.35 (m, 2H), 6.97 (d, J=8.3 Hz, 1H), 6.89 (d, J=7.1 Hz, 1H), 6.56 (d, J=7.4 Hz, 1H), 6.24 (dd, J=2.0, 10.1 Hz, 1H), 4.67 (s, 2H), 4.00-3.91 (m, 3H), 3.75-3.68 (m, 1H), 2.13-2.10 (m, 1H), 2.06-2.03 (m, 1H), 1.81-1.72 (m, 2H), 1.59-1.54 (m, 2H).

STEP B. To a solution of 2-[8-[(7-chloro-1-tetrahydropyran-2-yl-indazol-5-yl)amino]-1-oxo-2-isoquinolyl]-N-(2,2,2-trifluoroethyl)acetamide (36 mg, 0.07 mmol) in acetonitrile (1 mL) and methanol (1 mL) was added HCl (4 M in dioxane, 0.08 mL, 0.34 mmol) and the mixture was stirred overnight at rt. The mixture was concentrated under reduced pressure and the crude product was purified by reverse phase chromatography (12 g column, 20 to 60% acetonitrile in water, 0.1% formic acid) and dried under vacuum overnight to give 2-[8-[(7-chloro-1H-indazol-5-yl)amino]-1-oxo-2-isoquinolyl]-N-(2,2,2-trifluoroethyl)acetamide (7.5 mg, 0.02 mmol, 25% yield) as a pale brown solid.

UPLC-MS (ES$^+$, Method 1): 3.72 min, m/z 450.0 [M+H]$^+$.

$^1$H NMR (400 MHz, DMSO-$d_6$) δ 13.59 (s, 1H), 10.95 (s, 1H), 8.92 (t, J=6.4 Hz, 1H), 8.15 (s, 1H), 7.67 (s, 1H), 7.44-7.35 (m, 3H), 6.88 (t, J=8.5 Hz, 2H), 6.55 (d, J=7.4 Hz, 1H), 4.67 (s, 2H), 3.98 (q, J=5.4 Hz, 2H).

Examples synthesised following the same procedure as example 52 (scheme 7) replacing 7-chloro-1-tetrahydropyran-2-yl-indazol-5-amine in step A with the appropriate building block and replacing I-2 with I-8 when required are described in table 8.

TABLE 8

| Building block | Structure/Name | UPLCMS[1] ($ES^+$) | $^1H$ NMR (400 MHz, DMSO-$d_6$) |
|---|---|---|---|
| 6-methyl-1-tetrahydropyran-2-yl-indazol-5-amine | 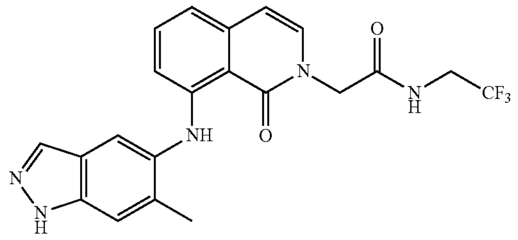 2-[8-[(6-methyl-1H-indazol-5-yl)amino]-1-oxo-2-isoquinolyl]-N-(2,2,2-trifluoroethyl)acetamide Example 65 | Method 1: 3.59 min, m/z 430.2 $[M + H]^+$ | 12.96 (s, 1H), 10.71 (s, 1H), 8.91 (t, J = 6.2 Hz, 1H), 7.98 (s, 1H), 7.68 (s, 1H), 7.50 (s, 1H), 7.35 (d, J = 7.3 Hz, 1H), 7.33 (t, J = 8.0 Hz, 1H), 6.78 (d, J = 7.0 Hz, 1H), 6.53-6.50 (m, 2H), 4.67 (s, 2H), 3.98 (dq, J = 6.4, 9.8 Hz, 2H), 2.30 (s, 3H). |
| 7-carbonitrile-1-tetrahydropyran-2-yl-indazol-5-amine | 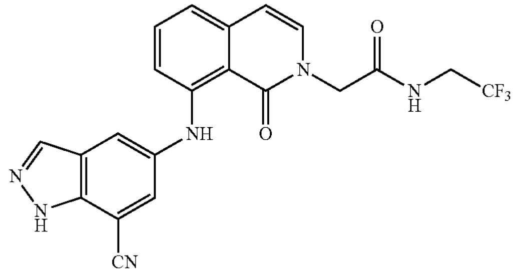 2-[8-[(7-cyano-1H-indazol-5-yl)amino]-1-oxo-2-isoquinolyl]-N-(2,2,2-trifluoroethyl)acetamide Example 66 | Method 1: 3.54 min, m/z 441.0 $[M + H]^+$ | 14.03 (s, 1H), 10.98 (s, 1H), 8.92 (t, J = 6.4 Hz, 1H), 8.27 (s, 1H), 8.09 (s, 1H), 7.89 (s, 1H), 7.45 – 7.37 (m, 2H), 6.91-6.87 (m, 2H), 6.56 (d, J = 7.4 Hz, 1H), 4.68 (s, 2H), 3.98 (dq, J = 6.4, 9.7 Hz, 2H). |
| 1-(tetrayhropyran-2-yl)-1H-pyrazolo[3,4-b]pyridin-5-amine + I-8 | 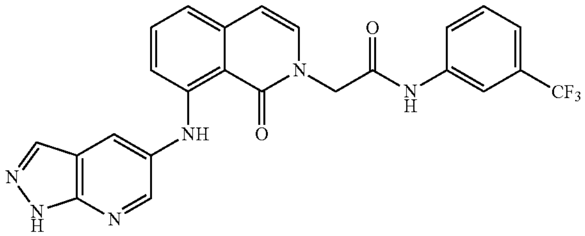 2-[1-oxo-8-(1H-pyrazolo[3,4-b]pyridin-5-ylamino)-2-isoquinolyl]-N-[3-(trifluoromethyl)phenyl]acetamide Example 22 | Method 1: 4.04 min, m/z 479.1 $[M + H]^+$ | 13.66 (s, 1H), 10.91 (s, 1H), 10.76 (s, 1H), 8.45 (d, J = 2.6 Hz, 1H), 8.17 (d, J = 2.1 Hz, 1H), 8.13 (s, 1H), 8.09 (d, J = 1.1 Hz, 1H), 7.78 (d, J = 8.7 Hz, 1H), 7.59 (t, J = 8.1 Hz, 1H), 7.45-7.39 (m, 3H), 6.89 (d, J = 7.4 Hz, 1H), 6.79 (d, J = 8.2 Hz, 1H), 6.60 (d, J = 7.4 Hz, 1H), 4.83 (s, 2H). |
| 7-methoxy-1-tetrahydropyran-2-yl-indazol-5-amine | 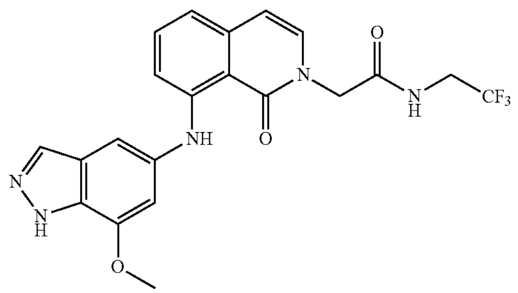 2-{8-[(7-methoxy-1H-indazol-5-yl)amino]1-oxo-1,2-dihydroisoquinolin-2-yl}-N-(2,2,2-trifluoroethyl)acetamide Example 89 | Method 3: 3.71 min, m/z 446.3 $[M + H]^+$ | 10.95 (s, 1H), 9.04 (t, J = 6.1 Hz, 1H), 8.02 (s, 1H), 7.47-7.38 (m, 2H), 7.27 (s, 1H), 7.01 (d, J = 8.0 Hz, 1H), 6.86 (d, J = 7.6 Hz, 1H), 6.76 (s, 1H), 6.57 (d, J = 7.2 Hz, 1H), 4.72 (s, 2H), 4.05-3.96 (m, 5H). |

TABLE 8-continued

| Building block | Structure/Name | UPLCMS[1] ($ES^+$) | $^1H$ NMR (400 MHz, DMSO-$d_6$) |
|---|---|---|---|
| methyl 1-(tetrahydropyran-2-yl)-1H-indazole-7-carboxylate | 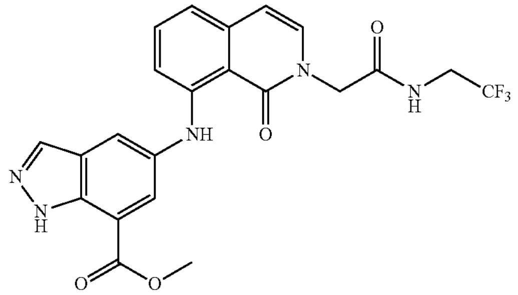 Methyl 5-[(1-oxo-2-{[(2,2,2-trifluoroethyl)carbamoyl]methyl}-1,2-dihydroisoquinolin-8-yl)amino]-1H-indazole-7-carboxylate Example 90 | Method 4: 1.76 min, m/z 474.1 | 13.28 (s, 1H), 11.05 (s, 1H), 8.95 (t, J = 6.2 Hz, 1H), 8.22 (s, 1H), 8.04 (d, J = 1.7 Hz, 1H), 7.90 (d, J = 2.0 Hz, 1H), 7.46-7.38 (m, 2H), 6.89 (d, J = 8.1 Hz, 2H), 6.57 (d, J = 7.3 Hz, 1H), 4.69 (s, 2H), 4.05 – 3.94 (m, 5H). |
| 7-cyclopropyl-1-tetrahydropyran-2-yl-indazol-5-amine | 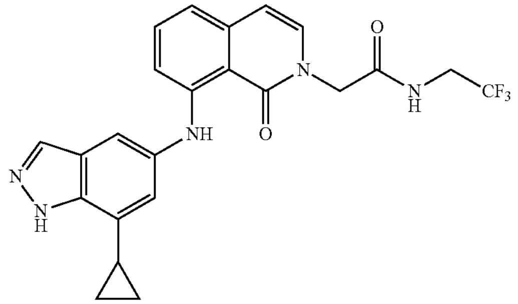 2-[8-[(7-cyclopropyl-1H-indazol-5-yl)amino]-1-oxo-2-isoquinolyl]-N-(2,2,2-trifluoroethyl)acetamide Example 120 | Method 3: 3.85 min, m/z 456.2 | 13.30 (s, 1H), 10.85 (s, 1H), 8.91 (t, J = 6.3 Hz, 1H), 8.03 (s, 1H), 7.46 (d, J = 1.8 Hz, 1H), 7.40-7.33 (m, 2H), 6.84 (d, J = 8.3 Hz, 1H), 6.80 (d, J = 7.6 Hz, 1H), 6.75 (s, J = 1.8 Hz, 1H), 6.52 (d, J = 7.3 Hz, 1H), 4.66 (s, 2H), 3.99 (m, J = 9.8, 6.2 Hz, 2H), 2.31 (m, J = 13.5, 8.6, 5.2 Hz, 1H), 1.09-1.00 (m, 2H), 0.87-0.79 (m, 2H). |
| Intermediate I-14 and 7-fluoro-N-methyl-1-tetrahydropyran-2-yl-indazol-5-amine (MI3) | 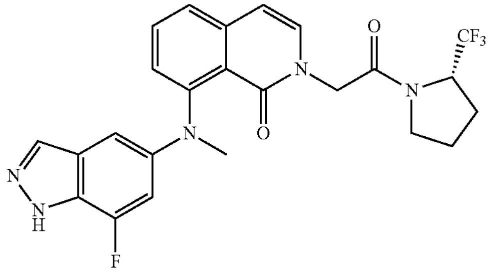 8-[(7-fluoro-1H-indazol-5-yl)-methyl-amino]-2-[2-oxo-2[(2S)-2-(trifluoromethyl)pyrrolidin-1-yl]ethyl]isoquinolin-1-one Example 149 | Method 4: 1.77 min, m/z 488.1 | 13.14 (s, 1H), 7.89 (s, 1H), 7.71 (t, J = 7.8 Hz, 1H), 7.57 (d, J = 7.9 Hz, 1H), 7.34 (d, J = 7.5 Hz, 1H), 7.26 (d, J = 7.6 Hz, 1H), 6.62 (d, J = 7.3 Hz, 1H), 6.55 (s, 1H), 6.35 (d, J = 13.9 Hz, 1H), 5.02-4.56 (m, 3H), 3.74-3.52 (m, 2H), 3.16 (s, 3H), 2.03 (d, J = 32.3 Hz, 4H). |

TABLE 8-continued

| Building block | Structure/Name | UPLCMS[1] ($ES^+$) | $^1H$ NMR (400 MHz, DMSO-$d_6$) |
|---|---|---|---|
| N,3-dimethyl-1-(tetrahydro-2H-pyran-2-yl)-1H-indazol-6- amine (MI2) | 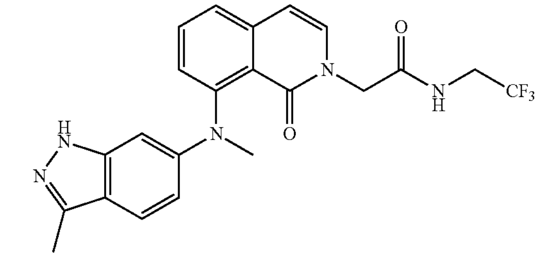 2-[8-[methyl-(3-methyl-1H-indazol-6-yl)amino]-1-oxo-2-isoquinolyl]-N-(2,2,2-trifluoroethyl)acetamide Example 157 | Method 3: 3.35 min, m/z 444.2 | 11.95 (s, 1H), 8.81 (t, J = 6.4 Hz, 1H), 7.77 (t, J = 7.8 Hz, 1H), 7.64 (d, J = 7.9 Hz, 1H), 7.46 (d, J = 7.3 Hz, 1H), 7.32 (s, 1H), 7.30 (s, 1H), 6.66 (d, J = 7.3 Hz, 1H), 6.38 (s, 1H), 6.28 (d, J = 8.8 Hz, 1H), 4.57 (s, 2H), 4.00-3.87 (m, 2H), 3.22 (s, 3H), 2.38 (s, 3H). |

[1]For examples where alternative HPLC and mass spectrometry methods were used, these are referred to in the individual example entries

Example 88, 2-[8-[methyl-(1-methylindazol-5-yl) amino]-1-oxo-2-isoquinolyl]-N-(2,2,2-trifluoroethyl) acetamide Scheme 8

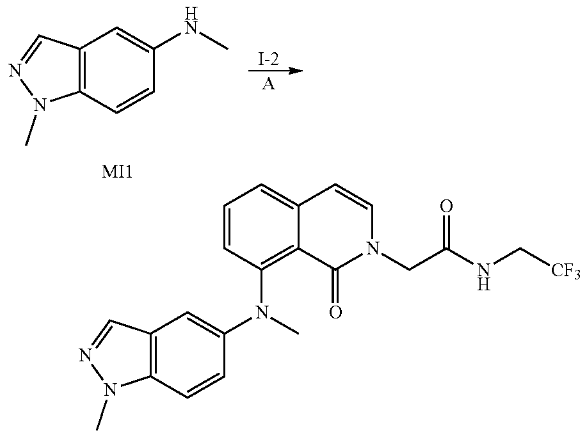

STEP A. A mixture of N,1-dimethyl-1H-indazol-5-amine (MI1, 67 mg, 0.42 mmol), 2-(8-bromo-1-oxoisoquinolin-2(1H)-yl)-N-(2,2,2-trifluoroethyl)acetamide (Intermediate I-2, 150 mg, 0.42 mmol), $Pd_2(dba)_3$ (38 mg, 0.042 mmol), Xantphos (24 mg, 0.042 mmol) and $Cs_2CO_3$ (243 mg, 0.75 mmol) in toluene (2 mL) was stirred at 110° C. under $N_2$ overnight. The mixture was concentrated under reduced pressure and purified by reverse phase prep-HPLC to give 2-[8-[methyl-(1-methylindazol-5-yl)amino]-1-oxo-2-isoquinolyl]-N-(2,2,2-trifluoroethyl)acetamide (25 mg, 0.056 mmol, 14% yield) as a white solid.

LC-MS (Method 3): 3.650 min, m/z, 444.3 [M+H].

$^1H$ NMR (400 MHz, DMSO) δ 8.79 (t, J=6.7 Hz, 1H), 7.81 (s, 1H), 7.67 (t, J=7.8 Hz, 1H), 7.52 (d, J=7.2 Hz, 1H), 7.43 (d, J=7.4 Hz, 1H), 7.33 (d, J=9.2 Hz, 1H), 7.21 (d, J=7.7 Hz, 1H), 6.86 (d, J=2.0 Hz, 1H), 6.69 (dd, J=2.1, 9.1 Hz, 1H), 6.61 (d, J=7.4 Hz, 1H), 4.55 (s, 2H), 3.96 (s, 3H), 3.94-3.86 (m, 2H), 3.19 (s, 3H).

Examples synthesised following the same procedure as example 88 (scheme 8) replacing N,1-dimethyl-1H-indazol-5-amine in step A with the appropriate aniline building block are described in table 9

TABLE 9

| Building block | Structure/Name | UPLCMS[1] ($ES^+$) | $^1H$ NMR (400 MHz, DMSO-$d_6$) |
|---|---|---|---|
| N7,N7,1-trimethylindazole-5,7-diamine | 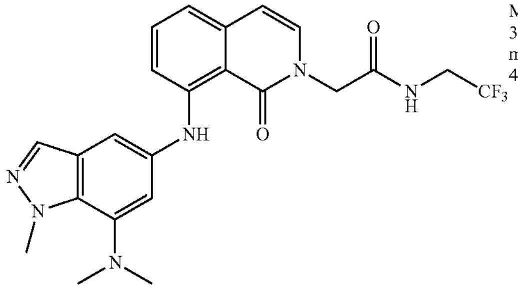 2-[8-[[7-(dimethylamino)-1-methyl-indazol-5-yl]amino]-1-oxo-2-isoquinolyl]-N-(2,2,2-trifluoroethyl)acetamide Example 117 | Method 3: 4.15 min, m/z 473.3 | 10.92 (s, 1H), 8.89 (t, J = 6.3 Hz, 1H), 7.95 (s, 1H), 7.42-7.29 (m, 3H), 6.96 (d, J = 8.2 Hz, 1H), 6.88-6.76 (m, 2H), 6.52 (d, J = 7.3 Hz, 1H), 4.65 (s, 2H), 4.24 (s, 3H), 3.97 (dd, J = 9.8, 6.4 Hz, 2H), 2.75 (s, 6H). |
| 5-amino-1-methyl-indazole-7-carbonitrile | 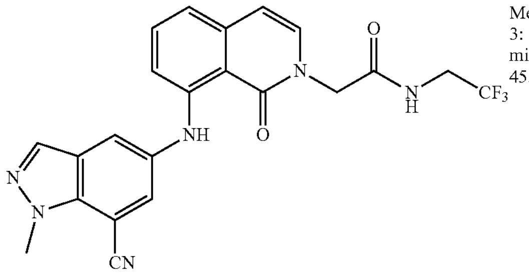 2-[8-[(7-cyano-1-methyl-indazol-5-yl)amino]-1-oxo-2-isoquinolyl]-N-(2,2,2-trifluoroethyl)acetamide Example 119 | Method 3: 3.95 min, m/z 455.2 | 10.99 (s, 1H), 8.91 (t, J = 6.3 Hz, 1H), 8.19 (s, 1H), 8.08 (d, J = 1.9 Hz, 1H), 7.92 (d, J = 1.9 Hz, 1H), 7.42 (t, J = 8.0 Hz, 1H), 7.37 (d, J = 7.4 Hz, 1H), 6.89 (dd, J = 8.0, 3.4 Hz, 2H), 6.55 (d, J = 7.3 Hz, 1H), 4.67 (s, 2H), 4.28 (s, 3H), 3.97 (dd, J = 9.9, 6.5 Hz, 2H). |
| 4-methyl-1H-indazol-6-amine | 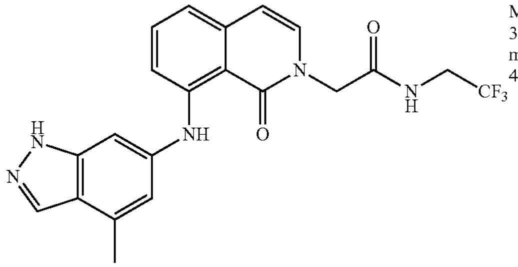 2-[8-[(4-methyl-1H-indazol-6-yl)amino]-1-oxo-2-isoquinolyl]-N-(2,2,2-trifluoroethyl)acetamide Example 147 | Method 3: 3.75 min, m/z 430.3 | 12.80 (s, 1H), 11.16 (s, 1H), 8.91 (t, J = 6.3 Hz, 1H), 8.02 (s, 1H), 7.47 (t, J = 8.0 Hz, 1H), 7.37 (d, J = 7.3 Hz, 1H), 7.25-7.20 (m, 2H), 6.90 (d, J = 7.7 Hz, 1H), 6.77 (s, 1H), 6.56 (d, J = 7.3 Hz, 1H), 4.67 (s, 2H), 3.97 (t, J = 9.8, 5.0 Hz, 2H), 2.52 (s, 3H). |

TABLE 9-continued

| Building block | Structure/Name | UPLCMS[1] ($ES^+$) | $^1H$ NMR (400 MHz, DMSO-$d_6$) |
|---|---|---|---|
| Intermediate I-14 and N, 1-dimethyl-1H-indazol-5-amine (MI1) | 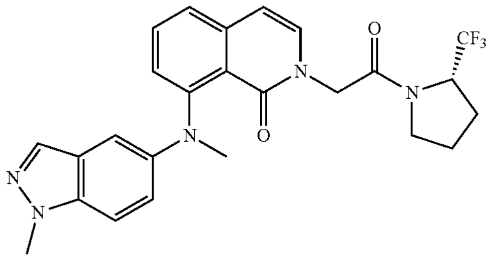 8-[methyl-(1-methylindazol-5-yl)amino]-2-[2-oxo-2-[(2S)-2-(trifluoromethyl)pyrrolidin-1-yl]ethyl]isoquinolin-1-one Example 126 | Method 3: 3.98 min, m/z 430.3 | 7.78 (s, 1H), 7.65 (t, J = 7.5 Hz, 1H), 7.50 (d, J = 7.9 Hz, 1H), 7.32 (m, J = 10.5, 10.0 Hz, 2H), 7.18 (d, J = 7.7 Hz, 1H), 6.83 (s, 1H), 6.65 (d, J = 9.3 Hz, 1H), 6.59 (d, J = 7.3 Hz, 1H), 5.07-4.58 (m, 3H), 3.93 (s, 3H), 3.62 (d, J = 26.3 Hz, 2H), 3.16 (s, 3H), 2.04 (m, J = 38.9 Hz, 4H). |

Example 9, N-isobutyl-2-[8-[(1-methylindazol-5-yl)amino]-1-oxo-2-isoquinolyl]acetamide Scheme 9

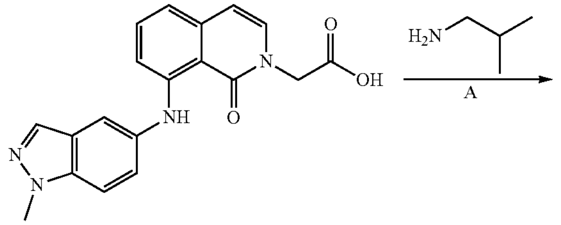

I-6

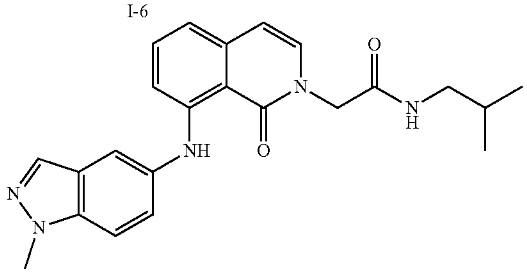

9

STEP A. To a solution of 2-[8-[(1-methylindazol-5-yl)amino]-1-oxo-2-isoquinolyl]acetic acid (Intermediate I-6, 30 mg, 0.09 mmol), Isobutylamine (0.01 mL, 0.1 mmol) and N,N-diisopropylethylamine (0.03 mL, 0.17 mmol) in DMF (2 mL) was added HATU (49 mg, 0.13 mmol) and the mixture was stirred at rt overnight. The mixture was partitioned between EtOAc and water and the layers separated. The organic layer was washed with brine, and the combined aqueous layers were extracted twice with EtOAc, dried over $Na_2SO_4$ and concentrated under reduced pressure. The crude product was purified by normal phase chromatography (4 g column, 70 to 100% EtOAc in petrol) to give N-isobutyl-2-[8-[(1-methylindazol-5-yl)amino]-1-oxo-2-isoquinolyl]acetamide (10 mg, 0.025 mmol, 29% yield) as a white solid.

UPLC-MS ($ES^+$, Method 1): 4.05 min, m/z 404.3 $[M+H]^+$.

$^1$H NMR (400 MHz, DMSO-$d_6$) δ 11.01 (s, 1H), 8.16 (t, J=5.7 Hz, 1H), 7.99 (d, J=0.9 Hz, 1H), 7.68 (d, J=8.9 Hz, 1H), 7.65 (d, J=1.9 Hz, 1H), 7.38 (t, J=8.1 Hz, 1H), 7.34-7.30 (m, 2H), 6.87 (d, J=8.3 Hz, 1H), 6.81 (d, J=7.0 Hz, 1H), 6.51 (d, J=7.4 Hz, 1H), 4.57 (s, 2H), 4.06 (s, 3H), 2.94 (t, J=6.3 Hz, 2H), 1.75-1.68 (m, 1H), 0.87 (d, J=6.7 Hz, 6H).

Examples synthesised following the same procedure as example 9 (scheme 9) replacing 7-isobutlylamine in step A with the appropriate amine building block or I-3 with I-13 are described in table 10.

TABLE 10

| Building block | Structure/Name | UPLCMS[1] ($ES^+$) | $^1$H NMR (400 MHz, DMSO-$d_6$) |
|---|---|---|---|
| 2,2-difluoro-ethylamine | 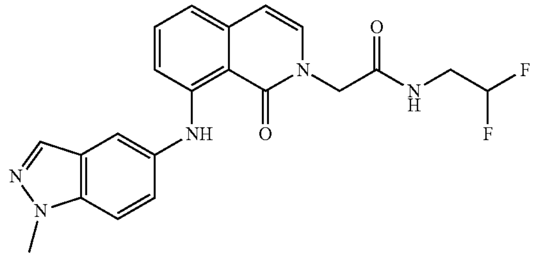 N-(2,2-difluoroethyl)-2-[8-[(1-methylindazol-5-yl)amino]-1-oxo-2-isoquinolyl]acetamide Example 10 | Method 1: 3.83 min, m/z 412.2 [M + H]$^+$ | 10.96 (s, 1H), 8.63 (t, J = 6.1 Hz, 1H), 7.99 (d, J = 0.9 Hz, 1H), 7.68 (d, J = 8.9 Hz, 1H), 7.65 (d, J = 1.9 Hz, 1H), 7.38 (t, J = 8.0 Hz, 1H), 7.35 (d, J = 7.3 Hz, 1H), 7.31 (dd, J = 2.0, 8.9 Hz, 1H), 6.87 (d, J = 7.4 Hz, 1H), 6.82 (d, J = 7.0 Hz, 1H), 6.52 (d, J = 7.4 Hz, 1H), 6.04 (tdd, J = 3.8, 55.8, 55.8 Hz, 1H), 4.64 (s, 2H), 4.06 (s, 3H), 3.60-3.51 (m, 2H). |
| morpholine | 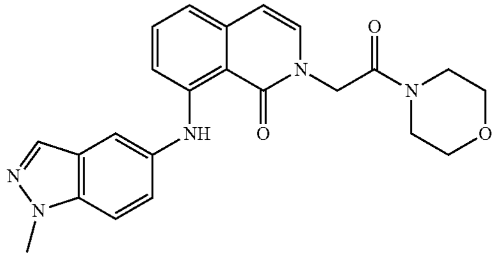 8-[(1-methylindazol-5-yl)amino]-2-(2-morpholino-2-oxo-ethyl)isoquinolin-1-one Example 11 | Method 1: 3.68 min, m/z 418.4 [M + H]$^+$ | 11.01 (s, 1H), 7.99 (d, J = 0.8 Hz, 1H), 7.68 (d, J = 8.8 Hz, 1H), 7.65 (d, J = 1.8 Hz, 1H), 7.39 (t, J = 8.0 Hz, 1H), 7.32 (dd, J = 2.1, 8.7 Hz, 1H), 7.28 (d, J = 7.3 Hz, 1H), 6.89 (d, J = 8.2 Hz, 1H), 6.82 (d, J = 7.7 Hz, 1H), 6.53 (d, J = 7.4 Hz, 1H), 4.87 (s, 2H), 4.06 (s, 3H), 3.70-3.67 (m, 2H), 3.60-3.58 (m, 4H), 3.47-3.44 (m, 2H). |
| 1,1,1-trifluoropropan-2-amine | 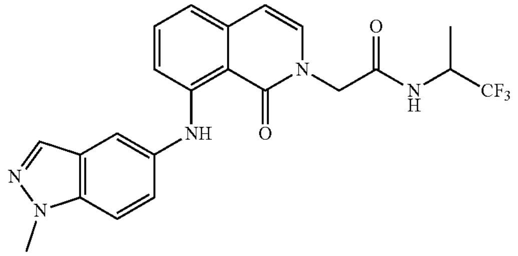 [SMILES: CC(NC(=O)Cn1ccc2cccc(Nc3ccc4c(cnn4C)c3)c2c1=O)C(F)(F)F] 2-[8-[(1-methylindazol-5-y)amino]-1-oxo-2-isoquinolyl]-N-(2,2,2-trifluoro-1-methyl-ethyl)acetamide Example 12 | Method 1: 4.11 min, m/z 444.2 [M + H]$^+$ | 10.94 (s, 1H), 8.83 (d, J = 8.8 Hz, 1H), 7.99 (d, J = 0.9 Hz, 1H), 7.68 (d, J = 8.8 Hz, 1H), 7.65 (d, J = 1.9 Hz, 1H), 7.38 (t, J = 7.8 Hz, 1H), 7.35 (d, J = 7.3 Hz, 1H), 7.32 (q, J = 3.6 Hz, 1H), 6.86 (d, J = 7.4 Hz, 1H), 6.82 (d, J = 7.0 Hz, 1H), 6.52 (d, J = 7.5 Hz, 1H), 4.65 (d, J = 4.5 Hz, 2H), 4.61 (t, J = 7.8 Hz, 1H), 4.06 (s, 3H), 1.29 (d, J = 7.0 Hz, 3H). |

TABLE 10-continued

| Building block | Structure/Name | UPLCMS[1] ($ES^+$) | $^1H$ NMR (400 MHz, DMSO-$d_6$) |
|---|---|---|---|
| N-methylpiperazine | 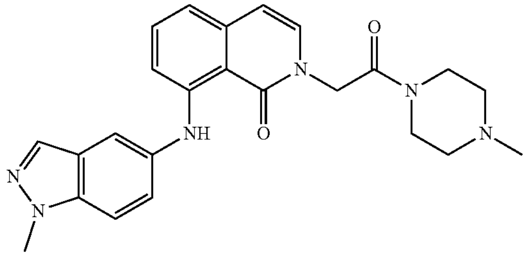 [SMILES: CN1CCN(C(=O)Cn2ccc3cccc(Nc4ccc5c(cnn5C)c4)c3c2=O)CC1] 8-[(1-methylindazol-5-yl)amino]-2-[2-(4-methylpiperazin-1-yl)-2-oxo-ethyl]isoquinolin-1-one Example 13 | Method 1: 3.05 min, m/z 431.4 $[M + H]^+$ | 11.01 (s, 1H), 7.99 (s, 1H), 7.68 (d, J = 8.9 Hz, 1H), 7.65 (d, J = 1.4 Hz, 1H), 7.38 (t, J = 8.0 Hz, 1H), 7.32 (dd, J = 2.0, 8.8 Hz, 1H), 7.28 (d, J = 7.3 Hz, 1H), 6.88 (d, J = 7.8 Hz, 1H), 6.82 (d, J = 7.6 Hz, 1H), 6.52 (d, J = 7.4 Hz, 1H), 4.86 (s, 2H), 4.06 (s, 3H), 3.55 (t, J = 4.8 Hz, 2H), 3.47 (t, J = 4.8 Hz, 2H), 2.40 (t, J = 4.7 Hz, 2H), 2.30 (t, J = 4.4 Hz, 2H), 2.22 (s, 3H). |
| ethylamine | 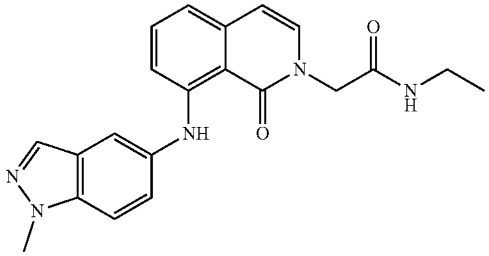 [SMILES: CCNC(=O)Cn1ccc2cccc(Nc3ccc4c(cnn4C)c3)c2c1=O] N-ethyl-2-[8-[(1-methylindazol-5-yl)amino]-1-oxo-2-isoquinolyl]acetamide Example 14 | Method 1: 3.67 min, m/z 376.3 $[M + H]^+$ | 11.00 (s, 1H), 8.17 (t, J = 5.5 Hz, 1H), 7.99 (d, J = 0.9 Hz, 1H), 7.68 (d, J = 8.9 Hz, 1H), 7.65 (d, J = 1.8 Hz, 1H), 7.38 (t, J = 8.0 Hz, 1H), 7.32 (d, J = 7.2 Hz, 1H), 7.32 (dd, J = 2.2, 9.0 Hz, 1H), 6.87 (d, J = 8.3 Hz, 1H), 6.81 (d, J = 7.4 Hz, 1H), 6.51 (d, J = 7.4 Hz, 1H), 4.54 (s, 2H), 4.06 (s, 3H), 3.17-3.09 (m, 2H), 1.06 (t, J = 7.2 Hz, 3H). |
| 4-amino tetrahydropyran | 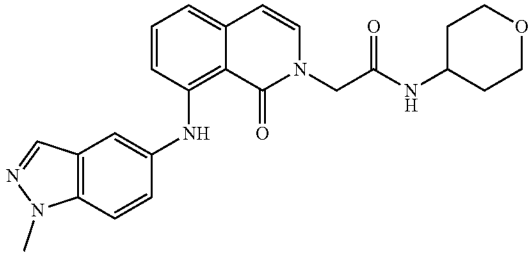 [SMILES: Cn1ncc2cc(Nc3cccc4ccn(CC(=O)NC5CCOCC5)c(=O)c34)ccc21] 2-[8-[(1-methylindazol-5-yl)amino]-1-oxo-2-isoquinolyl]-N-tetrahydropyran-4-yl-acetamide Example 15 | Method 1: 3.68 min, m/z 432.4 $[M + H]^+$ | 10.99 (s, 1H), 8.22 (d, J = 8.0 Hz, 1H), 7.99 (s, 1H), 7.68 (d, J = 9.4 Hz, 1H), 7.65 (s, 1H), 7.38 (t, J = 8.1 Hz, 1H), 7.32 (d, J = 7.3 Hz, 1H), 7.32 (dd, J = 2.6, 9.4 Hz, 1H), 6.86 (d, J = 8.3 Hz, 1H), 6.81 (d, J = 7.3 Hz, 1H), 6.51 (d, J = 7.4 Hz, 1H), 4.56 (s, 2H), 4.06 (s, 3H), 3.86-3.77 (m, 3H), 3.39-3.35 (m, 2H), 1.77-1.70 (m, 2H), 1.49-1.38 (m, 2H). |
| 1-cyclopropyl methanamine | 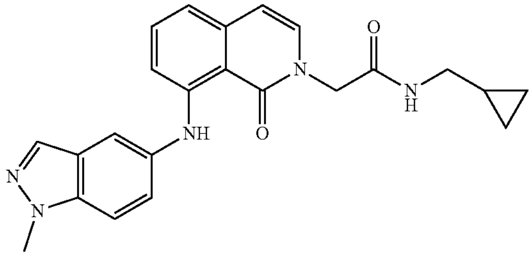 [SMILES: Cn1ncc2cc(Nc3cccc4ccn(CC(=O)NCC5CC5)c(=O)c34)ccc21] N-(cyclopropylmethyl)-2-[8-[(1-methylindazol-5-yl)aminol-1-oxo-2-isoquinolyl]acetamide Example 16 | Method 1: 3.95 min, m/z 402.3 $[M + H]^+$ | 11.00 (s, 1H), 8.28 (t, J = 5.7 Hz, 1H), 7.99 (d, J = 0.8 Hz, 1H), 7.68 (d, J = 8.9 Hz, 1H), 7.65 (d, J = 1.8 Hz, 1H), 7.38 (t, J = 7.9 Hz, 1H), 7.33 (d, J = 7.3 Hz, 2H), 7.32 (dd, J = 2.6, 8.4 Hz, 2H), 6.87 (d, J = 7.4 Hz, 1H), 6.82 (d, J = 7.1 Hz, 1H), 6.51 (d, J = 7.4 Hz, 1H), 4.57 (s, 2H), 4.06 (s, 3H), 3.00 (t, J = 6.2 Hz, 2H), 0.94-0.90 (m, 1H), 0.46-0.41 (m, 2H), 0.21-0.16 (m, 2H). |

TABLE 10-continued

| Building block | Structure/Name | UPLCMS[1] ($ES^+$) | $^1H$ NMR (400 MHz, DMSO-$d_6$) |
|---|---|---|---|
| cyclo-propylamine | 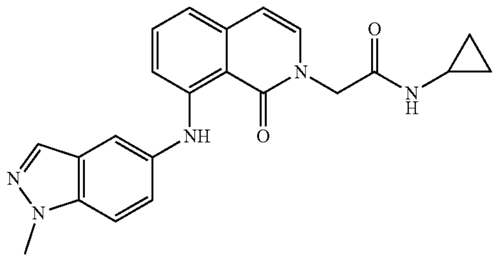 [SMILES: Cn1ncc2cc(Nc3cccc4ccn(CC(=O)NC5CC5)c(=O)c34)ccc21] N-cyclopropyl-2-[8-[(1-methylindazol-5-yl)amino]-1-oxo-2-isoquinolyl]acetamide Example 17 | Method 1: 3.75 min, m/z 388.3 $[M + H]^+$ | 10.99 (s, 1H), 8.28 (d, J = 4.3 Hz, 1H), 7.99 (s, 1H), 7.68 (d, J = 8.8 Hz, 1H), 7.65 (s, 1H), 7.38 (t, J = 8.0 Hz, 1H), 7.33 - 7.30 (m, 2H), 6.87 (d, J = 8.2 Hz, 1H), 6.81 (d, J = 7.7 Hz, 1H), 6.51 (d, J = 7.4 Hz, 1H), 4.50 (s, 2H), 4.06 (s, 3H), 2.01-1.98 (m, 1H), 0.67-0.61 (m, 2H), 0.46-0.41 (m, 2H). |
| 1-methylpiperidin-4-amine | 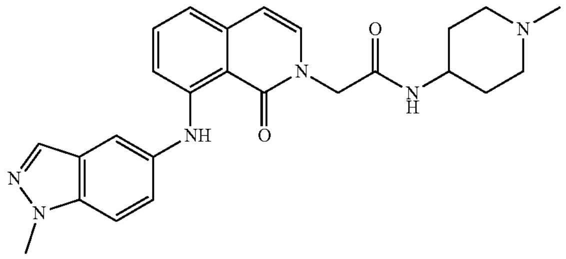 [SMILES: CN1CCC(NC(=O)Cn2ccc3cccc(Nc4ccc5c(cnn5C)c4)c3c2=O)CC1] 2-[8-[(1-methylindazol-5-y)amino]-1-oxo-2-isoquinolyl]-N-(1-methyl-4-piperidyl)acetamide Example 18 | Method 1: 3.00 min, m/z 445.5 $[M + H]^+$ | 10.99 (s, 1H), 8.15 (d, J = 7.6 Hz, 1H), 7.99 (s, 1H), 7.67 (d, J = 8.9 Hz, 1H), 7.65 (d, J = 1.8 Hz, 1H), 7.37 (t, J = 8.0 Hz, 1H), 7.33-7.30 (m, 2H), 6.86 (d, J = 8.3 Hz, 1H), 6.81 (d, J = 7.2 Hz, 1H), 6.50 (d, J = 7.4 Hz, 1H), 4.55 (s, 2H), 4.06 (s, 3H), 3.57-3.49 (m, 1H), 2.76-2.69 (m, 2H), 2.16 (s, 3H), 2.02-1.94 (m, 2H), 1.76-1.72 (m, 2H), 1.49-1.40 (m, 2H). |
| (1S)-2,2,2-trifluoro-1-methyl-ethylamine | 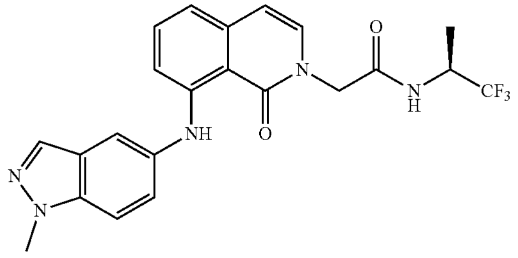 [SMILES: C[C@H](NC(=O)Cn1ccc2cccc(Nc3ccc4c(cnn4C)c3)c2c1=O)C(F)(F)F] 2-[8-[(1-methylindazol-5-yl)amino]-1-oxo-2-isoquinolyl]-N-[(1S)-2,2,2-trifluoro-1-methyl-ethyl]acetamide Example 19 | Method 1: 4.09 min, m/z 444.1 $[M + H]^+$ | 10.94 (s, 1H), 8.83 (d, J = 8.9 Hz, 1H), 7.99 (d, J = 0.9 Hz, 1H), 7.69-7.65 (m, 2H), 7.41-7.30 (m, 3H), 6.86 (d, J = 8.3 Hz, 1H), 6.82 (d, J = 7.0 Hz, 1H), 6.52 (d, J = 7.4 Hz, 1H), 4.67-4.60 (m, 3H), 4.06 (s, 3H), 1.29 (d, J = 7.0 Hz, 3H). |
| (1R)-2,2,2-trifluoro-1-methyl-ethylamine | 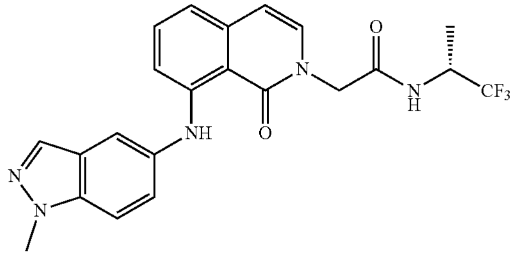 [SMILES: C[C@@H](NC(=O)Cn1ccc2cccc(Nc3ccc4c(cnn4C)c3)c2c1=O)C(F)(F)F] 2-[8-[(1-methylindazol-5-yl)amino]-1-oxo-2-isoquinolyl]-N-[(1R)-2,2,2-trifluoro-1-methyl-ethyl]acetamide Example 20 | Method 1: 4.11 min, m/z 444.2 $[M + H]^+$ | 10.94 (s, 1H), 8.83 (d, J = 8.9 Hz, 1H), 7.99 (d, J = 0.9 Hz, 1H), 7.68 (d, J = 8.8 Hz, 1H), 7.66 (d, J = 1.6 Hz, 1H), 7.38 (t, J = 8.1 Hz, 1H), 7.35 (d, J = 7.2 Hz, 1H), 7.32 (dd, J = 2.2, 8.9 Hz, 1H), 6.86 (d, J = 8.3 Hz, 1H), 6.82 (d, J = 7.0 Hz, 1H), 6.52 (d, J = 7.4 Hz, 1H), 4.67-4.60 (m, 3H), 4.06 (s, 3H), 1.29 (d, J = 7.0 Hz, 3H). |

TABLE 10-continued

| Building block | Structure/Name | UPLCMS[1] ($ES^+$) | $^1H$ NMR (400 MHz, DMSO-$d_6$) |
| --- | --- | --- | --- |
| 1-(trifluoromethyl) cyclo-propylamine | 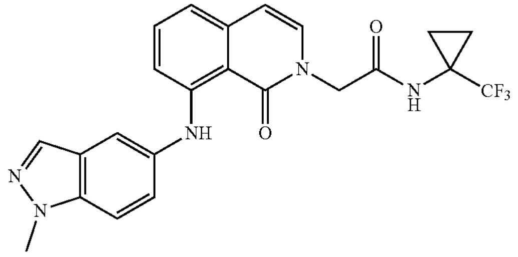 [SMILES: Cn1ncc2cc(Nc3cccc4ccn(CC(=O)NC5(C(F)(F)F)CC5)c(=O)c34)ccc21] 2-[8-[(1-methylindazol-5-yl)amino]-1-oxo-2-isoquinolyl]-N-[1-(trifluoromethyl)cyclopropyl]acetamide Example 21 | Method 1: 4.07 min, m/z 456.2 $[M + H]^+$ | 10.93 (s, 1H), 9.04 (s, 1H), 7.99 (s, 1H), 7.68 (d, J = 8.9 Hz, 1H), 7.65 (d, J = 1.8 Hz, 1H), 7.38 (t, J = 8.0 Hz, 1H), 7.34 – 7.30 (m, 2H), 6.86 (d, J = 8.3 Hz, 1H), 6.81 (d, J = 7.1 Hz, 1H), 6.52 (d, J = 7.4 Hz, 1H), 4.58 (s, 2H), 4.06 (s, 3H), 1.28-1.23 (m, 2H), 1.08-1.02 (m, 2H). |
| N-methyl-(2,2,2-trifluoroethyl) amine | 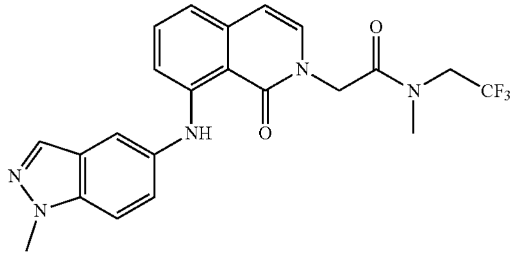 [SMILES: CN(CC(F)(F)F)C(=O)Cn1ccc2cccc(Nc3ccc4c(cnn4C)c3)c2c1=O] N-methyl-2-[8-[(1-methylindazol-5-yl)amino]-1-oxo-2-isoquinolyl]-N-(2,2,2-trifluoroethyl)acetamide Example 23 | Method 1: 4.13 min, m/z 444.3 $[M + H]^+$ | 10.97 (s, 1H), 7.99 (s, 1H), 7.68 (d, J = 8.8 Hz, 1H), 7.65 (d, J = 1.5 Hz, 1H), 7.39 (t, J = 8.0 Hz, 1H), 7.33-7.27 (m, 2H), 6.88 (d, J = 8.2 Hz, 1H), 6.82 (d, J = 7.7 Hz, 1H), 6.54 (d, J = 7.4 Hz, 1H), 4.96 (s, 2H), 4.22 (q, J = 9.6 Hz, 2H), 4.06 (s, 3H), 3.23 (s, 3H). |
| 3-aminopyridine | 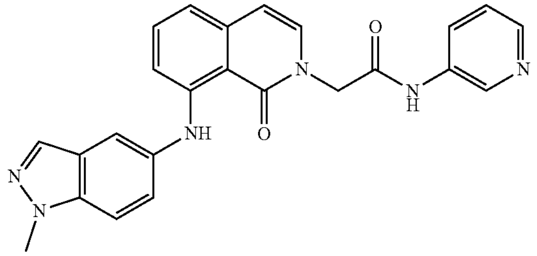 [SMILES: Cn1ncc2cc(Nc3cccc4ccn(CC(=O)Nc5cccnc5)c(=O)c34)ccc21] 2-[8-[(1-methylindazol-5-yl)amino]-1-oxo-2-isoquinolyl]-N-(3-pyridyl)acetamide Example 24 | Method 1: 3.34 min, m/z 425.4 $[M + H]^+$ | 10.92 (s, 1H), 10.68 (s, 1H), 8.81 (s, 1H), 8.31 (d, J = 4.6 Hz, 1H), 8.08 (d, J = 8.2 Hz, 1H), 7.98 (d, J = 0.9 Hz, 1H), 7.68 – 7.65 (m, 2H), 7.44-7.38 (m, 3H), 7.31 (dd, J = 2.1, 8.8 Hz, 1H), 6.88 (d, J = 8.3 Hz, 1H), 6.84 (d, J = 7.0 Hz, 1H), 6.57 (d, J = 7.7 Hz, 1H), 4.83 (s, 2H), 4.05 (s, 3H). |
| 5-aminopyrimidine | 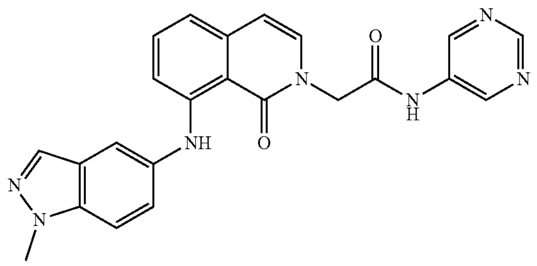 [SMILES: Cn1ncc2cc(Nc3cccc4ccn(CC(=O)Nc5cncnc5)c(=O)c34)ccc21] 2-[8-[(1-methylindazol-5-yl)amino]-1-oxo-2-isoquinolyl]-N-pyrimidin-5-yl-acetamide Example 25 | Method 1: 3.68 min, m/z 426.2 $[M + H]^+$ | 10.91 (s, 1H), 10.87 (s, 1H), 9.03 (s, 2H), 8.92 (s, 1H), 7.98 (d, J = 0.8 Hz, 1H), 7.68-7.64 (m, 2H), 7.44-7.38 (m, 2H), 7.31 (dd, J = 2.0, 8.9 Hz, 1H), 6.88 (d, J = 8.3 Hz, 1H), 6.85 (d, J = 7.7 Hz, 1H), 6.58 (d, J = 7.4 Hz, 1H), 4.86 (s, 2H), 4.05 (s, 3H). |

TABLE 10-continued

| Building block | Structure/Name | UPLCMS[1] ($ES^+$) | $^1H$ NMR (400 MHz, DMSO-$d_6$) |
|---|---|---|---|
| 4-aminopyridine | 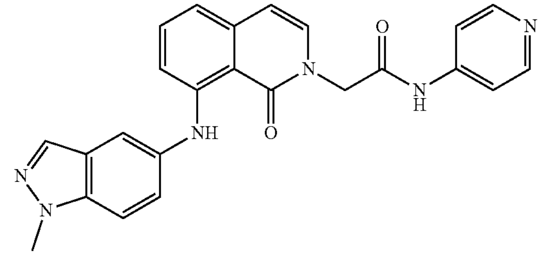 [SMILES: Cn1ncc2cc(Nc3cccc4ccn(CC(=O)Nc5ccncc5)c(=O)c34)ccc21] 2-[8-[(1-methylindazol-5-yl)amino]-1-oxo-2-isoquinolyl]-N-(4-pyridyl)acetamide Example 26 | Method 1: 3.25 min, m/z 425.4 $[M + H]^+$ | 10.91 (s, 1H), 10.79 (s, 1H), 8.47-8.44 (m, 2H), 7.98 (d, J = 0.8 Hz, 1H), 7.68-7.65 (m, 2H), 7.59-7.56 (m, 2H), 7.43-7.38 (m, 2H), 7.31 (dd, J = 2.1, 8.8 Hz, 1H), 6.88 (d, J = 8.4 Hz, 1H), 6.85 (d, J = 7.0 Hz, 1H), 6.58 (d, J = 7.4 Hz, 1H), 4.83 (s, 2H), 4.05 (s, 3H). |
| 3-methoxyaniline | 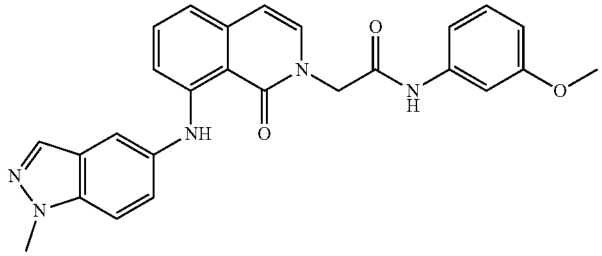 [SMILES: COc1cccc(NC(=O)Cn2ccc3cccc(Nc4ccc5c(cnn5C)c4)c3c2=O)c1] N-(3-methoxyphenyl)-2-[8-[(1-methylindazol-5-yl)amino]-1-oxo-2-isoquinolyl]acetamide Example 27 | Method 1: 4.27 min, m/z 454.2 $[M + H]^+$ | 10.96 (s, 1H), 10.37 (s, 1H), 7.98 (d, J = 0.9 Hz, 1H), 7.68-7.65 (m, 2H), 7.42-7.37 (m, 2H), 7.35-7.30 (m, 2H), 7.23 (t, J = 8.1 Hz, 1H), 7.13-7.11 (m, 1H), 6.88 (d, J = 8.3 Hz, 1H), 6.84 (d, J = 7.0 Hz, 1H), 6.65 (dd, J = 2.7, 8.1 Hz, 1H), 6.56 (d, J = 7.4 Hz, 1H), 4.78 (s, 2H), 4.05 (s, 3H), 3.72 (s, 3H). |
| 3-fluoroaniline | 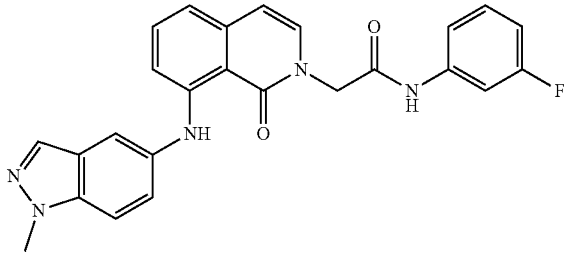 [SMILES: Cn1ncc2cc(Nc3cccc4ccn(CC(=O)Nc5cccc(F)c5)c(=O)c34)ccc21] N-(3-methoxyphenyl)-2-[8-[(1-methylindazol-5-yl)amino]-1-oxo-2-isoquinolyl]acetamide Example 29 | Method 1: 4.37 min, m/z 442.1 $[M + H]^+$ | 10.93 (s, 1H), 10.61 (s, 1H), 7.98 (d, J = 0.8 Hz, 1H), 7.68 – 7.64 (m, 2H), 7.60 (td, J = 2.2, 11.7 Hz, 1H), 7.42-7.39 (m, 2H), 7.37 (dd, J = 2.2, 6.2 Hz, 1H), 7.35-7.29 (m, 2H), 6.93 – 6.86 (m, 2H), 6.84 (d, J = 7.9 Hz, 1H), 6.57 (d, J = 7.7 Hz, 1H), 4.80 (s, 2H), 4.05 (s, 3H). |
| 4-(trifluoromethyl) aniline | 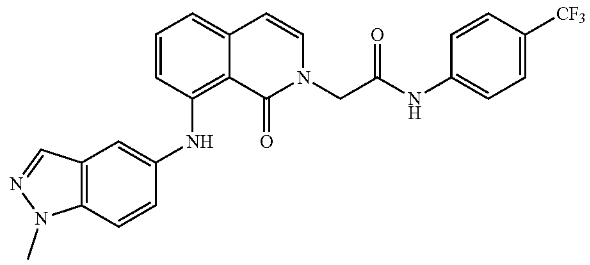 [SMILES: Cn1ncc2cc(Nc3cccc4ccn(CC(=O)Nc5ccc(C(F)(F)F)cc5)c(=O)c34)ccc21] 2-[8-[(1-methylindazol-5-yl)amino]-1-oxo-2-isoquinolyl]-N-[4-(trifluoromethyl)phenyl]acetamide Example 30 | Method 1: 4.68 min, m/z 492.1 $[M + H]^+$ | 10.93 (s, 1H), 10.76 (s, 1H), 7.98 (s, 1H), 7.82 (d, J = 8.5 Hz, 2H), 7.73-7.65 (m, 4H), 7.44-7.38 (m, 2H), 7.31 (dd, J = 2.0, 8.8 Hz, 1H), 6.88 (d, J = 8.3 Hz, 1H), 6.85 (d, J = 7.5 Hz, 1H), 6.57 (d, J = 7.4 Hz, 1H), 4.83 (s, 2H), 4.05 (s, 3H). |

TABLE 10-continued

| Building block | Structure/Name | UPLCMS[1] ($ES^+$) | $^1H$ NMR (400 MHz, DMSO-$d_6$) |
| --- | --- | --- | --- |
| 5-(trifluoromethyl) pyridin-3-amine | 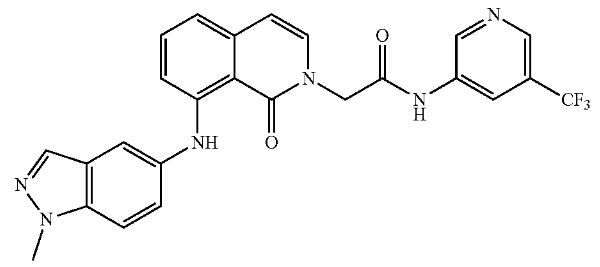 [SMILES: Cn1ncc2cc(Nc3cccc4ccn(CC(=O)Nc5cncc(C(F)(F)F)c5)c(=O)c34)ccc21] 2-[8-[(1-methylindazol-5-yl)amino]-1-oxo-2-isoquinolyl]-N-[5-(trifluromethyl)-3-pyridyl]acetamide Example 31 | Method 1: 4.37 min, m/z 493.2 $[M + H]^+$ | 11.04 (s, 1H), 10.91 (s, 1H), 8.96 (d, J = 2.4 Hz, 1H), 8.69 (s, 1H), 8.52 (t, J = 2.3 Hz, 1H), 7.98 (d, J = 0.9 Hz, 1H), 7.69-7.65 (m, 2H), 7.44-7.38 (m, 2H), 7.31 (dd, J = 2.0, 8.9 Hz, 1H), 6.88 (d, J = 8.3 Hz, 1H), 6.85 (d, J = 7.0 Hz, 1H), 6.58 (d, J = 7.4 Hz, 1H), 4.86 (s, 2H), 4.05 (s, 3H). |
| 3-acetylaniline | 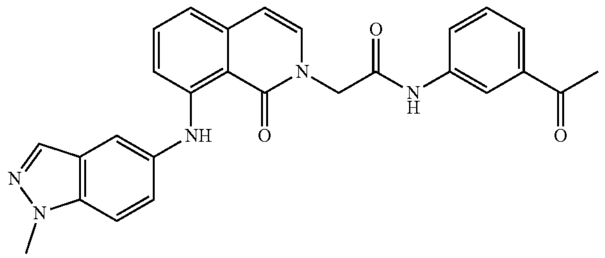 [SMILES: CC(=O)c1cccc(NC(=O)Cn2ccc3cccc(Nc4ccc5c(cnn5C)c4)c3c2=O)c1] N-(3-acetylphenyl)-2-[8-[(1-methylindazol-5-yl)amino]-1-oxo-2-isoquinolyl]acetamide Example 32 | Method 1: 3.93 min, m/z 466.2 $[M + H]^+$ | 10.94 (s, 1H), 10.61 (s, 1H), 8.22 (t, J = 1.8 Hz, 1H), 7.98 (d, J = 0.7 Hz, 1H), 7.85 (dd, J = 2.8, 8.2 Hz, 1H), 7.70-7.64 (m, 3H), 7.50 (t, J = 7.9 Hz, 1H), 7.44-7.38 (m, 2H), 7.31 (dd, J = 2.0, 8.8 Hz, 1H), 6.88 (d, J = 8.0 Hz, 1H), 6.84 (d, J = 7.3 Hz, 1H), 6.57 (d, J = 7.5 Hz, 1H), 4.81 (s, 2H), 4.05 (s, 3H), 2.56 (s, 3H). |
| 1-cyclopropyl-2,2,2-trifluoro-ethylamine | 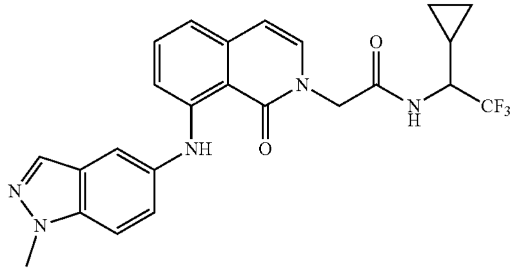 [SMILES: Cn1ncc2cc(Nc3cccc4ccn(CC(=O)NC(C5CC5)C(F)(F)F)c(=O)c34)ccc21] N-(1-cyclopropyl-2,2,2-trifluoro-ethly)-2-[8-[(1-methylindazol-5-yl)amino]-1-oxo-2-isoquinolyl]acetamide Example 33 | Method 1: 4.15 min, m/z 470.2 $[M + H]^+$ | 10.97 (s, 1H), 8.87 (d, J = 9.3 Hz, 1H), 7.99 (s, 1H), 7.70-7.64 (m, 2H), 7.42-7.30 (m, 3H), 6.84 (dd, J = 8.5, 19.9 Hz, 2H), 6.52 (d, J = 7.1 Hz, 1H), 4.68 (q, J = 13.8 Hz, 2H), 4.06 (s, 3H), 1.16-1.07 (m, 1H), 0.66-0.50 (m, 3H), 0.39-0.33 (m, 2H). |
| 3-amino-1-methylpyrazole | 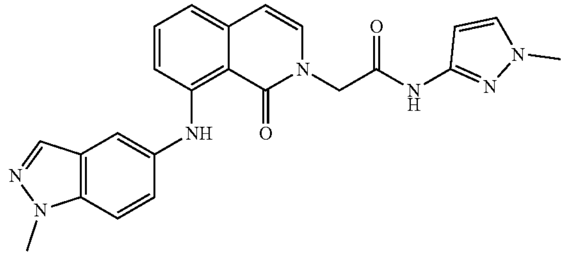 [SMILES: Cn1ccc(NC(=O)Cn2ccc3cccc(Nc4ccc5c(cnn5C)c4)c3c2=O)n1] 2-[8-[(1-methylindazol-5-yl)amino]-1-oxo-2-isoquinolyl]-N-(1-methylpyrazol-3-yl)acetamide Example 34 | Method 1: 3.67 min, m/z 428.3 $[M + H]^+$ | 10.96 (s, 1H), 10.80 (s, 1H), 7.98 (d, J = 0.9 Hz, 1H), 7.68-7.65 (m, 2H), 7.55 (d, J = 2.2 Hz, 1H), 7.41-7.36 (m, 2H), 7.31 (dd, J = 2.0, 8.9 Hz, 1H), 6.87 (d, J = 8.3 Hz, 1H), 6.82 (d, J = 7.1 Hz, 1H), 6.54 (d, J = 7.4 Hz, 1H), 6.40 (d, J = 2.2 Hz, 1H), 4.75 (s, 2H), 4.05 (s, 3H), 3.75 (s, 3H). |

TABLE 10-continued

| Building block | Structure/Name | UPLCMS[1] ($ES^+$) | $^1H$ NMR (400 MHz, DMSO-$d_6$) |
|---|---|---|---|
| 2,2,2-trifluoro-1-phenyl-ethylamine | 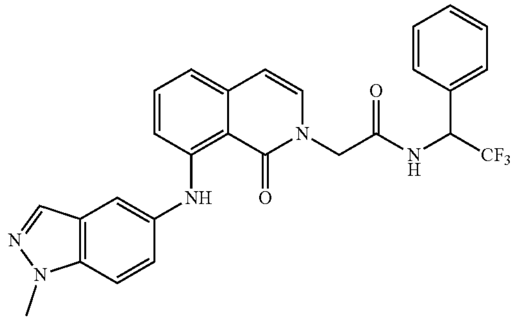 [SMILES: Cn1ncc2cc(Nc3cccc4ccn(CC(=O)NC(c5ccccc5)C(F)(F)F)c(=O)c34)ccc21] 2-[8-[(1-methylindazol-5-yl)amino]-1-oxo-2-isoquinolyl]-N-(2,2,2-trifluoro-1-phenyl-ethyl)acetamide Example 35 | Method 1: 4.49 min, m/z 506.2 $[M + H]^+$ | 10.90 (s, 1H), 9.53 (d, J = 9.4 Hz, 1H), 7.98 (s, 1H), 7.68-7.60 (m, 4H), 7.48-7.35 (m, 5H), 7.29 (dd, J = 2.2, 9.2 Hz, 1H), 6.83 (ddd, J = 7.8, 7.8, 7.8 Hz, 2H), 6.51 (d, J = 7.6 Hz, 1H), 5.85-5.76 (m, 1H), 4.76 (dd, J = 16.2, 21.2 Hz, 2H), 4.05 (s, 3H). |
| 5-amino-1-methylpyrazole | 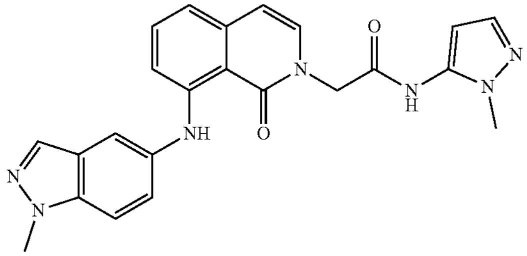 [SMILES: Cn1nccc1NC(=O)Cn1ccc2cccc(Nc3ccc4c(cnn4C)c3)c2c1=O] 2-[8-[(1-methylindazol-5-yl)amino]-1-oxo-2-isoquinolyl]-N-(2-methylpyrazol-3-yl)acetamide Example 36 | Method 1: 3.70 min, m/z 428.3 $[M + H]^+$ | 10.95 (s, 1H), 10.39 (s, 1H), 7.99 (s, 1H), 7.69-7.65 (m, 2H), 7.43-7.37 (m, 2H), 7.34-7.30 (m, 2H), 6.88 (d, J = 8.3 Hz, 1H), 6.84 (d, J = 7.5 Hz, 1H), 6.56 (d, J = 7.4 Hz, 1H), 6.21 (d, J = 1.8 Hz, 1H), 4.84 (s, 2H), 4.06 (s, 3H), 3.72 (s, 3H). |
| 4-aminoisoxazole | 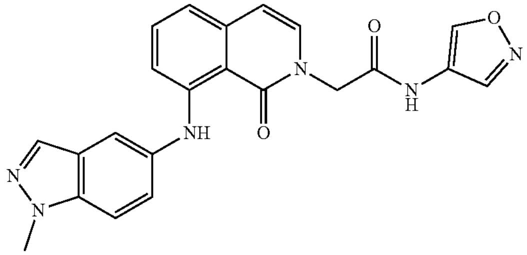 N-isoxazol-4-yl-2-[8-[(1-methylindazol-5-yl)amino]-1-oxo-2-isoquinolyl]acetamide Example 37 | Method 1: 3.86 min, m/z 425.1 $[M + H]^+$ | 10.91 (s, 1H), 10.70 (s, 1H), 9.11 (s, 1H), 8.67 (s, 1H), 7.98 (d, J = 0.9 Hz, 1H), 7.68-7.64 (m, 2H), 7.42-7.37 (m, 2H), 7.31 (dd, J = 2.0, 8.9 Hz, 1H), 6.88 (d, J = 8.2 Hz, 1H), 6.84 (d, J = 7.7 Hz, 1H), 6.57 (d, J = 7.4 Hz, 1H), 4.78 (s, 2H), 4.05 (s, 3H). |
| aniline | 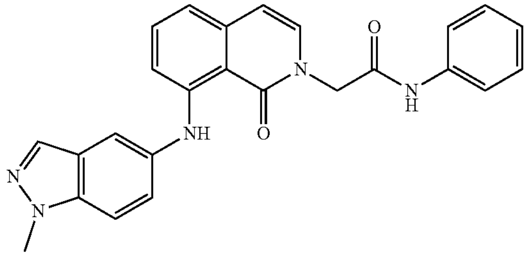 [SMILES: Cn1ncc2cc(Nc3cccc4ccn(CC(=O)Nc5ccccc5)c(=O)c34)ccc21] 2-[8-[(1-methylindazol-5-yl)amino]-1-oxo-2-isoquinolyl]-N-phenyl-acetamide Example 39 | Method 1: 4.27 min, m/z 424.1 $[M + H]^+$ | 10.96 (s, 1H), 10.37 (s, 1H), 7.98 (d, J = 0.8 Hz, 1H), 7.68-7.65 (m, 2H), 7.61 (d, J = 7.6 Hz, 2H), 7.43-7.37 (m, 2H), 7.35-7.30 (m, 3H), 7.07 (t, J = 7.4 Hz, 1H), 6.88 (d, J = 8.3 Hz, 1H), 6.84 (d, J = 7.0 Hz, 1H), 6.56 (d, J = 7.4 Hz, 1H), 4.79 (s, 2H), 4.05 (s, 3H). |

TABLE 10-continued

| Building block | Structure/Name | UPLCMS[1] ($ES^+$) | $^1H$ NMR (400 MHz, DMSO-$d_6$) |
|---|---|---|---|
| 4-amino-1-methylpyrazole | 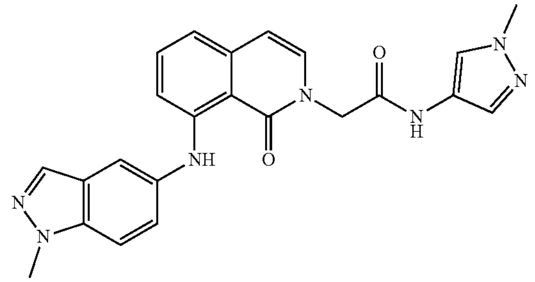 [SMILES: Cn1cc(NC(=O)Cn2ccc3cccc(Nc4ccc5c(cnn5C)c4)c3c2=O)cn1] 2-[8-[(1-methylindazol-5-yl)amino]-1-oxo-2-isoquinolyl]-N-(1-methylpyrazol-4-yl)acetamide Example 41 | Method 1: 3.66 min, m/z 428.2 $[M + H]^+$ | 10.96 (s, 1H), 10.33 (s, 1H), 7.98 (d, J = 1.0 Hz, 1H), 7.83 (s, 1H), 7.68-7.64 (m, 2H), 7.43 (d, J = 0.6 Hz, 1H), 7.41-7.37 (m, 2H), 7.31 (dd, J = 2.1, 9.0 Hz, 1H), 6.88 (d, J = 9.1 Hz, 1H), 6.83 (d, J = 7.0 Hz, 1H), 6.55 (d, J = 7.6 Hz, 1H), 4.72 (s, 2H), 4.05 (s, 3H), 3.78 (s, 3H). |
| 1-(trifluoromethyl) cyclopentamine | 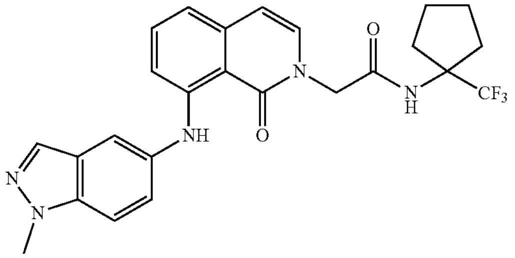 [SMILES: Cn1ncc2cc(Nc3cccc4ccn(CC(=O)NC5(C(F)(F)F)CCCC5)c(=O)c34)ccc21] 2-[8-[(1-methylindazol-5-yl)amino]-1-oxo-2-isoquinolyl]-N-[1-(trifluoromethyl)cyclopentyl]acetamide Example 42 | Method 1: 4.59 min, m/z 484.2 $[M + H]^+$ | 10.97 (s, 1H), 8.29 (s, 1H), 7.99 (s, 1H), 7.70-7.64 (m, 2H), 7.38 (t, J = 7.9 Hz, 1H), 7.34-7.30 (m, 2H), 6.86 (d, J = 8.2 Hz, 2H), 6.81 (d, J = 7.4 Hz, 2H), 6.51 (d, J = 7.3 Hz, 1H), 4.61 (s, 2H), 4.06 (s, 3H), 1.92-1.70 (m, 8H). |
| 2-(trifluoromethyl) morpholine | 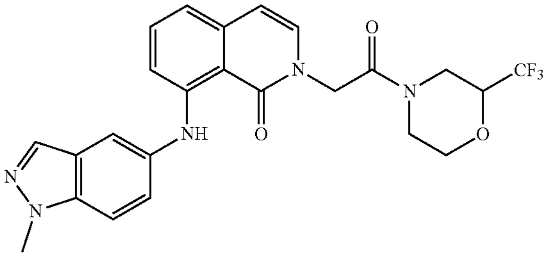 [SMILES: Cn1ncc2cc(Nc3cccc4ccn(CC(=O)N5CCOC(C(F)(F)F)C5)c(=O)c34)ccc21] 8-[(1-methylindazol-5-yl)aminio]-2-[2-oxo-2-[2-(trifluoromethyl)morpholin-4-yl]ethyl]isoquinolin-1-one Example 43 | Method 1: 4.23 min, m/z 486.2 $[M + H]^+$ | 10.99 (s, 1H), 7.99 (d, J = 0.7 Hz, 1H), 7.70-7.64 (m, 2H), 7.39 (t, J = 8.0 Hz, 1H), 7.31 (dd, J = 2.0, 8.8 Hz, 1H), 7.26 (t, J = 8.6 Hz, 1H), 6.89 (d, J = 8.3 Hz, 1H), 6.83 (d, J = 7.3 Hz, 1H), 6.54 (d, J = 7.4 Hz, 1H), 5.03-4.82 (m, 2H), 4.36-3.94 (m, 9H), 3.75-3.55 (m, 1H). |
| 3,3,3-trifluoro-propylamine | 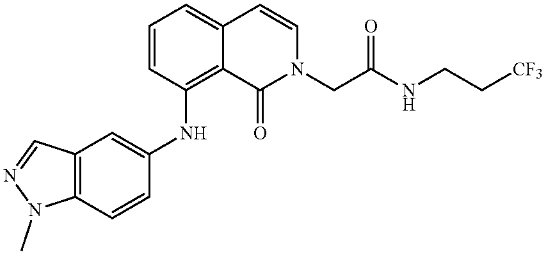 [SMILES: Cn1ncc2cc(Nc3cccc4ccn(CC(=O)NCCC(F)(F)F)c(=O)c34)ccc21] 2-[8-[(1-methylindazol-5-yl)amino]-1-oxo-2-isoquinolyl]-N-(3,3,3-trifluoropropyl)acetamide Example 44 | Method 1: 4.03 min, m/z 444.1 $[M + H]^+$ | 10.97 (s, 1H), 8.41 (t, J = 5.9 Hz, 1H), 7.99 (d, J = 1.0 Hz, 1H), 7.68 (d, J = 8.8 Hz, 1H), 7.65 (d, J = 1.8 Hz, 1H), 7.38 (t, J = 7.9 Hz, 1H), 7.34-7.30 (m, 2H), 6.87 (d, J = 7.3 Hz, 1H), 6.82 (d, J = 7.1 Hz, 1H), 6.52 (d, J = 7.5 Hz, 1H), 4.57 (s, 2H), 4.06 (s, 3H), 2.01 (t, J = 7.5 Hz, 2H), 0.86 (t, J = 6.9 Hz, 2H). |

TABLE 10-continued

| Building block | Structure/Name | UPLCMS[1] ($ES^+$) | $^1H$ NMR (400 MHz, DMSO-$d_6$) |
|---|---|---|---|
| (1S)-1-(trifluoromethyl) propylamine | 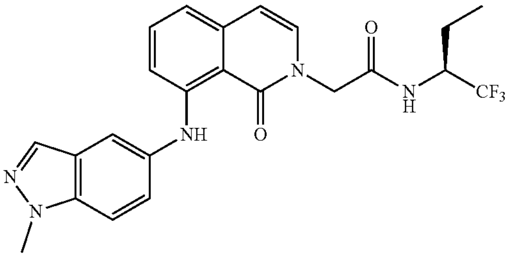 [SMILES: CC[C@H](NC(=O)Cn1ccc2cccc(Nc3ccc4c(cnn4C)c3)c2c1=O)C(F)(F)F] 2-[8-[(1-methylindazol-5-yl)amino]-1-oxo-2-isoquinolyl]-N-[(1S)-1-(trifluoromethyl)propyl] acetamide Example 45 | Method 1: 4.43 min, m/z 458.1 $[M + H]^+$ | 10.97 (s, 1H), 8.71 (d, J = 8.9 Hz, 1H), 7.99 (d, J = 1.0 Hz, 1H), 7.68 (d, J = 8.8 Hz, 1H), 7.65 (d, J = 1.8 Hz, 1H), 7.41-7.35 (m, 2H), 7.31 (dd, J = 2.1, 8.8 Hz, 1H), 6.86 (d, J = 8.3 Hz, 1H), 6.82 (d, J = 7.7 Hz, 1H), 6.53 (d, J = 7.4 Hz, 1H), 4.72 (d, J = 15.9 Hz, 1H), 4.64 (d, J = 16.0 Hz, 1H), 4.06 (s, 3H), 1.81- 1.74 (m, 1H), 1.60-1.53 (m, 2H), 0.99-0.94 (m, 3H). |
| 1-(trifluoromethyl) propylamine | 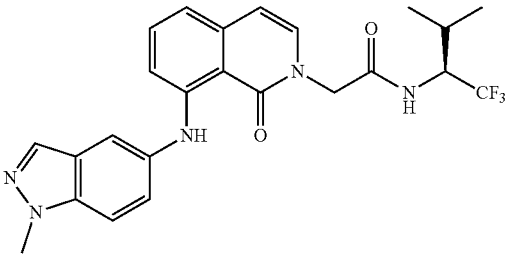 [SMILES: CC(C)[C@H](NC(=O)Cn1ccc2cccc(Nc3ccc4c(cnn4C)c3)c2c1=O)C(F)(F)F] 2-[8-[(1-methylindazol-5-yl)amino]-1-oxo-2-isoquinolyl]-N-[(S)-2-methyl-1-(trifluoromethyl)propyl]acetamide Example 46 | Method 1: 4.63 min, m/z 472.2 $[M + H]^+$ | 10.97 (s, 1H), 8.70 (d, J = 9.7 Hz, 1H), 7.99 (d, J = 0.9 Hz, 1H), 7.68 (d, J = 8.9 Hz, 1H), 7.65 (d, J = 1.9 Hz, 1H), 7.41-7.35 (m, 2H), 7.31 (dd, J = 2.0, 8.9 Hz, 1H), 6.86 (dd, J = 0.9, 8.3 Hz, 1H), 6.82 (dd, J = 0.8, 7.8 Hz, 1H), 6.53 (d, J = 7.5 Hz, 1H), 4.76 (d, J = 16.0 Hz, 1H), 4.68 (d, J = 16.1 Hz, 1H), 4.47-4.40 (m, 1H), 4.06 (s, 3H), 2.13-2.07 (m, 1H), 1.02-0.95 (m, 6H). |
| 3-(trifluoromethyl)-5-aminoisoxazole | 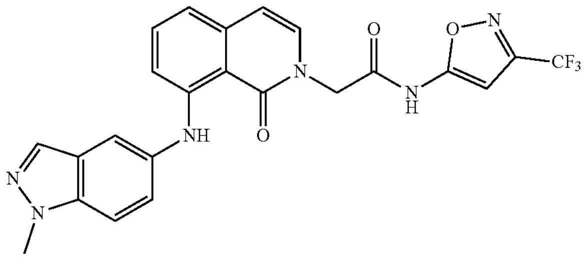 [SMILES: Cn1ncc2cc(Nc3cccc4ccn(CC(=O)Nc5cc(C(F)(F)F)no5)c(=O)c34)ccc21] 2-[8-[(1-methylindazol-5-yl)amino]-1-oxo-2-isoquinolyl]-N-[3-(trifluoromethyl)isoxazol-5-yl]acetamide | Method 1: 4.66 min, m/z 483.1 $[M + H]^+$ | 12.71 (s, 1H), 10.88 (s, 1H), 7.98 (d, J = 0.8 Hz, 1H), 7.68-7.64 (m, 2H), 7.43-7.38 (m, 2H), 7.31 (dd, J = 2.1, 8.9 Hz, 1H), 6.88 (d, J = 8.3 Hz, 1H), 6.84 (d, J = 8.2 Hz, 1H), 6.64 (s, 1H), 6.57 (d, J = 7.6 Hz, 1H), 4.85 (s, 2H), 4.05 (s, 3H). |
| (2S)-2-(trifluoromethyl) pyrrolidine | 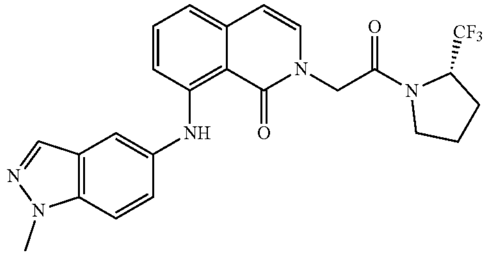 [SMILES: Cn1ncc2cc(Nc3cccc4ccn(CC(=O)N5CCC[C@H]5C(F)(F)F)c(=O)c34)ccc21] 8-[(1-methylindazol-5-yl)amino]-2-[2-oxo-2-[(2S)-2-trifluoromethyl)pyrrolidin-1-yl]ethyl]isoquinolin-1-one Example 49 | Method 1: 4.51 min, m/z 470.3 $[M + H]^+$ | 10.96 (s, 1H), 7.99 (d, J = 0.7 Hz, 1H), 7.69-7.64 (m, 2H), 7.39 (t, J = 8.0 Hz, 1H), 7.34-7.28 (m, 2H), 6.88 (d, J = 8.3 Hz, 1H), 6.82 (d, J = 7.3 Hz, 1H), 6.54 (d, J = 7.4 Hz, 1H), 4.90 (d, J = 16.5 Hz, 1H), 4.85 (d, J = 16.4 Hz, 1H), 4.82-4.75 (m, 1H), 4.06 (s, 3H), 3.77-3.69 (m, 2H), 2.12-2.03 (m, 4H). |

TABLE 10-continued

| Building block | Structure/Name | UPLCMS[1] (ES+) | 1H NMR (400 MHz, DMSO-$d_6$) |
|---|---|---|---|
| 2,2,2-trifluoro-1-(hydroxymethyl) ethylamine | 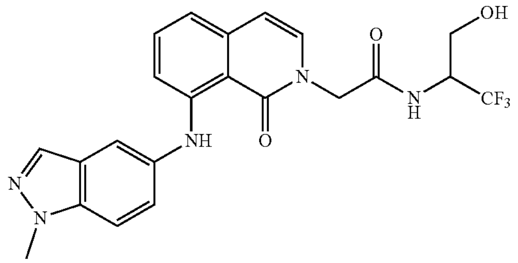 [SMILES: Cn1ncc2cc(Nc3cccc4ccn(CC(=O)NC(CO)C(F)(F)F)c(=O)c34)ccc21] 2-[8-[(1-methylindazol-5-yl)amino]-1-oxo-2-isoquinolyl]-N-[2,2,2-trifluoro-1-(hydroxymethyl)ethyl)acetamide Example 50 | Method 1: 4.02 min, m/z 460.1 $[M + H]^+$ | 10.96 (s, 1H), 8.83 (d, J = 9.3 Hz, 1H), 7.99 (d, J = 1.0 Hz, 1H), 7.69-7.65 (m, 2H), 7.40-7.30 (m, 3H), 6.86 (d, J = 7.6 Hz, 1H), 6.82 (d, J = 7.6 Hz, 1H), 6.52 (d, J = 7.6 Hz, 1H), 5.24 (t, J = 5.8 Hz, 1H), 4.70 (s, 2H), 4.57-4.53 (m, 1H), 4.06 (s, 3H), 3.66 (d, J = 26.8 Hz, 2H). |
| 2-hydroxy-2-methyl-propylamine | 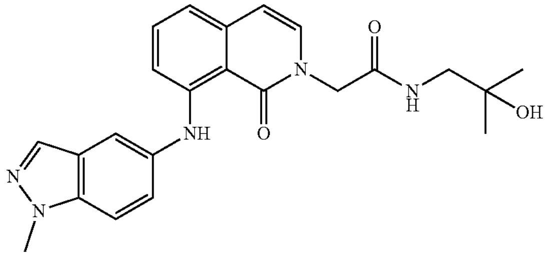 [SMILES: Cn1ncc2cc(Nc3cccc4ccn(CC(=O)NCC(C)(C)O)c(=O)c34)ccc21] N-(2-hydroxy-2-methyl-propyl)-2-[8-[(1-methylindazol-5-yl)amino]-1-oxo-2-isoquinolyl]acetamide Example 54 | Method 1: 3.44 min, m/z 420.3 $[M + H]^+$ | 11.01 (s, 1H), 8.07 (t, J = 6.0 Hz, 1H), 7.99 (s, 1H), 7.68 (d, J = 8.9 Hz, 1H), 7.65 (d, J = 1.7 Hz, 1H), 7.38 (t, J = 8.0 Hz, 1H), 7.35-7.29 (m, 2H), 6.87 (d, J = 8.3 Hz, 1H), 6.81 (d, J = 7.5 Hz, 1H), 6.51 (d, J = 7.4 Hz, 1H), 4.62 (s, 2H), 4.47 (s, 1H), 4.06 (s, 3H), 3.08 (d, J = 6.0 Hz, 2H), 1.09 (s, 6H). |
| 4-methoxyaniline | 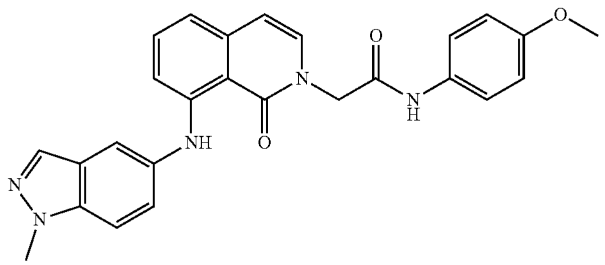 [SMILES: COc1ccc(NC(=O)Cn2ccc3cccc(Nc4ccc5c(cnn5C)c4)c3c2=O)cc1] N-(4-methoxyphenyl)-2-[8-[(1-methylindazol-5-yl)amino]-1-oxo-2-isoquinolyl]acetamide Example 55 | Method 1: 4.09 min, m/z 454.1 $[M + H]^+$ | 10.97 (s, 1H), 10.22 (s, 1H), 7.98 (s, 1H), 7.68-7.64 (m, 2H), 7.52 (d, J = 8.6 Hz, 2H), 7.42-7.37 (m, 2H), 7.31 (d, J = 9.5 Hz, 1H), 6.92-6.82 (m, 4H), 6.55 (d, J = 7.3 Hz, 1H), 4.76 (s, 2H), 4.05 (s, 3H), 3.73 (s, 3H). |
| 3-methoxy-5-aminopyridine | 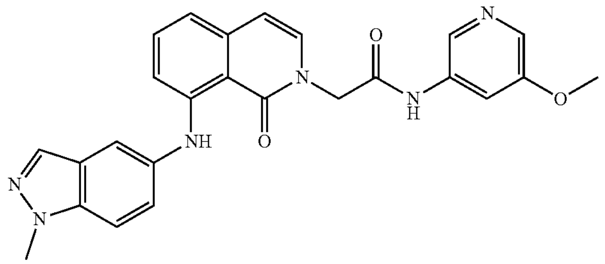 [SMILES: COc1cncc(NC(=O)Cn2ccc3cccc(Nc4ccc5c(cnn5C)c4)c3c2=O)c1] N-(5-methoxy-3-pyridyl)-2-[8-[(1-methylindazol-5-yl)amino]-1-oxo-2-isoquinolyl]acetamide Example 56 | Method 1: 3.38 min, m/z 455.4 $[M + H]^+$ | 10.93 (s, 1H), 10.66 (s, 1H), 8.34 (d, J = 2.0 Hz, 1H), 8.03 (d, J = 2.6 Hz, 1H), 7.98 (d, J = 1.0 Hz, 1H), 7.77 (t, J = 2.4 Hz, 1H), 7.68-7.65 (m, 2H), 7.43-7.38 (m, 2H), 7.31 (dd, J = 2.1, 8.8 Hz, 1H), 6.88 (d, J = 8.3 Hz, 1H), 6.84 (d, J = 7.0 Hz, 1H), 6.57 (d, J = 7.4 Hz, 1H), 4.82 (s, 2H), 4.05 (s, 3H), 3.80 (s, 3H). |

TABLE 10-continued

| Building block | Structure/Name | UPLCMS[1] (ES+) | 1H NMR (400 MHz, DMSO-d6) |
|---|---|---|---|
| (1S)-1-cyclopropyl-(2,2,2-trifluoro) ethylamine | 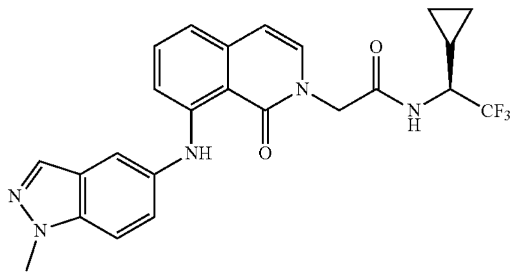 [SMILES: Cn1ncc2cc(Nc3cccc4ccn(CC(=O)N[C@@H](C5CC5)C(F)(F)F)c(=O)c34)ccc21] N-[(1S)-1-cyclopropyl-2,2,2-trifluoro-ethyl]-2-[8-[(1-methylindazol-5-yl)amino]-1-oxo-2-isoquinolyl]acetamide Example 57 | Method 1: 4.16 min, m/z 470.1 $[M + H]^+$ | 10.97 (s, 1H), 8.87 (d, J = 9.3 Hz, 1H), 7.99 (s, 1H), 7.70-7.64 (m, 2H), 7.42-7.30 (m, 3H), 6.84 (dd, J = 8.5, 19.9 Hz, 2H), 6.52 (d, J = 7.1 Hz, 1H), 4.68 (q, J = 13.8 Hz, 2H), 4.06 (s, 3H), 1.16-1.07 (m, 1H), 0.66-0.50 (m, 3H), 0.39-0.33 (m, 2H). |
| 6-(trifluoromethyl)-3-aminopyridine | 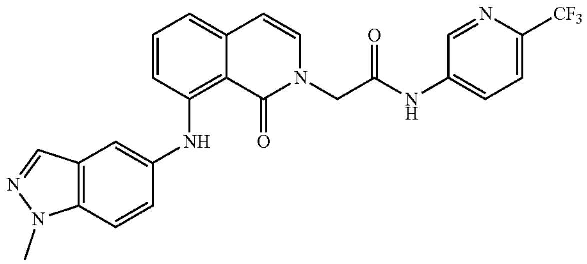 [SMILES: Cn1ncc2cc(Nc3cccc4ccn(CC(=O)Nc5ccc(C(F)(F)F)nc5)c(=O)c34)ccc21] 2-[8-[(1-methylindazol-5-yl)amino]-1-oxo-2-isoquinolyl]-N-[6-(trifluoromethyl)-3-pyridyl]acetamide Example 59 | Method 1: 5.49 min, m/z 493.1 $[M + H]^+$ | 11.05 (s, 1H), 10.91 (s, 1H), 8.92 (d, J = 2.4 Hz, 1H), 8.32 (dd, J = 2.1, 8.9 Hz, 1H), 7.98 (d, J = 0.9 Hz, 1H), 7.90 (d, J = 8.6 Hz, 1H), 7.68-7.65 (m, 2H), 7.44-7.38 (m, 2H), 7.31 (dd, J = 2.0, 8.8 Hz, 1H), 6.88 (d, J = 8.2 Hz, 1H), 6.85 (d, J = 7.1 Hz, 1H), 6.58 (d, J = 7.6 Hz, 1H), 4.87 (s, 2H), 4.05 (s, 3H). |
| (2S)-2-(1-hydroxy-1-methyl-ethyl) pyrrolidine | 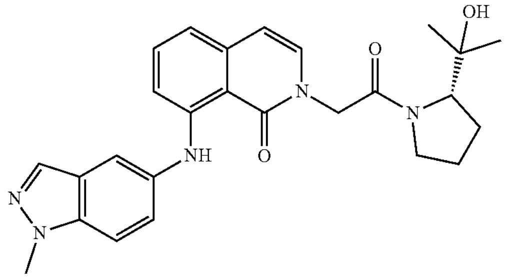 [SMILES: Cn1ncc2cc(Nc3cccc4ccn(CC(=O)N5CCC[C@H]5C(C)(C)O)c(=O)c34)ccc21] 2-[2-[(2S)-2-(1-hydroxy-1-methyl-ethyl)pyrrolidin-1-yl]-2-oxo-ethyl]-8-[(1-methylindazol-5-yl)amino]isoquinolin-1-one Example 60 | Method 1: 5.08 min, m/z 460.5 $[M + H]^+$ | 11.01 (s, 1H), 7.99 (s, 1H), 7.68 (d, J = 8.8 Hz, 1H), 7.65 (s, 1H), 7.38 (t, J = 7.9 Hz, 1H), 7.33-7.27 (m, 2H), 6.88 (d, J = 8.3 Hz, 1H), 6.82 (d, J = 7.3 Hz, 1H), 6.53 (d, J = 7.4 Hz, 1H), 5.18 (s, 1H), 4.88 (d, J = 16.2 Hz, 1H), 4.81 (d, J = 16.1 Hz, 1H), 4.06 (s, 3H), 4.00-3.98 (m, 1H), 3.78-3.77 (m, 1H), 3.51-3.49 (m, 1H), 2.02-2.01 (m, 1H), 1.89-1.85 (m, 3H), 1.06-1.04 (m, 6H). |

TABLE 10-continued

| Building block | Structure/Name | UPLCMS[1] ($ES^+$) | $^1H$ NMR (400 MHz, DMSO-$d_6$) |
| --- | --- | --- | --- |
| (2S)-2-(trifluoromethyl)-1-piperidine | 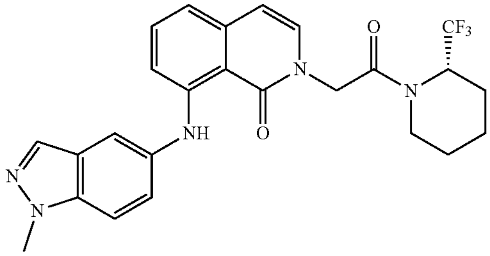 [SMILES: Cn1ncc2cc(Nc3cccc4ccn(CC(=O)N5CCCC[C@H]5C(F)(F)F)c(=O)c34)ccc21] 8-[(1-methylindazol-5-yl)amino]-2-[2-oxo-2-[(2S)-2-(trifluoromethyl)-1-piperidyl]ethyl]isoquinolin-1-one Example 61 | Method 1: 4.38 min, m/z 484.2 $[M + H]^+$ | 10.97 (s, 1H), 7.99 (s, 1H), 7.69-7.64 (m, 2H), 7.39 (t, J = 8.0 Hz, 1H), 7.32 (dd, J = 1.6, 8.9 Hz, 1H), 7.28 (d, J = 7.3 Hz, 1H), 6.88 (d, J = 8.1 Hz, 1H), 6.82 (d, J = 7.7 Hz, 1H), 6.53 (d, J = 7.3 Hz, 1H), 5.14-5.14 (m, 1H), 5.03 (d, J = 16.5 Hz, 1H), 4.95 (d, J = 16.3 Hz, 1H), 4.06 (s, 3H), 3.99 (d, J = 14.2 Hz, 1H), 3.21 (t, J = 12.3 Hz, 1H), 2.00-1.95 (m, 1H), 1.79-1.55 (m, 5H). |
| Methyl 3-aminopyridine-5-carboxylate | 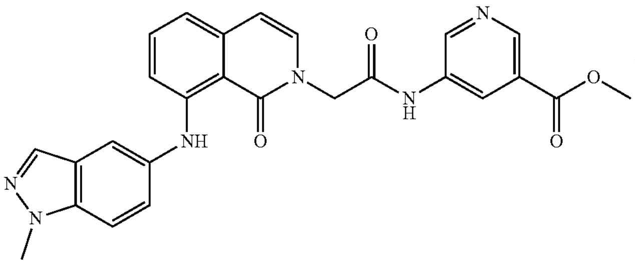 [SMILES: COC(=O)c1cncc(NC(=O)Cn2ccc3cccc(Nc4ccc5c(cnn5C)c4)c3c2=O)c1] methyl 5-[[2-[8[[(1-methylindazol-5-yl)amino]-1-oxo-2-isoquinolyl]acetyl]aminio]pyridine-3-carboxylate Example 63 | Method 1: 3.73 min, m/z 483.3 $[M + H]^+$ | 10.92 (s, 1H), 10.88 (s, 1H), 8.95 (d, J = 2.8 Hz, 1H), 8.80 (d, J = 1.8 Hz, 1H), 8.65 (t, J = 2.4 Hz, 1H), 7.98 (s, 1H), 7.68-7.65 (m, 2H), 7.44-7.38 (m, 2H), 7.31 (dd, J = 1.9, 8.9 Hz, 1H), 6.88 (d, J = 8.2 Hz, 1H), 6.85 (d, J = 7.7 Hz, 1H), 6.58 (d, J = 7.6 Hz, 1H), 4.85 (s, 2H), 4.05 (s, 3H), 3.89 (s, 3H). |
| 3,5-dimethyl-isoxazol-4-amine | 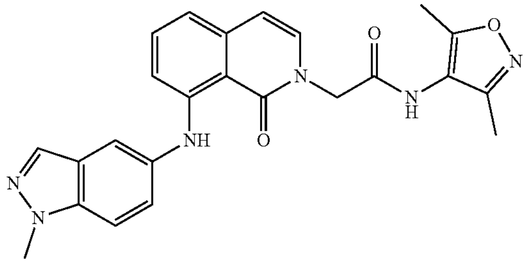 [SMILES: Cc1noc(C)c1NC(=O)Cn1ccc2cccc(Nc3ccc4c(cnn4C)c3)c2c1=O] N-(3,5-dimethylisoxazol-4-yl)-2-[8-[(1-methylindazol-5-yl)amino]-1-oxo-2-isoquinolyl]acetamide Example 69 | Method 1: 3.64 min, m/z 443.2 $[M + H]^+$ | 10.99 (s, 1H), 9.70 (s, 1H), 7.99 (d, J = 0.9 Hz, 1H), 7.68 (d, J = 8.9 Hz, 1H), 7.65 (d, J = 1.7 Hz, 1H), 7.42-7.37 (m, 2H), 7.31 (dd, J = 1.9, 8.9 Hz, 1H), 6.88 (d, J = 8.3 Hz, 1H), 6.83 (d, J = 7.1 Hz, 1H), 6.55 (d, J = 7.4 Hz, 1H), 4.78 (s, 2H), 4.06 (s, 3H), 2.28 (s, 3H), 2.12 (s, 3H). |
| Methyl pyrrolidine-3-carboxylate | 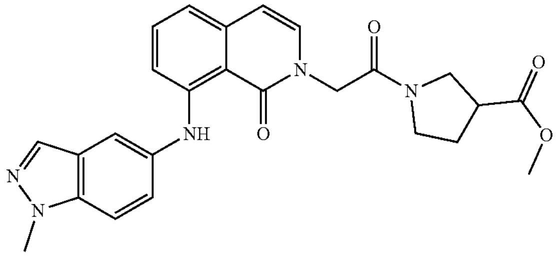 [SMILES: COC(=O)C1CCN(C(=O)Cn2ccc3cccc(Nc4ccc5c(cnn5C)c4)c3c2=O)C1] methyl 1-[2-[8-[(1-methylindazol-5-yl)amino]-1-oxo2-isoquinolyl]acetyl]pyrrolidine-3-carboxylate Example 73 | Method 1: 3.66 min, m/z 460.8 $[M + H]^+$ | 11.00 (s, 1H), 7.99 (d, J = 0.9 Hz, 1H), 7.67 (d, J = 8.9 Hz, 1H), 7.65 (d, J = 1.8 Hz, 1H), 7.38 (t, J = 8.0 Hz, 1H), 7.31 (dd, J = 2.0, 8.9 Hz, 1H), 7.28 (d, J = 7.3 Hz, 1H), 6.88 (d, J = 8.3 Hz, 1H), 6.82 (d, J = 7.2 Hz, 1H), 6.52 (d, J = 7.4 Hz, 1H), 4.82-4.71 (m, 2H), 4.06 (s, 3H), 3.89-3.68 (m, 1H), 3.67 (d, J = 9.8 Hz, 3H). 3.64-3.58 (m, 1H), 3.53-3.42 (m, 1H) 3.40-3.17 (m, 1H), 2.31-2.22 (m, 1H), 2.19-2.10 (m, 1H), 2.07-1.95 (m, 1H) |

TABLE 10-continued

| Building block | Structure/Name | UPLCMS[1] ($ES^+$) | $^1H$ NMR (400 MHz, DMSO-$d_6$) |
|---|---|---|---|
| 3-aminoisoxazole | 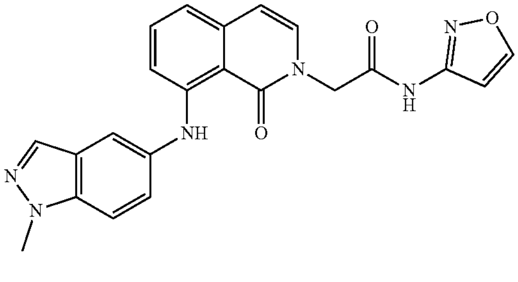 [SMILES: Cn1ncc2cc(Nc3cccc4ccn(CC(=O)Nc5ccon5)c(=O)c34)ccc21] N-isoxazol-3-yl-2-[8-[(1-methylindazol-5-yl)amino]-1-oxo-2-isoquinolyl]acetamide Example 74 | Method 1: 3.66 min, m/z 415.6 $[M + H]^+$ | 11.52 (s, 1H), 10.90 (s, 1H), 8.82 (d, J = 1.8 Hz, 1H), 7.98 (d, J = 1.0 Hz, 1H), 7.68-7.65 (m, 2H), 7.42-7.37 (m, 2H), 7.32 (dd, J = 2.1, 8.8 Hz, 1H), 6.91 − 6.86 (m, 2H), 6.83 (d, J = 7.1 Hz, 1H), 6.56 (d, J = 7.4 Hz, 1H), 4.83 (s, 2H), 4.05 (s, 3H). |
| 3-[(4-methylpiperazin-1-yl)methyl]-5-(trifluoromethyl) aniline | 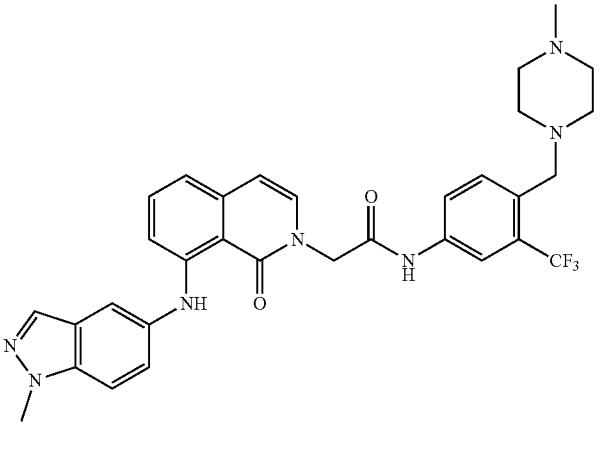 [SMILES: CN1CCN(Cc2ccc(NC(=O)Cn3ccc4cccc(Nc5ccc6c(cnn6C)c5)c4c3=O)cc2C(F)(F)F)CC1] 2-[8-[(1-methylindazol-5-yl)amino]-1-oxo-2-isoquinolyl]-N-[4-[(4-methylpiperazin-1-yl)methyl]-3-trifuoromethyl)phenyl]acetamide Example76 | Method 1: 3.32 min, m/z 604.9 $[M + H]^+$ | 10.93 (s, 1H), 10.77 (s, 1H), 8.28 (s, 1H), 8.09 (d, J = 1.9 Hz, 1H), 7.97 (d, J = 0.8 Hz, 1H), 7.78 (dd, J = 1.4, 8.6 Hz, 1H), 7.70-7.64 (m, 3H), 7.43-7.37 (m, 2H), 7.31 (dd, J = 2.0, 8.8 Hz, 1H), 6.88 (d, J = 8.3 Hz, 1H), 6.84 (d, J = 7.1 Hz, 1H), 6.57 (d, J = 7.4 Hz, 1H), 4.81 (s, 2H), 4.05 (s, 3H), 3.54 (s, 2H), 2.34 −2.33 (m, 7H), 2.15 (s, 3H). |
| 1-methyl-1H-imidazol-2-amine | 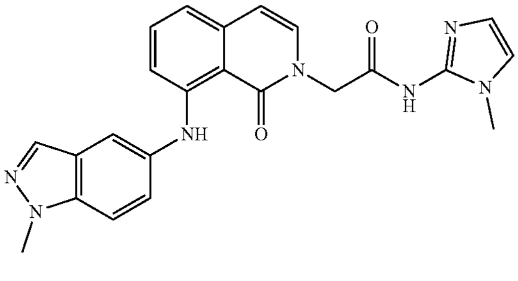 [SMILES: Cn1ccnc1NC(=O)Cn1ccc2cccc(Nc3ccc4c(cnn4C)c3)c2c1=O] N-(1-methylimidazol-2-yl)-2-[8-[(1-methylindazol-5-yl)amino]-1-oxo-2-isoquinolyl]acetamide Example 77 | Method 1: 2.84 min, m/z 428.8 $[M + H]^+$ | 11.94 (s, 0.5H), 11.09 (s, 1H), 10.52 (s, 0.5H), 7.98 (s, 1H), 7.69-7.65 (m, 2H), 7.42-7.35 (m, 2H), 7.31 (dd, J = 1.9, 8.8 Hz, 1H), 7.05-7.04 (m, 1H), 6.88 (d, J = 8.2 Hz, 1H), 6.82 (d, J = 7.5 Hz, 1H), 6.77 (d, J = 1.1 Hz, 1H), 6.53 (d, J = 7.0 Hz, 1H), 4.77-4.76 (m, 2H), 4.06 (s, 3H), 2.55 (s, 3H). |

TABLE 10-continued

| Building block | Structure/Name | UPLCMS[1] ($ES^+$) | $^1H$ NMR (400 MHz, DMSO-$d_6$) |
|---|---|---|---|
| 3-(4-methyl-1H-imidazol-1-yl)-5-(trifluoromethyl) aniline | 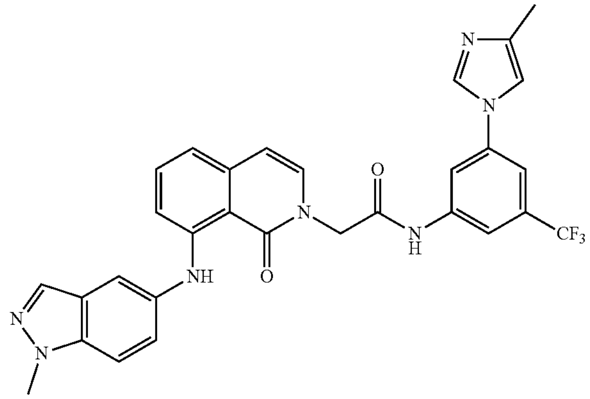 [SMILES: Cc1cn(-c2cc(NC(=O)Cn3ccc4cccc(Nc5ccc6c(cnn6C)c5)c4c3=O)cc(C(F)(F)F)c2)cn1] N-[3-(4-methylimidazol-1-yl)-5-(trifluoromethyl)phenyl]-2-[8-[(1-methylindazol-5-yl)amino]-1-oxo-2-isoquinolyl]acetamide Example 79 | Method 1: 3.39 min, m/z 572.9 $[M + H]^+$ | 10.93 (m, 2H), 8.20 (s, 1H), 8.05 (s, 1H), 7.97 (s, 1H), 7.93 (s, 1H), 7.72 (s, 1H), 7.66 (d, J = 9.9 Hz, 2H), 7.47-7.38 (m, 3H), 7.31 (d, J = 8.5 Hz, 1H), 6.87 (dd, J = 8.2, 14.0 Hz, 2H), 6.59 (d, J = 7.1 Hz, 1H), 4.84 (s, 2H), 4.04 (s, 3H), 2.16 (s, 3H). |
| 4-acetylpiperidine | 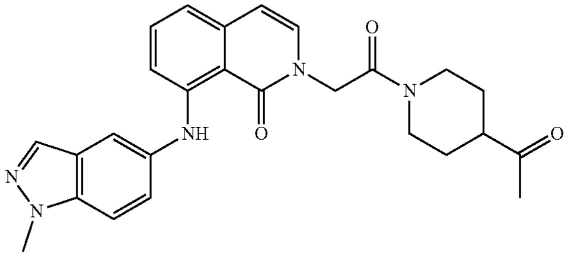 [SMILES: CC(=O)C1CCN(C(=O)Cn2ccc3cccc(Nc4ccc5c(cnn5C)c4)c3c2=O)CC1] 2-[2-(4-acetyl-1-piperidyl)-2-oxo-ethyl]-8-[(1-methylindazol-5-yl)amino]isoquinolin-1-one Example 80 | Method 1: 3.64 min, m/z 458.7 $[M + H]^+$ | 11.01 (s, 1H), 7.99 (s, 1H), 7.69-7.64 (m, 2H), 7.38 (t, J = 8.0 Hz, 1H), 7.31 (dd, J = 2.0, 8.8 Hz, 1H), 7.28 (d, J = 7.3 Hz, 1H), 6.88 (d, J = 8.3 Hz, 1H), 6.82 (d, J = 7.6 Hz, 1H), 6.52 (d, J = 7.4 Hz, 1H), 4.88 (d, J = 16.2 Hz, 1H), 4.83 (d, J = 15.7 Hz, 1H), 4.29-4.26 (m, 1H), 4.06 (s, 3H), 4.00-3.93 (m, 1H), 3.20-3.13 (m, 1H), 2.77-2.69 (m, 2H), 2.16 (s, 3H), 1.95-1.85 (m, 2H), 1.57-1.48 (m, 1H), 1.35-1.23 (m, 1H). |
| 1-methyl-1H-imidazol-4-amine | 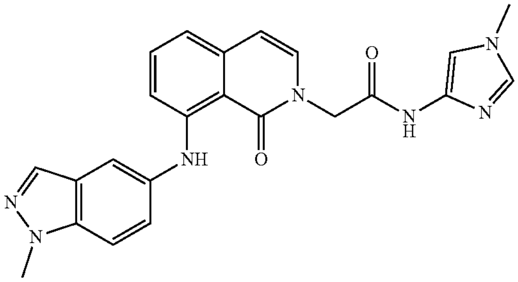 N-(1-methylimidazol-4-yl)-2-[8-[(1-methylindazol-5-yl)amino]-1-oxo-2-isoquinolyl]acetamide Example 81 | Method 1: 2.98 min, m/z 438.6 $[M + H]^+$ | 10.97 (s, 1H), 10.65 (s, 1H), 7.98 (d, J = 0.9 Hz, 1H), 7.68-7.64 (m, 2H), 7.41-7.36 (m, 3H), 7.31 (dd, J = 2.0, 8.9 Hz, 1H), 7.12 (d, J = 1.5 Hz, 1H), 6.87 (d, J = 8.3 Hz, 1H), 6.82 (d, J = 7.5 Hz, 1H), 6.53 (d, J = 7.4 Hz, 1H), 4.75 (s, 2H), 4.05 (s, 3H), 3.60 (s, 3H). |
| 3-(trifluoromethyl) morpholine | 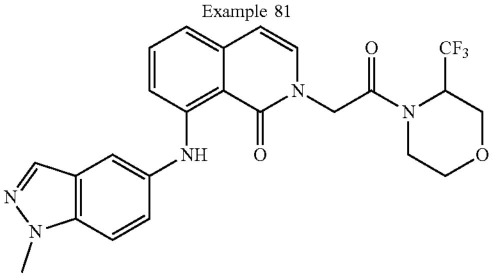 8-[(1-methylindazol-5-yl)amino]-2-[2-oxo-2-[3-(trifluoromethyl)morpholin-4-yl]ethyl]isoquinolin-1-one Example 87 | Method 1: 3.98 min, m/z 486.6 $[M + H]^+$ | 10.97 (s, 1H), 7.99 (d, J = 0.9 Hz, 1H), 7.69 – 7.66 (m, 2H), 7.39 (t, J = 8.0 Hz, 1H), 7.32 (dd, J = 2.1, 8.8 Hz, 1H), 7.28 (d, J = 7.3 Hz, 1H), 6.89 (d, J = 8.4 Hz, 1H), 6.82 (d, J = 7.1 Hz, 1H), 6.55 (d, J = 7.4 Hz, 1H), 5.14-4.77 (m, 3H), 4.18-4.11 (m, 1H), 4.06 (s, 3H), 3.99-3.90 (m, 2H), 3.80-3.66 (m, 1H), 3.60-3.43 (m, 2H). |

TABLE 10-continued

| Building block | Structure/Name | UPLCMS[1] ($ES^+$) | $^1H$ NMR (400 MHz, DMSO-$d_6$) |
|---|---|---|---|
| (2S)-2-(trifluoromethyl) pyrrolidine + I-13 | 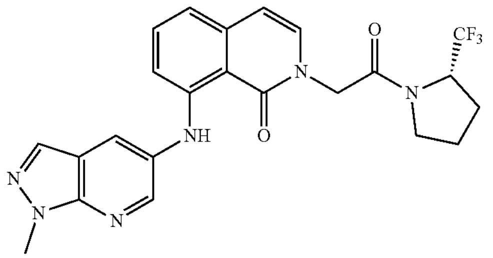 [SMILES: Cn1ncc2cc(Nc3cccc4ccn(CC(=O)N5CCC[C@H]5C(F)(F)F)c(=O)c34)cnc21] 8-[(1-methylpyrazolo[3,4-b]pyridin-5-yl)amino]-2-[2-oxo-2-[(2S)-2-(trifluoromethyl)pyrrolidin-1-yl]ethyl]isoquinolin-1-one Example 78 | Method 1: 3.91 min, m/z 471.6 $[M + H]^+$ | 10.99 (s, 1H), 8.51 (d, J = 2.3 Hz, 1H), 8.19 (d, J = 2.3 Hz, 1H), 8.10 (s, 1H), 7.40 (t, J = 8.0 Hz, 1H), 7.32 (d, J = 7.3 Hz, 1H), 6.88 (d, J = 7.7 Hz, 1H), 6.80 (d, J = 8.3 Hz, 1H), 6.57 (d, J = 7.4 Hz, 1H), 4.91-4.88 (m, 2H), 4.79-4.77 (m, 1H), 4.08 (s, 3H), 3.70-3.69 (m, 2H), 2.08-2.03 (m, 4H). |
| piperidine | 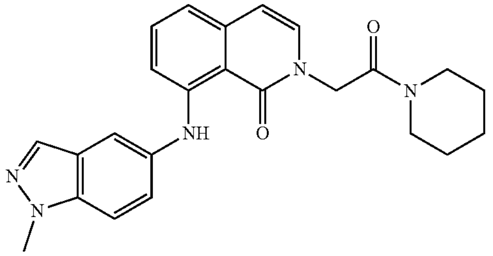 [SMILES: Cn1ncc2cc(Nc3cccc4ccn(CC(=O)N5CCCCC5)c(=O)c34)ccc21] 8-[(1-methyl-1H-indazol-5-yl)amino]-2-[2-oxo-2-piperidin-1-yl)ethyl]-1,2-dihydroisoquinolin-1-one Example 93 | Method 4: 1.92 min, m/z 416.2 $[M + H]^+$ | 10.97 (s, 1H), 7.94 (s, 1H), 7.64-7.60 (m, 2H), 7.33 (t, J = 8.0 Hz, 1H), 7.27 (dd, J = 1.9, 8.8 Hz, 1H), 7.23 (d, J = 7.5 Hz, 1H), 6.83 (d, J = 8.1 Hz, 1H), 6.77 (d, J = 7.3 Hz, 1H), 6.46 (d, J = 7.4 Hz, 1H), 4.79 (s, 2H), 4.01 (s, 3H), 3.48-3.39 (m, 4H), 1.61-1.52 (m, 4H), 1.47-1.38 (m, 2H). |
| pyrrolidine | 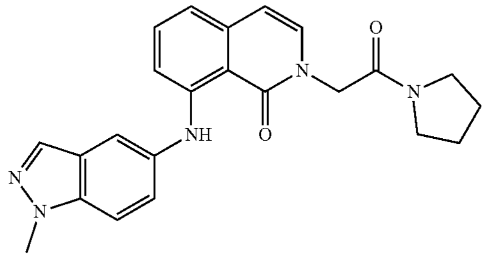 [SMILES: Cn1ncc2cc(Nc3cccc4ccn(CC(=O)N5CCCC5)c(=O)c34)ccc21] 8-[(1-methyl-1H-indazol-5-yl)amino]-2-[2-oxo-2-(pyrrolidin-1-yl)ethyl]-1,2-dihydroisoquinolin-1-one Example 94 | Method 4: 1.75 min, m/z 402.1 $[M + H]^+$ | 10.96 (s, 1H), 7.94 (s, 1H), 7.64-7.59 (m, 2H), 7.34 (t, J = 7.9 Hz, 1H), 7.27 (dd, J = 1.9, 8.7 Hz, 1H), 7.23 (d, J = 7.4 Hz, 1H), 6.83 (d, J = 8.3 Hz, 1H), 6.77 (d, J = 7.6 Hz, 1H), 6.47 (d, J = 7.3 Hz, 1H), 4.69 (s, 2H), 4.01 (s, 3H), 3.50 (t, J = 6.8 Hz, 2H), 3.29 (t, J = 6.9 Hz, 2H), 1.95-1.86 (m, 2H), 1.81-1.72 (m, 2H). |
| 5-aminooxazole | 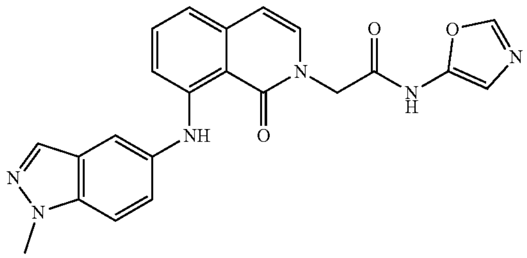 [SMILES: Cn1ncc2cc(Nc3cccc4ccn(CC(=O)Nc5cnco5)c(=O)c34)ccc21] 2-{8-[(1-methyl-1H-indazol-5-yl)amino]-1-oxo-1,2-dihydroisoquinolin-2-yl}-N-(1,3-oxazol-5-yl)acetamide Example 95 | Method 4: 2.04 min, m/z 415.2 | 10.92 (s, 1H), 10.69 (s, 1H), 9.12 (s, 1H), 8.68 (s, 1H), 7.99 (s, 1H), 7.70-7.65 (m, 2H), 7.44-7.38 (m, 2H), 7.32 (dd, J = 2.0, 8.7 Hz, 1H), 6.89 (d, J = 9.3 Hz, 1H), 6.86 (d, J = 8.1 Hz, 1H), 6.58 (d, J = 7.3 Hz, 1H), 4.80 (s, 2H), 4.07 (s, 3H). |

TABLE 10-continued

| Building block | Structure/Name | UPLCMS[1] ($ES^+$) | $^1$H NMR (400 MHz, DMSO-$d_6$) |
|---|---|---|---|
| cis-3,5-dimethyl-morpholine | 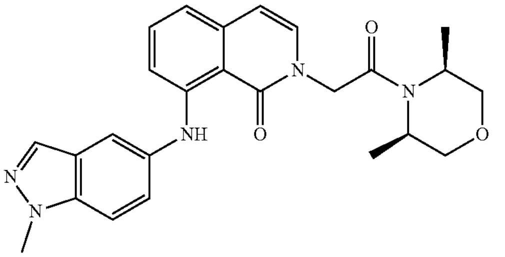 [SMILES: C[C@@H]1COC[C@H](C)N1C(=O)Cn1ccc2cccc(Nc3ccc4c(cnn4C)c3)c2c1=O] 2-{2-[(3R,5S)-3,5-dimethylmorphin-4-yl]-2-oxoethyl}-8-[(1-methyl-1H-indazol-5-yl)amino]-1,2-dihydroisoquinolin-1-one Example 96 | Method 4: 2.18 min, m/z 446.3 $[M + H]^+$ | 10.99 (s, 1H), 8.00 (s, 1H), 7.70-7.67 (m, 2H), 7.39 (t, J = 8.0 Hz, 1H), 7.34 (s, 1H), 7.33 (s, 1H), 6.87 (d, J = 8.2 Hz, 1H), 6.83 (d, J = 7.6 Hz, 1H), 6.54 (d, J = 7.6 Hz, 1H), 4.93-4.81 (m, 2H), 4.19-4.19 (m, 1H), 4.07 (s, 3H), 4.02-4.02 (m, 1H), 3.77-3.71 (m, 2H), 3.56-3.55 (m, 2H), 1.48-1.20 (m, 6H). |
| 3-oxa-8-azabicyclo [3.2.1] octane | 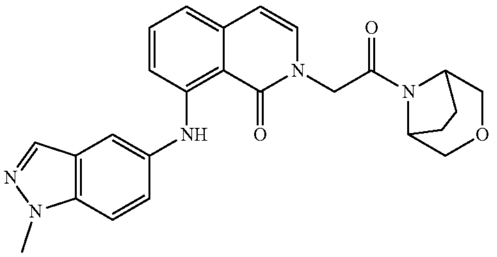 [SMILES: Cn1ncc2cc(Nc3cccc4ccn(CC(=O)N5C6CCC5COC6)c(=O)c34)ccc21] 8-[(1-methyl-1H-indazol-5-yl)amino]-2-(2-{3-oxa-8-azabicyclo[3.2.1]octan-8-yl}-2-oxoethyl)-1,2-dihydroisoquinolin-1-one Example 97 | Method 3: 3.73 min, m/z 444.4 $[M + H]^+$ | 11.01 (s, 1H), 8.00 (s, 1H), 7.72-7.66 (m, 2H), 7.44-7.31 (m, 3H), 6.89 (d, J = 8.2 Hz, 1H), 6.84 (d, J = 7.6 Hz, 1H), 6.55 (d, J = 7.8 Hz, 1H), 4.89-4.78 (m, 2H), 4.44-4.37 (m, 2H), 4.08 (s, 3H), 3.81-3.74 (m, 1H), 3.68-3.62 (m, 1H), 3.62-3.54 (m, 2H), 2.07-1.98 (m, 2H), 1.94-1.79 (m, 2H). |
| 3,5-dimethyl-1H-pyrazole | 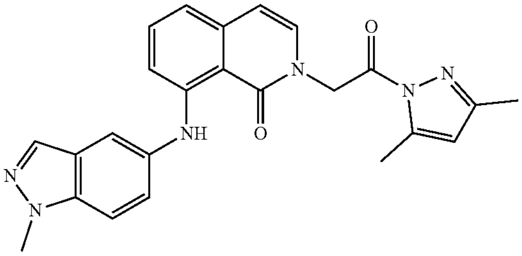 [SMILES: Cc1cc(C)n(C(=O)Cn2ccc3cccc(Nc4ccc5c(cnn5C)c4)c3c2=O)n1] 2-[2-(3,5-dimethyl-1H-pyrazol-1-yl)-2-oxoethyl]-8-[(1-methyl-1H-indazol-5-yl)amino]-1,2-dihydroisoquinolin-1-one Example 98 | Method 3: 4.46 min, m/z 425.2 $[M - H]^-$ | 10.92 (s, 1H), 8.02 (s, 1H), 7.73-7.68 (m, 2H), 7.49-7.42 (m, 2H), 7.35 (d, J = 10.6 Hz, 1H), 6.94 (d, J = 8.3 Hz, 1H), 6.89 (d, J = 7.7 Hz, 1H), 6.63 (d, J = 7.4 Hz, 1H), 6.34 (s, 1H), 5.54 (s, 2H), 4.09 (s, 3H), 2.53 (s, 3H), 2.30 (s, 3H). |
| 3-amino-5-(trifluoromethyl) pyridine + I-13 | 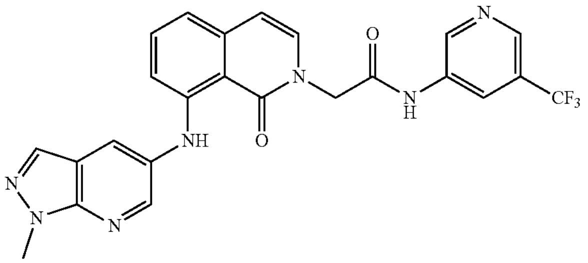 [SMILES: Cn1ncc2cc(Nc3cccc4ccn(CC(=O)Nc5cncc(C(F)(F)F)c5)c(=O)c34)cnc21] 2-[8-({1-methyl-1H-pyrazolo[3,4-b]pyridine-5-5-yl}amino)1-oxo-1,2-dihydroisoquinolin-2-yl]-N-[5-(trifluoromethyl)pyridine-3-yl]acetamide Example 99 | Method 3: 3.90 min, m/z 494.3 $[M + H]^+$ | 11.05 (s, 1H), 10.94 (s, 1H), 8.98 (d, J = 2.4 Hz, 1H), 8.71 (s, 1H), 8.54 - 8.50 (m, 2H), 8.20 (d, J = 2.3 Hz, 1H), 8.10 (s, 1H), 7.48-7.41 (m, 2H), 6.92 (d, J = 7.6 Hz, 1H), 6.82 (d, J = 8.8 Hz, 1H), 6.63 (d, J = 7.3 Hz, 1H), 4.90 (s, 2H), 4.09 (s, 3H). |

TABLE 10-continued

| Building block | Structure/Name | UPLCMS[1] ($ES^+$) | $^1H$ NMR (400 MHz, DMSO-$d_6$) |
|---|---|---|---|
| 4-aminoisoxazole + I-13 | 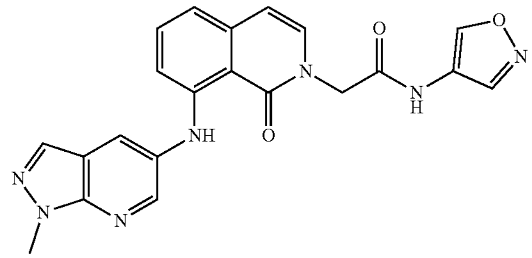 [SMILES: Cn1ncc2cc(Nc3cccc4ccn(CC(=O)Nc5cnoc5)c(=O)c34)cnc21] 2-{8-({1-methyl-1H-pyrazolo[3,4-b]pyridine-5-5-yl}amino)1-oxo-1,2-dihydroisoquinolin-2-yl}-N-(1,2-(trifluoromethyl)pyridine-3-oxozaol-4-yl)acetamide Example 101 | Method 3: 3.57 min, m/z 416.3 $[M + H]^+$ | 10.96 (s, 1H), 10.71 (s, 1H), 9.13 (s, 1H), 8.69 (s, 1H), 8.52 (d, J = 2.2 Hz, 1H), 8.20 (d, J = 2.8 Hz, 1H), 8.11 (s, 1H), 7.47-7.41 (m, 2H), 6.92 (d, J = 8.2 Hz, 1H), 6.83 (d, J = 8.2 Hz, 1H), 6.62 (d, J = 7.4 Hz, 1H), 4.83 (s, 2H), 4.10 (s, 3H). |
| 3-(2-aminopropan-2-yl)aniline | 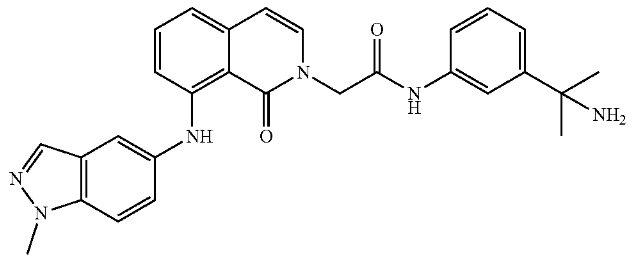 [SMILES: Cn1ncc2cc(Nc3cccc4ccn(CC(=O)Nc5cccc(C(C)(C)N)c5)c(=O)c34)ccc21] N-[3-(2-aminopropan-2-yl)phenyl-2-{8-[(1-methyl-1H-indazol-5-yl)amino]-1-oxo-1,2-dihydroisoquinolin-2-yl}acetamide Example 103 | Method 3: 2.78 min, m/z 481.3 $[M + H]^+$ | 10.99-10.87 (m, 2H), 8.34 (s, 1H), 7.98-7.89 (m, 2H), 7.68-7.58 (m, 4H), 7.45-7.35 (m, 2H), 7.35-7.17 (m, 3H), 6.87 (d, J = 8.2 Hz, 1H), 6.83 (d, J = 7.7 Hz, 1H), 6.54 (d, J = 5.7 Hz, 1H), 4.77 (s, 2H), 4.04 (s, 3H), 1.57 (s, 6H). |
| 3-[(dimethylamino) methyl]aniline | 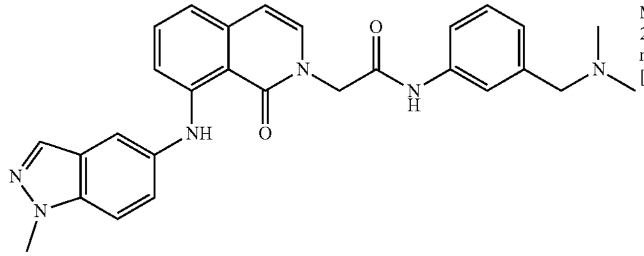 N-{3-[(dimethylamino)methyl]phenyl}-2-{8-[(1-methyl-1H-indazol-5-yl)amino]-1-oxo-1,2-dihydroisoquinolin-2-yl}acetamide Example 104 | Method 3: 2.77 min, m/z 481.3 [M + H]+ | 10.97 (s, 1H), 10.39 (s, 1H), 7.99 (s, 1H), 7.69-7.65 (m, 3H), 7.51 (d, J = 8.1 Hz, 1H), 7.44-7.38 (m, 2H), 7.35-7.28 (m, 2H), 7.03 (d, J = 7.6 Hz, 1H), 6.89 (d, J = 8.2 Hz, 1H), 6.85 (d, J = 7.7 Hz, 1H), 6.57 (d, J = 7.3 Hz, 1H), 4.80 (s, 2H), 4.06 (s, 3H), 3.54 (s, 2H), 2.27 (s, 6H). |

TABLE 10-continued

| Building block | Structure/Name | UPLCMS[1] ($ES^+$) | $^1H$ NMR (400 MHz, DMSO-$d_6$) |
|---|---|---|---|
| 4-[(dimethylamino) methyl]-3-(trifluoromethyl) aniline | 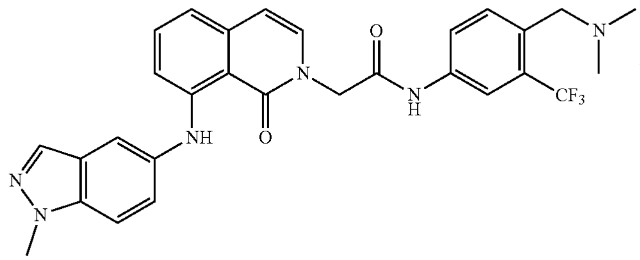 [SMILES: CN(C)Cc1ccc(NC(=O)Cn2ccc3cccc(Nc4ccc5c(cnn5C)c4)c3c2=O)cc1C(F)(F)F] N-[4-[(dimethylamino)methyl]-3-(trifluoromethyl)phenyl]-2-[8-[(1-methylindazol-5-yl)amino]-1-oxo-2-isoquinolyl]acetamide Example 112 | Method 3: 2.92 min, m/z 549.4 $[M + H]^+$ | 10.92 (s, 1H), 10.69 (s, 1H), 8.07 (d, J = 2.2 Hz, 1H), 7.97 (s, 1H), 7.77 (dd, J = 8.5, 2.2 Hz, 1H), 7.70 - 7.62 (m, 3H), 7.39 (dd, J = 8.8, 7.5 Hz, 2H), 7.30 (dd, J = 8.8, 2.0 Hz, 1H), 6.85 (dd, J = 14.8, 7.9 Hz, 2H), 6.56 (d, J = 7.3 Hz, 1H), 4.80 (s, 2H), 4.04 (s, 3H), 2.15 (s, 6H). |
| 3-(trifluoromethyl) piperidine | 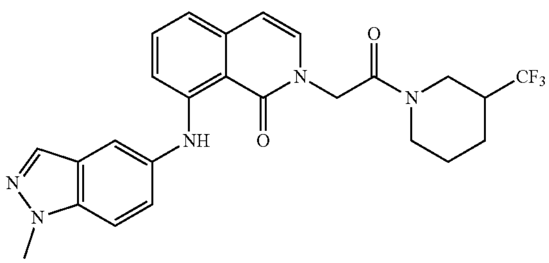 [SMILES: Cn1ncc2cc(Nc3cccc4ccn(CC(=O)N5CCCC(C(F)(F)F)C5)c(=O)c34)ccc21] 8-[(1-methylindazol-5-yl)amino]-2-[2-oxo-2-[3-trifluoromethyl)-1-piperidyl]ethyl]isoquinolin-1-one Example 121 | Method 3: 4.22 min, m/z 484.3 $[M + H]^+$ | 11.00 (s, 1H), 7.99 (s, 1H), 7.70-7.65 (m, 2H), 7.40 (t, J = 7.3 Hz, 1H), 7.33-7.27 (m, 2H), 6.88 (d, J = 7.8 Hz, 1H), 6.83 (d, J = 7.4 Hz, 1H), 6.54 (d, J = 7.0 Hz, 1H), 4.89 (s, 2H), 4.45-4.42 (m, 1H), 4.07 (s, 3H), 3.97-3.93 (m, 1H), 3.25-3.15 (m, 1H), 2.83-2.71 (m, 1H), 2.42-2.37 (m, 1H), 2.03-1.98 (m, 1H), 1.85-1.82 (m, 1H), 1.62-1.58 (m, 2H). |
| (2S)-2-(difluoromethyl) pyrrolidine | 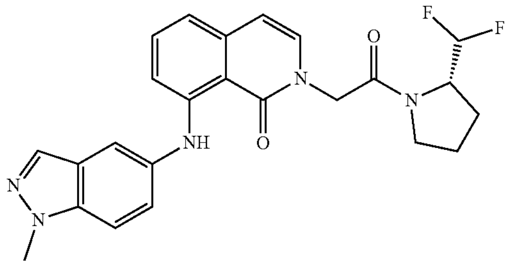 [SMILES: Cn1ncc2cc(Nc3cccc4ccn(CC(=O)N5CCC[C@H]5C(F)F)c(=O)c34)ccc21] 2-[2-[(2S)-2-(difluoromethyl)pyrrolidin-1-yl]-2-oxo-ethyl]-8-[(1-methylindazol-5-yl)amino]isoquinolin-1-one Example 131 | Method 3: 4.08 min, m/z 451.2 $[M + H]^+$ | 10.95 (d, J = 11.1 Hz, 1H), 7.98 (s, 1H), 7.69-7.62 (m, 2H), 7.38 (t, J = 8.0 Hz, 1H), 7.33-7.26 (m, 2H), 6.84 (m, J = 24.0, 8.0 Hz, 2H), 6.52 (d, J = 7.1 Hz, 1H), 6.41-6.03 (m, 1H), 4.96-4.75 (m, 2H), 4.28 (d, J = 25.2 Hz, 1H), 4.05 (s, 3H), 3.71-3.51 (m, 2H), 2.09-1.86 (m, 4H). |

TABLE 10-continued

| Building block | Structure/Name | UPLCMS[1] ($ES^+$) | $^1H$ NMR (400 MHz, DMSO-$d_6$) |
|---|---|---|---|
| 4-[2-(dimethylamino)ethyl]-3-(trifluoromethyl)aniline | 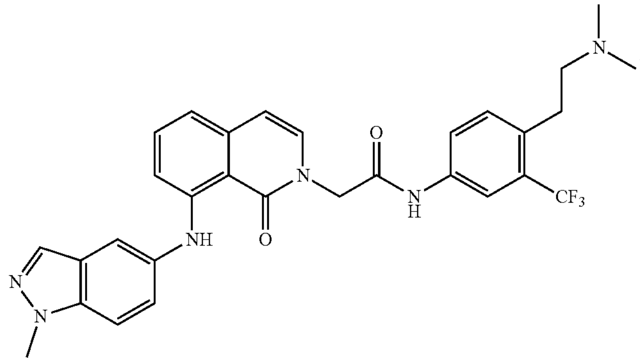 [SMILES: CN(C)CCc1ccc(NC(=O)Cn2ccc3cccc(Nc4ccc5c(cnn5C)c4)c3c2=O)cc1C(F)(F)F]<br>N-[4-[(dimethylamino)ethyl]-3-(trifluoromethyl)phenyl]-2-[8-[(1-methylindazol-5-yl)amino]-1-oxo-2-isoquinolyl]acetamide<br>Example 133 | Method 4: 1.48 min, m/z 563.3 $[M + H]^+$ | 10.92 (s, 1H), 10.62 (s, 1H), 8.04 (d, J = 2.3 Hz, 1H), 7.97 (s, 1H), 7.72 (dd, J = 8.4, 2.2 Hz, 1H), 7.65 (d, J = 9.0 Hz, 2H), 7.46 (d, J = 8.5 Hz, 1H), 7.39 (t, J = 7.8 Hz, 2H), 7.30 (dd, J = 8.8, 2.1 Hz, 1H), 6.85 (dd, J = 15.1, 8.0 Hz, 2H), 6.56 (d, J = 7.4 Hz, 1H), 4.79 (s, 2H), 4.04 (s, 3H), 2.81 (t, J = 7.8 Hz, 2H), 2.45 (t, J = 7.9 Hz, 2H), 2.20 (s, 6H) |
| (2S)-2-(fluoromethyl)pyrrolidine | 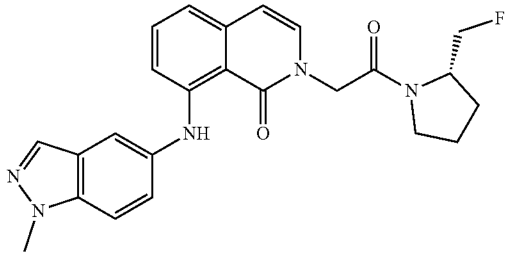 [SMILES: Cn1ncc2cc(Nc3cccc4ccn(CC(=O)N5CCC[C@H]5CF)c(=O)c34)ccc21]<br>2-[2-[(2S)-2-(fluoromethyl)pyrrolidin-1-yl]-2-oxo-ethyl]-8-[(1-methylindazol-5-yl)amino]isoquinolin-1-one<br>Example 136 | Method 3: 4.95 min, m/z 434.2 $[M + H]^+$ | 10.97 (d, J = 11.5 Hz, 1H), 7.98 (d, J = 1.0 Hz, 1H), 7.69-7.63 (m, 2H), 7.37 (m, J = 8.0, 2.2 Hz, 1H), 7.33-7.26 (m, 2H), 6.84 (m, J = 24.4, 8.0 Hz, 2H), 6.52 (d, J = 7.3 Hz, 1H), 4.79 (s, 2H), 4.62-4.38 (m, 2H), 4.15 (d, J = 23.3 Hz, 1H), 4.05 (s, 3H), 3.63-3.42 (m, 2H), 2.08-1.82 (m, 4H). |
| 1,2,3,5,6,7-hexahydro-pyrrolizin-8-ylmethanamine | 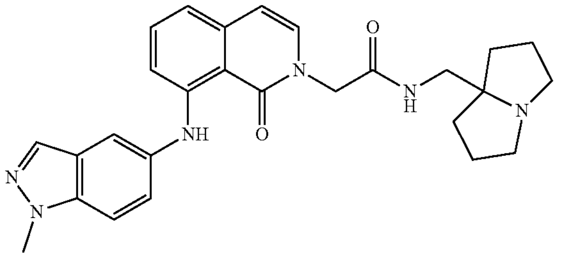 [SMILES: Cn1ncc2cc(Nc3cccc4ccn(CC(=O)NCC56CCCN5CCC6)c(=O)c34)ccc21]<br>N-1,2,3,5,6,7-hexahydropyrrolizin-8-ylmethyl)-2-[8-[(1-methylindazol-5-yl)amino]-1-oxo-2-isoquinolyl]acetamide<br>Example 138 | Method 3: 2.72 min, m/z 471.3 $[M + H]^+$ | 10.97 (s, 1H), 8.59 (s, 1H), 8.27 (s, 1H), 7.98 (s, 1H), 7.68-7.62 (m, 2H), 7.39-7.27 (m, 3H), 6.86 (d, J = 8.3 Hz, 1H), 6.81 (d, J = 7.7 Hz, 1H), 6.51 (d, J = 7.3 Hz, 1H), 4.60 (s, 2H), 4.05 (s, 3H), 3.25 (d, J = 5.9 Hz, 2H), 3.20-3.13 (m, 2H), 2.76 (d, J = 5.5 Hz, 2H), 1.90-1.73 (m, 6H), 1.62 (d, J = 6.5 Hz, 2H). |

TABLE 10-continued

| Building block | Structure/Name | UPLCMS[1] ($ES^+$) | $^1H$ NMR (400 MHz, DMSO-$d_6$) |
|---|---|---|---|
| Intermediate I-18 and isoxazol-4-amine | 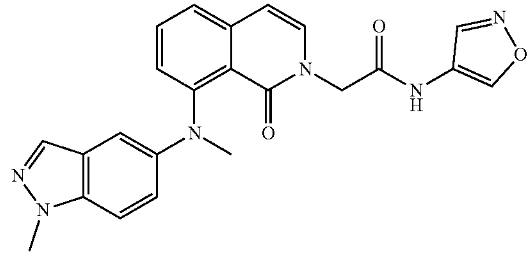 [SMILES: CN(c1ccc2c(cnn2C)c1)c1cccc2ccn(CC(=O)Nc3cnoc3)c(=O)c12] N-isoxazol-4-yl-2-[8-[methyl-(1-methylindazol-5-yl)amino]-1-oxo-2-isoquinolyl]acetamide Example 140 | Method 3: 3.59 min, m/z 429.0 $[M + H]^+$ | 10.57 (s, 1H), 9.02 (s, 1H), 8.59 (s, 1H), 8.32 (s, 1H), 7.77 (s, 1H), 7.66 (t, J = 7.8 Hz, 1H), 7.51 (d, J = 7.9, 1.3 Hz, 1H), 7.44 (d, J = 7.3 Hz, 1H), 7.29 (d, J = 9.2 Hz, 1H), 7.19 (dd, J = 7.7, 1.2 Hz, 1H), 6.82 (d, J = 2.2 Hz, 1H), 6.66 (dd, J = 9.1, 2.3 Hz, 1H), 6.62 (d, J = 7.3 Hz, 1H), 4.64 (s, 2H), 3.92 (s, 3H), 3.16 (s, 3H). |
| 1-(2-piperidyl) ethanone | 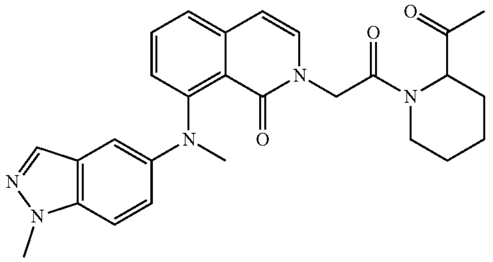 2-[2-(2-acetyl-1-piperidyl)-2-oxo ethyl]-8-[(1-methylindazol-5-yl)amino]isoquinolin-1-one Example 141 | Method 3: 3.95 min, m/z 458.2 $[M + H]^+$ | 10.98 (d, J = 9.5 Hz, 1H), 7.98 (d, J = 0.9 Hz, 1H), 7.69-7.63 (m, 2H), 7.37 (t, J = 8.0 Hz, 1H), 7.33-7.23 (m, 2H), 6.89-6.83 (m, 1H), 6.83-6.79 (m, 1H), 6.51 (d, J = 7.4 Hz, 1H), 5.03-4.67 (m, 3H), 4.05 (s, 4H), 3.20-2.52 (m, 1H), 2.36-2.08 (m, 4H), 1.75-1.45 (m, 4H), 1.36-1.20 (m, 2H). |
| Intermediate I-18 and (S)-2-Amino-1,1,1-trifluoropropane hydrochloride | 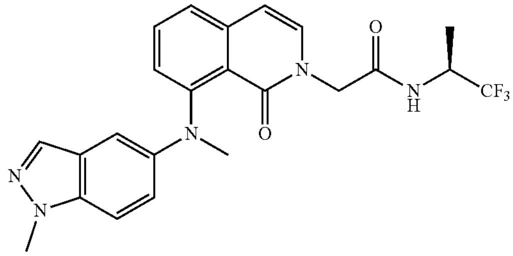 [SMILES: C[C@H](NC(=O)Cn1ccc2cccc(N(C)c3ccc4c(cnn4C)c3)c2c1=O)C(F)(F)F] 2-[8-[methyl-(1-methylindazol-5-yl)amino]-1-oxo-2-isoquinolyl]-N-[(1S)-2,2,2-trifluoro-1-methyl-ethyl]acetamide Example 143 | Method 3: 3.82 min, m/z 458.2 $[M + H]^+$ | 8.68 (d, J = 8.8 Hz, 1H), 7.78 (s, 1H), 7.64 (t, J = 7.8 Hz, 1H), 7.49 (dd, J = 8.0, 1.3 Hz, 1H), 7.38 (d, J = 7.3 Hz, 1H), 7.30 (d, J = 9.1 Hz, 1H), 7.18 (d, J = 7.7, 1.2 Hz, 1H), 6.83 (d, J = 2.2 Hz, 1H), 6.66 (dd, J = 9.1, 2.3 Hz, 1H), 6.57 (d, J = 7.3 Hz, 1H), 4.58-4.44 (m, 3H), 3.93 (s, 3H), 3.16 (s, 3H), 1.20 (d, J = 7.0 Hz, 3H). |
| Intermediate I-18 and 3-(Trifluoro-methyl) aniline | 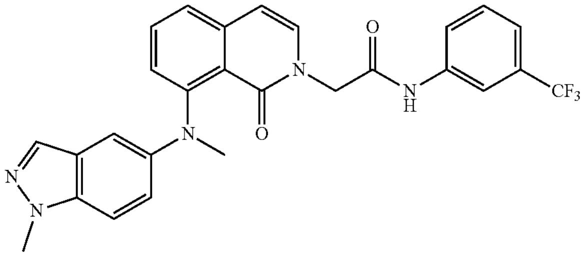 [SMILES: CN(c1ccc2c(cnn2C)c1)c1cccc2ccn(CC(=O)Nc3cccc(C(F)(F)F)c3)c(=O)c12] 2-[8-[methyl-(1-methylindazol-5-yl)amino]-1-oxo-2-isoquinolyl]-N-[3-(trifluoromethyl)phenyl]acetamide Example 144 | Method 3: 4.18 min, m/z 506.0 $[M + H]^+$ | 10.60 (s, 1H), 8.05 (s, 1H), 7.77 (s, 1H), 7.67 (q, J = 7.8 Hz, 2H), 7.53 (d, J = 9.9, 7.6 Hz, 2H), 7.45 (d, J = 7.3 Hz, 1H), 7.39 (d, J = 7.9 Hz, 1H), 7.29 (d, J = 9.2 Hz, 1H), 7.19 (d, J = 7.6 Hz, 1H), 6.83 (s, 1H), 6.68-6.61 (m, 2H), 4.68 (s, 2H), 3.91 (s, 3H), 3.17 (s, 3H). |

TABLE 10-continued

| Building block | Structure/Name | UPLCMS[1] ($ES^+$) | $^1H$ NMR (400 MHz, DMSO-$d_6$) |
|---|---|---|---|
| 3-[(dimethyl-amino) methyl]-5-(trifluoro-methyl) aniline | 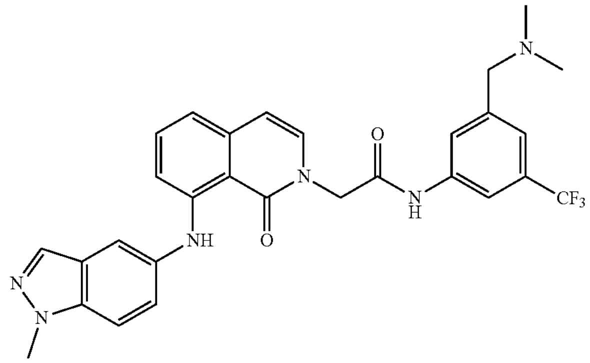 [SMILES: CN(C)Cc1cc(NC(=O)Cn2ccc3cccc(Nc4ccc5c(cnn5C)c4)c3c2=O)cc(C(F)(F)F)c1]<br>N-[3-[(dimethylamino)methyl]-5-(trifluoromethyl)phenyl]-2-[8-[(1-methylindazol-5-yl)amino]-1-oxo-2-isoquinolyl]acetamide<br>Example 154 | Method 3: 2.92 min, m/z 549.2 $[M + H]^+$ | 10.91-10.86 (m, 1H), 8.04 (s, 1H), 8.01 (s, 1H), 7.97 (s, 1H), 7.68-7.62 (m, 3H), 7.43-7.37 (m, 2H), 7.32-7.27 (m, 1H), 6.91-6.83 (m, 2H), 6.58 (d, J = 7.3 Hz, 1H), 4.83 (s, 2H), 4.37 (s, 2H), 4.05 (s, 3H), 2.75 (s, 6H). |
| Intermediate I-19 and isoxazol-4-amine | 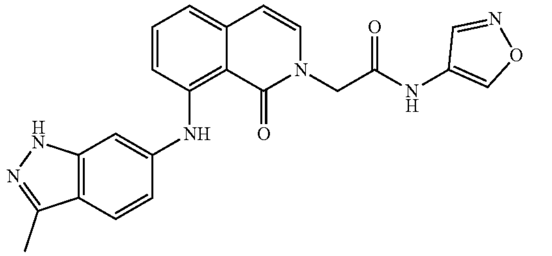 [SMILES: Cc1n[nH]c2cc(Nc3cccc4ccn(CC(=O)Nc5cnoc5)c(=O)c34)ccc12]<br>N-isoxazol-4-yl-2-[8-[(3-methyl-1H-indazol-6-yl)amino]-1-oxo-2-isoquinolyl]acetamide<br>Example 158 | Method 3: 3.55 min, m/z 415.1 $[M + H]^+$ | 12.40 (s, 1H), 11.13 (s, 1H), 10.73 (s, 1H), 9.09 (s, 1H), 8.66 (s, 1H), 7.64 (d, J = 8.5 Hz, 1H), 7.50-7.40 (m, 2H), 7.32 (s, 1H), 7.20 (d, J = 8.2 Hz, 1H), 6.97-6.90 (m, 2H), 6.59 (d, J = 7.3 Hz, 1H), 4.79 (s, 2H), 2.45 (s, 3H). |
| Intermediate I-19 and 3-(Trifluoro-methyl) aniline | 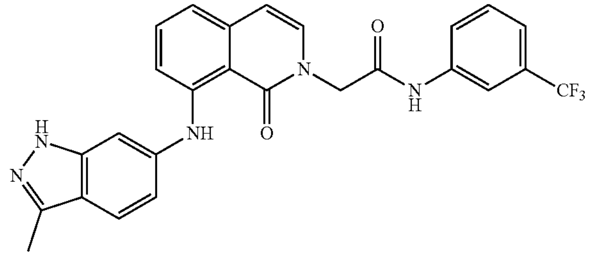 [SMILES: Cc1n[nH]c2cc(Nc3cccc4ccn(CC(=O)Nc5cccc(C(F)(F)F)c5)c(=O)c34)ccc12]<br>2-[8-[(3-methyl-1H-indazol-6-yl)amino]-1-oxo-2-isoquinolyl]-N-[3-(trifluoromethyl)phenyl]acetamide<br>Example 159 | Method 3: 4.08 min, m/z 492.2 $[M + H]^+$ | 12.42 (s, 1H), 11.17 (s, 1H), 10.76 (s, 1H), 8.14 (s, 1H), 7.78 (d, J = 7.6 Hz, 1H), 7.66 (d, J = 8.4 Hz, 1H), 7.60 (t, J = 7.9 Hz, 1H), 7.50 (t, J = 8.0 Hz, 1H), 7.44 (d, J = 7.4 Hz, 2H), 7.35 (s, 1H), 7.22 (d, J = 8.1 Hz, 1H), 7.00-6.92 (m, 2H), 6.62 (d, J = 7.2 Hz, 1H), 4.84 (s, 2H), 2.47 (s, 3H). |

[1]For examples where alternative HPLC and mass spectrometry methods were used, these are referred to in the individual example entries Example 27, 2-[1-oxo-8-(1H-pyrazolo[3,4-b]pyridin-5-ylamino)-2-isoquinolyl]-N-[(1 S)-2,2,2-trifluoro-1-methyl-ethyl]acetamide Scheme 10

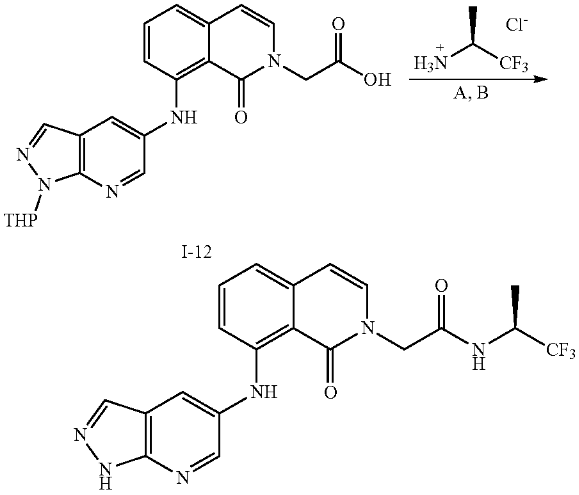

I-12

27

STEP A. To a solution of 2-[1-oxo-8-[(1-tetrahydropyran-2-ylpyrazolo[3,4-b]pyridin-5-yl)amino]-2-isoquinolyl]acetic acid (Intermediate I-12, 50 mg, 0.12 mmol), (S)-2-Amino-1,1,1-trifluoropropane hydrochloride (20 mg, 0.13 mmol) and N,N-diisopropylethylamine (0.05 mL, 0.3 mmol) in DMF (2 mL) was added HATU (68 mg, 0.18 mmol) and the mixture was stirred at rt overnight. The mixture was diluted with EtOAc, washed three times with Brine, dried over $Na_2SO_4$ and concentrated under reduced pressure. The crude product was purified by normal phase chromatography (12 g column, 10 to 90% EtOAc in petrol) to give 2-[1-oxo-8-[(1-tetrahydropyran-2-ylpyrazolo[3,4-b]pyridin-5-yl)amino]-2-isoquinolyl]-N-[(1S)-2,2,2-trifluoro-1-methyl-ethyl]acetamide (50 mg, 0.1 mmol, 82% yield) as a brown solid.

UPLC-MS ($ES^+$, Method 2): 1.89 min, m/z 515.4 $[M+H]^+$.

$^1$H NMR (400 MHz, DMSO-$d_6$) δ 11.00 (s, 1H), 8.84 (d, J=8.8 Hz, 1H), 8.53 (d, J=2.4 Hz, 1H), 8.22 (d, J=2.3 Hz, 1H), 8.18 (s, 1H), 7.42-7.36 (m, 2H), 6.89 (d, J=7.2 Hz, 1H), 6.82 (d, J=7.5 Hz, 1H), 6.56 (d, J=7.4 Hz, 1H), 6.02 (dd, J=2.2, 10.4 Hz, 1H), 4.69-4.62 (m, 3H), 3.98-3.93 (m, 1H), 3.71-3.70 (m, 1H), 2.08-2.04 (m, 1H), 1.98-1.91 (m, 2H), 1.83-1.76 (m, 2H), 1.66-1.56 (m, 3H).

STEP B. To a solution of 2-[1-oxo-8-[(1-tetrahydropyran-2-ylpyrazolo[3,4-b]pyridin-5-yl)amino]-2-isoquinolyl]-N-[(1S)-2,2,2-trifluoro-1-methyl-ethyl]acetamide (50 mg, 0.1 mmol) in acetonitrile (2 mL) was added HCl (4 M in dioxane, 0.12 mL, 0.5 mmol), the mixture was stirred overnight at rt. The mixture was concentrated under reduced pressure and purified by reverse phase chromatography (12 g column, 20 to 60% acetonitrile in water, 0.1% formic acid), then dried under vacuum overnight to give 2-[1-oxo-8-(1H-pyrazolo[3,4-b]pyridin-5-ylamino)-2-isoquinolyl]-N-[(1S)-2,2,2-trifluoro-1-methyl-ethyl]acetamide (22 mg, 0.05 mmol, 53% yield) as a pale yellow solid.

UPLC-MS ($ES^+$, Method 1): 3.70 min, m/z 431.1 $[M+H]^+$.

$^1$H NMR (400 MHz, DMSO-$d_6$) δ 13.67 (s, 1H), 10.94 (s, 1H), 8.84 (d, J=8.8 Hz, 1H), 8.46 (d, J=2.4 Hz, 1H), 8.18 (d, J=2.3 Hz, 1H), 8.11 (s, 1H), 7.42-7.35 (m, 2H), 6.87 (d, J=7.6 Hz, 1H), 6.78 (d, J=8.3 Hz, 1H), 6.55 (d, J=7.4 Hz, 1H), 4.72-4.57 (m, 3H), 1.29 (d, J=7.0 Hz, 3H).

Examples synthesised following the same procedure as example 27 (scheme 10) replacing (S)-2-amino-1,1,1-trifluoropropane hydrochloride in step A with the appropriate amine building block are described in table 11.

TABLE 11

| Building block | Structure/Name | UPLCMS[1] ($ES^+$) | $^1$H NMR (400 MHz, DMSO-$d_6$) |
|---|---|---|---|
| (2S)-2-(trifluoromethyl) pyrrolidine | 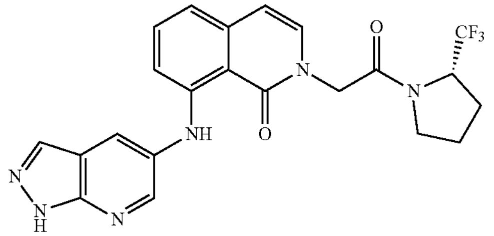 2-[2-oxo-2-[(2S)-2-(trifluoromethyl)pyrrolidin-1-yl]ethyl]-8-(1H-pyrazolo[3,4-b]pyridin-5-ylamino)isoquinolin-1-one Example 67 | Method 1: m/z 457.3 3.57 min, $[M + H]^+$ | 13.67 (s, 1H), 10.96 (s, 1H), 8.45 (d, J = 2.3 Hz, 1H), 8.18 (d, J = 2.3 Hz, 1H), 8.11 (s, 1H), 7.40 (t, J = 8.0 Hz, 1H), 7.32 (d, J = 7.3 Hz, 1H), 6.87 (d, J = 7.7 Hz, 1H), 6.79 (d, J = 8.2 Hz, 1H), 6.57 (d, J = 7.4 Hz, 1H), 4.91-4.87 (m, 2H), 4.79-4.78 (m, 1H), 3.71-3.69 (m, 2H), 2.09-2.07 (m, 4H). |

TABLE 11-continued

| Building block | Structure/Name | UPLCMS[1] (ES+) | $^1$H NMR (400 MHz, DMSO-$d_6$) |
|---|---|---|---|
| 4-aminoisoxazole | 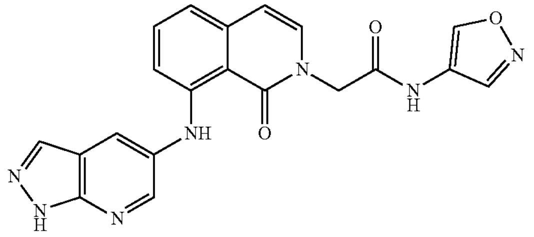 N-isoxazol-4-yl-2-[1-oxo-8-(1H-pyrazolo[3,4-b]pyridin-5-ylamino)-2-isoquinolyl]acetamide Example 71 | Method 1: 3.09 min, m/z 402.1 [M + H]$^+$ | 13.68 (s, 1H), 10.91 (s, 1H), 10.82 (s, 1H), 9.11 (s, 1H), 8.68 (s, 1H), 8.54 (s, 1H), 8.45 (d, J = 2.4 Hz, 1H), 8.17 (d, J = 2.3 Hz, 1H), 8.10 (s, 1H), 7.44-7.38 (m, 2H), 6.89 (d, J = 7.7 Hz, 1H), 6.79 (d, J = 8.3 Hz, 1H), 6.59 (d, J = 7.4 Hz, 1H), 4.80 (s, 2H). |
| 3-amino-5-(trifluoromethyl) pyridine | 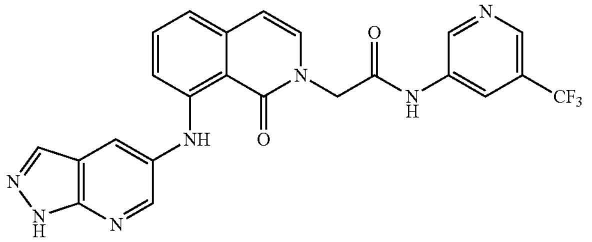 2-[1-oxo-8-(1H-pyrazolo[3,4-b]pyridin-5-ylamino)-2-isoquinolyl]-N-[5-(trifluoromethyl)-3-pyridyl]acetamide Example 72 | Method 1: 3.59 min, m/z 480.5 [M + H]$^+$ | 13.66 (s, 1H), 11.05 (s, 1H), 10.90 (s, 1H), 8.96 (d, J = 2.2 Hz, 1H), 8.70 (d, J = 1.0 Hz, 1H), 8.52 (t, J = 1.8 Hz, 1H), 8.45 (d, J = 2.4 Hz, 1H), 8.17 (d, J = 2.1 Hz, 1H), 8.10 (d, J = 0.7 Hz, 1H), 7.46-7.39 (m, 2H), 6.90 (d, J = 7.6 Hz, 1H), 6.80 (d, J = 8.3 Hz, 1H), 6.61 (d, J = 7.4 Hz, 1H), 4.88 (s, 2H). |

[1]For examples where alternative HPLC and mass spectrometry methods were used, these are referred to in the individual example entries Example 38, N-[3-(1-hydroxy-1-methyl-ethyl)phenyl]-2-[8-[(1-methylindazol-5-yl)amino]-1-oxo-2-isoquinolyl]acetamide Scheme 11

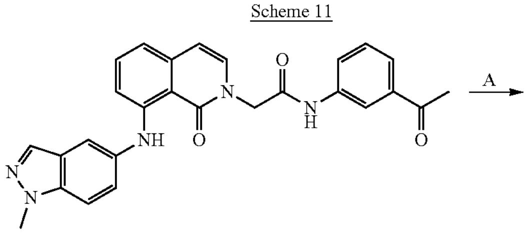

32

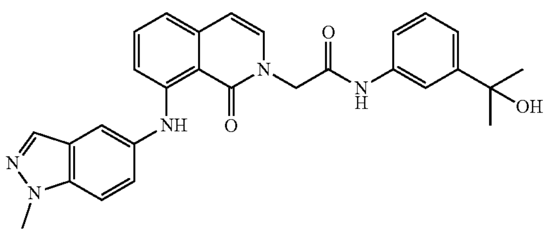

38

STEP A. A solution of N-(3-acetylphenyl)-2-[8-[(1-methylindazol-5-yl)amino]-1-oxo-2-isoquinolyl]acetamide (30 mg, 0.06 mmol) in THE (2 mL) under $N_2$ was cooled to 0° C. and bromo(methyl) magnesium (1M in THF, 0.14 mL, 0.14 mmol) was added dropwise. The mixture was stirred at 0° C. for 2 h. The reaction was quenched by adding 1 mL MeOH, then it was warmed to rt and concentrated under reduced pressure. The crude product was purified by reverse phase chromatography (12 g column, 20 to 60% acetonitrile in water, 0.1% formic acid), then dried under vacuum overnight to give N-[3-(1-hydroxy-1-methyl-ethyl)phenyl]-2-[8-[(1-methylindazol-5-yl)amino]-1-oxo-2-isoquinolyl] acetamide (10 mg, 0.021 mmol, 32% yield) as an off-white solid.

UPLC-MS (ES$^+$, Method 1): 4.20 min m/z 482.2 [M+H]$^+$. $^1$H NMR (400 MHz, DMSO-$d_6$) θ 10.96 (s, 1H), 10.33 (s, 1H), 7.97 (s, 1H), 7.71 (s, 1H), 7.68-7.64 (m, 2H), 7.48 (d, J=8.2 Hz, 1H), 7.42-7.37 (m, 2H), 7.31 (d, J=1.4 Hz, 1H), 7.24 (t, J=7.9 Hz, 1H), 7.15 (d, J=8.5 Hz, 1H), 6.88 (d, J=8.3 Hz, 1H), 6.84 (d, J7.7 Hz, 1H), 6.56 (d, J7.3 Hz, 1H), 5.01 (s, 1H), 4.78 (s, 2H), 4.05 (s, 3H), 1.40 (d, 6H).

Examples synthesised following the same procedure as example 38 (scheme 11) replacing N-(3-acetylphenyl)-2-[8-[(1-methylindazol-5-yl)amino]-1-oxo-2-isoquinolyl] acetamide in step A with the appropriate corresponding ketone or ester examples are entered in table 12.

TABLE 12

| Starting material | Structure/Name | UPLCMS[1] (ES$^+$) | $^1$H NMR (400 MHz, DMSO-d$_6$) |
|---|---|---|---|
| N-(4-acetylphenyl)-2-[8-[(1-methylindazol-5-yl)amino]-1-oxo-2-isoquinolyl]acetamide | 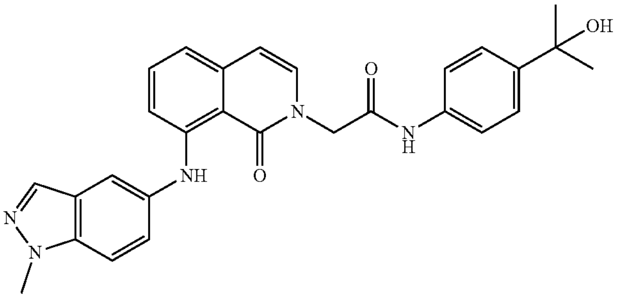<br>N-[4-(1-hydroxy-1-methyl-ethyl)phenyl]-2-[8-[(1-methylindazol-5-yl)amino]-1-oxo-2-isoquinolyl]acetamide<br>Example 53 | Method 1: 3.85 min, m/z 482.1 [M + H]$^+$ | 10.97 (s, 1H), 10.31 (s, 1H), 7.98 (s, 1H), 7.68-7.64 (m, 2H), 7.52 (d, J = 8.7 Hz, 2H), 7.43-7.37 (m, 4H), 7.32 (dd, J = 2.1, 8.7 Hz, 1H), 6.89 (d, J = 7.7 Hz, 1H), 6.84 (d, J = 7.8 Hz, 1H), 6.56 (d, J = 7.4 Hz, 1H), 4.94 (s, 1H), 4.78 (s, 2H), 4.05 (s, 3H), 1.40 (s, 6H). |
| methyl 5-[2-[8-[(1-methylindazol-5-yl)amino]-1-oxo-2-isoquinolyl]acetyl]amino]pyridine-3-carboxylate | 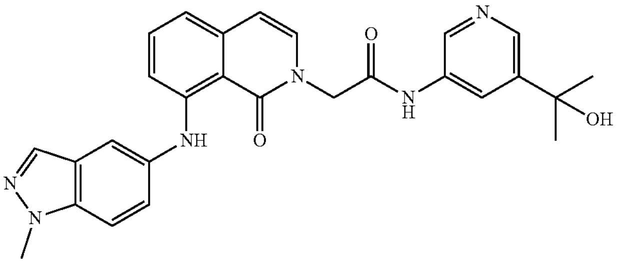<br>N-[5-(1-hydroxy-1-methyl-ethyl)-3-pyridyl]-2-[8-[(1-methylindazol-5-yl)amino]-1-oxo-2-isoquinolyl]acetamide<br>Example 62 | Method 1: 3.06 min, m/z 483.3 [M + H]$^+$ | 10.94 (s, 1H), 10.57 (s, 1H), 8.64 (d, J = 2.6 Hz, 1H), 8.39 (d, J = 1.7 Hz, 1H), 8.13 (t, J = 2.3 Hz, 1H), 7.98 (s, 1H), 7.68-7.65 (m, 2H), 7.43-7.37 (m, 2H), 7.32 (dd, J = 1.7, 8.7 Hz, 1H), 6.88 (d, J = 8.2 Hz, 1H), 6.85 (d, J = 7.7 Hz, 1H), 6.57 (d, J = 7.2 Hz, 1H), 5.22 (s, 1H), 4.82 (s, 2H), 4.05 (s, 3H), 1.44 (s, 6H). |
| methyl 1-[2-[8-[(1-methylindazol-5-yl)amino]-1-oxo-2-isoquinolyl]acetyl]pyrrolidine-3-carboxylate | 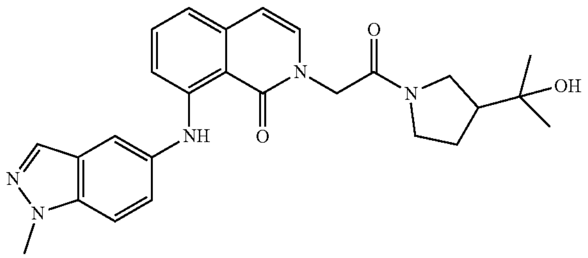<br>2-[2-[3-(1-hydroxy-1-methyl-ethyl)pyrrolidin-1-yl]-2-oxo-ethyl]-8-[(1-methylindazol-5-yl)aminolisoquinolin-1-one<br>Example 75 | Method 1: 3.54 min, m/z 460.8 [M + H]$^+$ | 11.01 (s, 1H), 7.99 (s, 1H), 7.69-7.64 (m, 2H), 7.38 (t, J = 8.0 Hz, 1H), 7.33-7.27 (m, 2H), 6.88 (d, J = 8.5 Hz, 1H), 6.82 (d, J = 7.5 Hz, 1H), 6.52 (d, J = 7.3 Hz, 1H), 4.80-4.67 (m, 2H), 4.42 (d, J = 28.7 Hz, 1H), 4.06 (s, 3H), 3.66-3.55 (m, 1H), 3.50-3.38 (m, 1H), 3.20-3.11 (m, 1H), 2.21-2.10 (m, 1H), 2.01-1.87 (m, 2H), 1.80-1.66 (m, 1H), 1.15 (s, 3H), 1.12 (d, J = 3.3 Hz, 3H). |
| 2-[2-(4-acetyl-1-piperidyl)-2-oxo-ethyl]-8-[(1-methylindazol-5-yl)amino]isoquinolin-1-one | 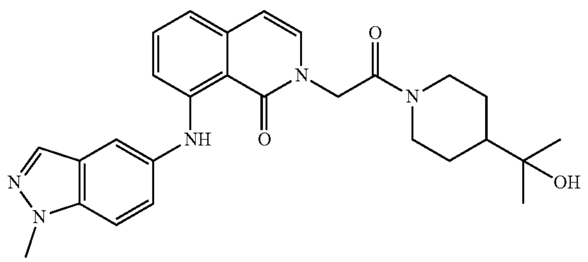<br>2-[2-[4-(1-hydroxy-1-methyl-ethyl)-1-piperidyl]-2-oxo-ethyl]-8-[(1-methylindazol-5-yl)amino]isoquinolin-1-one<br>Example 82 | Method 1: 3.64 min, m/z 474.8 [M + H]$^+$ | 11.02 (s, 1H), 7.99 (d, J = 0.8 Hz, 1H), 7.67 (d, J = 8.9 Hz, 1H), 7.65 (d, J = 2.0 Hz, 1H), 7.38 (t, J = 8.0 Hz, 1H), 7.33-7.27 (m, 2H), 6.88 (d, J = 8.3 Hz, 1H), 6.82 (d, J = 7.1 Hz, 1H), 6.51 (d, J = 7.4 Hz, 1H), 4.85 (s, 2H), 4.46-4.41 (m, 1H), 4.20 (s, 1H), 4.06 (s, 3H), 4.02-4.01 (m, 1H), 3.05-2.98 (m, 1H), 1.83-1.79 (m, 1H), 1.75-1.70 (m, 1H), 1.49-1.42 (m, 1H), 1.32-1.22 (m, 2H), 1.13-1.08 (m, 1H), 1.06 (s, 6H). |

TABLE 12-continued

| Starting material | Structure/Name | UPLCMS[1] ($ES^+$) | $^1$H NMR (400 MHz, DMSO-$d_6$) |
| --- | --- | --- | --- |
| 8-[(1-methylindazol-5-yl)amino]-2-[2-oxo-2-(4-oxo-1-piperidyl)ethyl] isoquinolin-1-one | 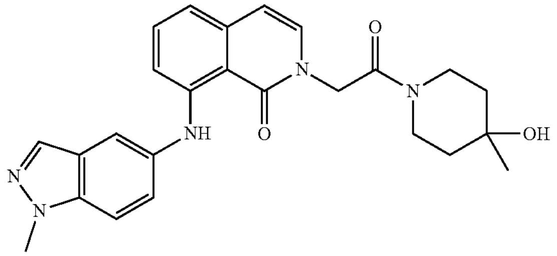 2-[2-(4-hydroxy-4-methyl-1-piperidyl)-2-oxo-ethyl]-8-[(1-methylindazol-5-yl)aminolisoquinolin-1-one Example 84 | Method 1: 3.47 min, m/z 446.7 $[M + H]^+$ | 11.02 (s, 1H), 7.99 (d, J = 0.9 Hz, 1H), 7.69-7.64 (m, 2H), 7.38 (t, J = 8.0 Hz, 1H), 7.31 (dd, J = 2.0, 8.9 Hz, 1H), 7.28 (d, J = 7.3 Hz, 1H), 6.87 (d, J = 8.3 Hz, 1H), 6.81 (d, J = 8.0 Hz, 1H), 6.51 (d, J = 7.4 Hz, 1H), 4.85 (s, 2H), 4.46 (s, 1H), 4.06 (s, 3H), 3.94-3.90 (m, 1H), 3.67-3.62 (m, 1H), 3.47-3.38 (m, 1H), 3.13-3.05 (m, 1H), 1.59-1.53 (m, 2H), 1.51-1.45 (m, 1H), 1.42-1.33 (m, 1H), 1.17 (s, 3H). |
| Methyl 5-[(1-oxo-2-{[(2,2,2-trifluoroethyl) carbamoyl]methyl}-1,2-dihydroisoquinolin-8-yl)amino]-1H-indazole-7-carboxylate | 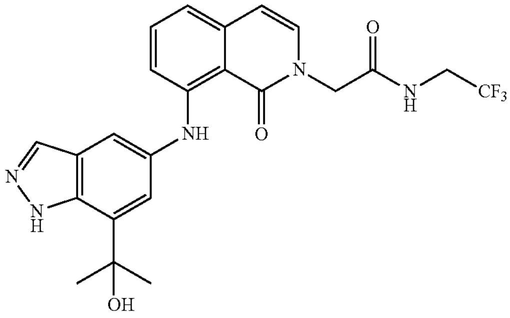 2-(8-{[7-(2-hydroxypropan-2-yl)-1H-indazol-5-yl]amino}-1-oxo-1,2-dihydroisoquinolin-2-yl)-N-(2,2,2-trifluoroethyl)acetamide Example 92 | Method 3: 3.60 min, m/z 472.3 $[M - H]^-$ | 12.69 (s, 1H), 10.97 (s, 1H), 8.91 (t, J = 6.4 Hz, 1H), 8.02 (s, 1H), 7.55 (s, 1H), 7.43-7.35 (m, 2H), 7.18 (s, 1H), 6.95 (d, J = 8.3 Hz, 1H), 6.82 (d, J = 8.3 Hz, 1H), 6.54 (d, J = 7.4 Hz, 1H), 5.42 (s, 1H), 4.68 (s, 2H), 4.05-3.94 (m, 2H), 1.62 (s, 6H). |
| N-(3-acetylphenyl)-2-[1-ox0-8-[(1-tetrahydropyran-2-ylpyrazolo[3,4-b]pyridin-5-yl)amino]-2-isoquinolyl]acetamide (Final THP deprotection required) | 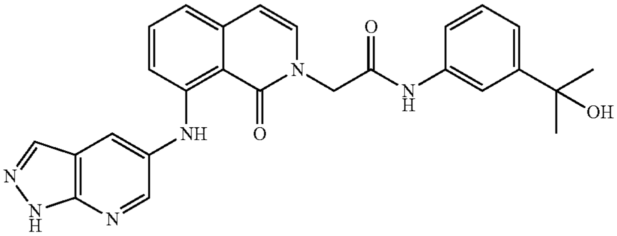 N-[3-(1-hydroxy-1-methyl-ethyl)phenyl]-2-[1-oxo-8-(1H-pyrazolo[3,4-b]pyridin-5-ylamino)-2-isoquinolyl]acetamide Example 106 | Method 3: 3.33 min, m/z 469.6 | 13.64 (s, 1H), 10.96 (s, 1H), 10.33 (s, 1H), 8.45 (d, J = 2.4 Hz, 1H), 8.17 (d, J = 2.3 Hz, 1H), 8.09 (s, 1H), 7.71 (s, 1H), 7.49 (d, J = 8.0 Hz, 1H), 7.44-7.38 (m, 2H), 7.24 (t, J = 7.9 Hz, 1H), 7.16 (d, J = 8.0 Hz, 1H), 6.89 (d, J = 7.1 Hz, 1H), 6.79 (d, J = 7.6 Hz, 1H), 6.58 (d, J = 7.4 Hz, 1H), 4.99 (s, 1H), 4.79 (s, 2H), 1.41 (s, 6H). |
| N-(3-acetylphenyl)-2-[8-[(1-methylpyrazolo[3,4-b]pyridin-5-yl)amino]-1-oxo-2-isoquinolyl]acetamide | 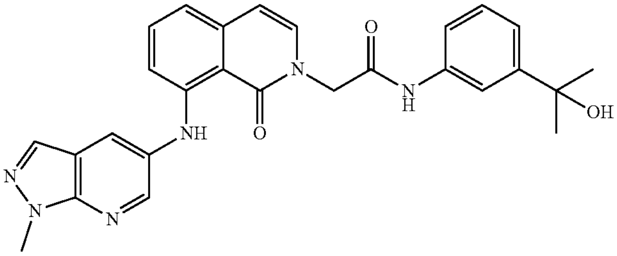 N-[3-(1-hydroxy-1-methyl-ethyl)phenyl]-2-[8-[(1-methylpyrazolo[3,4-b]pyridin-5-yl)amino]-1-oxo-2-isoquinolyl]acetamide Example 111 | Method 3: 3.67 min, m/z 483.4 | 10.98 (s, 1H), 10.32 (s, 1H), 8.49 (s, 1H), 8.18 (s, 1H), 8.08 (s, 1H), 7.71 (s, 1H), 7.49-7.38 (m, 3H), 7.25-7.14 (m, 2H), 6.90 (d, 1H), 6.81 (d, 1H), 6.57 (d, 1H), 4.99 (s, 1H), 4.78 (s, 2H), 4.06 (s, 3H), 1.4 (s, 6H). |

TABLE 12-continued

| Starting material | Structure/Name | UPLCMS[1] (ES$^+$) | $^1$H NMR (400 MHz, DMSO-$d_6$) |
|---|---|---|---|
| N-(3-acetylphenyl)-2-[8-[methyl-(1-methylindazol-5-yl)amino]-1-oxo-2-isoquinolyl]acetamide | 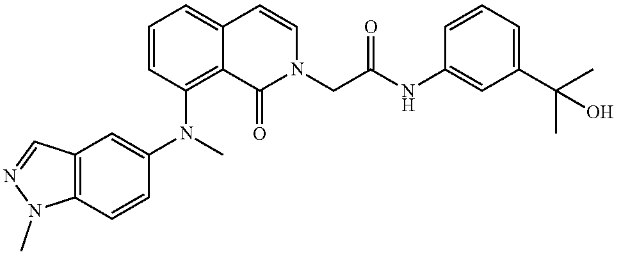 N-[3-(1-hydroxy-1-methyl-ethyl)phenyl]-2-[8-[methyl-(1-methylindazol-5-yl)amino]-1-oxo-2-isoquinolyl]acetamide Example 142 | Method 3: 3.68 min, m/z 496.0 | 10.18 (s, 1H), 7.77 (s, 1H), 7.70-7.62 (m, 2H), 7.54-7.49 (m, 1H), 7.44 (d, J = 7.3Hz, 1H), 7.40 (d, J = 8.1 Hz, H), 7.29 (d, J = 9.1 Hz, 1H), 7.19 (dt, J = 7.9, 4.1 Hz, 2H), 7.11 (d, J = 7.8 Hz, 1H), 6.82 (d, J = 2.2 Hz, 1H), 6.65 (dd, J = 9.1, 2.3 Hz, 1H), 6.61 (d, J = 7.4 Hz, 1H), 4.95 (s, 1H), 4.63 (s, 2H), 3.92 (s, 3H), 3.17 (s, 3H), 1.37 (s, 6H). |
| methyl 2-[1-[2-[8-[(1-methylindazol-5-yl)amino]-1-oxo-2-isoquinolyl]acetyl] pyrrolidin-2-yl]acetate | 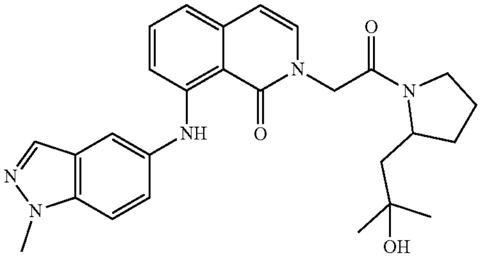 2-[2-[2-(2-hydroxy-2-methyl-propyl)pyrrolidin-1-yl]-2-oxo-ethyl]-8-[(1-methylindazol-5-yl)amino]isoquinolin-1-one Example 148 | Method 3: 3.88 min, m/z 474.3 | 10.98 (d, J = 12.2 Hz, 1H), 7.98 (s, 1H), 7.72-7.60 (m, 2H), 7.40-7.24 (m, 3H), 6.90-6.78 (m, 2H), 6.51 (d, J = 7.3 Hz, 1H), 4.77 (d, J = 41.4 Hz, 2H), 4.21 (s, 1H), 4.05 (s, 4H), 3.58-3.45 (m, 1H), 2.05-1.64 (m, 5H), 1.41 (dd, J = 13.4, 9.6 Hz, 1H), 1.27-1.05 (m, 6H). |
| N-(3-acetylphenyl)-2-[7-fluoro-8-[(1-methylindazol-5-yl)amino]-1-oxo-2-isoquinolyl]acetamide | 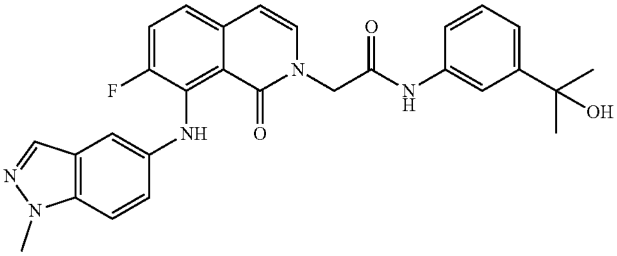 2-[7-fluoro-8-[(1-methylindazol-5-yl)amino]-1-oxo-2-isoquinolyl]-N-[3-(1-hydroxy-1-methyl-ethyl)phenyl]acetamide Example 152 | Method 4: 1.38 min, m/z 500.0 | 10.67 (s, 1H), 10.37 (s, 1H), 7.93 (s, 1H), 7.74 (s, 1H), 7.64-7.56 (m, 2H), 7.53-7.47 (m, 2H), 7.30-7.17 (m, 5H), 6.73 (d, J = 7.6 Hz, 1H), 5.04 (s, 1H), 4.83 (s, 2H), 4.06 (s, 3H), 1.44 (s, 6H). |
| methyl 1-[2-[8-[(1-methylindazol-5-yl)amino]-1-oxo-2-isoquinolyl]acetyl] piperidine-2-carboxylate | 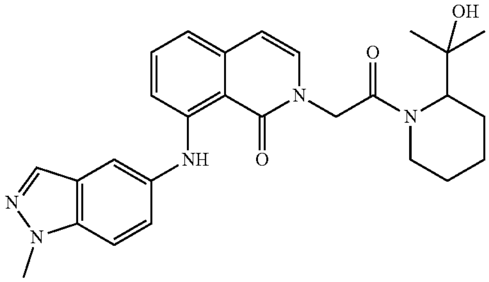 2-[2-[2-(1-hydroxy-1-methyl-ethyl)-1-piperidyl]-2-oxo-ethyl]-8-[(1-methylindazol-5-yl)amino]isoquinolin-1-one Example 156 | Method 3: 3.92 min, m/z 474.2 | 11.04-10.98 (m, 1H), 7.98 (s, 1H), 7.70-7.62 (m, 2H), 7.36 (t, J = 8.0 Hz, 1H), 7.33-7.28 (m, 1H), 7.28-7.22 (m, 1H), 6.88-6.77 (m, 2H), 6.50 (d, J = 7.3 Hz, 1H), 4.96-4.80 (m, 2H), 4.64-4.42 (m, 1H), 4.32-4.12 (m, 1H), 4.05 (s, 3H), 3.73-3.56 (m, 2H), 2.06-1.90 (m, 2H), 1.71-1.36 (m, 4H), 1.30-1.03 (m, 6H). |

TABLE 12-continued

| Starting material | Structure/Name | UPLCMS[1] ($ES^+$) | $^1H$ NMR (400 MHz, DMSO-$d_6$) |
|---|---|---|---|
| N-(3-acetylphenyl)-2-[8-[(3-methyl-1H-indazol-6-yl)amino]-1-oxo-2-isoquinolyl]acetamide | 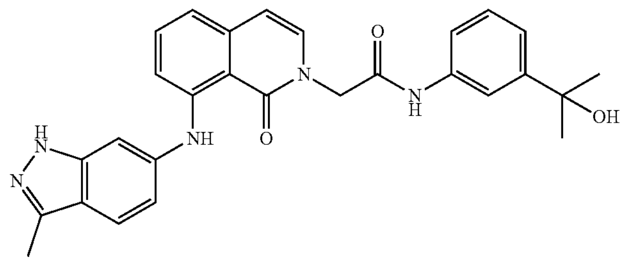 N-[3-(1-hydroxy-1-methyl-ethyl)phenyl]-2-[8-[(3-methyl-1H-indazol-6-yl)amino]-1-oxo-2-isoquinolyl]acetamide Example 161 | Method 3: 61 min, m/z 482.2 | 12.45 (s, 1H), 11.25 (s, 1H), 10.37 (s, 1H), 7.76 (s, 1H), 7.70 (d, J = 8.4 Hz, 1H), 7.57-7.51 (m, 2H), 7.48 (d, J = 7.3 Hz, 1H), 7.39 (s, 1H), 7.32-7.23 (m, 2H), 7.21 (d, J = 7.7 Hz, 1H), 7.04-6.96 (m, 2H), 6.64 (d, J = 7.2 Hz, 1H), 5.05 (s, 1H), 4.84 (s, 2H), 2.51 (s, 3H), 1.46 (s, 6H). |

[1]For examples where alternative HPLC and mass spectrometry methods were used, these are referred to in the individual example entries

Example 47, 2-[6-fluoro-8-[(1-methylindazol-5-yl)amino]-1-oxo-2-isoquinolyl]-N-(2,2,2-trifluoroethyl)acetamide Scheme 12

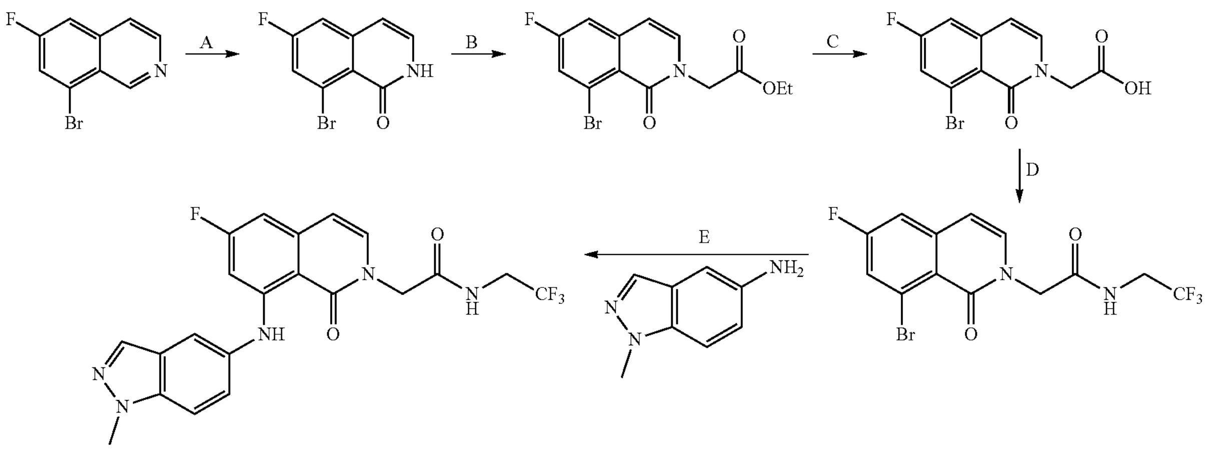

47

STEP A. To a solution of 8-Bromo-6-fluoroisoquinoline (1.0 g, 4.4 mmol) in dichloromethane (25 mL) at 0° C. was added m-chloroperbenzoic acid (1.53 g, 8.9 mmol) and the mixture was stirred for 4 h slowly warming to rt. The reaction was quenched with saturated aqueous $Na_2S_2O_3$, the layers were separated, the organic layer was washed with saturated aqueous $NaHCO_3$, and the combined aqueous layers were extracted with dichloromethane. The organic layers were combined, dried over $Na_2SO_4$, and concentrated under reduced pressure to give the intermediate N-oxide as a pale orange solid.

The N-oxide was dissolved in acetic anhydride (20 mL, 212 mmol) and the mixture was heated to 140° C. and stirred for 3 h, then cooled to rt and concentrated under reduced pressure. The resulting brown oil was dissolved in methanol (20 mL) and saturated aqueous $NaHCO_3$ (20 mL, 88 mmol) was added. The mixture was stirred at rt overnight, then concentrated under reduced pressure, and neutralised by dropwise addition of 2M HCl until pH 6. The resulting brown solid was collected by filtration, then dissolved in methanol and concentrated under reduced pressure to give 8-bromo-6-fluoro-2H-isoquinolin-1-one (963 mg, 4.0 mmol, 90% yield) as a brown solid.

UPLC-MS ($ES^+$, Method 2): 1.62 min, m/z 241.8/243.8 $[M+H]^+$.

$^1H$ NMR (400 MHz, DMSO-$d_6$) δ 11.34 (s, 1H), 7.64 (dd, J=2.6, 8.6 Hz, 1H), 7.55 (dd, J=2.6, 9.4 Hz, 1H), 7.25 (app t, J=6.5 Hz, 1H), 6.54 (dd, J=1.3, 7.1 Hz, 1H).

STEP B. To a solution of 8-bromo-6-fluoro-2H-isoquinolin-1-one (963 mg, 4.0 mmol) in dichloromethane (15 mL) were added ethyl bromoacetate (0.9 mL, 8.0 mmol) and $Cs_2CO_3$ (3.25 g, 10.0 mmol), and the mixture was stirred at rt overnight. Water was added, the layers were separated, the aqueous layer was extracted with dichloromethane and the combined organic layers were washed with Brine, dried over $Na_2SO_4$, and concentrated under reduced pressure. The crude product was purified by normal phase chromatography (25 g column, 10 to 90% EtOAc in petrol) to give ethyl 2-(8-bromo-6-fluoro-1-oxo-2-isoquinolyl)acetate (1.1 g, 3.35 mmol, 84% yield) as an orange solid.

UPLC-MS ($ES^+$, Method 2): 1.82 min, m/z 328.0/329.9 $[M+H]^+$.

$^1$H NMR (400 MHz, DMSO-$d_6$) δ 7.73 (dd, J=2.6, 8.6 Hz, 1H), 7.60-7.56 (m, 2H), 6.66 (d, J=7.4 Hz, 1H), 4.71 (s, 2H), 4.17 (q, J=7.1 Hz, 2H), 1.23 (t, J=7.1 Hz, 3H).

STEP C. To a mixture of ethyl 2-(8-bromo-6-fluoro-1-oxo-2-isoquinolyl)acetate (500 mg, 1.5 mmol) in methanol (4 mL) was added a solution of lithium hydroxide (109 mg, 4.6 mmol) in water (4 mL) and the mixture was stirred at rt overnight. The mixture was concentrated under reduced pressure, then it was neutralised by dropwise addition of 2M HCl until pH 4. The resulting precipitate was collected by filtration, dissolved in methanol and concentrated under reduced pressure to give 2-(8-bromo-6-fluoro-1-oxo-2-isoquinolyl)acetic acid (445 mg, 1.5 mmol, 97% yield) as a pale yellow solid.

UPLC-MS ($ES^+$, Method 2): 1.57 min, m/z 299.9/301.9 $[M+H]^+$.

$^1$H NMR (400 MHz, DMSO-$d_6$) δ 13.03 (s, 1H), 7.72 (dd, J=2.6, 8.6 Hz, 1H), 7.59-7.55 (m, 2H), 6.63 (d, J=7.4 Hz, 1H), 4.63 (s, 2H).

STEP D. To a solution of 2-(8-bromo-6-fluoro-1-oxo-2-isoquinolyl)acetic acid (445 mg, 1.5 mmol), trifluoroethylamine (220 mg, 2.2 mmol), N,N-diisopropylethylamine (0.5 mL, 3.0 mmol) and trifluoroethylamine (0.18 mL, 2.2 mmol) in dichloromethane (10 mL) was added HATU (846 mg, 2.2 mmol). The mixture was stirred at rt overnight. Water was added, the layers were separated, the organic layer was washed with Brine and the combined aqueous layers were extracted with dichloromethane. The organic layers were combined, dried over $Na_2SO_4$, and concentrated under reduced pressure. The crude product was purified by normal phase chromatography (12 g column, 10 to 100% EtOAc in petrol) to give 2-(8-bromo-6-fluoro-1-oxo-2-isoquinolyl)-N-(2,2,2-trifluoroethyl)acetamide (434 mg, 1.1 mmol, 77% yield) as a pale orange solid.

UPLC-MS ($ES^+$, Method 2): 1.73 min, m/z 381.0/382.9 $[M+H]^+$.

$^1$H NMR (400 MHz, DMSO-$d_6$) δ 8.91 (t, J=6.2 Hz, 1H), 7.70 (dd, J=2.6, 8.6 Hz, 1H), 7.58-7.53 (m, 2H), 6.62 (d, J=7.4 Hz, 1H), 4.63 (s, 2H), 3.97 (dq, J=6.4, 9.8 Hz, 2H).

STEP E. 2-(8-bromo-6-fluoro-1-oxo-2-isoquinolyl)-N-(2,2,2-trifluoroethyl)acetamide (50 mg, 0.12 mmol), 1-methyl-1h-indazol-5-amine (21 mg, 0.14 mmol), tris(dibenzylideneacetone)dipalladium (0) (5.4 mg, 0.01 mmol), 4,5-Bis (diphenylphosphino)-9,9-dimethylxanthene (6.7 mg, 0.01 mmol) and $Cs_2CO_3$ (77 mg, 0.24 mmol) were dissolved in toluene (2 mL), the vial was sealed and degassed, and the mixture was stirred at 110° C. overnight. The mixture was concentrated under reduced pressure and purified by normal phase chromatography (12 g column, 10 to 100% EtOAc in petrol). The purified product was triturated with isopropanol, then dried under vacuum overnight to give 2-[6-fluoro-8-[(1-methylindazol-5-yl)amino]-1-oxo-2-isoquinolyl]-N-(2,2,2-trifluoroethyl) acetamide (30 mg, 0.067 mmol, 57% yield) as a white solid.

UPLC-MS ($ES^+$, Method 1): 4.32 min, m/z 448.1 $[M+H]^+$.

$^1$H NMR (400 MHz, DMSO-$d_6$) δ 11.13 (s, 1H), 8.93 (t, J=6.3 Hz, 1H), 8.02 (s, 1H), 7.74-7.68 (m, 2H), 7.43 (d, J=7.3 Hz, 1H), 7.34 (dd, J=1.7, 8.8 Hz, 1H), 6.63 (dd, J=2.1, 9.4 Hz, 1H), 6.54 (d, J=7.4 Hz, 1H), 6.45 (dd, J=2.1, 12.4 Hz, 1H), 4.67 (s, 2H), 4.07 (s, 3H), 3.98 (dq, J=6.4, 9.7 Hz, 2H).

The following examples (table 13) were prepared according to the route described in scheme 12 for example 47, replacing 8-Bromo-6-fluoroisoquinoline in step A with the appropriate fluorinated 8-bromoisoquinoline starting material in step A and/or substituting trifluoroethylamine for the appropriate amine building block in step D or 1-methyl-1 h-indazol-5-amine for the appropriate aniline building block in step E.

TABLE 13

| Starting material | Structure/Name | UPLCMS ($ES^+$) | $^1$H NMR (400 MHz, DMSO-$d_6$) |
|---|---|---|---|
| 8-Bromo-5-fluoroisoquinoline | 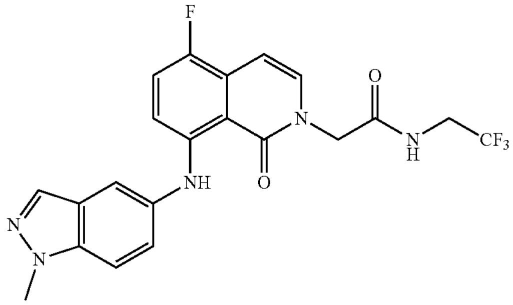 2-[5-fluoro-8-[(1-methylindazol-5-yl)amino]-1-oxo-2-isoquinolyl]-N-(2,2,2-trifluoroethyl)acetamide Example 64 | Method 1: 3.91 min, m/z 448.1 $[M + H]^+$ | 10.64 (s, 1H), 8.94 (t, J = 6.2 Hz, 1H), 7.98 (d, J = 1.0 Hz, 1H), 7.69-7.64 (m, 2H), 7.49 (d, J = 7.5 Hz, 1H), 7.37-7.29 (m, 2H), 6.82 (dd, J = 4.3, 9.2 Hz, 1H), 6.62 (d, J = 7.4 Hz, 1H), 4.70 (s, 2H), 4.06 (s, 3H), 4.03-3.93 (m, 2H). |

TABLE 13-continued

| Starting material | Structure/Name | UPLCMS (ES$^+$) | $^1$H NMR (400 MHz, DMSO-$d_6$) |
|---|---|---|---|
| 8-Bromo-7-fluoroisoquinoline | 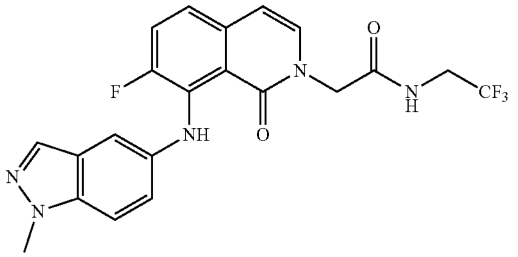 2-[7-fluoro-8-[(1-methylindazol-5-yl)amino]-1-oxo-2-isoquinolyl]-N-(2,2,2-trifluoroethyl)acetamide Example 58 | Method 1: 3.80 min, m/z 448.2 [M + H]$^+$ | 10.59 (d, J = 2.1 Hz, 1H), 8.92 (t, J = 6.3 Hz, 1H), 7.89 (s, 1H), 7.58-7.52 (m, 2H), 7.40 (d, J = 7.3 Hz, 1H), 7.22-7.16 (m, 2H), 7.13 (dd, J = 4.3, 8.6 Hz, 1H), 6.66 (d, J = 7.3 Hz, 1H), 4.67 (s, 2H), 4.02 (s, 3H), 3.96 (q, J = 5.4 Hz, 2H). |
| 8-Bromo-7-fluoroisoquinoline and (2S)-2-(trifluoromethyl) pyrrolidine (Step D) | 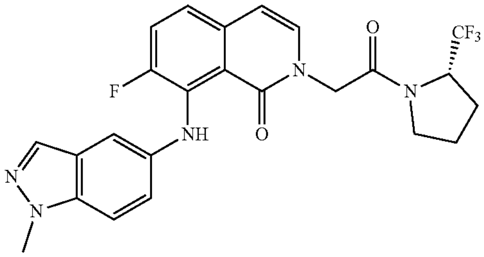 7-fluoro-8-[(1-methylindazol-5-yl)amino]-2-[2-oxo-2-[(2S)-2-(trifluoromethyl)pyrrolidin-1-yl]ethyl]isoquinolin-1-one Example 130 | Method 4: 2.20 min, m/z 488.2 [M + H]$^+$ | 10.59 (d, J = 17.0 Hz, 1H), 7.91-7.87 (m, 1H), 7.59-7.50 (m, 2H), 7.32 (d, J = 7.2 Hz, 1H), 7.22 (s, 1H), 7.20-7.10 (m, 2H), 6.66 (d, J = 7.4 Hz, 1H), 5.07-4.71 (m, 3H), 4.01 (s, 3H), 3.81-3.58 (m, 2H), 2.19-1.91 (m, 4H). |
| 8-Bromo-7-fluoroisoquinoline and (1S)-2,2,2-trifluoro-1-methyl-ethylamine (Step D) | 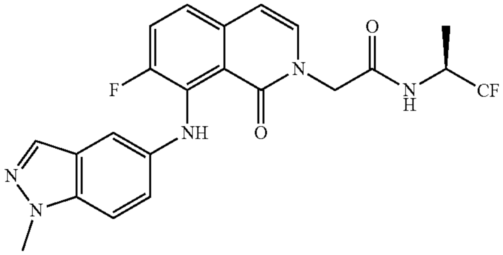 2-[7-fluoro-8-[(1-methylindazol-5-yl)amino]-1-oxo-2-isoquinolyl]-N-[(1S)-2,2,2-trifluoro-1-methyl-ethyl]acetamide Example 137 | Method 3: 3.88 min, m/z 462.2 [M + H]$^+$ | 10.59 (d, J = 2.3 Hz, 1H), 8.81 (d, J = 8.8 Hz, 1H), 7.89 (s, 1H), 7.54 (dt, J = 8.5, 6.3 Hz, 2H), 7.37 (d, J = 7.3 Hz, 1H), 7.25-7.06 (m, 3H), 6.64 (d, J = 7.4 Hz, 1H), 4.78-4.44 (m, 3H), 4.01 (s, 3H), 1.26 (d, J = 7.0 Hz, 3H). |
| 8-Bromo-7-fluoroisoquinoline and 3-(Trifluoromethyl) aniline (Step D) | 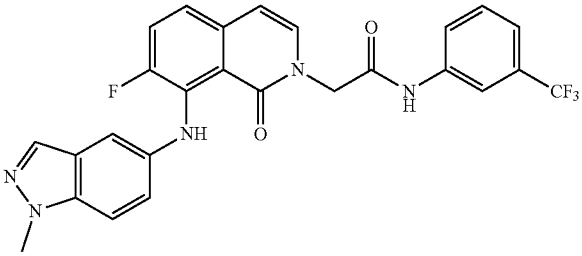 2-[7-fluoro-8-[(1-methylindazol-5-yl)amino]-1-oxo-2-isoquinolyl]-N-[3-(trifluoromethyl)phenyl]acetamide Example 146 | Method 3: 4.22 min, m/z 510.2 [M + H]$^+$ | 10.79 (s, 1H), 10.58 (d, J = 2.4 Hz, 1H), 8.09 (s, 1H), 7.88 (s, 1H), 7.76 (d, J = 8.4 Hz, 1H), 7.60-7.50 (m, 3H), 7.45 (d, J = 7.3 Hz, 1H), 7.41 (d, J = 7.7 Hz, 1H), 7.23-7.20 (m, 1H), 7.18-7.13 (m, 2H), 6.69 (d, J = 7.4 Hz, 1H), 4.83 (s, 2H), 4.00 (s, 3H). |

TABLE 13-continued

| Starting material | Structure/Name | UPLCMS ($ES^+$) | $^1H$ NMR (400 MHz, DMSO-$d_6$) |
|---|---|---|---|
| 8-Bromo-7-fluoroisoquinoline and 3-methyl-1H-indazol-6-amine (Step E) | 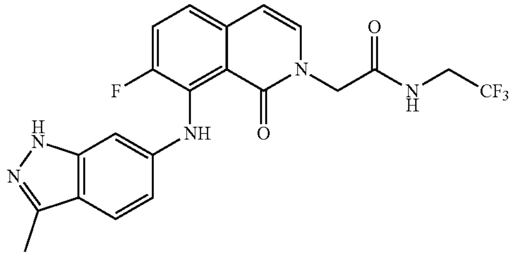 2-[7-fluoro-8-[(3-methyl-1H-indazol-6-yl)amino]-1-oxo-2-isoquinolyl]-N-(2,2,2-trifluoroethyl)acetamide Example 150 | Method 4: 1.62 min, m/z 448.1 $[M + H]^+$ | 12.25 (s, 1H), 10.54 (s, 1H), 8.91 (t, J = 6.4 Hz, 1H), 7.62 (dd, J = 12.0, 8.4 Hz, 1H), 7.54 (d, J = 8.4 Hz, 1H), 7.40 (d, J = 7.2 Hz, 1H), 7.24 (dd, J = 8.8, 4.4 Hz, 1H), 6.78 (dd, J = 8.8, 2.8 Hz, 2H), 6.68 (d, J = 7.6 Hz, 1H), 4.67 (s, 2H), 3.99-3.89 (m, 2H), 2.42 (s, 3H). |
| 8-Bromo-7-fluoroisoquinoline and 1-methylpyrazolo[3,4-b]pyridin-5-amine (Step E) | 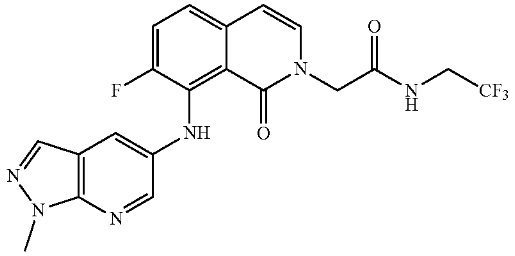 2-[7-fluoro-8-[(1-methylpyrazolo[3,4-b]pyridin-5-yl)amino]-1-oxo-2-isoquinolyl]-N-(2,2,2-trifluoroethyl)acetamide Example 135 | Method 4: 1.59 min, m/z 449.1 $[M + H]^+$ | 10.71 (s, 1H), 8.90 (d, J = 6.7 Hz, 1H), 8.44 (s, 1H), 8.00 (s, 1H), 7.72 (d, J = 3.2 Hz, 1H), 7.59-7.53 (m, 1H), 7.41 (d, J = 3.6 Hz, 1H), 7.16 (dd, J = 8.4, 4.0 Hz, 1H), 6.67 (d, J = 6.4 Hz, 1H), 4.69 (s, 2H), 4.04 (s, 3H), 4.0-3.91 (m, 2H). |
| 8-Bromo-7-fluoroisoquinoline and 7-chloro-1-methyl-indazol-5-amine | 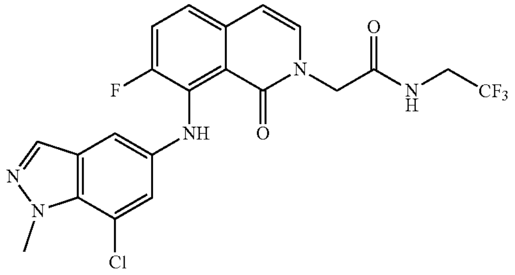 2-[8-[(7-chloro-1-methyl-indazol-5-yl)amino]-7-fluoro-1-oxo-2-isoquinolyl]-N-(2,2,2-trifluoroethyl)acetamide Example 160 | Method 3: 4.02 min, m/z 482.1 $[M + H]^+$ | 10.54 (s, 1H), 8.91 (t, J = 6.3 Hz, 1H), 7.97 (s, 1H), 7.61-7.56 (m, 1H), 7.40 (d, J = 7.3 Hz, 1H), 7.25 (s, 1H), 7.21-7.18 (m, 2H), 6.67 (d, J = 7.3 Hz, 1H), 4.67 (s, 2H), 4.27 (s, 3H), 4.00-3.90 (m, 2H). |

Example 51, 2-[8-[(1-methylindazol-5-yl)amino]-1-oxo-2-isoquinolyl]-N-(2,2,2-trifluoroethyl) propanamide Scheme 13

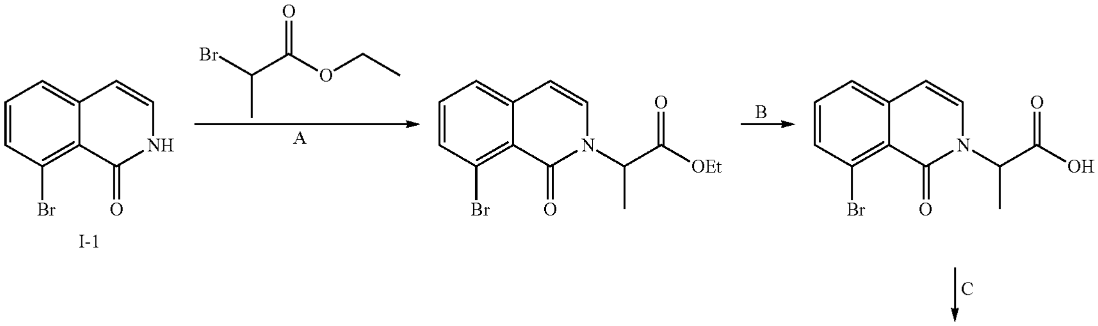

-continued

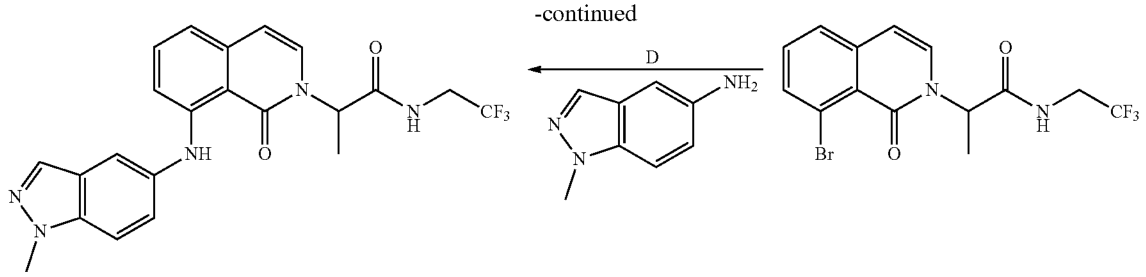

51

STEP A. To a solution of 8-bromo-2H-isoquinolin-1-one (Intermediate I-1, 250 mg, 1.1 mmol) in DMF (5 mL) were added ethyl 2-bromopropionate (0.2 mL, 1.7 mmol) and $Cs_2CO_3$ (727 mg, 2.2 mmol) and the mixture was stirred at rt overnight. The mixture was diluted with EtOAc, washed three times with Brine, dried over $Na_2SO_4$ and concentrated under reduced pressure. The crude product was purified by normal phase chromatography (25 g column, 10 to 90% EtOAc in petrol) to give ethyl 2-(8-bromo-1-oxo-2-isoquinolyl)propanoate (155 mg, 0.48 mmol, 43% yield) as a yellow oil.

UPLC-MS ($ES^+$, Method 2): 1.83 min, m/z 324.0/325.9 $[M+H]^+$.

$^1H$ NMR (400 MHz, DMSO-$d_6$) δ 7.75 (dd, J=1.2, 7.7 Hz, 1H), 7.68 (dd, J=1.1, 8.0 Hz, 1H), 7.57-7.52 (m, 2H), 6.69 (d, J=7.5 Hz, 1H), 5.21 (q, J=7.2 Hz, 1H), 4.18-4.08 (m, 2H), 1.58 (d, J=7.2 Hz, 3H), 1.16 (t, J=7.1 Hz, 3H).

STEP B. To a mixture of ethyl 2-(8-bromo-1-oxo-2-isoquinolyl)propanoate (155 mg, 0.48 mmol) in methanol (3 mL) was added a solution of lithium hydroxide (34 mg, 1.4 mmol) in water (3 mL) and the mixture was stirred at rt overnight. The mixture was concentrated under reduced pressure, then it was neutralised by dropwise addition of 2M HCl until pH 4. The resulting precipitate was collected by filtration, dissolved in methanol and concentrated under reduced pressure to give 2-(8-bromo-1-oxo-2-isoquinolyl) propanoic acid (145 mg, 0.48 mmol, 100% yield) as a white solid.

UPLC-MS ($ES^+$, Method 2): 1.56 min, m/z 295.9/297.9 $[M+H]^+$.

$^1H$ NMR (400 MHz, DMSO-$d_6$) δ 12.91 (s, 1H), 7.75 (d, J=7.8 Hz, 1H), 7.67 (d, J=7.0 Hz, 1H), 7.56-7.51 (m, 2H), 6.66 (d, J=7.4 Hz, 1H), 5.20 (q, J=7.3 Hz, 1H), 1.57 (d, J=7.4 Hz, 3H).

STEP C. To a solution of 2-(8-bromo-1-oxo-2-isoquinolyl)propanoic acid (145 mg, 0.48 mmol), N,N-diisopropylethylamine (0.17 mL, 0.98 mmol) and trifluoroethylamine (0.06 mL, 0.73 mmol) in DMF (3 mL) was added HATU (279 mg, 0.73 mmol), and the mixture was stirred at rt overnight. The mixture was diluted with EtOAc and washed three times with Brine, dried over $Na_2SO_4$ and concentrated under reduced pressure. The crude product was purified by normal phase chromatography (12 g column, 10 to 90% EtOAc in petrol) to give 2-(8-bromo-1-oxo-2-isoquinolyl)-N-(2,2,2-trifluoroethyl)propanamide (149 mg, 0.39 mmol, 81% yield) as a pale yellow solid.

UPLC-MS ($ES^+$, Method 2): 1.71 min, m/z 377.0/378.9 $[M+H]^+$.

$^1H$ NMR (400 MHz, DMSO-$d_6$) δ 8.90 (t, J=6.2 Hz, 1H), 7.74 (dd, J=1.2, 7.7 Hz, 1H), 7.67 (dd, J=1.2, 8.1 Hz, 1H), 7.53 (t, J=7.8 Hz, 1H), 7.49 (d, J=7.5 Hz, 1H), 6.66 (d, J=7.6 Hz, 1H), 5.45 (q, J=7.3 Hz, 1H), 3.98-3.89 (m, 2H), 1.55 (d, J=7.3 Hz, 3H).

STEP D. 2-(8-bromo-1-oxo-2-isoquinolyl)-N-(2,2,2-trifluoroethyl)propanamide (50 mg, 0.13 mmol), 1-methyl-1h-indazol-5-amine (21 mg, 0.15 mmol), tris(dibenzylideneacetone)dipalladium (0) (6.1 mg, 0.01 mmol), 4,5-Bis (diphenylphosphino)-9,9-dimethylxanthene (7.7 mg, 0.01 mmol) and $Cs_2CO_3$ (86 mg, 0.27 mmol) were dissolved in toluene (2 mL), the vial was sealed and degassed, and the mixture was stirred at 110° C. overnight. The mixture was filtered through a Celite pad washing with methanol and concentrated under reduced pressure. The crude product was purified by reverse phase chromatography (12 g column, 25 to 65% acetonitrile in water, 0.1% formic acid), then dried under vacuum overnight to give 2-[8-[(1-methylindazol-5-yl)amino]-1-oxo-2-isoquinolyl]-N-(2,2,2-trifluoroethyl) propanamide (39 mg, 0.09 mmol, 66% yield) as a white solid.

UPLC-MS ($ES^+$, Method 1): 4.44 min, m/z 444.3 $[M+H]^+$.

$^1H$ NMR (400 MHz, DMSO-$d_6$) δ 10.99 (s, 1H), 8.89 (t, J=6.4 Hz, 1H), 7.99 (s, 1H), 7.70-7.64 (m, 2H), 7.41-7.34 (m, 2H), 7.31 (dd, J=1.9, 8.8 Hz, 1H), 6.86 (d, J=8.3 Hz, 1H), 6.82 (d, J=7.3 Hz, 1H), 6.57 (d, J=7.6 Hz, 1H), 5.49 (q, J=7.3 Hz, 1H), 4.06 (s, 3H), 4.02-3.87 (m, 2H), 1.58 (d, J=7.3 Hz, 3H).

The following examples (table 14) were prepared according to the route described in scheme 13 for example 51, replacing ethyl 2-bromopropionate in with the appropriate electrophile starting material in step A.

TABLE 14
| Starting material | Structure/Name | UPLCMS ($ES^+$) | $^1H$ NMR (400 MHz, DMSO-$d_6$) |
|---|---|---|---|
| Ethyl bromofluoroacetate | 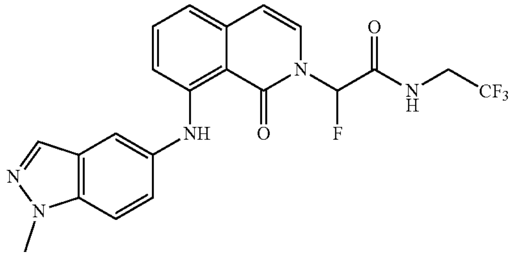 2-fluoro-2-[8-[(1-methylindazol-5-yl)amino]-1-oxo-2-isoquinolyl]-N-(2,2,2-trifluoroethyl)acetamide Example 122 | Method 3: 4.05 min, m/z 448.0 $[M + H]^+$ | 10.60 (s, 1H), 9.33 (t, J = 6.4 Hz, 1H), 8.01 (s, 1H), 7.72-7.66 (m, 2H), 7.45 (t, J = 7.9 Hz, 1H), 7.33 (dd, J = 1.5, 8.9 Hz, 1H), 7.25 (d, J = 7.4 Hz, 1H), 6.90-6.82 (m, 2H), 6.63 (d, J = 7.6 Hz, 1H), 4.10-3.91 (m, 6H). |
Example 8, 2-[5-methyl-8-[(1-methylindazol-5-yl)amino]-1-oxo-2-isoquinolyl]-N-(2,2,2-trifluoroethyl)acetamide
Scheme 14
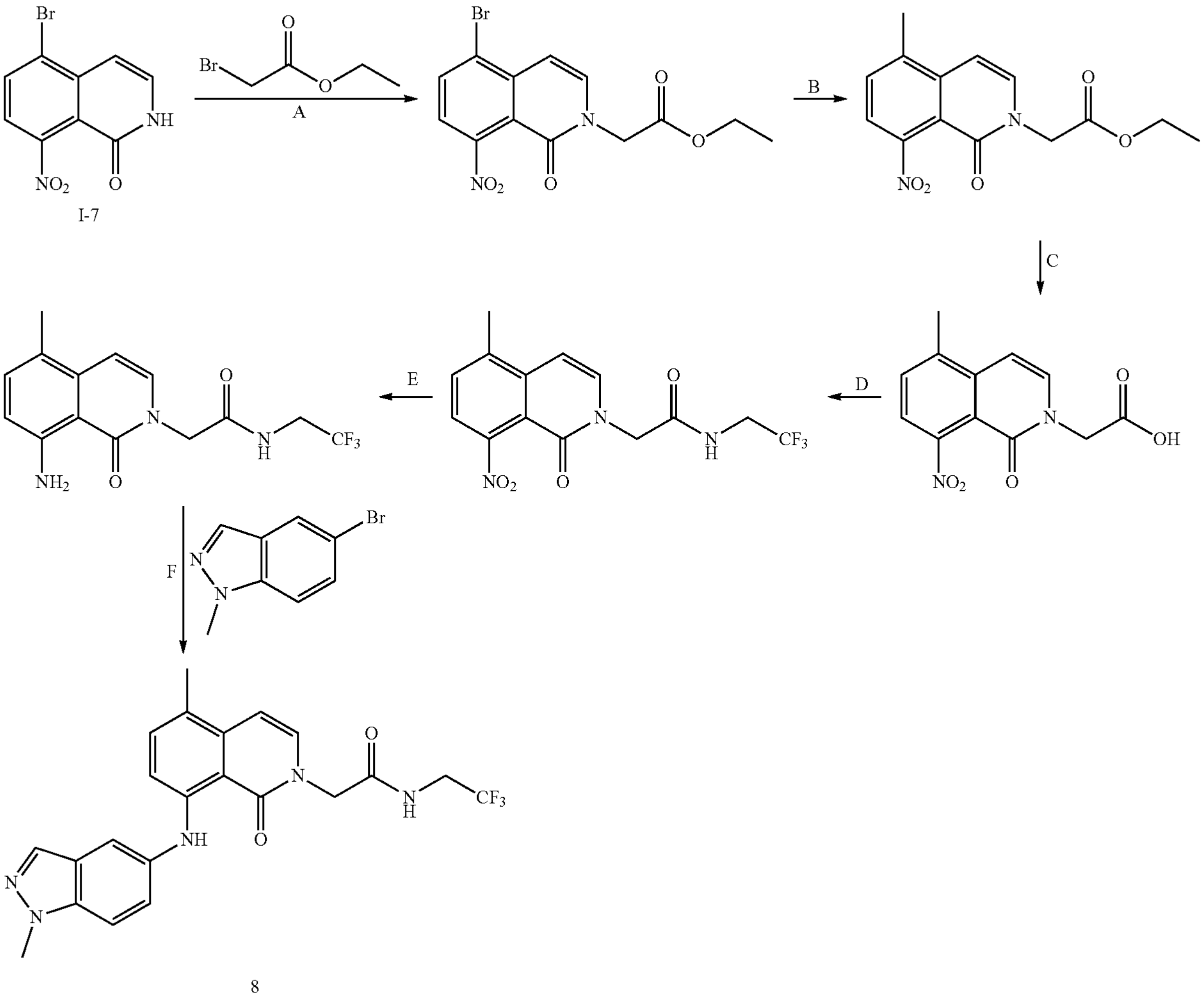
I-7
8

STEP A. To a solution of 5-bromo-8-nitro-2H-isoquinolin-1-one (160 mg, 0.6 mmol) in DMF (10 mL) were added ethyl bromoacetate (0.13 mL, 1.2 mmol) and $Cs_2CO_3$ (484 mg, 1.5 mmol), the mixture was heated to 90° C. and stirred overnight. The mixture was cooled to rt and diluted with EtOAc, washed three times with Brine, dried over $Na_2SO_4$ and concentrated under reduced pressure. The crude product was purified by normal phase chromatography (25 g column, 0 to 5% methanol in dichloromethane) to give ethyl 2-(5-bromo-8-nitro-1-oxo-2-isoquinolyl)acetate (107 mg, 0.3 mmol, 51% yield) as a yellow solid.

UPLC-MS ($ES^+$, Method 2): 1.68 min, m/z 355.0/357.0 $[M+H]^+$.

$^1$H NMR (400 MHz, DMSO-$d_6$) δ 8.28 (d, J=8.2 Hz, 1H), 7.82 (d, J=7.7 Hz, 1H), 7.78 (d, J=8.3 Hz, 1H), 6.95 (d, J=7.7 Hz, 1H), 4.82 (s, 2H), 4.17 (q, J=7.1 Hz, 2H), 1.22 (t, J=7.1 Hz, 3H).

STEP B. Methylboronic acid (0.08 mL, 2.8 mmol), $K_2CO_3$ (584 mg, 4.2 mmol) and ethyl 2-(5-bromo-8-nitro-1-oxo-2-isoquinolyl)acetate (500 mg, 1.4 mmol) were dissolved in 1,4-Dioxane (6 mL) and Water (1 mL). The solution was degassed, [1,1'-Bis(diphenylphosphino)ferrocene]Palladium (II) chloride dichloromethane complex (115 mg, 0.14 mmol) was added and the mixture was stirred at 110° C. for 4 h. The mixture was cooled to rt, diluted with methanol and quenched with 2 M HCl, filtered through a Celite pad washing with methanol and concentrated under reduced pressure. EtOAc and water were added, the layers were separated, and the organic layer was washed with brine. The combined aqueous layers were extracted with EtOAc. The organic layers were combined, dried over $Na_2SO_4$, and concentrated under reduced pressure. The crude product was purified by normal phase chromatography (25 g column, 0 to 5% methanol in dichloromethane) to give ethyl 2-(5-methyl-8-nitro-1-oxo-2-isoquinolyl)acetate (191 mg, 0.66 mmol, 47% yield) as a yellow solid.

UPLC-MS ($ES^+$, Method 2): 1.59 min, m/z 291.2 $[M+H]^+$.

$^1$H NMR (400 MHz, DMSO-$d_6$) δ 7.74 (d, J=8.1 Hz, 1H), 7.70 (d, J=7.7 Hz, 1H), 7.67 (d, J=7.7 Hz, 1H), 6.86 (d, J=7.6 Hz, 1H), 4.79 (s, 2H), 4.16 (q, J=7.5 Hz, 2H), 2.57 (s, 3H), 1.21 (t, J=7.1 Hz, 3H).

STEP C. To a mixture of ethyl 2-(5-methyl-8-nitro-1-oxo-2-isoquinolyl)acetate (191 mg, 0.7 mmol) in methanol (4 mL) and THE (2 mL) was added a solution of lithium hydroxide (47 mg, 2.0 mmol) in water (2 mL) and the mixture was stirred at rt overnight. The mixture was concentrated under reduced pressure, then it was neutralised by dropwise addition of 2M HCl until pH 4. The resulting precipitate was collected by filtration, dissolved in methanol and concentrated under reduced pressure to give 2-(5-methyl-8-nitro-1-oxo-2-isoquinolyl)acetic acid (145 mg, 0.55 mmol, 84% yield) as a yellow solid.

UPLC-MS ($ES^+$, Method 2): 1.37 min, m/z 263.0 $[M+H]^+$.

$^1$H NMR (400 MHz, DMSO-$d_6$) δ 13.12 (s, 1H), 7.75-7.65 (m, 3H), 6.83 (d, J=7.6 Hz, 1H), 4.70 (s, 2H), 2.57 (s, 3H).

STEP D. To a solution of 2-(5-methyl-8-nitro-1-oxo-2-isoquinolyl)acetic acid (145 mg, 0.55 mmol), N,N-diisopropylethylamine (0.2 mL, 1.1 mmol) and trifluoroethylamine (0.07 mL, 0.83 mmol) in dichloromethane (8 mL) was added HATU (315 mg, 0.83 mmol. The mixture was stirred at rt overnight. The mixture was diluted with dichloromethane, water was added, and the layers were separated. The aqueous layer was extracted with dichloromethane, the combined organic layers were washed with Brine, dried over $Na_2SO_4$, and concentrated under reduced pressure. The crude product was purified by normal phase chromatography (25 g column, 0 to 5% methanol in dichloromethane) to give 2-(5-methyl-8-nitro-1-oxo-2-isoquinolyl)-N-(2,2,2-trifluoroethyl)acetamide (190 mg, 0.55 mmol, 100% yield) as a pale yellow solid.

UPLC-MS ($ES^+$, Method 2): 1.55 min, m/z 344.1 $[M+H]^+$.

$^1$H NMR (400 MHz, DMSO-$d_6$) δ 8.94 (t, J=6.2 Hz, 1H), 7.72 (d, J=7.8 Hz, 1H), 7.68-7.62 (m, 2H), 6.81 (d, J=7.6 Hz, 1H), 4.70 (s, 2H), 3.97 (dq, J=6.4, 9.7 Hz, 2H), 2.56 (s, 3H).

STEP E. A solution of 2-(5-methyl-8-nitro-1-oxo-2-isoquinolyl)-N-(2,2,2-trifluoroethyl)acetamide (190 mg, 0.55 mmol) in methanol (8 mL) was purged with three cycles of vac/$N_2$. Palladium (10 wt. % on carbon, 29 mg, 0.03 mmol) was added, followed by another 3 vac/$N_2$ cycles, then the mixture was put under $H_2$ atmosphere (3×H2/vac cycles) and stirred at rt for 1 h. The mixture was filtered through a Celite pad washing with methanol, concentrated under reduced pressure, and purified on an SCX column, eluting first with methanol then 7 M ammonia in methanol. The basic layer was concentrated under reduced pressure to give 2-(8-amino-5-methyl-1-oxo-2-isoquinolyl)-N-(2,2,2-trifluoroethyl) acetamide (143 mg, 0.46 mmol, 82% yield) as a brown solid.

UPLC-MS ($ES^+$, Method 2): 1.47 min, m/z 314.3 $[M+H]^+$.

$^1$H NMR (400 MHz, DMSO-$d_6$) δ 8.84 (t, J=5.6 Hz, 1H), 7.28 (d, J=7.6 Hz, 1H), 7.16 (d, J=8.2 Hz, 1H), 7.03 (br s, 2H), 6.51 (d, J=7.8 Hz, 1H), 6.43 (d, J=7.6 Hz, 1H), 4.58 (s, 2H), 4.00-3.92 (m, 2H), 2.24 (s, 3H).

STEP F. 2-(8-amino-5-methyl-1-oxo-2-isoquinolyl)-N-(2,2,2-trifluoroethyl)acetamide (40 mg, 0.13 mmol), tbubrettphos (6 mg, 0.01 mmol), $K_2CO_3$ (35 mg, 0.26 mmol), acetic acid (glacial) (5 µL, 0.06 mmol) and 5-bromo-1-methyl-1H-indazole (30 mg, 0.14 mmol) were dissolved in tert-butanol (2 mL). The solution was degassed, tris(dibenzylideneacetone)dipalladium (0) (6 mg, 0.01 mmol) was added, the vial was sealed and the mixture was stirred at 110° C. overnight. The mixture was filtered through a Celite pad, washing with methanol, then concentrated under reduced pressure. The crude product was purified by reverse phase chromatography (12 g column, 20 to 60% acetonitrile in water, 0.1% formic acid), then dried under vacuum overnight to give 2-[5-methyl-8-[(1-methylindazol-5-yl)amino]-1-oxo-2-isoquinolyl]-N-(2,2,2-trifluoroethyl)acetamide (34 mg, 0.08 mmol, 60% yield) as a pale yellow solid.

UPLC-MS ($ES^+$, Method 1): 4.07 min, m/z 444.1 $[M+H]^+$.

$^1$H NMR (400 MHz, DMSO-$d_6$) δ 10.88 (s, 1H), 8.91 (t, J=6.4 Hz, 1H), 7.97 (d, J=0.9 Hz, 1H), 7.65 (d, J=8.8 Hz, 1H), 7.62 (d, J=2.0 Hz, 1H), 7.44 (d, J=7.6 Hz, 1H), 7.31-7.26 (m, 2H), 6.85 (d, J=8.3 Hz, 1H), 6.59 (d, J=7.6 Hz, 1H), 4.68 (s, 2H), 4.05 (s, 3H), 3.98 (dq, J=6.4, 9.7 Hz, 2H), 2.32 (s, 3H).

Example 125, 1-Methyl-5-[[1-oxo-2-[2-oxo-2-(2,2,2-trifluoroethylamino)ethyl]-8-isoquinolyl]amino]indazole-7-carboxamide Scheme 15

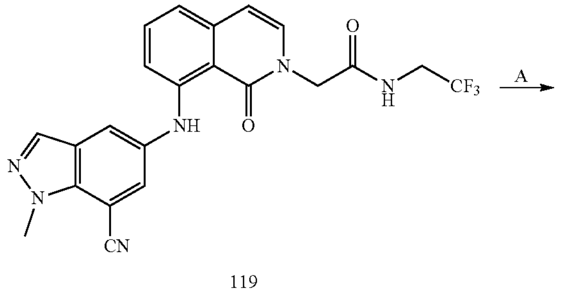

119

-continued

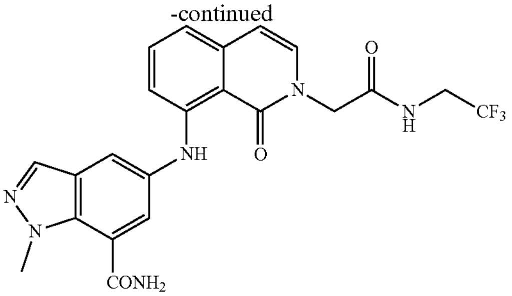

125

STEP A. A mixture of 2-(8-((7-cyano-1-methyl-1H-indazol-5-yl)amino)-1-oxoisoquinolin-2(1H)-yl)-N-(2,2,2-trifluoroethyl)acetamide (Example 119, 8 mg, 0.018 mol) and $K_2CO_3$ (0.5 mg, 0.0035 mmol) in water (0.5 mL) and DMSO (0.5 mL) was stirred at 150° C. under microwave irradiation for 0.5 h. The mixture was purified by prep-HPLC to give 1-methyl-5-[[1-oxo-2-[2-oxo-2-(2,2,2-trifluoroethylamino) ethyl]-8-isoquinolyl]amino] indazole-7-carboxamide (Example 125, 2.3 mg, 0.005 mmol, 28% yield) as yellow solid.

UPLC-MS ($ES^+$, Method 3): 3.35 min, m/z 473.2 $[M+H]^+$.

$^1H$ NMR (400 MHz, DMSO-$d_6$) δ 11.04 (s, 1H), 8.91 (t, J=6.2 Hz, 1H), 8.20 (s, 1H), 8.08 (s, 1H), 7.79 (s, 1H), 7.69 (s, 1H), 7.47-7.36 (m, 3H), 7.01 (d, J=8.3 Hz, 1H), 6.88 (d, J=7.6 Hz, 1H), 6.56 (d, J=7.4 Hz, 1H), 4.69 (s, 2H), 4.09 (s, 3H), 4.03-3.93 (m, 2H).

The following examples (table 15) were prepared according to the route described in scheme 15 for example 125, replacing 2-(8-((7-cyano-1-methyl-1H-indazol-5-yl) amino)-1-oxoisoquinolin-2(1H)-yl)-N-(2,2,2-trifluoroethyl) acetamide with the appropriate cyano starting material in step A.

TABLE 15

| Starting material | Structure/Name | UPLCMS ($ES^+$) | $^1H$ NMR (400 MHz, DMSO-$d_6$) |
|---|---|---|---|
| 2-[8-[(7-cyano-1-tetrahydropyran-2-yl-indazol-5-yl)amino]-1-oxo-2-isoquinolyl]-N-(2,2,2-trifluoroethyl)acetamide (final THP deprotection required) | 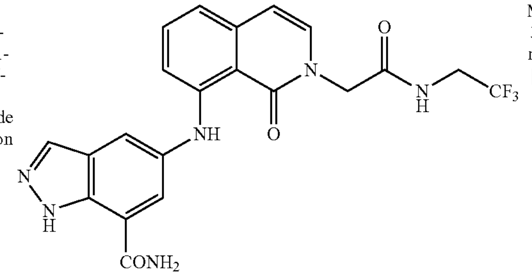 5-[1-oxo-2-[2-oxo-2-(2,2,2-trifluoroethylamino)ethyl]-8-isoquinolyl]amino]-1H-indazole-7-carboxamide Example 105 | Method 3: 3.19 min, m/z 459.4 $[M + H]^+$ | 13.01 (s, 1H), 10.98 (s, 1H), 8.92 (t, J = 6.2 Hz, 1H), 8.19 (s, 1H), 8.09 (s, 1H), 7.88-7.88 (m, 2H), 7.50 (s, 1H), 7.43-7.36 (m, 2H), 6.85 (t, J = 7.2 Hz, 2H), 6.54 (d, J = 7.4 Hz, 1H), 4.68 (s, 2H), 3.98 (dq, J = 6.3, 9.8 Hz, 2H). |

DDR1 and DDR2 Biochemical Assay Method

The capacity of compounds to bind to DDR1 and DDR2 was quantified using a LanthaScreen Eu Kinase Binding Assay. Recombinant human DDR1 (2.5 nM; aa440-876 containing a GST tag) and DDR2 (1.75 nM; aa427-855 containing a GST tag) were diluted in assay buffer (50 mM HEPES pH7.3, 10 mM MgCl2, 1 mM EGTA and 0.01% Tween) with various concentrations of compound in a 384-well plate and a volume of 5 uL. After a 30-minute incubation at room temperature, 2.5 uL of Eu-anti GST antibody (diluted to 1 nM in assay buffer) plus Kinase Tracer 178 (diluted in assay buffer to 5 nM for DDR1 and 10 nM for DDR2) were added to the plate. Following 60-minute incubation at room temperature, time-resolved fluorescence was measured on a BMG Labtech PHERAstar plate reader. DMSO (1%) and reference compound (1 μM) were used to generate the Max and Min assay signals, respectively. Data was analysed using a four-parameter logistic model to calculate IC50 values, with at least two independent replicates were performed for each compound.

BIOLOGICAL ACTIVITY VALUES

The following table shows the $pIC_{50}$ values for the above examples against the DDR1 and DDR2 kinases (A: $pIC_{50}$>8; B: 8≥$pIC_{50}$>7; C: 7≥$pIC_{50}$>6; D: $pIC_{50}$≤6; ND: not determined).

| Example number | DDR1 $pIC_{50}$ | DDR2 $pIC_{50}$ |
|---|---|---|
| 1 | B | D |
| 2 | B | D |
| 3 | B | C |
| 4 | C | D |
| 5 | B | B |
| 6 | B | B |
| 7 | C | D |
| 8 | D | D |
| 9 | B | C |
| 10 | B | C |
| 11 | C | C |
| 12 | B | B |
| 13 | D | D |
| 14 | C | D |
| 15 | C | D |
| 16 | B | C |
| 17 | C | D |
| 18 | D | D |

-continued

| Example number | DDR1 $pIC_{50}$ | DDR2 $pIC_{50}$ |
|---|---|---|
| 19 | A | B |
| 20 | C | C |
| 21 | B | C |
| 22 | B | D |
| 23 | B | C |
| 24 | C | D |

-continued

| Example number | DDR1 $pIC_{50}$ | DDR2 $pIC_{50}$ |
|---|---|---|
| 25 | C | D |
| 26 | D | D |
| 27 | B | C |
| 28 | A | B |
| 29 | B | D |
| 30 | A | D |
| 31 | A | A |
| 32 | A | B |
| 33 | B | C |
| 34 | C | D |
| 35 | B | C |
| 36 | B | C |
| 37 | A | B |
| 38 | A | B |
| 39 | B | D |
| 40 | C | C |
| 41 | C | D |
| 42 | B | C |
| 43 | B | D |
| 44 | C | D |
| 45 | B | B |
| 46 | B | B |
| 47 | C | D |
| 48 | B | B |
| 49 | A | B |
| 50 | D | D |
| 51 | D | D |
| 52 | A | B |
| 53 | B | B |
| 54 | C | D |
| 55 | B | D |
| 56 | B | B |
| 57 | A | B |
| 58 | B | B |
| 59 | B | C |
| 60 | C | D |
| 61 | A | B |
| 62 | B | B |
| 63 | B | B |
| 64 | B | C |
| 65 | C | C |
| 66 | A | B |
| 67 | B | C |
| 68 | D | D |
| 69 | C | C |
| 70 | D | D |
| 71 | B | C |
| 72 | A | B |
| 73 | C | D |
| 74 | B | C |
| 75 | C | C |
| 76 | B | B |
| 77 | D | D |
| 78 | B | C |
| 79 | B | C |
| 80 | C | D |
| 81 | B | D |
| 82 | C | D |
| 83 | A | B |
| 84 | C | D |
| 85 | A | C |
| 86 | A | ND |
| 87 | B | C |
| 88 | B | C |
| 89 | B | D |
| 90 | A | B |
| 91 | B | D |
| 92 | C | D |
| 93 | C | C |
| 94 | C | D |
| 95 | B | C |
| 96 | C | D |
| 97 | C | D |
| 98 | B | B |
| 99 | B | B |
| 100 | B | C |
| 101 | B | C |

-continued

| Example number | DDR1 $pIC_{50}$ | DDR2 $pIC_{50}$ |
|---|---|---|
| 102 | A | C |
| 103 | A | B |
| 104 | B | C |
| 105 | B | C |
| 106 | A | C |
| 107 | D | D |
| 108 | D | D |
| 109 | D | D |
| 110 | D | D |
| 111 | B | C |
| 112 | A | B |
| 113 | A | B |
| 114 | A | C |
| 115 | B | C |
| 116 | A | B |
| 117 | ND | D |
| 118 | D | D |
| 119 | A | D |
| 120 | A | B |
| 121 | B | C |
| 122 | C | D |
| 123 | A | B |
| 124 | C | D |
| 125 | C | D |
| 126 | B | B |
| 127 | A | B |
| 128 | B | C |
| 129 | A | B |
| 130 | A | B |
| 131 | A | B |
| 132 | D | D |
| 133 | B | C |
| 134 | A | B |
| 135 | B | C |
| 136 | A | B |
| 137 | A | B |
| 138 | D | D |
| 139 | C | D |
| 140 | B | B |
| 141 | C | D |
| 142 | B | C |
| 143 | B | C |
| 144 | B | C |
| 145 | A | B |
| 146 | B | ND |
| 147 | B | C |
| 148 | C | D |
| 149 | B | B |
| 150 | A | B |
| 151 | A | B |
| 152 | A | B |
| 153 | C | D |
| 154 | A | B |
| 155 | A | ND |
| 156 | D | D |
| 157 | B | C |
| 158 | B | B |
| 159 | B | C |
| 160 | A | B |
| 161 | A | B |

The invention claimed is:

1. A compound of formula (I) or a pharmaceutically acceptable salt thereof:

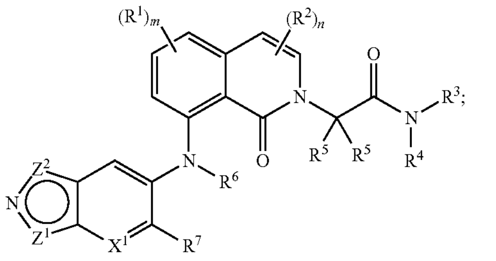

(I)

wherein $Z^1$ and $Z^2$ are each selected from —$CR^{8a}$— and —$NR^{8b}$—, wherein one of $Z^1$ and $Z^2$ is —$CR^{8a}$— and the other is —$NR^{8b}$—; and wherein the ring comprising $Z^1$ and $Z^2$ is a pyrazole;

$X^1$ is independently selected from $CR^{7a}$ and N;

$R^1$ and $R^2$ are each independently selected at each occurrence from halo, nitro, cyano, $NR^9R^{10}$, $OR^{11}$, $SR^9$, $SO_2NR^9R^9$, $SO_2R^9$, $CO_2R^9$, $C(O)R^9$, $CONR^9R^9$, $C_1$-$C_4$-alkyl, $C_1$-$C_4$-alkyl substituted with $NR^9R^{10}$, $C_1$-$C_4$-alkyl substituted with $OR^{11}$, $C_2$-$C_4$-alkenyl, $C_2$-$C_4$-alkynyl, $C_1$-$C_4$-haloalkyl and cyclopropyl;

$R^3$ is independently selected from H and $C_1$-$C_4$-alkyl;

$R^4$ is independently selected from $C_1$-$C_6$-alkyl, $C_1$-$C_6$-haloalkyl, $C_0$-$C_4$-alkylene-$R^{4a}$; wherein $R^{4a}$ is independently selected from: $C_3$-$C_8$-cycloalkyl, phenyl, 5-, 6-, 9- or 10-membered heteroaryl and 4- to 10-membered heterocycloalkyl; wherein said heterocycloalkyl or heteroaryl group may be monocyclic or bicyclic; wherein said cycloalkyl or heterocycloalkyl group is optionally substituted with a single $R^{12}$ group and/or from 1 to 4 $R^{13}$ groups and wherein said phenyl or heteroaryl group is optionally substituted with a single $R^{12}$ group and/or from 1 to 3 $R^{14}$ groups;

or $R^3$ and $R^4$, together with the nitrogen atom to which they are attached together form a 4- to 10-membered heterocycloalkyl group or a 5-, or 9-membered heteroaryl group; wherein said heterocycloalkyl or heteroaryl group may be monocyclic or bicyclic; wherein said heterocycloalkyl group is optionally substituted with a single $R^{12}$ group and/or from 1 to 4 $R^{13}$ groups and wherein said heteroaryl group is optionally substituted with a single $R^{12}$ group and/or from 1 to 3 $R^{14}$ groups;

$R^5$ is independently at each occurrence selected from H, halo and $C_1$-$C_4$-alkyl, or the two $R^5$ groups and the carbon atom to which they are attached may together form a $C_3$-$C_6$ cycloalkyl ring;

$R^6$ is independently selected from H, $C_1$-$C_4$-alkyl, $C_1$-$C_4$-haloalkyl and cyclopropyl;

$R^7$ and $R^{7a}$ are each independently selected from H, halo, nitro, cyano, $NR^9R^{10}$, $OR^{11}$, $SR^9$, $SO_2NR^9R^9$, $SO_2R^9$, $CO_2R^9$, $C(O)R^9$, $CONR^9R^9$, $C_1$-$C_4$-alkyl, $C_1$-$C_4$-alkyl substituted with $NR^9R^{10}$, $C_1$-$C_4$-alkyl substituted with $OR^{11}$, $C_2$-$C_4$-alkenyl, $C_2$-$C_4$-alkynyl, $C_1$-$C_4$-haloalkyl and cyclopropyl;

$R^{8a}$ is independently selected from H, halo, nitro, cyano, $NR^9R^{10}$, $OR^{11}$, $SR^9$, $SO_2NR^9R^9$, $SO_2R^9$, $CO_2R^9$, $C(O)R^9$, $CONR^9R^9$, $C_1$-$C_4$-alkyl, $C_1$-$C_4$-alkyl substituted with $NR^9R^{10}$, $C_1$-$C_4$-alkyl substituted with $OR^{11}$, $C_2$-$C_4$-alkenyl, $C_2$-$C_4$-alkynyl, $C_1$-$C_4$-haloalkyl and $C_0$-$C_4$-alkylene-$R^{8c}$;

$R^{8b}$ is independently selected from H, $C_1$-$C_4$-alkyl, $C_2$-$C_4$-alkyl substituted with $NR^9R^{10}$, $C_2$-$C_4$-alkyl substituted with $OR^{11}$, $C_3$-$C_4$-alkenyl, $C_3$-$C_4$-alkynyl, $C_1$-$C_4$-haloalkyl and $C_0$-$C_4$-alkylene-$R^{8c}$;

$R^{8c}$ is independently selected from $C_3$-$C_6$-cycloalkyl and 3- to 7-membered heterocycloalkyl; wherein said heterocycloalkyl group is attached to the $C_0$-$C_4$-alkylene via a carbon atom in the heterocycloalkyl ring; wherein said cycloalkyl or heterocycloalkyl group is optionally substituted with from 1 to 4 $R^{13}$ groups;

$R^9$ is independently at each occurrence selected from H and $C_1$-$C_4$-alkyl; or two $R^9$ groups, together with the nitrogen atom to which they are attached together form a $C_5$-$C_8$-heterocycloalkyl group optionally substituted with from 0 to 4 $R^{13}$ groups;

$R^{10}$ is independently at each occurrence selected from H, $C_1$-$C_4$-alkyl, C(O)—$C_1$-$C_4$-alkyl and $S(O)_2$—$C_1$-$C_4$-alkyl; or $R^9$ and $R^{10}$, together with the nitrogen atom to which they are attached together form a $C_5$-$C_8$-heterocycloalkyl group optionally substituted with from 0 to 4 $R^{13}$ groups;

$R^{11}$ is independently at each occurrence selected from H, $C_1$-$C_4$-alkyl, C(O)—$C_1$-$C_4$-alkyl and $C_1$-$C_4$-haloalkyl;

$R^{12}$ is independently selected from $C_3$-$C_6$-cycloalkyl, phenyl, 5- or 6-membered heteroaryl and 3- to 6-membered-heterocycloalkyl; wherein said cycloalkyl or heterocycloalkyl group is optionally substituted with from 1 to 4 $R^{13}$ groups and wherein said phenyl or heteroaryl group is optionally substituted with from 1 to 3 $R^{14}$ groups;

$R^{13}$ is independently at each occurrence selected from =O, halo, nitro, cyano, $NR^8R^9$, $OR^{14}$, $SR^8$, $SO_2NR^8R^8$, $CO_2R^8$, $C(O)R^8$, $CONR^8R^8$, $C_1$-$C_4$-alkyl, $C_1$-$C_4$-alkyl substituted with $OR^{11}$, $C_1$-$C_4$-alkyl substituted with $NR^9R^{10}$, $C_2$-$C_4$-alkenyl, $C_2$-$C_4$-alkynyl, $C_1$-$C_4$-haloalkyl, $C_6$-$C_{10}$-aryl, and $C_3$-$C_6$-cycloalkyl;

$R^{14}$ is independently at each occurrence selected from halo, nitro, cyano, $NR^8R^9$, $OR^{10}$, $SR^8$, $SO_2R^8$, $SO_2NR^8R^8$, $CO_2R^8$, $C(O)R^8$, $CONR^8R^9$, $C_1$-$C_4$-alkyl, $C_2$-$C_4$-alkenyl, $C_2$-$C_4$-alkynyl, $C_1$-$C_4$-haloalkyl, $C_1$-$C_4$-alkyl substituted with $OR^{11}$, $C_1$-$C_4$-alkyl substituted with $NR^8R^9$ and cyclopropyl;

m is an integer selected from 0, 1, 2 and 3;

n is an integer selected from 0, 1 and 2;

wherein any of the aforementioned alkyl, alkylene or cyclopropyl groups is optionally substituted, where chemically possible, by 1 to 5 substituents which are each independently at each occurrence selected from the group consisting of: halo, oxo, fluoro, nitro, cyano, $NR^aR^b$, $OR^a$, $SR^a$, $CO_2R^a$, $C(O)R^a$, $CONR^aR^a$, $C_1$-$C_4$-alkyl, $C_1$-$C_4$-haloalkyl and cyclopropyl; wherein $R^a$ is independently at each occurrence selected from H, $C_1$-$C_4$-alkyl and $C_1$-$C_4$-haloalkyl; and $R^b$ is independently at each occurrence selected from H, $C_1$-$C_4$-alkyl, C(O)—$C_1$-$C_4$-alkyl and $S(O)_2$-$C_1$-$C_4$-alkyl.

2. The compound of claim 1 wherein $Z^1$ is $NR^{8b}$ and $Z^2$ is CH.

3. The compound of claim 1, wherein $Z^1$ is $CR^{8a}$ and $Z^2$ is NH.

4. The compound of claim 1, wherein m is 0.

5. The compound of claim 1, wherein m is 1.

6. The compound of claim 5, wherein the single $R^1$ group is F and is situated ortho to $NR^6$.

7. The compound of claim 1, wherein n is 0.

8. The compound of claim 1, wherein $R^5$ is at each occurrence H.

9. The compound of claim 1, wherein $R^6$ is H.

10. The compound of claim 1, wherein $R^7$ is H.

11. The compound of claim 1, wherein $X^1$ is N.

12. The compound of claim 1, wherein $X^1$ is $CR^{7a}$.

13. The compound of claim 1, wherein $R^3$ is H and $R^4$ is selected from $C_1$-$C_6$-alkyl, $C_1$-$C_6$-haloalkyl and $C_0$-$C_4$-alkylene-$R^{4a}$.

14. The compound of claim 13, wherein $R^4$ is selected from $C_1$-$C_6$-alkyl and $C_1$-$C_6$-haloalkyl.

15. The compound of claim 13, wherein $R^4$ is $R^{4a}$.

16. The compound of claim 15, wherein $R^{4a}$ is selected from $C_3$-$C_8$-cycloalkyl and 4- to 10-membered heterocycloalkyl, wherein said cycloalkyl or heterocycloalkyl group is optionally substituted with from 1 to 4 $R^{13}$ groups.

17. The compound of claim 15, wherein $R^{4a}$ is independently selected from: phenyl and 5- or 6-membered heteroaryl; wherein said phenyl or heteroaryl group is optionally substituted with a single $R^{12}$ group and/or from 1 to 3 $R^{14}$ groups.

18. The compound of claim 1, wherein $R^3$ and $R^4$, together with the nitrogen atom to which they are attached together form a monocyclic 4- to 7-membered heterocycloalkyl group optionally substituted with from 1 to 4 $R^{13}$ groups.

19. The compound of claim 1, wherein $NR^3R^4$ has the formula

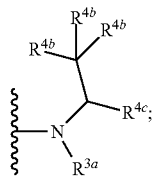

wherein $R^{4b}$ is at each occurrence selected from H and F; wherein at least two $R^{4b}$ groups are F, $R^{3a}$ is independently selected from H and $C_1$-$C_4$-alkyl;

$R^{4c}$ is independently selected from H, $C_1$-$C_4$-alkyl and $C_4$-$C_6$-cycloalkyl; or $R^{3a}$ and $R^{4c}$, together with the carbon and nitrogen to which they are attached, form a 4- to 6-membered heterocycloalkyl group.

20. The compound of claim 1, wherein the compound of formula (I) is selected from:

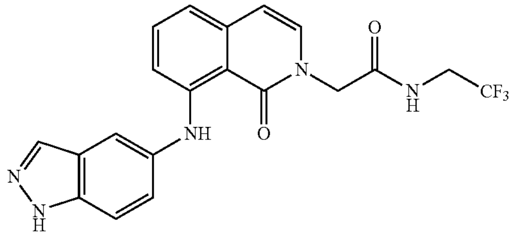

-continued

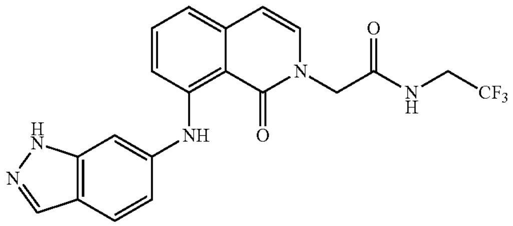

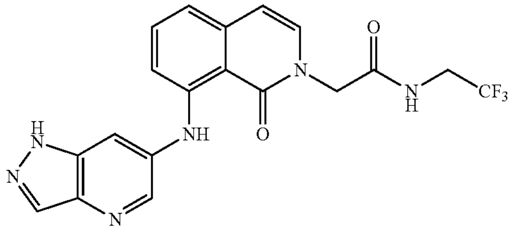

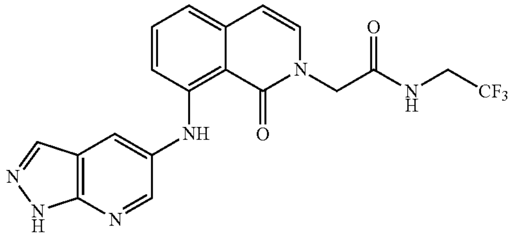

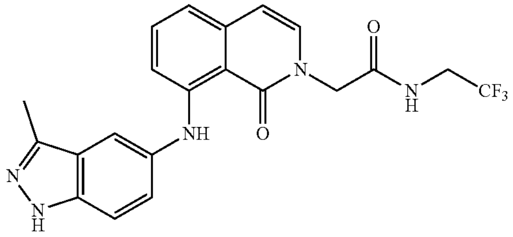

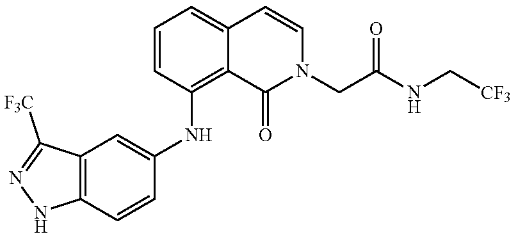

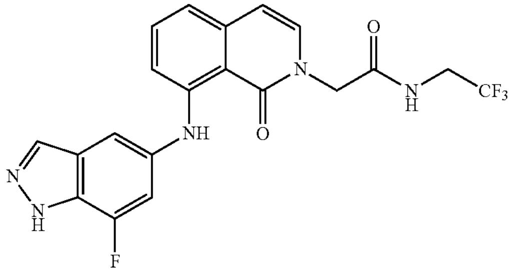

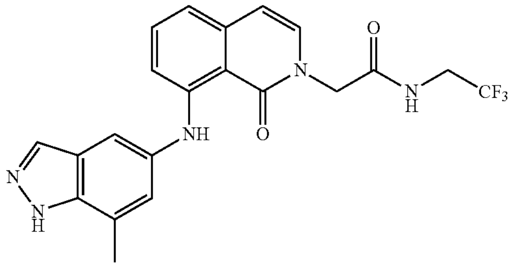

-continued
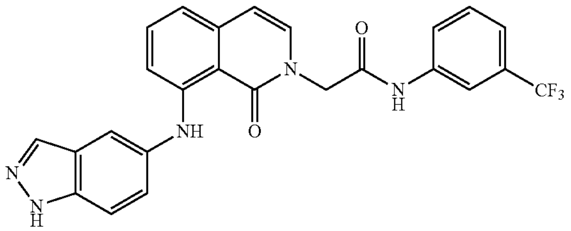
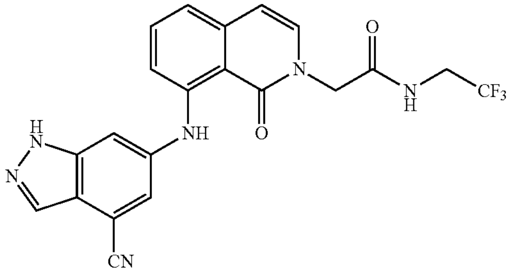
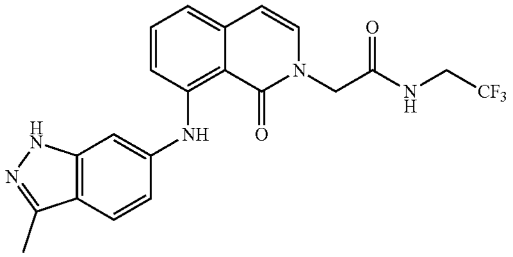
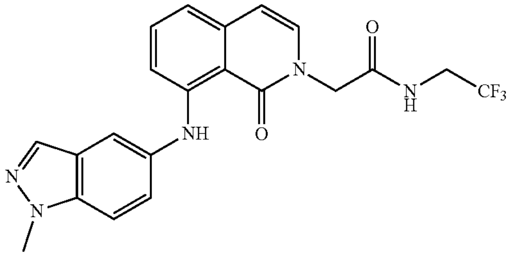
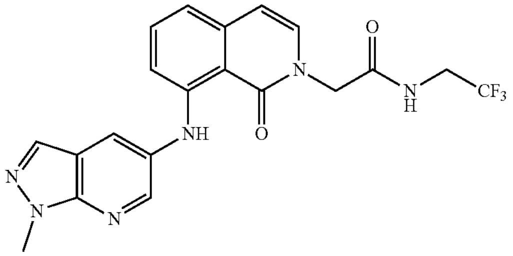
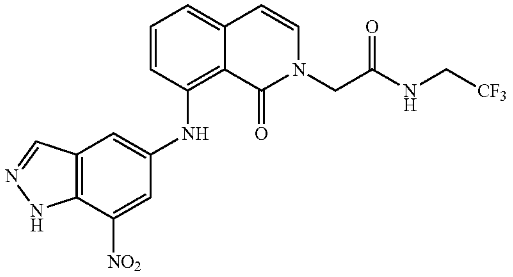
-continued
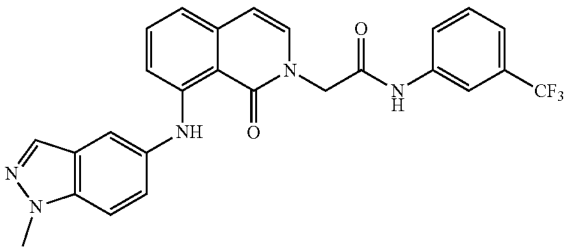
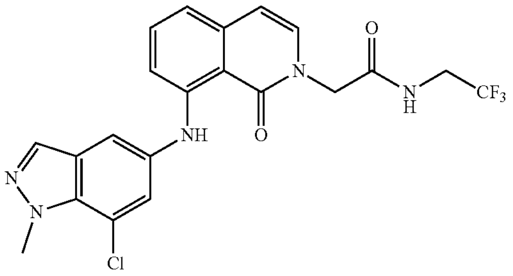
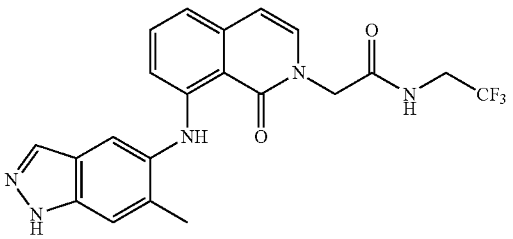
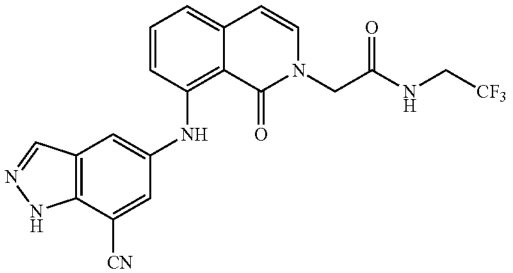
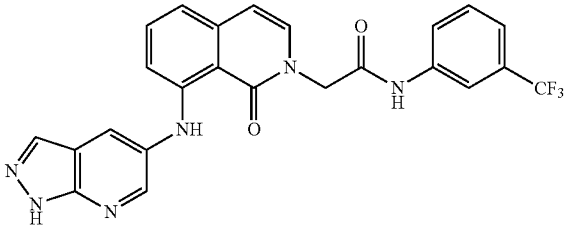
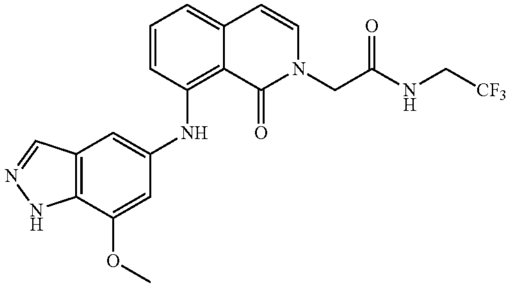

-continued
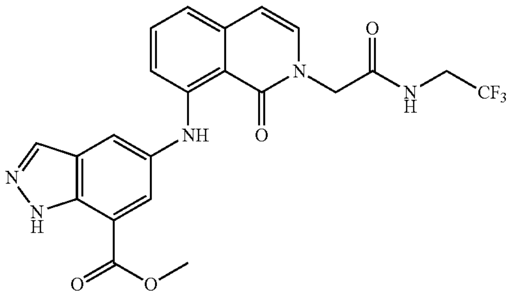
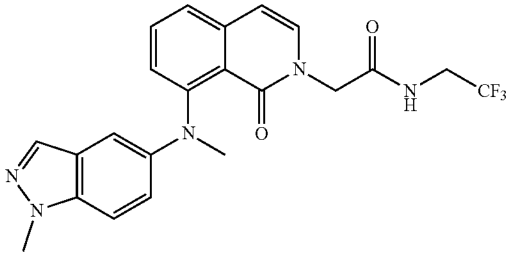
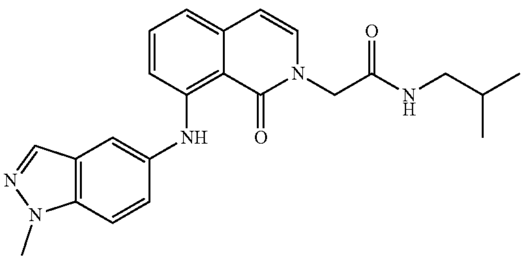
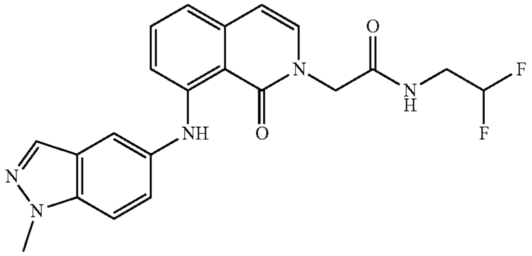
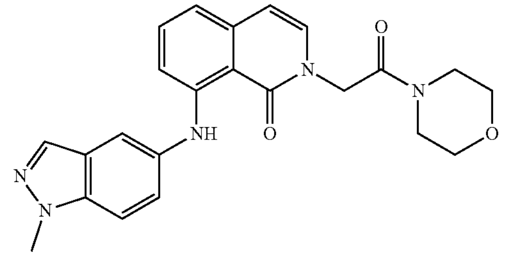
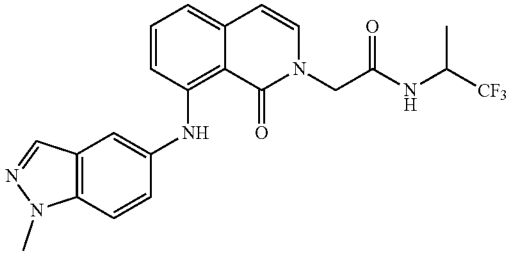
-continued
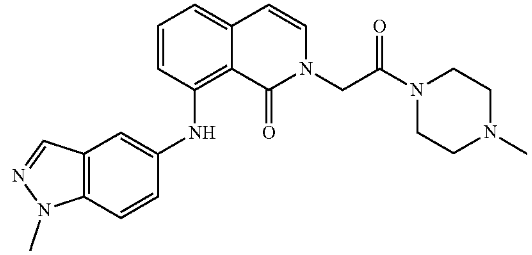
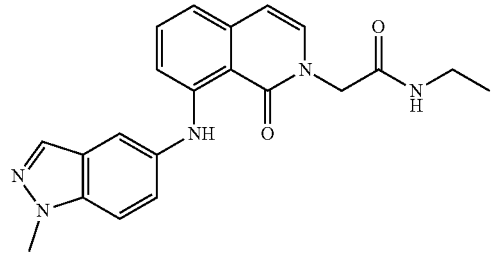
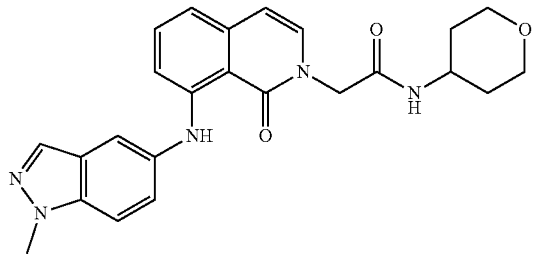
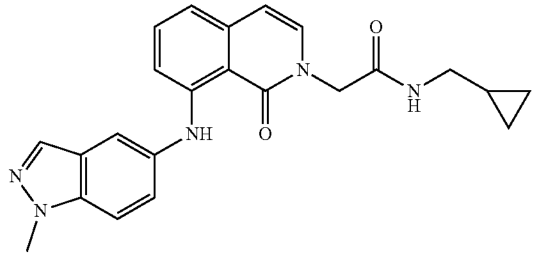
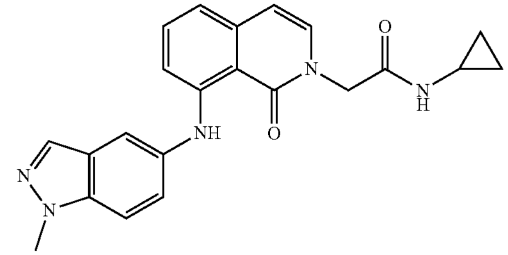
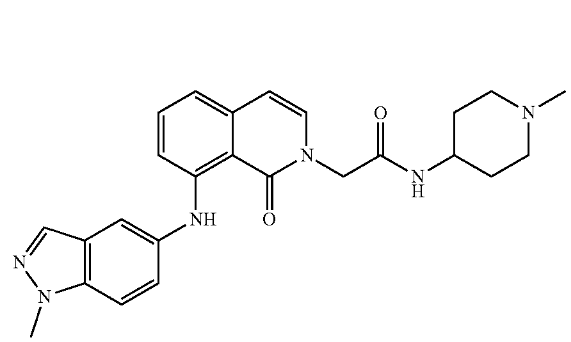

-continued
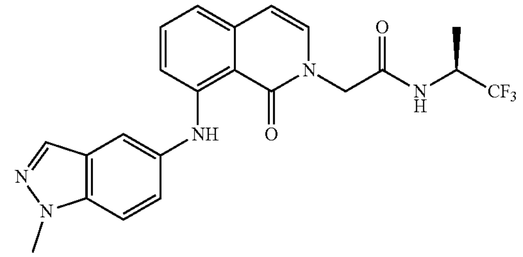
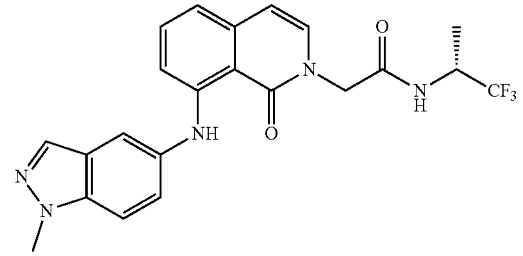
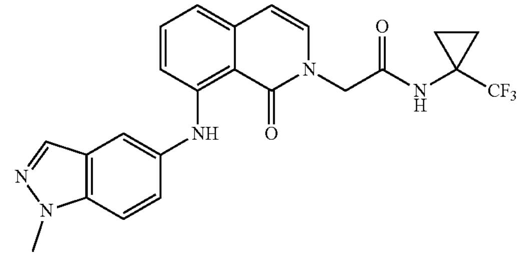
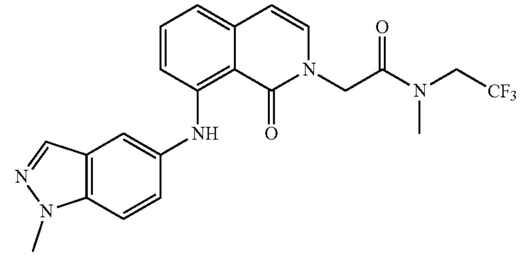
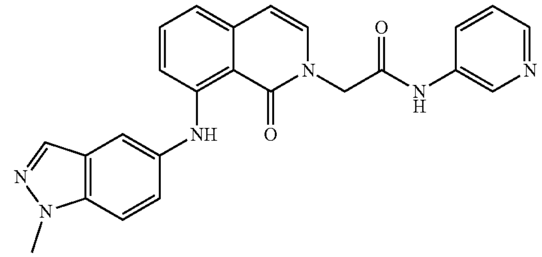
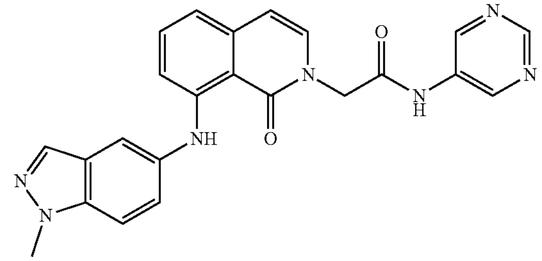
-continued
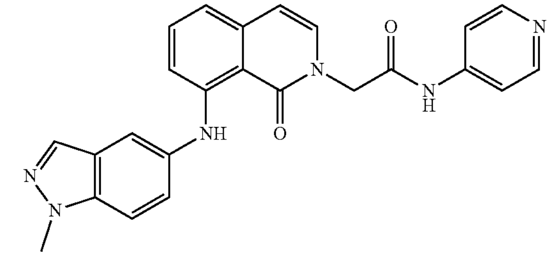
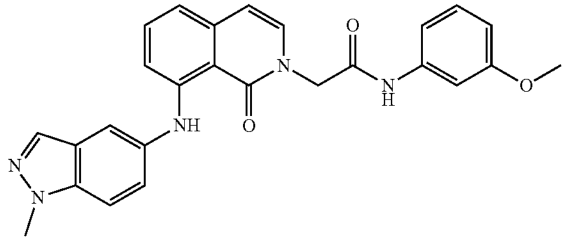
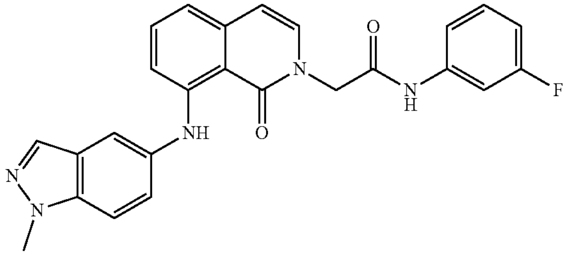
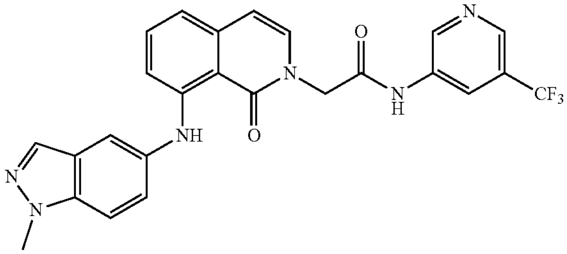
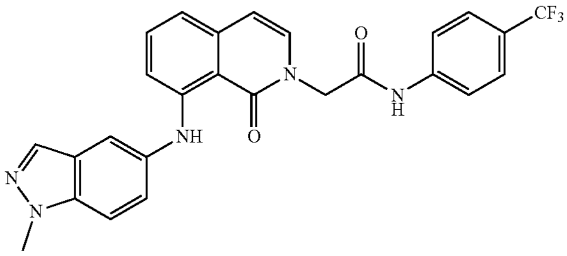
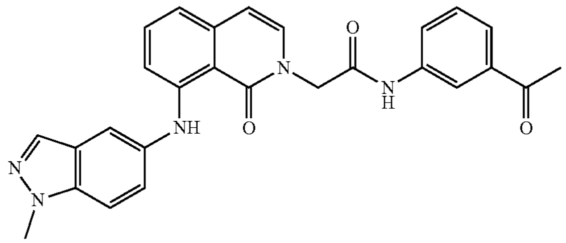

-continued
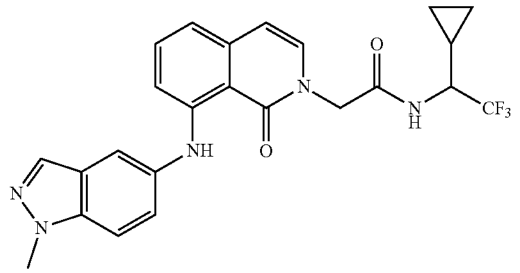
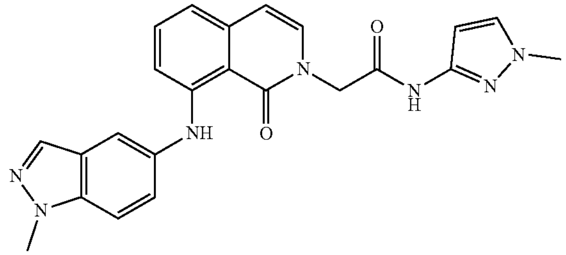
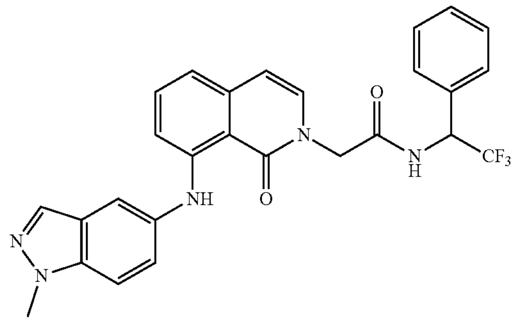
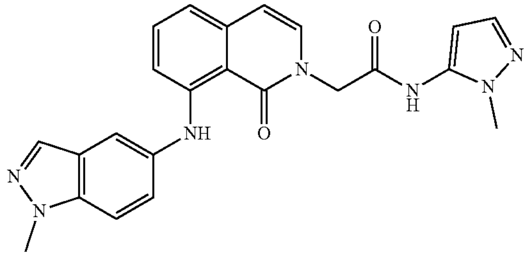
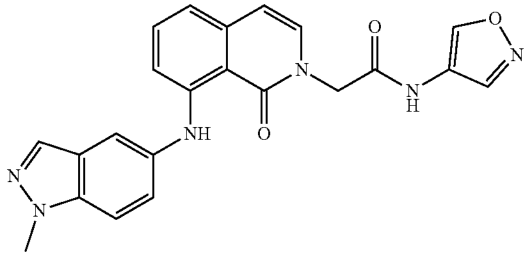
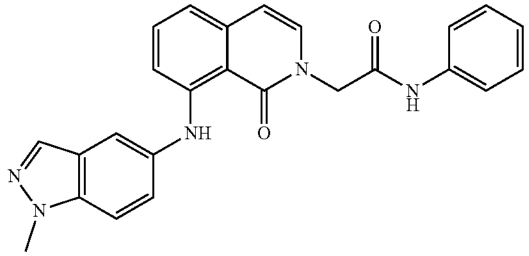
-continued
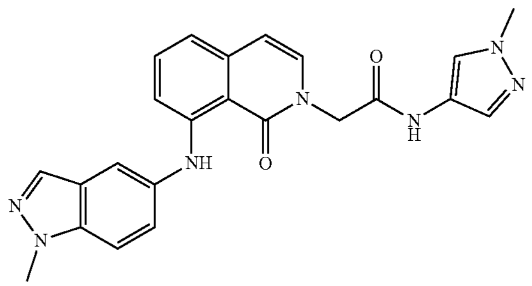
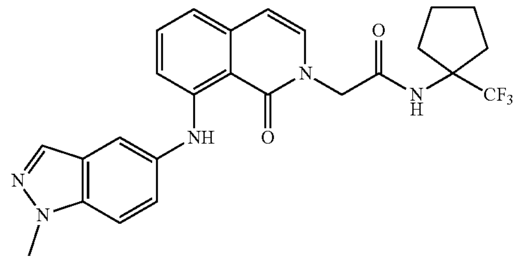
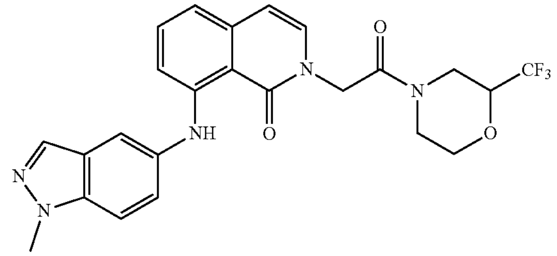
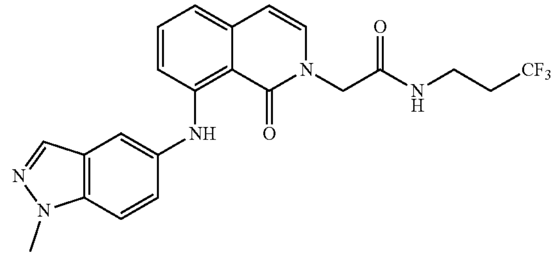
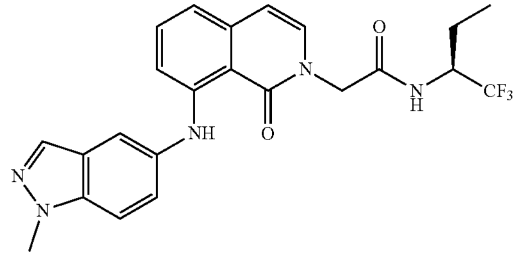
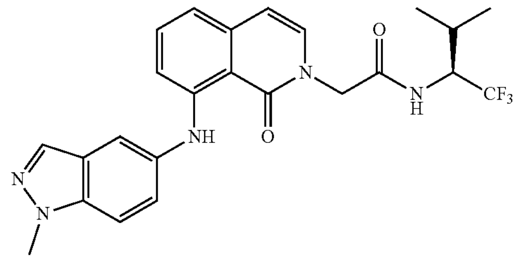

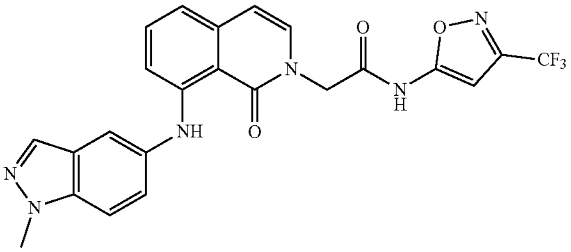
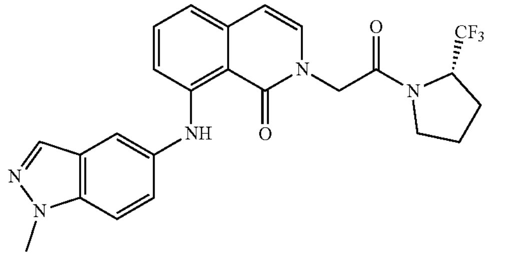
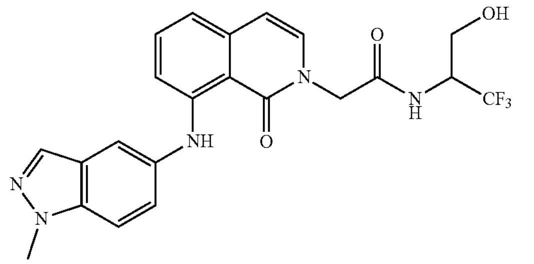
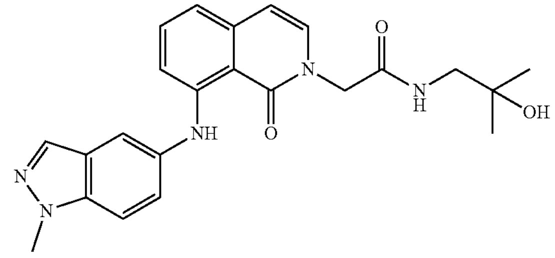
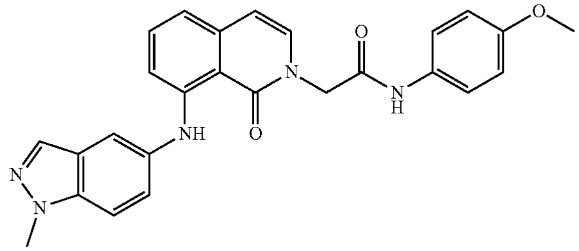
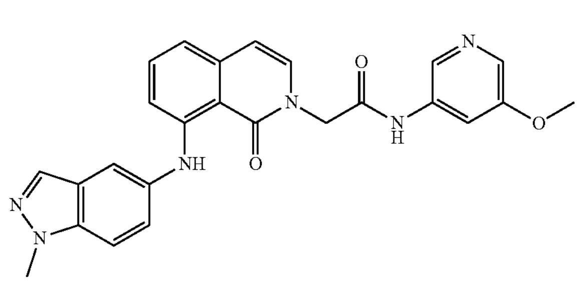
-continued
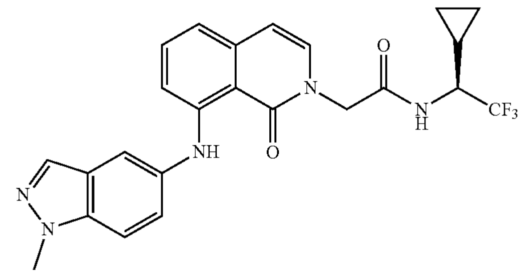
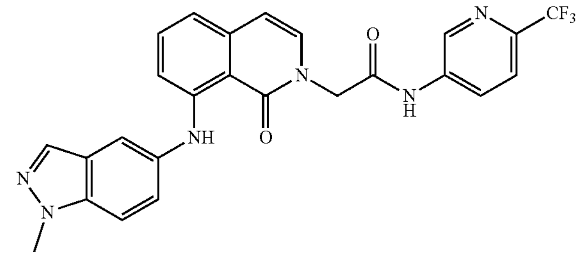
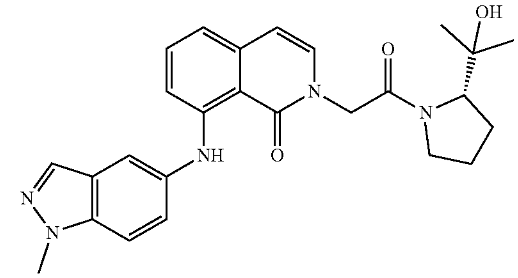
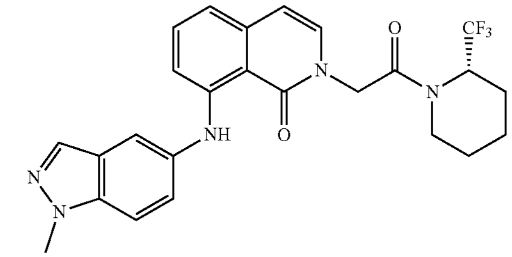
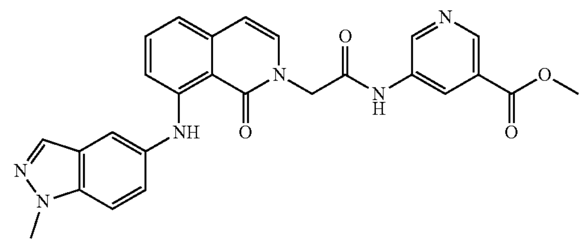
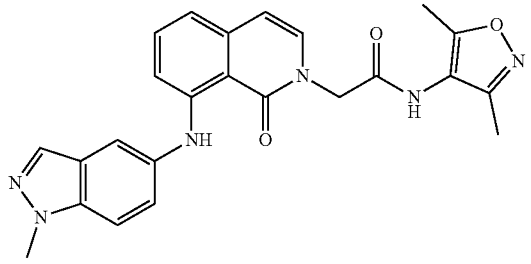

-continued
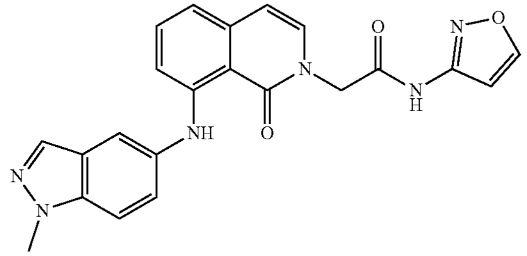
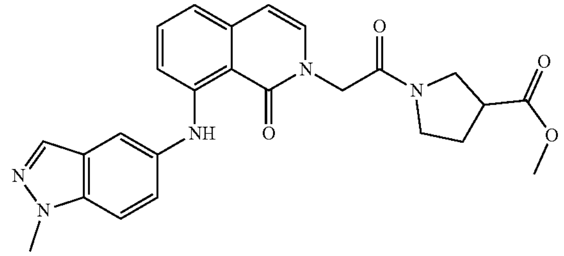
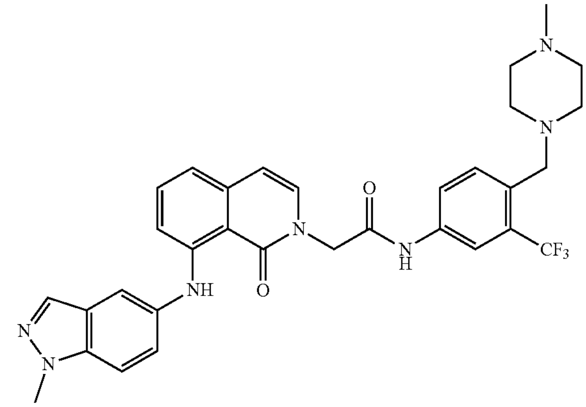
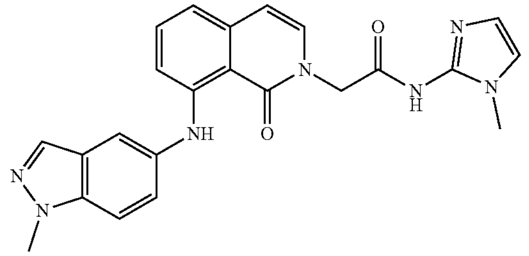
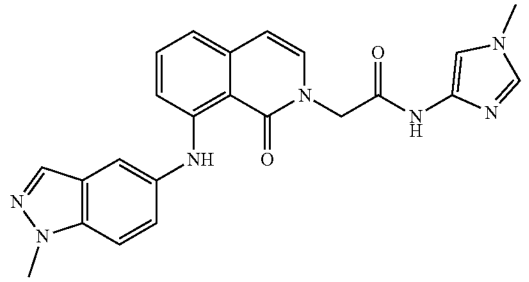
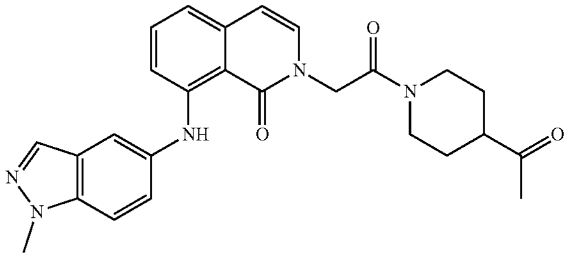
-continued
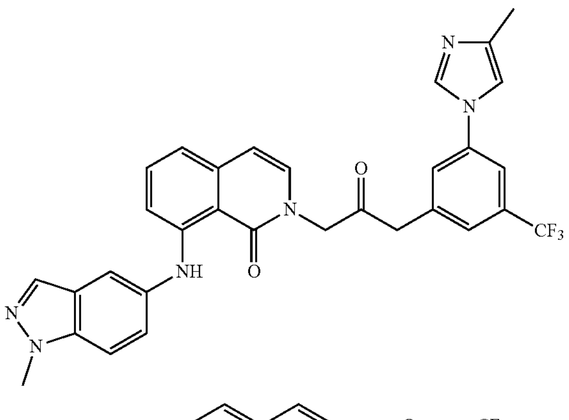
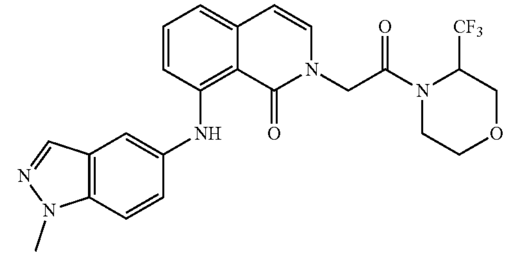
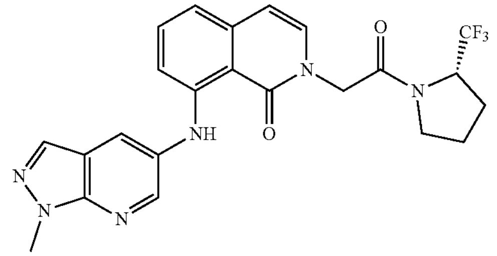
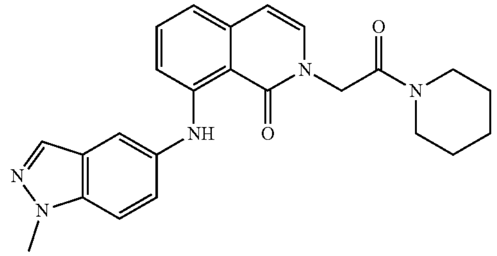
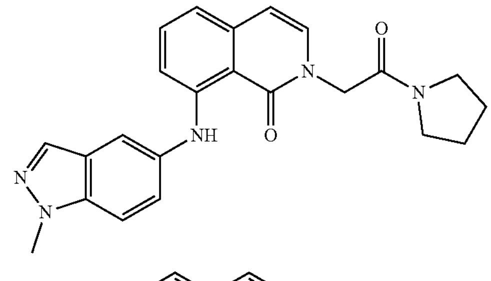
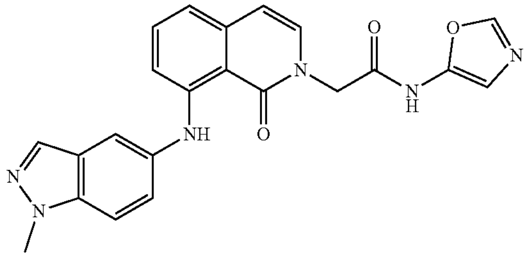

-continued
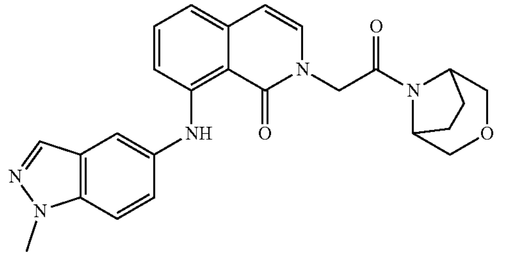
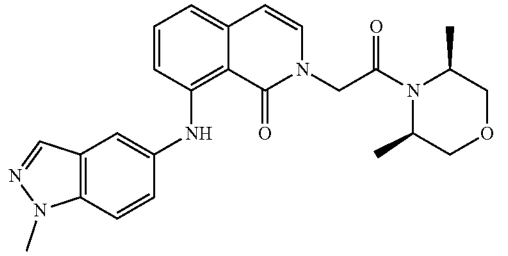
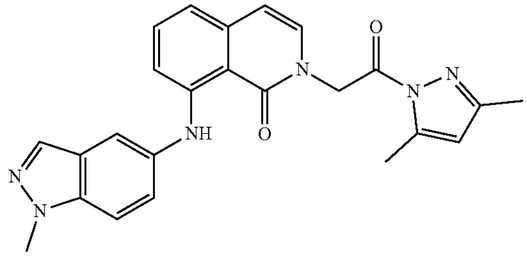
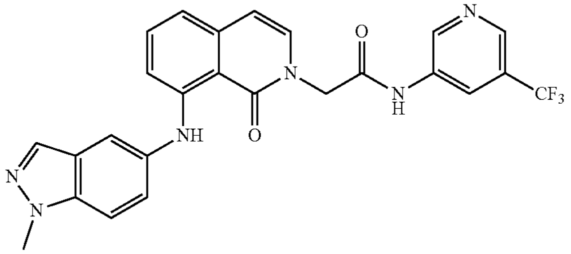
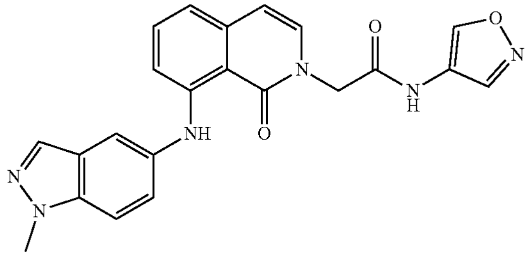
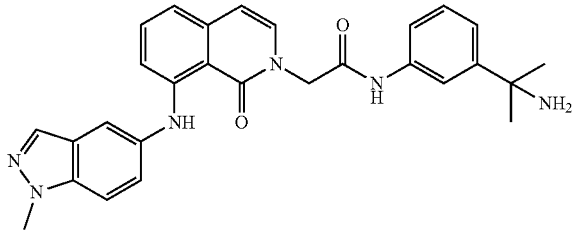
-continued
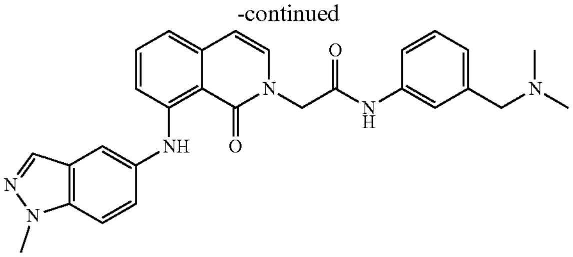
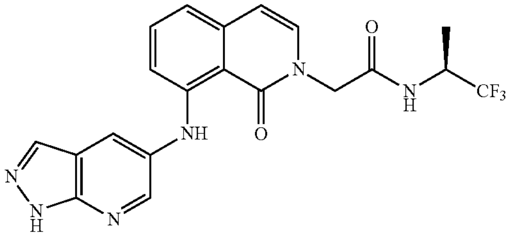
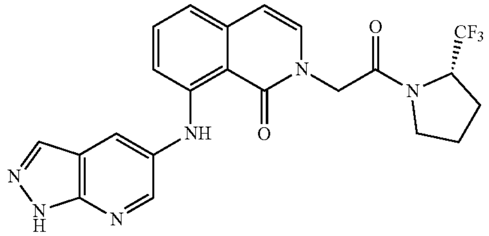
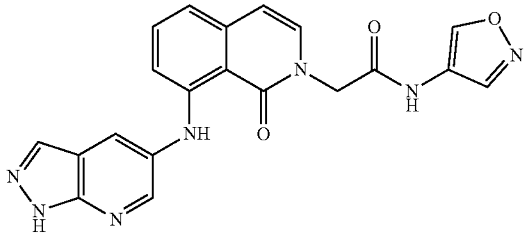
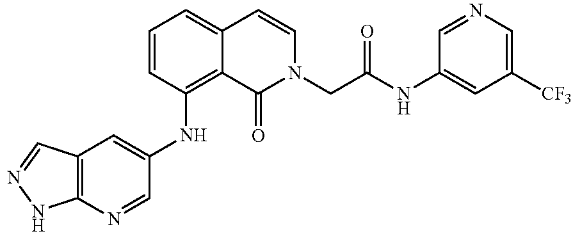
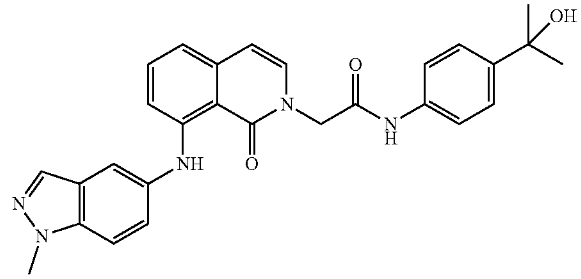
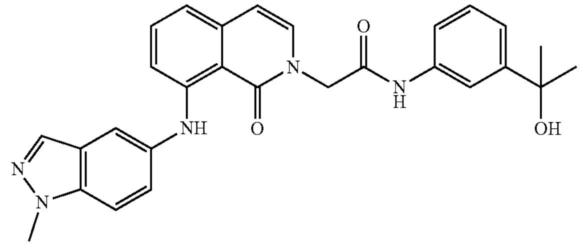

-continued
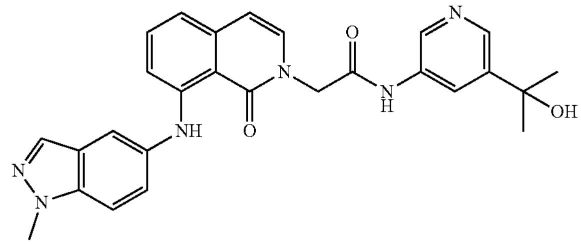
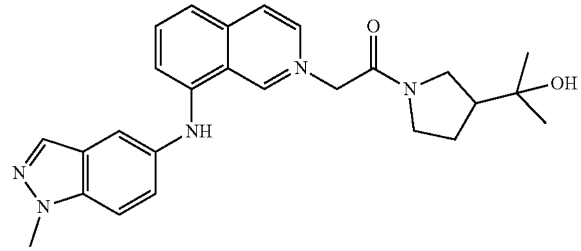
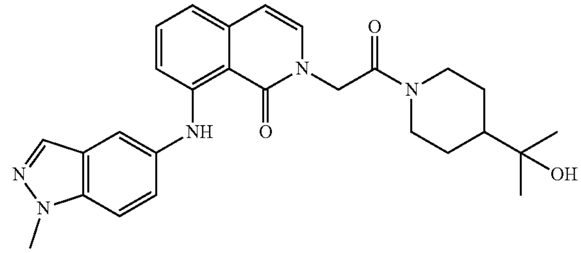
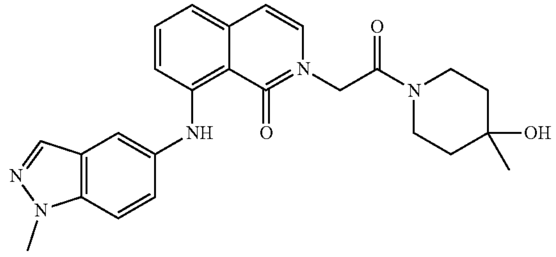
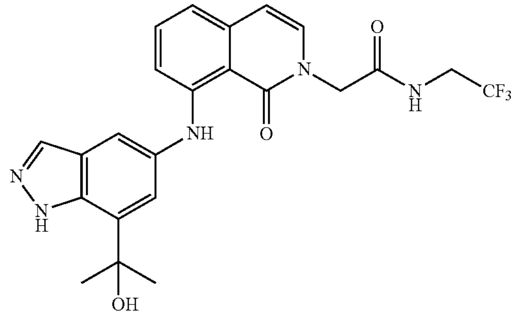
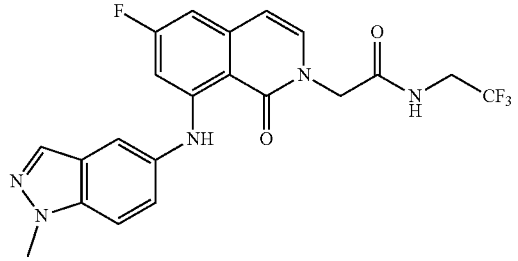
-continued
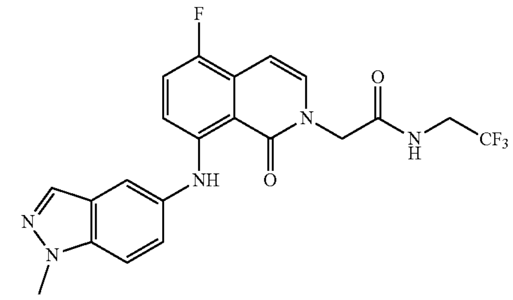
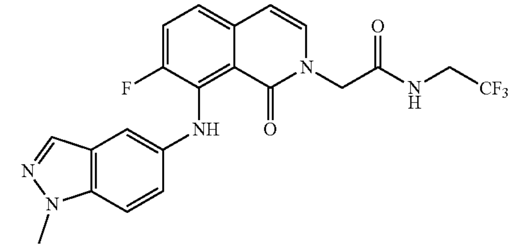
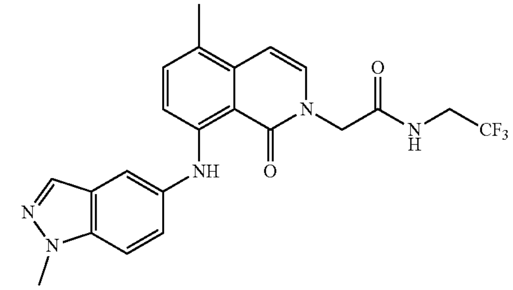
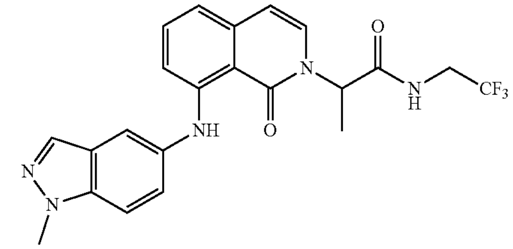
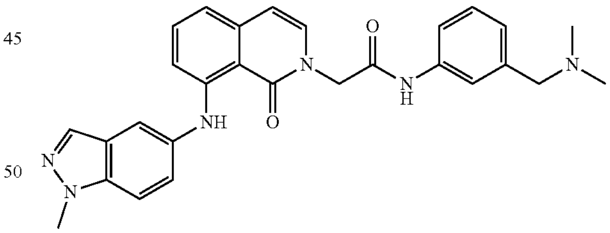
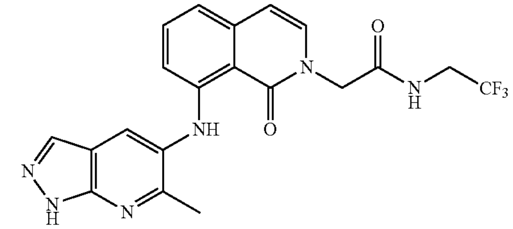

-continued
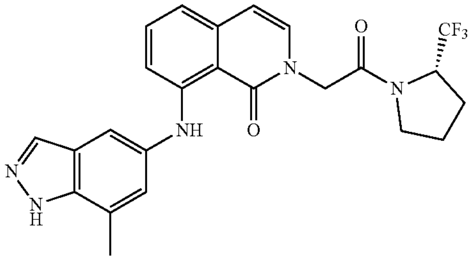
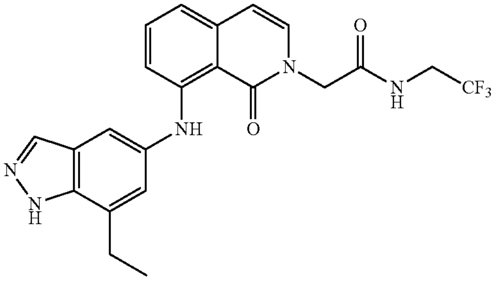
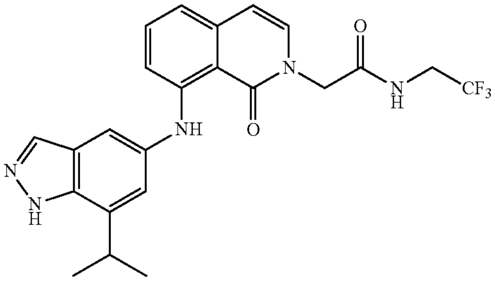
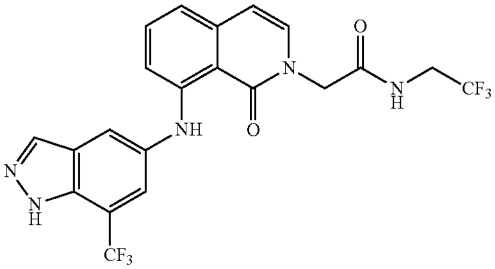
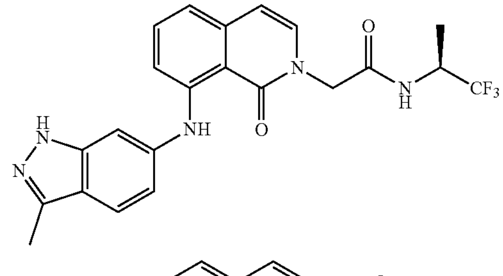
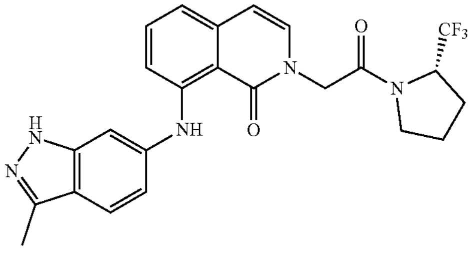
-continued
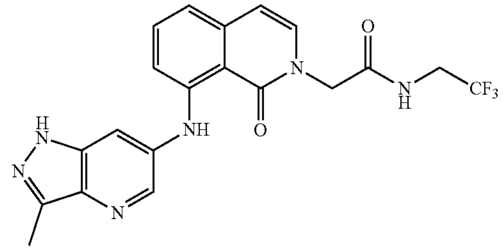
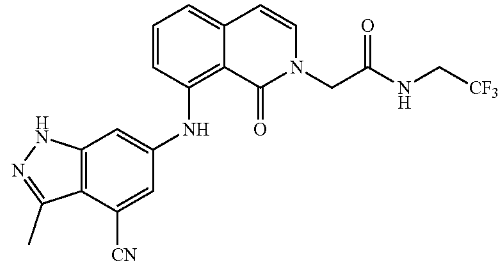
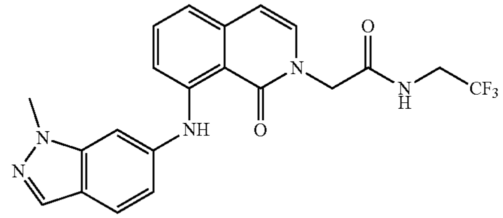
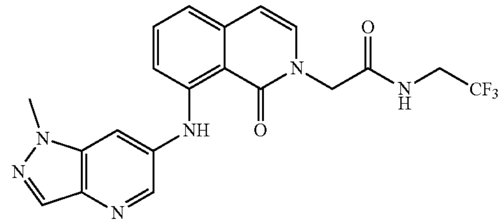
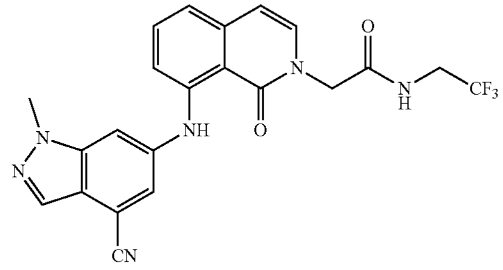
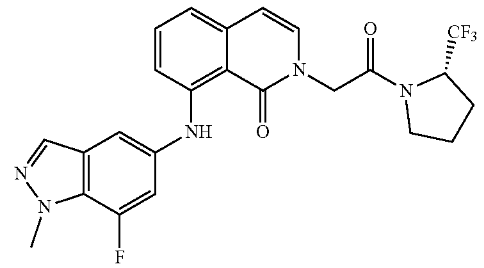

-continued
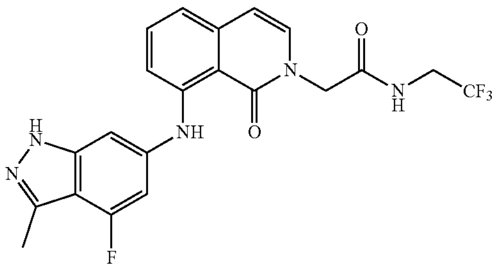
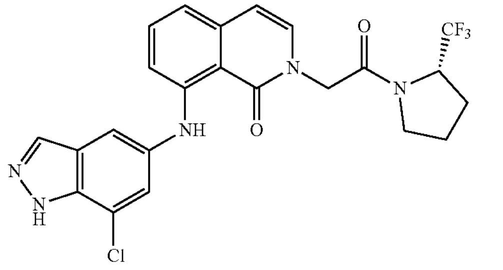
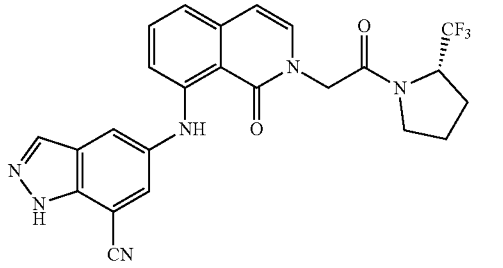
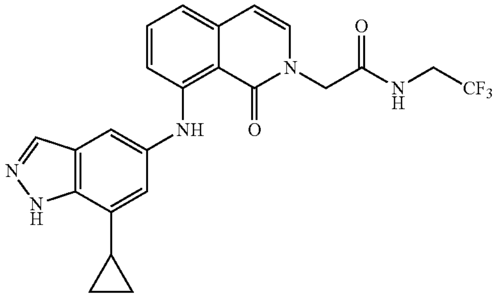
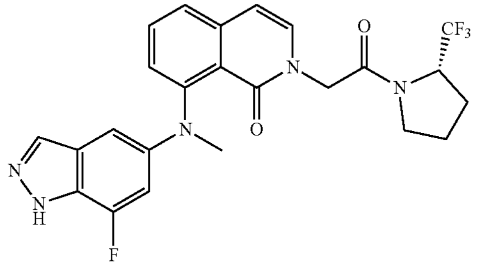
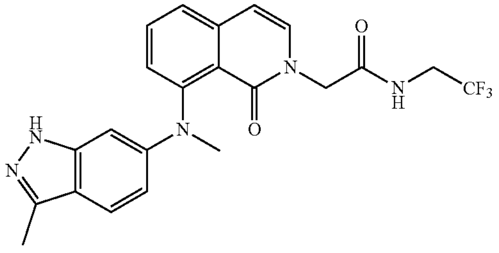
-continued
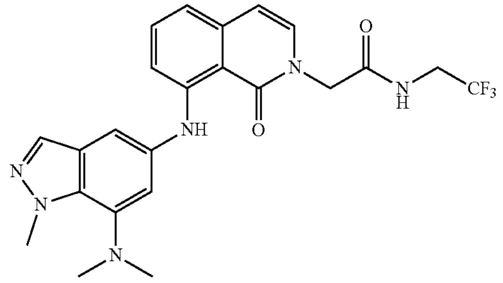
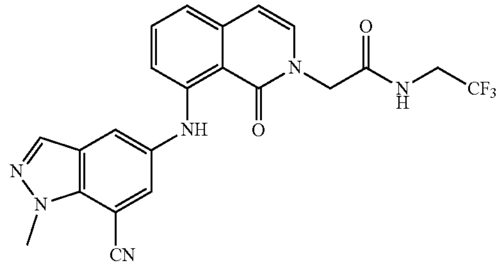
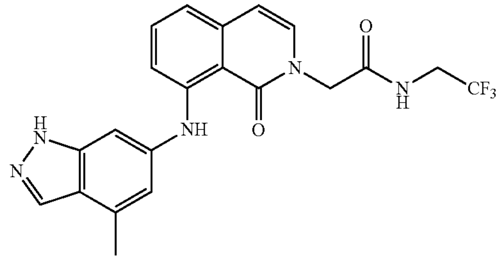
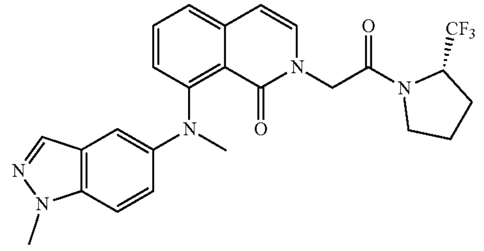
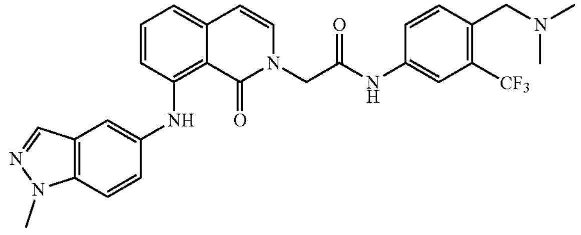
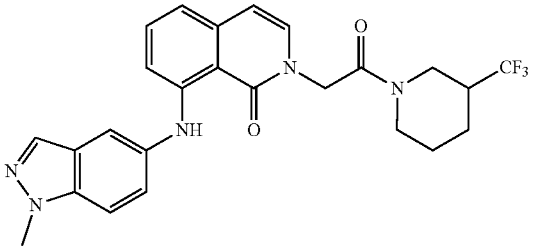

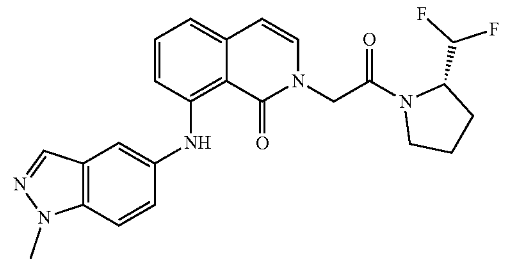
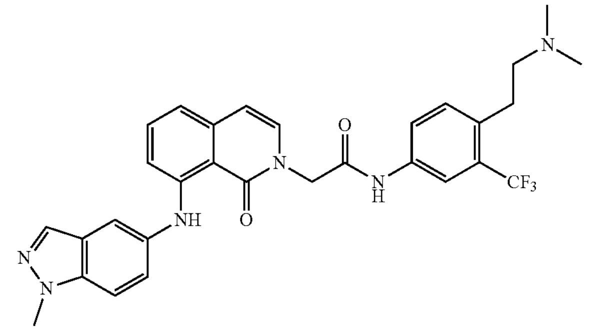
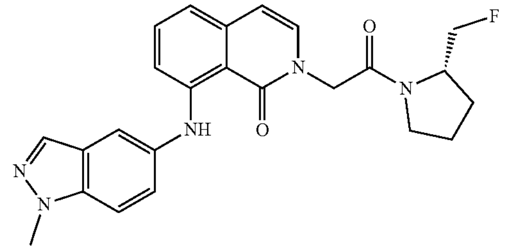
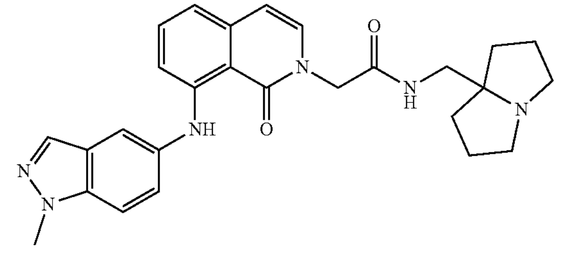
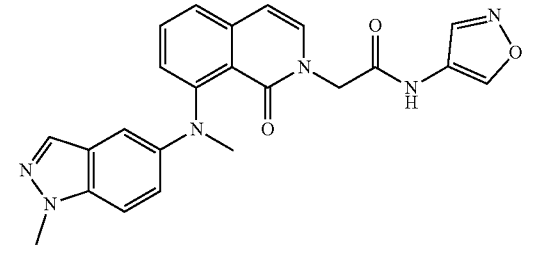
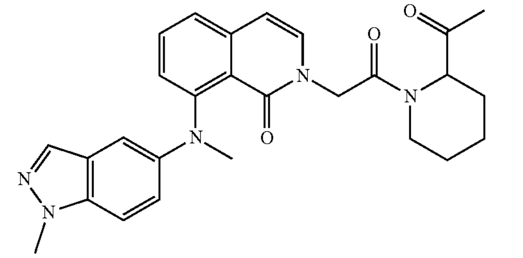
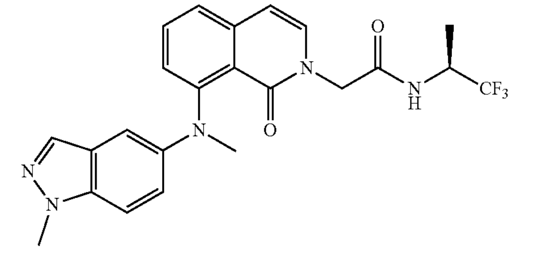
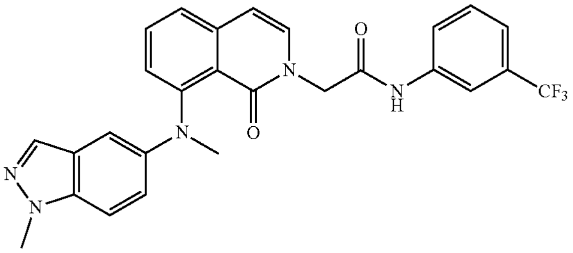
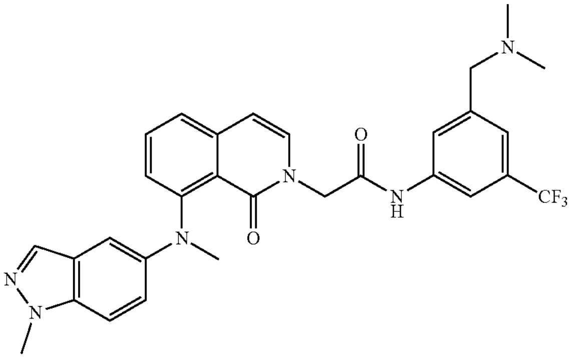
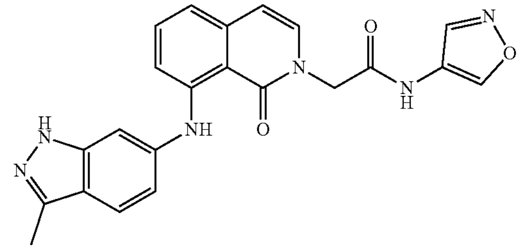
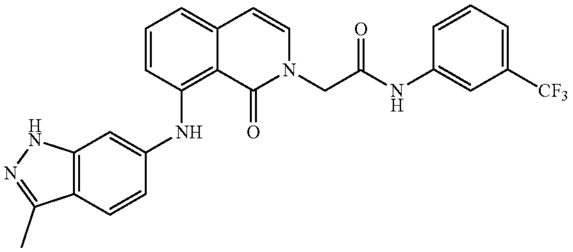
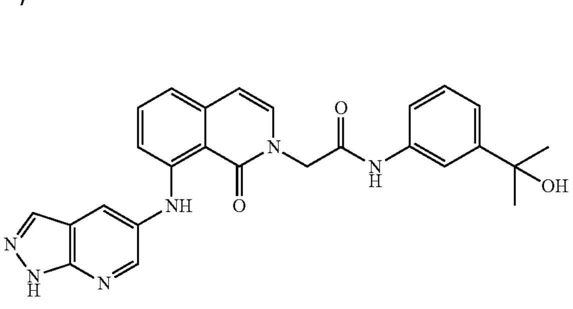

-continued
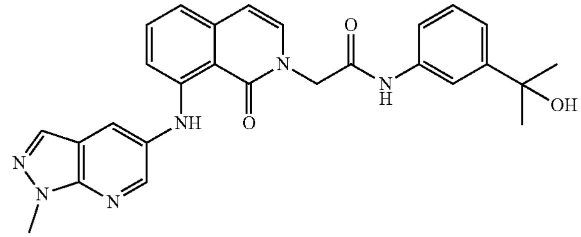
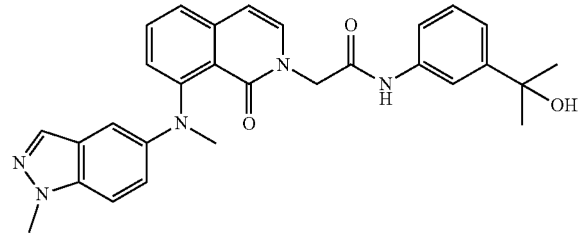
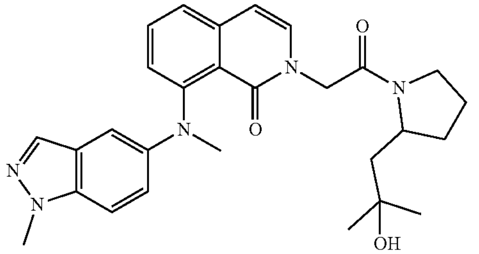
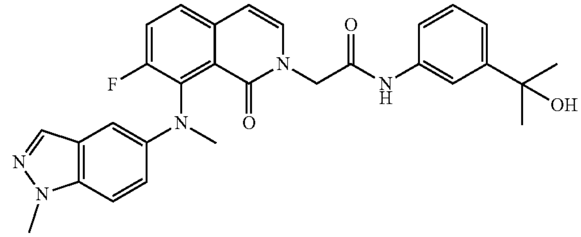
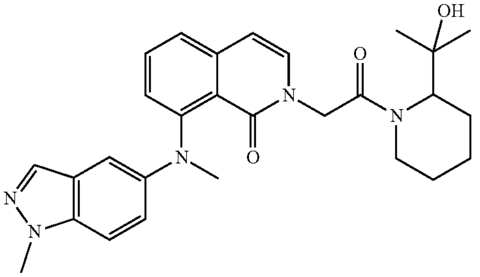
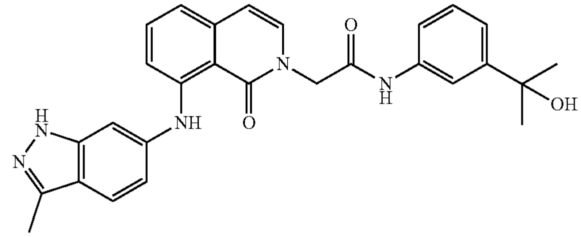
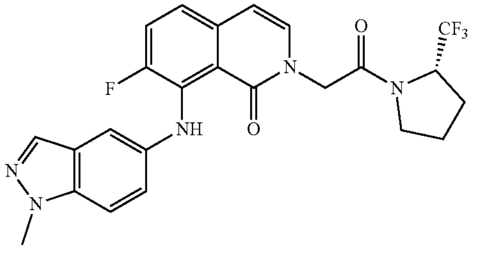
-continued
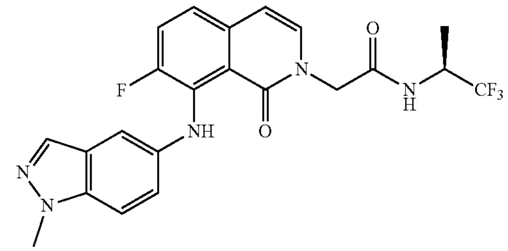
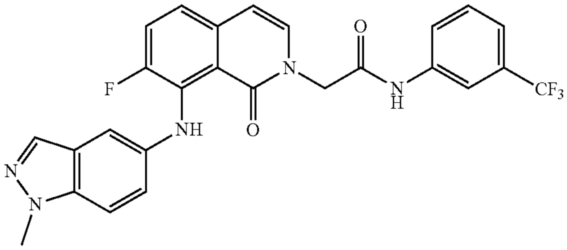
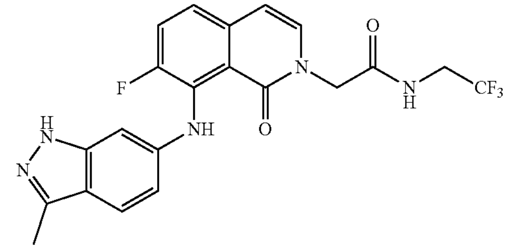
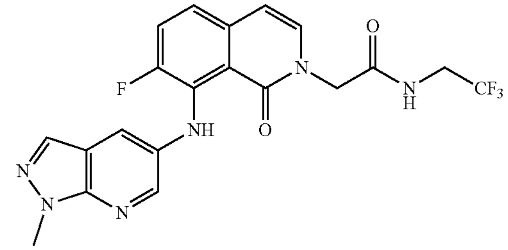
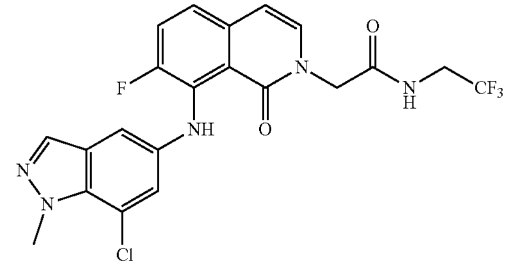
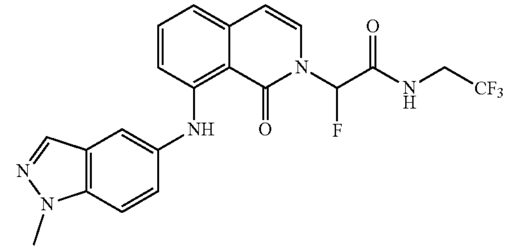

-continued

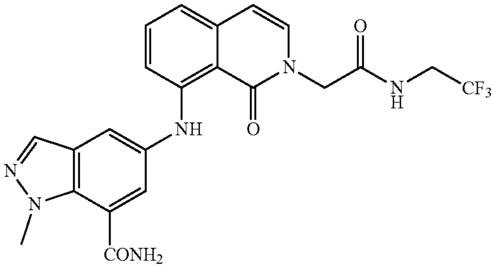

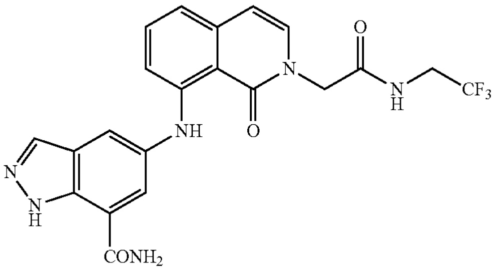

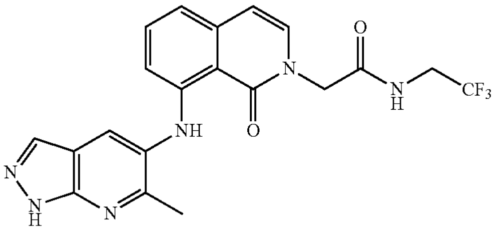

-continued

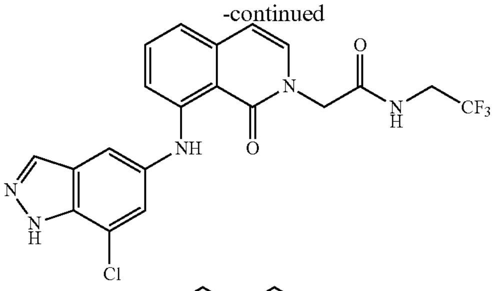

and

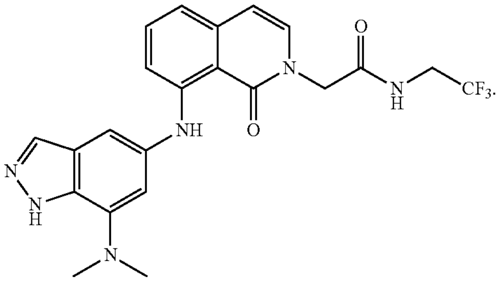

.

21. A pharmaceutical composition, comprising a compound of claim 1; and a pharmaceutically acceptable excipient.

22. A method of treating a disease or disorder selected from renal conditions, liver conditions, inflammatory conditions, cardiovascular conditions, acute and chronic organ transplant rejection, fibrotic diseases and cancer, comprising administering to a subject in need thereof a therapeutically effective amount of a compound of claim 1.

* * * * *